(12) United States Patent
Devy et al.

(10) Patent No.: US 8,008,445 B2
(45) Date of Patent: Aug. 30, 2011

(54) METALLOPROTEINASE 9 BINDING PROTEINS

(75) Inventors: Laetitia Devy, Somerville, MA (US); David Buckler, Chester, NJ (US); Edward H. Cohen, Belmont, MA (US)

(73) Assignee: Dyax Corp., Cambridge, MA (US)

( * ) Notice: Subject to any disclaimer, the term of this patent is extended or adjusted under 35 U.S.C. 154(b) by 163 days.

(21) Appl. No.: 12/396,740

(22) Filed: Mar. 3, 2009

(65) Prior Publication Data

US 2009/0311245 A1    Dec. 17, 2009

Related U.S. Application Data

(60) Provisional application No. 61/033,075, filed on Mar. 3, 2008, provisional application No. 61/054,938, filed on May 21, 2008, provisional application No. 61/138,297, filed on Dec. 17, 2008.

(51) Int. Cl.
*C12P 21/08* (2006.01)
(52) U.S. Cl. .................. 530/387.3; 530/391.7
(58) Field of Classification Search ............... 530/387.3, 530/391.7
See application file for complete search history.

(56) References Cited

U.S. PATENT DOCUMENTS

| | | | |
|---|---|---|---|
| 2002/0159971 A1 | 10/2002 | Houde et al. | |
| 2004/0115202 A1 | 6/2004 | Chen | |
| 2004/0146499 A1* | 7/2004 | Wood et al. | 424/94.65 |
| 2005/0118632 A1 | 6/2005 | Chen et al. | |
| 2006/0062777 A1 | 3/2006 | Brooks et al. | |
| 2006/0063204 A1 | 3/2006 | Valkirs et al. | |
| 2006/0142550 A1 | 6/2006 | Chang | |
| 2007/0203209 A1 | 8/2007 | Bartolini et al. | |
| 2007/0207184 A1 | 9/2007 | Ruane et al. | |
| 2007/0258987 A1 | 11/2007 | Francisco et al. | |
| 2009/0186031 A1 | 7/2009 | Wood | |
| 2009/0203060 A1 | 8/2009 | Wood | |
| 2009/0297449 A1 | 12/2009 | Devy et al. | |

FOREIGN PATENT DOCUMENTS

| | | |
|---|---|---|
| WO | 9957315 | 11/1999 |
| WO | 0190047 | 11/2001 |
| WO | 2009079581 | 6/2009 |
| WO | 2009079585 | 6/2009 |
| WO | 2009111508 | 9/2009 |
| WO | 2010048432 | 4/2010 |

OTHER PUBLICATIONS

Ueda et al., "Surviving gene expression in endometrosis," J. Clin. Endocr. Metab., 2002, vol. 87, pp. 3452-3459.
Vadillo-Ortega et al., "92-kd type IV collagenase (matrix metalloproteinase-9) activity in human amniochorion increases with labor," Am. J. Pathol., Jan. 1995, vol. 146(1), pp. 148-156.
Van Den Steen et al., "Neutrophil gelatinase B poteniates interleukin-8 tenfold by aminoterminal processing, whereas it degrades CTAP-III, PF-4, and GRO-alpha and leaves RANTES and MCP-2 intact," Blood, 2000, vol. 96, pp. 2673-2681.
Vu et al., "MMP-9/gelatinase B is a key regulator of growth plate angiogenesis and apoptosis o hypertrophic chondrocytes," Cell, 1998, vol. 93, pp. 411-422.
Wang et al., "Lipoprotein receptor-mediated induction of matrix metalloproteinase by tissue plasminogen activator," Nature Med., 2003, vol. 9, pp. 1313-1317.
Yan et al., "Repression of 92-kDa type IV collagenase expression by MTA1 is mediated through direct interactions with the promoter via a mechanism, which is both dependent on and independent of histone deacetylation," J. Biol. Chem., 2003, vol. 278, pp. 2309-2316.
Yu et al., "Cell surface-localized matrix metalloproteinase-9 proteolytically activates TGF-beta and promotes tumor invasion and angiogenesis," Genes Dev., 2000, vol. 14, pp. 163-176.
Zhao et al., "Activation of pro-gelatinase B by endometase/matrilysin-2 promotes invasion of human prostate cancer cells," J. Biol. Chem., Apr. 25, 2003, vol. 278(17), pp. 15056-15064.
International Search Report and Written Opinion from corresponding International Application No. PCT/US09/35840, dated Jun. 1, 2009.
Bergers et al., "Extrinsic Regulators of Epithelial Tumor Progression: Metalloproteinases", Current Opinion in Genetics and Development, 10:120-127, 2000.
Nagase et al., "Nomenclature and Glossary of the Matrix Metalloproteinases", Matrix, Supplemental No. 1:421-424, 1992.
Itoh, "MT1-MMP: A Key Regulator of Cell Migration in Tissue", IUBMB Life, 58(10):589-596, Oct. 2006.
Jiang et al., "Expression of Membrane Type-1 Matrix Metalloproteinase, MT1-MMP in Human Breast Cancer and its Impact on Invasiveness of Breast Cancer Cells", Int. J. Mol. Med., 17:583-590, 2006.
Paquette et al., "In Vitro Irradiation of Basement Membrane Enhances the Invasiveness of Breast Cancer Cells", British Journal of Cancer, 97:1505-1512, 2007.
Shinoda et al., "A Novel Matrix Metalloproteinase Inhibitor, FYK-1388 Suppresses Tumor Growth, Metastasis and Angiogenesis by Human Fibrosarcoma Cell Line", Int'l Journal of Oncology, 22:281-288, 2003.
Choi et al., "Expression of Matrix Metalloproteinases in the Muscle of Patients with Inflammatory Myopathies", Neurology, vol. 54, Issue 1, Jan. 2000.
Andrews et al., "Gelatinase B (MMP-9) is not essential in the normal kidney and does not influence progression of renal disease in a mouse model of Alport syndrome," Am. J. Pathol., Jul. 2000, vol. 157(1), pp. 303-311. Buisson-Legendre et al., "Relationship Between Cell-Associated Matrix Metalloproteinase 9 and Psoriatic Keratinocyte Growth," Journal of Investigative Dermatology, 2000, vol. 115, pp. 213-218.
Collier et al., "On the structure and chromosome location of the 72- and 92-kDa human type IV collagenase genes," Genomics, 1991, vol. 9, pp. 429-434.
Coussens et al., "MMP-9 supplied by bone marrow-derived cells contributes to skin carcinogenesis," Cell, 2000, vol. 103, pp. 481, 490.
Davis et al., "Matrix metalloproteinase-1 and -9 activation by plasmin regulates a novel endothelial cell-mediated mechanism of collagen gel contraction and capillary tube regression in three-dimensional collagen matrices," J. Cell. Sci., Mar. 2001, vol. 114(Pt. 5), pp. 917-930.

(Continued)

*Primary Examiner* — Misook Yu
*Assistant Examiner* — Brad Duffy
(74) *Attorney, Agent, or Firm* — Lando & Anastasi, LLP

(57) ABSTRACT

Proteins that bind to matrix metalloproteinase 9 and methods of using such proteins are described.

4 Claims, 10 Drawing Sheets

OTHER PUBLICATIONS

Di Carlo et al., "Urinary gelatinase activities (matrix metalloproteinases 2 and 9) in human bladder tumors," Oncol. Rep., 2006, vol. 15, pp. 1321-1326.

Dubois et al., Resistance of young gelatinase B-deficient mice to experimental autoimmune encephalomyelitis and necrotizing tail lesions, 1999, J. Clin. Invest. vol. 104, pp. 1507-1515.

Gijbels et al., "Gelatinase in the cerebrospinal fluid of patients with multiple sclerosis and other inflammatory neurological disorders," J. Neuroimmun. 1992, vol. 41, p. 29-34.

Gijbels et al., "Gelatinase B is present in the cerebrospinal fluid during experimental autoimmune encephalomyelitis and cleaves myelin basic protein," J. Neurosci. Res., 1993, vol. 36, pp. 432-440.

Gu et al., "S-nitrosylation of matrix metalloproteinases: signaling pathway to neuronal cell death," Science, 2002, vol. 297, pp. 1186-1190.

Gursoy-Ozdemir et al., Cortical spreading depression activates and upregulates MMP-9, J. Clin. Invest. 2004, vol. 113, pp. 1447-1455.

Graubert et al., "Cloning and Expression of the cDNA Encoding Mouse Neutrophil Gelatinase: Demonstration of Coordinate Secondary Granule Protein Gene Expression During Terminal Neutrophil Maturation," Blood, Nov. 15, 1993, vol. 82, No. 10, pp. 3192-3197.

Hayashidani et al., "Targeted deletion of MMP-2 attenuates early LV rupture and late remodeling after experimental myocardial infarction," 2003, Am. J. Physiol. Heart Circ. Physiol. vol. 285, pp. H1229-H1235.

Heymans et al., "Loss or inhibition of uPA or MMP-9 attenuates LV remodeling and dysfunction after acute pressure overload in mice," 2005, Am. J. Pathol., vol. 166, pp. 15-25.

Heymans et al., "Inhibition of plasminogen activators or matrix metalloproteinases prevents cardiac rupture but impairs therapeutic angiogenesis and causes cardiac failure," Nat. Med., 1999, vol. 5, pp. 1135-1142.

Heymans et al., "Inhibition of urokinase-type plasminogen activator or matrix metalloproteinases prevents cardiace injury and dysfunction during viral myocarditis," 2006, Circulation, vol. 114, pp. 565-573.

Heissig et al., Recruitment of stem and progenitor cells from the bone marrow niche requires MMP-9 mediated release of Kit-ligand, Cell, 2002, vol. 109, pp. 625-637.

Huhtala et al., Complete structure of the human gene for 92-kDa type IV collagenase: divergent regulation of expression for the 92- and 72-kilodalton enzyme genes in HT-1080 cells, J. Biol. Chem., 1991, vol. 266, pp. 16485-16490.

Hudson et al., "Effects of selective matrix metalloproteinase inhibitor (PG-116800) to prevent ventricular remodeling after myocardial infarction: results of the PREMIER (Prevention of Myocardial Infarction Early Remodeling) trial," J. Am. Coll. Cardiol., 2006, vol. 48, pp. 15-20.

Johnson et al., "Matrix metalloproteinase-2 and -9 differentially regulate smooth muscle cell migration and cell-mediated collagen organization," Arterioscler Thromb Vasc. Biol., 2004, vol. 24, pp. 54-60.

Kaliski et al., "Angiogenesis and tumor growth inhibition by a matrix metalloproteinase inhibitor targeting radiation-induced invasion," Mol. Cancer Ther., 2005, vol. 4, pp. 1717-1728.

Kawamura et al., "In situ gelatinolytic activity correlates with tumor progression and prognosis in patients with bladder cancer," J. Urol., 2004, vol. 172, pp. 1480-1484.

Kelly et al., Increased matrix metalloproteinase-9 in the airway after allergen challenge, 2000, Am. J. Resp. Crit. Care Med., 2000, vol. 162, pp. 1157-1161.

Kenagy et al., "Primate smooth muscle cell migration from aortic explants is mediated by endogenous platelet-derived growth factor and basic fibroblast growth factor acting through matrix metalloproteinases 2 and 9," Circulation, Nov. 18, 1997, vol. 96(10), pp. 3555-3560.

Koivunen et al., "Tumor targeting with a selective gelantinase inhibitor," Nature Biotechnology, Aug. 1999, vol. 17, pp. 768-774.

Lambert et al., "MMP-2 and MMP-9 synergize in promoting choroidal neovascularization," Faseb J., 2003, vol. 17, pp. 2290-2292.

La Rocca et al., "Zymographic detection and clinical correlations of MMP-2 and MMP-9 in breast cancer sera," Br. J. Cancer, 2004, vol. 90, pp. 1414-1421.

Larsen et al., "The expression of matrix metalloproteinase-12 by oligodendrocytes regulates their maturation and morphological differentiation," J. Neurosci., Sep. 1, 2004, vol. 24(35), pp. 7597-7603.

Laterveer et al., Rapid mobilization of hematopoietic progenitor cells in Rhesus monkeys by a single intraveneous injection interleukin-8, of interleukin-8, Blood, 1996, vol. 87, pp. 781-788.

Lee et al., "Matrix metalloproteinase-9 and spontaneous hemorrhage in an animal model of cerebral amyloid angiopathy," Ann. Neurol., 2003, vol. 54, pp. 379-382.

Linn et al., "Reassignment of the 92-kDa type IV collagenase gene (CLG4B) to human chromosome 20," Cytogent. Cell Genet., 1996, vol. 72, pp. 159-161.

Lin et al., "Salvianolic acid B attenuates MMP-2 and MMP-9 expression in vivo in apolipoprotein-E-deficient mouse aorta and in vitro in LPS-treated human aortic smooth muscle cells," J. Cell Biochem., 2007, vol. 100, pp. 372-384.

Masson et al., "Contribution of host MMP-2 and MMP-9 to promote tumor vascularization and invasion of malignant keratinocytes," Faseb J., 2005, vol. 19, pp. 234-236.

Matsuyama et al., "Matrix metalloproteinases as novel disease markers in Takayasu arteritis," Circulation, 2003, vol. 108, pp. 1469-1473.

Minematsu et al., Genetic polymorphism in matrix metalloproteinase-9 and pulmonary emphysema, Biochem. Biophys. Res. Commun., 2001, vol. 289, pp. 116-119.

NCBI Locus CAC07541, retrieved from http://www.ncbi.nlm.nih.gov/protein/9997653, retrieved May 14, 2009.

NCBI Locus NP_038627, retrieved from http://www.ncbi.nlm.nih.gov/protein/7305277, retrieved May 14, 2009.

Opdenakker et al., "The molecular basis of leukocytosis," Immun. Today, 1998, vol. 9, pp. 182-189.

Opdenakker et al., "Cytokine-mediated regulation of human leukocyte gelatinases and role in arthritis," Lymphokine Cytokine Res., 1991, vol. 10, pp. 317-324.

Osman et al., "Expression of matrix metalloproteinases and tissue inhibitors of metalloproteinases define the migratory characteristics of human monocyte-derived dendritic cells," Immunology, 2002, vol. 105, pp. 73-82.

Oulu Univeristy Library, Matrix metalloproteinases (MMPs) and their specific tissue inhibitors (TIMPs) in mature human odontoblasts and pulp tissue, 2003, http://herkules.oulufi/isbn9514270789/html/x561.html, retrieved on May 12, 2005, 9 pages.

Peterson et al., "Matrix metalloproteinase inhibition attenuates left ventricular remodeling and dysfunction in a rat model of progressive heart failure," 2001, Circulation, vol. 103, pp. 2303-2309.

Price et al., "Identification of a matrix-degrading phenotype in human tuberculosis in vitro and in vivo," J. Immun., 2001, vol. 166, pp. 4223-4230.

Pruijt et al., Prevention of interleukin-8-induced mobilization of hematopoietic progenitor cells in rhesus monkeys by inhibitory antibodies against the metalloproteinase gelatinase B (MMP-9), Proc. Nat. Acad. Sci., 1999, vol. 96, pp. 10863-10868.

Ramos-Desimone et al., "Inhibition of Matrix Metalloproteinase 9 Activation by a Specific Monoclonal Antibody," Hybridoma, 1993, vol. 12, No. 4, pp. 349-363.

Romanic et al., "Matrix metalloproteinase expression increases after cerebral focal ischemia in rats: inhibition of matrix metalloproteinase-9 reduces infarct size," Stroke, May 1998, vol. 29(5), pp. 1020-1030.

Seftor et al., "Cooperative interactions of laminin 5 gamma2 chain, matrix metalloproteinase-2, and membrane type-1 matrix/metalloproteinase are required for mimicry of embryonic vasculogenesis by aggressive melanoma," Cancer Res., Sep. 1, 2001, vol. 61(17), pp. 6322-6327.

St. Jean et al., "Characterization of a dinucleotide repeat in the 92 kDa type IV collagenase gene (CLG4B), localization of CLG4B to chromosome 20 and the role of CLG4B in aortic aneurismal disease," Ann. Hum. Genet., 1995, vol. 59, pp. 17-24.

Turner et al., "Role of matrix metalloproteinase 9 in pituitary tumor behavior," J. Clin. Endocr. Metab., 2000, vol. 85, pp. 2931-2935.

* cited by examiner

| | Dilution enzyme | Substrate used | % Activity at 1µM final | % Activity at 500nM final |
|---|---|---|---|---|
| Hu-MMP1 | 1/300 | M2350 | 108 | |
| Hu-MMP2 | 1/500 | M2350 | 107 | |
| Hu-MMP3 | 1/200 | M2225 | 112 | |
| Hu-MMP7 | 1/500 | M2350 | 111 | |
| Hu-MMP8 | 1/1000 | M2350 | 104 | |
| Hu-MMP9 | 1/500 | M2350 | 6 | |
| Mouse-MMP9 | 1/20000 | M2350 | 3 | |
| Hu-MMP10 | 1/100 | M2350 | 110 | |
| Hu-MMP12 | 1/500 | | ND | 104 |
| Hu-MMP13 | 1/5000 | M2350 | 100 | |
| Hu-MMP14 | 1/1000 | M2350 | 105 | |

SEQUENCE LISTING

<160> NUMBER OF SEQ ID NOS: 960

<210> SEQ ID NO 1
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met His Ser Phe Cys Ala Phe Lys Ala Glu Thr Gly Pro Cys Arg Ala
1               5                   10                  15

Arg Phe Asp Arg Trp Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
    50                  55

<210> SEQ ID NO 2
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
ttctattctc acagtgcaca gagcgaattg actcagccac cgtcagcgtc tgcggccccc         60
gggcagaggg tcaccatctc ttgttctgga agcagctcca acatcggaag taacactgta        120

```
acctggtacc agaagctccc aggaacggcc cccaagctcc tcatttacaa taattatgag    180
cggccctcag gggtccctgc ccgattctct ggctccaagt ctggcacctc agcctccctg    240
gccatcagtg gctccagtc tgaggatgag gctgattatt actgtgcaac atgggatgac    300
agcctgattg ccaattacgt cttcggaagt gggaccaagg tcaccgtcct aggtcagccc    360
aaggccaacc cc                                                        372
```

```
<210> SEQ ID NO 3
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Phe Tyr Ser His Ser Ala Gln Ser Glu Leu Thr Gln Pro Pro Ser Ala
1               5                   10                  15

Ser Ala Ala Pro Gly Gln Arg Val Thr Ile Ser Cys Ser Gly Ser Ser
            20                  25                  30

Ser Asn Ile Gly Ser Asn Thr Val Thr Trp Tyr Gln Lys Leu Pro Gly
        35                  40                  45

Thr Ala Pro Lys Leu Leu Ile Tyr Asn Asn Tyr Glu Arg Pro Ser Gly
    50                  55                  60

Val Pro Ala Arg Phe Ser Gly Ser Lys Ser Gly Thr Ser Ala Ser Leu
65                  70                  75                  80

Ala Ile Ser Gly Leu Gln Ser Glu Asp Glu Ala Asp Tyr Tyr Cys Ala
                85                  90                  95

Thr Trp Asp Asp Ser Leu Ile Ala Asn Tyr Val Phe Gly Ser Gly Thr
            100                 105                 110

Lys Val Thr Val Leu Gly Gln Pro Lys Ala Asn Pro
        115                 120
```

```
<210> SEQ ID NO 4
<211> LENGTH: 483
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atgaagaagc tcctctttgc tatcccgctc gtcgttcctt ttgtggccca gccggccatg     60
gccgaagttc aattgttaga gtctggtggc ggtcttgttc agcctggtgg ttctttacgt    120
ctttcttgcg ctgcttccgg attcactttc tctccttacc ttatgaattg ggttcgccaa    180
gctcctggta aagtttgga gtgggttcct ctatctatt cttctggtgg cggtactggt    240
tatgctgact ccgttaaagg tcgcttcact atctctagag acaactctaa gaatactctc    300
tacttgcaga tgaacagctt aagggctgag gacacggccg tgtattactg tgcgagaata    360
taccatagca gcagtggacc tttctacggt atggacgtct ggggccaagg gaccacggtc    420
accgtctcaa gcgcctccac caagggccca tcggtcttcc cgctagcacc tcctccaag    480 agc                                                                 483
```

```
<210> SEQ ID NO 5
<211> LENGTH: 161
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 5

Met Lys Lys Leu Leu Phe Ala Ile Pro Leu Val Val Pro Phe Val Ala
1               5                   10                  15

Gln Pro Ala Met Ala Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Pro Tyr Leu Met Asn Trp Val Arg Gln Ala Pro Gly Lys
50                  55                  60

Gly Leu Glu Trp Val Ser Ser Ile Tyr Ser Ser Gly Gly Thr Gly
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Ile Tyr His Ser Ser Gly Pro Phe
        115                 120                 125

Tyr Gly Met Asp Val Trp Gly Gln Gly Thr Thr Val Thr Val Ser Ser
130                 135                 140

Ala Ser Thr Lys Gly Pro Ser Val Phe Pro Leu Ala Pro Ser Ser Lys
145                 150                 155                 160

Ser

<210> SEQ ID NO 6
<211> LENGTH: 148
<212> TYPE: PRT
<213> ORGANISM: Homo sapiens

<400> SEQUENCE: 6

Met Ala Arg Lys Gly Ala Arg Arg Pro Arg Gln Gly Pro Gly Ser His
1               5                   10                  15

Lys Trp Leu Gln Pro Gly Ser Arg Arg Glu Lys Glu Arg Ile Pro Gln
            20                  25                  30

Pro Pro Pro Pro Ala Arg Pro Arg Asp Ala Ala Pro Arg Arg Val
        35                  40                  45

Leu Val Pro Ala Val Arg Val Pro Glu Ser Gly His Phe Ala Gly
    50                  55                  60

Arg Pro Trp Ala Pro Gln Cys His Pro Lys Gly Leu Arg Arg Pro Ser
65                  70                  75                  80

Ala Glu Ser His Ser Val Ala Gln Ala Gly Val Gln Cys His Asp Leu
                85                  90                  95

Gly Ser Leu Gln Pro Pro Pro Ser Ser Gly Asp Ser Pro Ala Ser
            100                 105                 110

Ala Ser Arg Val Ala Gly Ile Thr Thr Val Pro Gly Thr Leu Ser
        115                 120                 125

Ala Leu Asp Asp Cys Cys Leu Ile Thr Glu Leu Pro Tyr Lys Pro Pro
130                 135                 140

Ala Val Leu Tyr
145

<210> SEQ ID NO 7
<211> LENGTH: 1955
<212> TYPE: DNA
```

<213> ORGANISM: Homo sapiens

<400> SEQUENCE: 7

```
acactttgcg ttccgcggcc ccggcccctt ggtttcctag tcctggctcc attccctct      60
caggcctagg gctgggaccc ctccccgccc ccggtcttgg ccctgccccc ttcaacagac     120
ggtccgcccc ggcccctccc cctcgtcccg cccggccctg gcaggccccg ccccctgcgg     180
cctctacctt tgacgtcttc ccccgggagg tggcgggggt ctgcgaccga atgccggcgg     240
gactctgggt cagggcttct ggcgggccct gcgggggggca gcgaggtgac cgtgaacctg     300
cggctcatgg cgcggaaagg agccaggcgg ccgcggcaag gtccgggatc gcacaagtgg     360
ctgcaaccag gctctaggag ggagaaagag cggatccccc aaccccctcc gcccgcccgc     420
cccccgcgag acgcggcgcc gcgcagggtc ctagtgcccg ctgtgcgaag ggttcctgaa     480
tctggccact tcgctgggag gccctgggct ccccagtgcc acccgaaggg cctgaggagg     540
ccatctgcag aatctcactc tgtcgcccag gccgagtgc agtgtcatga tcttggctca     600
ctgcaacctc cgcctcccag ttcaggagat tctcctgcct cagcctcccg ggtggctggg     660
attacaagca cagtgcctgg cacattatcg gcacttgatg actgttgtct aataactgag     720
cttccataca aaccacctgc cgtcctgtac tgaaggagaa agagcttcca gccggggagg     780
caggaaatct gggtcctggt cttggttgca tccctgactt cctaaatgac ctggagaagg     840
cctctgcctc tgctgggatc ttgtctgtgc tgggcatttt gtttccattt ccaagggctt     900
tttcttcctc gctcagaatt tgaccactca ctaagaggag cttagtgtgg tgtctcacga     960
agggatcctc ctcagccctc acctcggtac tggaagacgt cgtgcgtgtc caaaggcacc    1020
ccggggaaca tccggtccac ctcgctggcg ctccggggat ccaccatctg cgccttcacg    1080
tcgaacctgc gggcaggcgc ggaggagaca ggtgctgagc cggctagcgg acggaccgac    1140
ggcgccgggg ctcccctgc cggcggccgc ggcggcgctc acctccagag gcgccgcccg    1200
ctgaacagca gcatcttccc cctgccactc cggagggccc cggtcacctg gccacgtcg    1260
gcgcccaggc ccagcttgtc cagacgcctc gggcccagca ccgacgcgcc tgtgtacacc    1320
cacacctggc gccctgcagg ggaggagggt cacgtcggtt tgggggcgca gagggagcac    1380
gtactcctag aacgcgagga gggagattcc ggcgaggcct ttcctagccc gcgtgcccgc    1440
agtccctgca acccaggggc agaggcgctg gtagagcga cgcgagggcg tggagaggag    1500
ggggcagaaa ctcagccgcc cctacgtttg ctaaactgcg tccgccaggg ggcgtatttt    1560
tctaaaacgc acaagacgtt tcgtgggtta tcgatggtct cttgagcctc cttgactgat    1620
ggggattgac cgggcggggg agggaaagta ggtaactaac cagagaagaa gaaaagcttc    1680
ttggagagcg gctcctcaaa gaccgagtcc agcttgcggg gcagcgcggg ccacttgtcg    1740
gcgataagga agggccctg cggccggctc cccctgccct cagagaatcg ccagtacttc    1800
ctgagaaagc gaggagggaa aggacgggct ctaagccttg gacacagggc cagtgggcgg    1860
gaagggacgg gcagcccctc cgcaaagccc cctcccgcat ccacacaacc ccgcctcctc    1920
acccatcctt gaacaaatac agctggttcc caatc                              1955
```

<210> SEQ ID NO 8
<211> LENGTH: 730
<212> TYPE: PRT
<213> ORGANISM: Mus musculus

<400> SEQUENCE: 8

```
Met Ser Pro Trp Gln Pro Leu Leu Leu Ala Leu Leu Ala Phe Gly Cys
1               5                   10                  15
```

```
Ser Ser Ala Ala Pro Tyr Gln Arg Gln Pro Thr Phe Val Phe Pro
            20                  25                  30

Lys Asp Leu Lys Thr Ser Asn Leu Thr Asp Thr Gln Leu Ala Glu Ala
 35                  40                  45

Tyr Leu Tyr Arg Tyr Gly Tyr Thr Arg Ala Ala Gln Met Met Gly Glu
 50                  55                  60

Lys Gln Ser Leu Arg Pro Ala Leu Leu Met Leu Gln Lys Gln Leu Ser
 65                  70                  75                  80

Leu Pro Gln Thr Gly Glu Leu Asp Ser Gln Thr Leu Lys Ala Ile Arg
                 85                  90                  95

Thr Pro Arg Cys Gly Val Pro Asp Val Gly Arg Phe Gln Thr Phe Lys
                100                 105                 110

Gly Leu Lys Trp Asp His His Asn Ile Thr Tyr Trp Ile Gln Asn Tyr
            115                 120                 125

Ser Glu Asp Leu Pro Arg Asp Met Ile Asp Asp Ala Phe Ala Arg Ala
130                 135                 140

Phe Ala Val Trp Gly Glu Val Ala Pro Leu Thr Phe Thr Arg Val Tyr
145                 150                 155                 160

Gly Pro Glu Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Ala Gly Val Gln Gly Asp Ala His Phe Asp Asp Asp Glu
            195                 200                 205

Leu Trp Ser Leu Gly Lys Gly Val Val Ile Pro Thr Tyr Tyr Gly Asn
210                 215                 220

Ser Asn Gly Ala Pro Cys His Phe Pro Phe Thr Phe Glu Gly Arg Ser
225                 230                 235                 240

Tyr Ser Ala Cys Thr Thr Asp Gly Arg Asn Asp Gly Thr Pro Trp Cys
                245                 250                 255

Ser Thr Thr Ala Asp Tyr Asp Lys Asp Gly Lys Phe Gly Phe Cys Pro
                260                 265                 270

Ser Glu Arg Leu Tyr Thr Glu His Gly Asn Gly Glu Gly Lys Pro Cys
            275                 280                 285

Val Phe Pro Phe Ile Phe Glu Gly Arg Ser Tyr Ser Ala Cys Thr Thr
290                 295                 300

Lys Gly Arg Ser Asp Gly Tyr Arg Trp Cys Ala Thr Thr Ala Asn Tyr
305                 310                 315                 320

Asp Gln Asp Lys Leu Tyr Gly Phe Cys Pro Thr Arg Val Asp Ala Thr
                325                 330                 335

Val Val Gly Gly Asn Ser Ala Gly Glu Leu Cys Val Phe Pro Phe Val
            340                 345                 350

Phe Leu Gly Lys Gln Tyr Ser Ser Cys Thr Ser Asp Gly Arg Arg Asp
            355                 360                 365

Gly Arg Leu Trp Cys Ala Thr Thr Ser Asn Phe Asp Thr Asp Lys Lys
        370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Leu Tyr Ser Tyr Leu Glu Gly Phe Pro Leu Asn
                420                 425                 430

Lys Asp Asp Ile Asp Gly Ile Gln Tyr Leu Tyr Gly Arg Gly Ser Lys
```

```
                    435                 440                 445
Pro Asp Pro Arg Pro Ala Thr Thr Thr Thr Glu Pro Gln Pro Thr
    450                 455                 460

Ala Pro Pro Thr Met Cys Pro Thr Ile Pro Pro Thr Ala Tyr Pro Thr
465                 470                 475                 480

Val Gly Pro Thr Val Gly Pro Thr Gly Ala Pro Ser Pro Gly Pro Thr
                485                 490                 495

Ser Ser Pro Ser Pro Gly Pro Thr Gly Ala Pro Ser Pro Gly Pro Thr
            500                 505                 510

Ala Pro Pro Thr Ala Gly Ser Ser Glu Ala Ser Thr Glu Ser Leu Ser
        515                 520                 525

Pro Ala Asp Asn Pro Cys Asn Val Asp Val Phe Asp Ala Ile Ala Glu
    530                 535                 540

Ile Gln Gly Ala Leu His Phe Phe Lys Asp Gly Trp Tyr Trp Lys Phe
545                 550                 555                 560

Leu Asn His Arg Gly Ser Pro Leu Gln Gly Pro Phe Leu Thr Ala Arg
                565                 570                 575

Thr Trp Pro Ala Leu Pro Ala Thr Leu Asp Ser Ala Phe Glu Asp Pro
            580                 585                 590

Gln Thr Lys Arg Val Phe Phe Phe Ser Gly Arg Gln Met Trp Val Tyr
        595                 600                 605

Thr Gly Lys Thr Val Leu Gly Pro Arg Ser Leu Asp Lys Leu Gly Leu
    610                 615                 620

Gly Pro Glu Val Thr His Val Ser Gly Leu Leu Pro Arg Arg Leu Gly
625                 630                 635                 640

Lys Ala Leu Leu Phe Ser Lys Gly Arg Val Trp Arg Phe Asp Leu Lys
                645                 650                 655

Ser Gln Lys Val Asp Pro Gln Ser Val Ile Arg Val Asp Lys Glu Phe
            660                 665                 670

Ser Gly Val Pro Trp Asn Ser His Asp Ile Phe Gln Tyr Gln Asp Lys
        675                 680                 685

Ala Tyr Phe Cys His Gly Lys Phe Phe Trp Arg Val Ser Phe Gln Asn
    690                 695                 700

Glu Val Asn Lys Val Asp His Glu Val Asn Gln Val Asp Asp Val Gly
705                 710                 715                 720

Tyr Val Thr Tyr Asp Leu Leu Gln Cys Pro
                725                 730

<210> SEQ ID NO 9
<211> LENGTH: 3185
<212> TYPE: DNA
<213> ORGANISM: Mus musculus

<400> SEQUENCE: 9
ctcaccatga gtccctggca gcccctgctc ctggctctcc tggctttcgg ctgcagctct     60
gctgcccctt accagcgcca gccgactttt gtggtcttcc ccaaagacct gaaaacctcc    120
aacctcacgg acacccagct ggcagaggca tacttgtacc gctatggtta cacccgggcc    180
gcccagatga tgggagagaa gcagtctcta cggccggctt gctgatgct  tcagaagcag    240 ctctccctgc cccagactgg tgagctggac agccagacac taaaggccat cgaacacca     300 cgctgtggtg tcccagacgt gggtcgattc caaaccttca aaggcctcaa gtgggaccat    360
cataacatca catactggat ccaaaactac tctgaagact gccgcgaga catgatcgat     420 gacgccttcg cgcgcgcctt cgcggtgtgg ggcgaggtgg caccctcac cttcacccgc    480
```

-continued

```
gtgtacggac ccgaagcgga cattgtcatc cagtttggtg tcgcggagca cggagacggg    540
tatcccttcg acggcaagga cggccttctg cacacagcct ttcccctgg cgccggcgtt     600 cagggagatg cccatttcga cgacgacgag ttgtggtcgc tgggcaaagg cgtcgtgatc    660
cccacttact atgaaactc aaatggtgcc ccatgtcact ttcccttcac cttcgaggga     720
cgctcctatt cggcctgcac cacagacggc cgcaacgacg gcacgccttg gtgtagcaca    780
acagctgact acgataagga cggcaaattt ggtttctgcc ctagtgagag actctacacg    840
gagcacggca acggagaagg caaaccctgt gtgttcccgt tcatctttga gggccgctcc    900
tactctgcct gcaccactaa aggccgctcg gatggttacc gctggtgcgc caccacagcc    960
aactatgacc aggataaact gtatggcttc tgccctaccc gagtggacgc gaccgtagtt   1020
gggggcaact cggcaggaga gctgtgcgtc ttccccttcg tcttcctggg caagcagtac   1080
tcttcctgta ccagcgacgg ccgcagggat gggcgcctct ggtgtgcgac cacatcgaac   1140
ttcgacactg acaagaagtg gggtttctgt ccagaccaag ggtacagcct gttcctggtg   1200
gcagcgcacg agttcggcca tgcactgggc ttagatcatt ccagcgtgcc ggaagcgctc   1260
atgtacccgc tgtatagcta cctcgagggc ttccctctga ataaagacga catagacggc   1320
atccagtatc tgtatggtcg tggctctaag cctgacccaa ggcctccagc caccaccaca   1380
actgaaccac agccgacagc acctcccact atgtgtccca ctatacctcc cacggcctat   1440
cccacagtgg gccccacggt tgggccctaca ggcgcccct cacctggccc cacaagcagc   1500
ccgtcacctg gcctacagg cgcccctca cctggccta cagcgccccc tactgcgggc   1560
tcttctgagg cctctacaga gtctttgagt ccggcagaca atccttgcaa tgtggatgtt   1620
tttgatgcta ttgctgagat ccagggcgct ctgcatttct tcaaggacgg ttggtactgg   1680
aagttcctga atcatagagg aagcccatta cagggcccct tccttactgc ccgcacgtgg   1740
ccagccctgc ctgcaacgct ggactccgcc tttgaggatc cgcagaccaa gagggttttc   1800
ttcttctctg gacgtcaaat gtgggtgtac acaggcaaga ccgtgctggg ccccaggagt   1860
ctggataagt tgggtctagg cccagaggta acccacgtca gcgggcttct cccgcgtcgt   1920
ctcgggaagg ctctgctgtt cagcaagggg cgtgtctgga gattcgactt gaagtctcag   1980
aaggtggatc cccagagcgt cattcgcgtg gataaggagt tctctggtgt gccctggaac   2040
tcacacgaca tcttccagta ccaagacaaa gcctatttct gccatggcaa attcttctgg   2100
cgtgtgagtt tccaaaatga ggtgaacaag gtggaccatg aggtgaacca ggtggacgac   2160
gtgggctacg tgacctacga cctcctgcag tgcccttgaa ctagggctcc ttctttgctt   2220
caaccgtgca gtgcaagtct ctagagacca ccaccaccac caccacacac aaaccccatc   2280
cgagggaaag gtgctagctg gccaggtaca gactggtgat ctcttctaga gactgggaag   2340
gagtggaggc aggcagggct ctctctgccc accgtccttt cttgttggac tgtttctaat   2400
aaacacggat ccccaacctt ttccagctac tttagtcaat cagcttatct gtagttgcag   2460
atgcatccga gcaagaagac aactttgtag ggtggattct gacctttat ttttgtgtgg   2520 cgtctgagaa ttgaatcagc tggcttttgt gacaggcact tcaccggcta aaccacctct   2580
cccgactcca gccctttta ttattatgta tgaggttatg ttcacatgca tgtatttaac   2640
ccacagaatg cttactgtgt gtcggcgcg gctccaaccg ctgcataaat attaaggtat   2700
tcagttgccc ctactggaag gtattatgta actatttctc tcttacattg gagaacacca   2760
ccgagctatc cactcatcaa acatttattg agagcatccc tagggagcca ggctctctac   2820
tgggcgttag ggacagaaat gttggttctt ccttcaagga ttgctcagag attctccgtg   2880
```

-continued

```
tcctgtaaat ctgctgaaac cagacccag actcctctct ctcccgagag tccaactcac    2940
tcactgtggt tgctggcagc tgcagcatgc gtatacagca tgtgtgctag agaggtagag    3000
ggggtctgtg cgttatggtt caggtcagac tgtgtcctcc aggtgagatg accctcagc    3060 tggaactgat ccaggaagga taaccaagtg tcttcctggc agtctttttt aaataaatga    3120
ataaatgaat atttacttaa aaaaaaaaaa aaaaaaaaa aaaaaaaaa aaaaaaaaa     3180 aaaaa                                                                3185
```

```
<210> SEQ ID NO 10
<211> LENGTH: 730
<212> TYPE: PRT
<213> ORGANISM: Mus musculus

<400> SEQUENCE: 10
```

```
Met Ser Pro Trp Gln Pro Leu Leu Leu Ala Leu Leu Ala Phe Gly Cys
 1               5                  10                  15

Ser Ser Ala Ala Pro Tyr Gln Arg Gln Pro Thr Phe Val Val Phe Pro
            20                  25                  30

Lys Asp Leu Lys Thr Ser Asn Leu Thr Asp Thr Gln Leu Ala Glu Ala
        35                  40                  45

Tyr Leu Tyr Arg Tyr Gly Tyr Thr Arg Ala Ala Gln Met Met Gly Glu
    50                  55                  60

Lys Gln Ser Leu Arg Pro Ala Leu Leu Met Leu Gln Lys Gln Leu Ser
65                  70                  75                  80

Leu Pro Gln Thr Gly Glu Leu Asp Ser Gln Thr Leu Lys Ala Ile Arg
                85                  90                  95

Thr Pro Arg Cys Gly Val Pro Asp Val Gly Arg Phe Gln Thr Phe Lys
            100                 105                 110

Gly Leu Lys Trp Asp His His Asn Ile Thr Tyr Trp Ile Gln Asn Tyr
        115                 120                 125

Ser Glu Asp Leu Pro Arg Asp Met Ile Asp Asp Ala Phe Ala Arg Ala
    130                 135                 140

Phe Ala Val Trp Gly Glu Val Ala Pro Leu Thr Phe Thr Arg Val Tyr
145                 150                 155                 160

Gly Pro Glu Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Ala Gly Val Gln Gly Asp Ala His Phe Asp Asp Asp Glu
        195                 200                 205

Leu Trp Ser Leu Gly Lys Gly Val Val Ile Pro Thr Tyr Tyr Gly Asn
    210                 215                 220

Ser Asn Gly Ala Pro Cys His Phe Pro Phe Thr Phe Glu Gly Arg Ser
225                 230                 235                 240

Tyr Ser Ala Cys Thr Thr Asp Gly Arg Asn Asp Gly Thr Pro Trp Cys
                245                 250                 255

Ser Thr Thr Ala Asp Tyr Asp Lys Asp Gly Lys Phe Gly Phe Cys Pro
            260                 265                 270

Ser Glu Arg Leu Tyr Thr Glu His Gly Asn Gly Glu Gly Lys Pro Cys
        275                 280                 285

Val Phe Pro Phe Ile Phe Glu Gly Arg Ser Tyr Ser Ala Cys Thr Thr
    290                 295                 300

Lys Gly Arg Ser Asp Gly Tyr Arg Trp Cys Ala Thr Thr Ala Asn Tyr
305                 310                 315                 320
```

```
Asp Gln Asp Lys Leu Tyr Gly Phe Cys Pro Thr Arg Val Asp Ala Thr
                325                 330                 335

Val Val Gly Gly Asn Ser Ala Gly Glu Leu Cys Val Phe Pro Phe Val
                340                 345                 350

Phe Leu Gly Lys Gln Tyr Ser Ser Cys Thr Ser Asp Gly Arg Arg Asp
                355                 360                 365

Gly Arg Leu Trp Cys Ala Thr Thr Ser Asn Phe Asp Thr Asp Lys Lys
            370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Leu Tyr Ser Tyr Leu Glu Gly Phe Pro Leu Asn
                420                 425                 430

Lys Asp Asp Ile Asp Gly Ile Gln Tyr Leu Tyr Gly Arg Gly Ser Lys
                435                 440                 445

Pro Asp Pro Arg Pro Pro Ala Thr Thr Thr Thr Glu Pro Gln Pro Thr
            450                 455                 460

Ala Pro Pro Thr Met Cys Pro Thr Ile Pro Pro Thr Ala Tyr Pro Thr
465                 470                 475                 480

Val Gly Pro Thr Val Gly Pro Thr Gly Ala Pro Ser Pro Gly Pro Thr
                485                 490                 495

Ser Ser Pro Ser Pro Gly Pro Thr Gly Ala Pro Ser Pro Gly Pro Thr
                500                 505                 510

Ala Pro Pro Thr Ala Gly Ser Ser Glu Ala Ser Thr Glu Ser Leu Ser
            515                 520                 525

Pro Ala Asp Asn Pro Cys Asn Val Asp Val Phe Asp Ala Ile Ala Glu
530                 535                 540

Ile Gln Gly Ala Leu His Phe Phe Lys Asp Gly Trp Tyr Trp Lys Phe
545                 550                 555                 560

Leu Asn His Arg Gly Ser Pro Leu Gln Gly Pro Phe Leu Thr Ala Arg
                565                 570                 575

Thr Trp Pro Ala Leu Pro Ala Thr Leu Asp Ser Ala Phe Glu Asp Pro
            580                 585                 590

Gln Thr Lys Arg Val Phe Phe Phe Ser Gly Arg Gln Met Trp Val Tyr
                595                 600                 605

Thr Gly Lys Thr Val Leu Gly Pro Arg Ser Leu Asp Lys Leu Gly Leu
            610                 615                 620

Gly Pro Glu Val Thr His Val Ser Gly Leu Leu Pro Arg Arg Leu Gly
625                 630                 635                 640

Lys Ala Leu Leu Phe Ser Lys Gly Arg Val Trp Arg Phe Asp Leu Lys
                645                 650                 655

Ser Gln Lys Val Asp Pro Gln Ser Val Ile Arg Val Asp Lys Glu Phe
                660                 665                 670

Ser Gly Val Pro Trp Asn Ser His Asp Ile Phe Gln Tyr Gln Asp Lys
            675                 680                 685

Ala Tyr Phe Cys His Gly Lys Phe Phe Trp Arg Val Ser Phe Gln Asn
690                 695                 700

Glu Val Asn Lys Val Asp His Glu Val Asn Gln Val Asp Asp Val Gly
705                 710                 715                 720

Tyr Val Thr Tyr Asp Leu Leu Gln Cys Pro
                725                 730

<210> SEQ ID NO 11
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Phe Leu Gly
1

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (7-methoxycoumarin-4-yl)acetic acid-Pro
<220> FEATURE:
<221> NAME/KEY: MOD_RES
<222> LOCATION: (4)..(4)
<223> OTHER INFORMATION: Cys(methoxybenzyl)
<220> FEATURE:
<221> NAME/KEY: MOD_RES
<222> LOCATION: (8)..(8)
<223> OTHER INFORMATION: 2,3-diaminopropionic acid(2,4-dinitrophenyl)
<220> FEATURE:
<223> OTHER INFORMATION: C-term amidated

<400> SEQUENCE: 12

Pro Leu Ala Cys Trp Ala Arg Xaa
1               5

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ala Ser Gln Gly Ile Ser Asn Tyr Leu Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ala Ser Asn Leu Gln Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Gln Tyr Lys Thr Tyr Pro Phe Thr
```

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Tyr Arg Met His
1               5

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Ile Gly Ser Ser Gly Gly Pro Thr Ala Tyr Ala Asp Ser Val Lys
1               5                   10                  15

Gly

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Arg Ala Gly Thr Phe Phe Asp Ser
1               5

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ser Ser Gln Ser Leu Val Ser Ser Asn Gly Asn Thr Tyr Leu Asn
1               5                   10                  15

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Tyr Lys Val Ser Asn Arg Asp Ser
1               5

<210> SEQ ID NO 21
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 21

Met Gln Gly Thr His Trp Pro Tyr Thr
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met Tyr Arg Met Met
1               5

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr Ile Gly Ser Ser Gly Gly Met Thr Ser Tyr Ala Asp Ser Val Lys
1               5                   10                  15

Gly

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Ser Val Phe Arg Gly Glu Arg Asp Ala Phe Asp Ile
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ala Ser Gln Ser Ile Ser Ser Ser Phe Leu Ala
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Ala Ser Ser Arg Ala Thr
1               5
```

```
<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Gln Thr Tyr Ser Thr Pro Leu Thr
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Tyr Ser Met Val
1               5

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Val Ile Ser Pro Ser Gly Gly Tyr Thr Gly Tyr Ala Asp Ser Val Lys
1               5                   10                  15

Gly

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Met Arg Val Pro Ala Ala Ile Gly Gly Trp Leu Asp Pro
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Ala Ser Gln Asn Ile Gly Lys Phe Leu Ala
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 32

Gly Ala Ser Thr Leu Gln Leu
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Lys Tyr Asp Ser Ala Leu Trp Thr
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Tyr Gly Met Trp
1               5

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Ile Ser Pro Ser Gly Gly Trp Thr Phe Tyr Ala Asp Ser Val Lys
1               5                   10                  15

Gly

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Val Lys Val Arg His Gly Gly Gly Phe Asp Tyr
1               5                   10

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Lys Ser Ser Gln Asn Val Leu Leu Ser Ser Asn Ser Lys Asn Tyr Leu
1               5                   10                  15

Ala
```

```
<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Trp Ala Ser Thr Arg Glu Ser
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Gln Tyr Tyr Ser Ile Pro Trp Ser
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asn Tyr Arg Met Ser
1               5

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ser Ile Gly Ser Ser Gly Gly Gln Thr Met Tyr Ala Asp Ser Val Lys
1               5                   10                  15
Gly

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser His Pro Val Ser Gly Gly Val Phe Asp Phe
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 43

Arg Ala Ser Gln Gly Ile Ser Ser Trp Leu Ala
1               5                   10

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Tyr Ala Thr Ser Ser Leu Gln Ser
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Gln Ser Lys Ser Phe Pro Pro Thr
1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Tyr Arg Met Asn
1               5

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Tyr Ile Gly Ser Ser Gly Gly Asn Thr Ala Tyr Ala Asp Ser Val Lys
1               5                   10                  15

Gly

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Arg Ile Gly Val Gly Ala Lys Gly Gly Thr Phe Asp Ile
1               5                   10                  15

<210> SEQ ID NO 49
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Ala Ser Gln Ser Val Ser Ser Tyr Leu Ala
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asp Ala Ser Asn Arg Ala Thr
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Gln Arg Ser Asn Trp Pro Leu Thr
1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

His Tyr Arg Met Tyr
1               5

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Tyr Ile Gly Ser Ser Gly Gly Met Thr Ser Tyr Ala Asp Ser Val Lys
1               5                   10                  15

Gly

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54
```

```
Ser Asp Arg Ser Gly Asp Asn Tyr Tyr Gly Met Asp Tyr
1               5                   10
```

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

```
Arg Ala Ser Gln Ser Ile Ser Ser Asp Leu Asn
1               5                   10
```

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

```
Ala Ala Ser Ser Leu Gln Ser
1               5
```

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

```
Gln Gln Ser Tyr Ser Thr Pro Val Thr
1               5
```

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

```
Asp Tyr Arg Met Phe
1               5
```

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

```
Ser Ile Ser Ser Ser Gly Gly Phe Thr Asn Tyr Ala Asp Ser Val Lys
1               5                   10                  15

Gly
```

<210> SEQ ID NO 60
<211> LENGTH: 14
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 60

Asp Gln Gly Gly Thr Val Val Val Ala Thr Ala Asp Tyr
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Ala Ser Gln Ser Ile Ser Ser Trp Leu Ala
1               5                   10

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Ala Ser Ser Leu Glu Ser
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Gln Tyr Asn Ser Tyr Pro Trp Thr
1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Lys Tyr Lys Met Phe
1               5

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Ile Gly Ser Ser Gly Gly Ala Thr Ser Tyr Ala Asp Ser Val Lys
1               5                   10                  15
```

Gly

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Gly Phe Trp Ser Gly Tyr Tyr Gly Tyr
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Ala Ser Glu Thr Val Arg Tyr Gly Gln Val Ala
1               5                   10

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Ala Ser Lys Arg Ala Thr
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Gln Arg Ser Asn Trp Pro Leu Thr
1               5

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Leu Tyr Arg Met Asn
1               5

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 71

Tyr Ile Gly Ser Ser Gly Gly Ala Thr Ala Tyr Ala Asp Ser Val Lys
1               5                   10                  15
Gly

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ser Met Arg Gly Gly His Leu Asp Ser
1               5

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Gly Asp Lys Leu Gly Asp Lys Tyr Ala Ser
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Asp Arg Lys Arg Pro Ser
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Ala Trp Asp Ser Asn Thr Val Val
1               5

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

His Tyr Asp Met Trp
1               5

<210> SEQ ID NO 77
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Arg Ile Val Pro Ser Gly Gly Leu Thr Thr Tyr Ala Asp Ser Val Lys
1               5                   10                  15
Gly

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

His Ser Phe Trp Ser Gly Tyr Tyr Gly Ala Phe Asp Ile
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Arg Ala Ser Gln Gly Ile Ser Ser Trp Leu Ala
1               5                   10

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Ala Ser Thr Leu Gln Ser
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Pro Thr Tyr Ser Thr Ser Trp Thr
1               5

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82
```

```
Thr Tyr Ser Met Val
1               5

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Arg Ile Gly Ser Ser Gly Gly Asp Thr Phe Tyr Ala Asp Ser Val Lys
1               5                   10                  15

Gly

<210> SEQ ID NO 84
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Asp Arg Ala Asp Thr Val Val Thr Ala Gly Gly Asp Tyr Tyr Tyr Tyr
1               5                   10                  15

Tyr Gly Met Asp Val
            20

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Ala Ser Gln Ser Ile Ser Ser Trp Leu Ala
1               5                   10

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Lys Ala Ser Ser Leu Glu Ser
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gln Gln Tyr Asn Ser Tyr Pro Trp Thr
1               5
```

```
<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asn Tyr Lys Met His
1               5

<210> SEQ ID NO 89
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ser Ile Gly Ser Ser Gly Gly Met Thr Ser Tyr Ala Asp Ser Val Lys
1               5                   10                  15

Gly

<210> SEQ ID NO 90
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Asp Trp Gln His Leu Ala Gly Asp Ala Phe Asp Phe
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Ala Ser Gln Gly Ile Arg Asn Asp Leu Gly
1               5                   10

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ala Ala Ser Ser Leu Gln Ser
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 93

Gln Gln Leu Asn Ser Tyr Pro Pro Thr
1               5

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Pro Tyr Arg Met His
1               5

<210> SEQ ID NO 95
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Ile Gly Ser Ser Gly Gly Ala Thr Ser Tyr Ala Asp Ser Val Lys
1               5                   10                  15

Gly

<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asp Gly Ile Ala Val Ala Gly Ile Ala Phe Asp Ile
1               5                   10

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Arg Ala Ser Gln Asp Ile Arg Ser Ser Leu Ala
1               5                   10

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Ala Ser Ser Leu Gln Ser
1               5

<210> SEQ ID NO 99
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gln Gln Ala Asn Ser Phe Pro Pro Thr
1               5

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Tyr Arg Met Gln
1               5

<210> SEQ ID NO 101
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Tyr Ile Gly Ser Ser Gly Gly Met Thr Ser Tyr Ala Asp Ser Val Lys
1               5                   10                  15
Gly

<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Ser Trp Arg Gly Gly Ser Gln Tyr Phe Asp Tyr
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Arg Ala Ser Gln Ser Ile Ser Ser Tyr Leu Asn
1               5                   10

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104
```

```
Ala Ala Ser Ser Leu Gln Ser
1               5
```

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

```
Gln Gln Ser Tyr Ser Thr Pro Arg Thr
1               5
```

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

```
His Tyr Val Met Ser
1               5
```

<210> SEQ ID NO 107
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

```
Ser Ile Gly Ser Ser Gly Gly Asp Thr His Tyr Ala Asp Ser Val Lys
1               5                   10                  15

Gly
```

<210> SEQ ID NO 108
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

```
Val Trp Ile Ser Gly Ser Tyr Leu Asp Ala Phe Asp Ile
1               5                   10
```

<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

```
Arg Ala Ser Gln Ser Ile Ser Ser His Leu Ala
1               5                   10
```

<210> SEQ ID NO 110
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 110

Gly Ala Ser Asn Arg Ala Thr
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gln Gln Arg Ser Asn Trp Pro Pro Thr
1               5

<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ala Tyr Arg Met Gln
1               5

<210> SEQ ID NO 113
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Tyr Ile Gly Ser Ser Gly Gly Gln Thr Ser Tyr Ala Asp Ser Val Lys
1               5                   10                  15

Gly

<210> SEQ ID NO 114
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Asp Pro Val Gly Ala Lys Tyr Tyr Gly Met Asp Val
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Arg Ala Ser Gln Ser Val Ser Ser Tyr Leu Ala
1               5                   10
```

```
<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Asp Ala Ser Asn Arg Ala Thr
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Gln Arg Ser Asn Trp Pro Ile Thr
1               5

<210> SEQ ID NO 118
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ala Tyr Gly Met Val
1               5

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Val Ile Arg Ser Ser Gly Gly Pro Thr Ser Tyr Ala Asp Ser Val Lys
1               5                   10                  15

Gly

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ala Gly Gly Gly Thr Tyr Leu Asp Tyr
1               5

<210> SEQ ID NO 121
<211> LENGTH: 11
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 121

Arg Ala Ser Gln Ser Val Ser Ser Asn Leu Ala
1               5                   10

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gly Ala Ser Thr Arg Ala Thr
1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

His Gln Tyr Asn Asp Trp Pro Leu Thr
1               5

<210> SEQ ID NO 124
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Pro Tyr Lys Met Tyr
1               5

<210> SEQ ID NO 125
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Tyr Ile Gly Ser Ser Gly Gly Met Thr Ser Tyr Ala Asp Ser Val Lys
1               5                   10                  15

Gly

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Arg Gly Tyr Ser Ser Gly Pro Leu Arg Tyr
1               5                   10

```
<210> SEQ ID NO 127
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Arg Ala Ser Gln Ser Ile Ser Ser Thr Ile Thr Tyr Leu Asn
1               5                   10

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ala Ala Ser Asn Arg Ala Thr
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gln Gln Arg Ser Asn Trp Pro Pro Thr
1               5

<210> SEQ ID NO 130
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Asp Tyr Lys Met Trp
1               5

<210> SEQ ID NO 131
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ser Ile Arg Ser Ser Gly Gly Pro Ile Gly Tyr Ala Asp Ser Val Lys
1               5                   10                  15
Gly

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 132

Glu Thr Asn Gln Met Gly Met Asp Val
1               5

<210> SEQ ID NO 133
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Arg Ala Ser Gln Ser Val Ser Ser Tyr Leu Ala
1               5                   10

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Asp Ala Ser Asn Arg Ala Thr
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gln Gln Arg Gly Asn Trp Pro Ile Thr
1               5

<210> SEQ ID NO 136
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Pro Tyr Arg Met Ser
1               5

<210> SEQ ID NO 137
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ser Ile Gly Ser Ser Gly Gly Gln Thr Ser Tyr Ala Asp Ser Val Lys
1               5                   10                  15

Gly

<210> SEQ ID NO 138
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Glu Pro Pro Gly Tyr Tyr Phe Asp Ser
1               5

<210> SEQ ID NO 139
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Arg Ala Ser Gln Ser Val Ser Ser Ser Tyr Leu Ala
1               5                   10

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Asp Ala Ser Asn Arg Ala Thr
1               5

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gln Gln Arg Ser Asn Trp Pro Ile Thr
1               5

<210> SEQ ID NO 142
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asn Tyr Arg Met His
1               5

<210> SEQ ID NO 143
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Trp Ile Ser Ser Ser Gly Gly Pro Thr Ser Tyr Ala Asp Ser Val Lys
1               5                   10                  15
```

Gly

<210> SEQ ID NO 144
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Gly Ser Tyr Arg His Asn Asn Val Phe Asp Ile
1               5                   10

<210> SEQ ID NO 145
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Arg Ala Ser Gln Thr Val Ser Arg Asn Tyr Leu Ala
1               5                   10

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Asp Ala Ser Lys Arg Ala Thr
1               5

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gln Gln Arg Ser Asn Trp Pro Pro Thr
1               5

<210> SEQ ID NO 148
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Leu Tyr Arg Met Val
1               5

<210> SEQ ID NO 149
<211> LENGTH: 17
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 149

Ser Phe Gly Pro Ser Gly Gly Pro Thr Met Tyr Ala Asp Ser Val Lys
1               5                   10                  15
Gly

<210> SEQ ID NO 150
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Arg Gly Tyr Thr Val Asp Val Asn Ala Phe Asp Ile
1               5                   10

<210> SEQ ID NO 151
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Arg Ala Ser Gln Ser Val Ser Ser Asn Leu Ala
1               5                   10

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Ala Ser Thr Arg Ala Thr
1               5

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gln Gln Tyr Asn Lys Trp Pro Gln Thr
1               5

<210> SEQ ID NO 154
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ile Tyr Arg Met His
1               5

```
<210> SEQ ID NO 155
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Tyr Ile Gly Ser Ser Gly Gly Asn Thr Ser Tyr Ala Asp Ser Val Lys
1               5                   10                  15

Gly

<210> SEQ ID NO 156
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Glu Trp Val Gly Ser Ser Ala Ala Leu Asp Tyr
1               5                   10

<210> SEQ ID NO 157
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Lys Ser Ser Gln Ser Val Leu Tyr Ser Ser Asn Asn Lys Asn Tyr Leu
1               5                   10                  15

Ala

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Trp Ala Ser Thr Arg Glu Ser
1               5

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gln Gln Ser Tyr Ser Thr Pro Leu Thr
1               5

<210> SEQ ID NO 160
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
                                peptide

<400> SEQUENCE: 160

Ala Tyr Arg Met His
1               5

<210> SEQ ID NO 161
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Tyr Ile Gly Ser Ser Gly Gly Met Thr Thr Tyr Ala Asp Ser Val Lys
1               5                   10                  15

Gly

<210> SEQ ID NO 162
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ser Thr Val Thr Thr Leu Asp Tyr
1               5

<210> SEQ ID NO 163
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Arg Ala Ser Gln Ser Val Arg Ser Tyr Leu Ala
1               5                   10

<210> SEQ ID NO 164
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Asp Val Ser Asn Arg Ala Thr
1               5

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gln Gln Arg Ser Asn Trp Pro Leu Thr
1               5
```

```
<210> SEQ ID NO 166
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Met Tyr Arg Met Ile
1               5

<210> SEQ ID NO 167
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Trp Ile Gly Ser Ser Gly Gly Gln Thr Ser Tyr Ala Asp Ser Val Lys
1               5                   10                  15

Gly

<210> SEQ ID NO 168
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Gly Leu Trp Cys Asp Asn
1               5

<210> SEQ ID NO 169
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Arg Ala Ser Gln Ser Val Ser Ser Ser Tyr Leu Ala
1               5                   10

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Ala Ser Ser Arg Ala Ile
1               5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 171

Gln Gln Tyr Gly Ser Ser Thr Arg Thr
1               5

<210> SEQ ID NO 172
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gln Tyr Arg Met Phe
1               5

<210> SEQ ID NO 173
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Tyr Ile Gly Ser Ser Gly Gly Met Thr Ser Tyr Ala Asp Ser Val Lys
1               5                   10                  15

Gly

<210> SEQ ID NO 174
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ser Met Gly Tyr Gly Asp Ala Phe Asp Ile
1               5                   10

<210> SEQ ID NO 175
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Arg Ala Ser Gln Thr Ile Ser Ser Tyr Tyr Leu Ala
1               5                   10

<210> SEQ ID NO 176
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Ala Ser Ser Arg Ala Ala
1               5

<210> SEQ ID NO 177
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gln Gln Tyr Gly Val Ser Pro Pro Tyr Ser
1               5                   10

<210> SEQ ID NO 178
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Tyr Tyr Asn Met Val
1               5

<210> SEQ ID NO 179
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Val Ile Ser Pro Ser Gly Gly Trp Thr Pro Tyr Ala Asp Ser Val Lys
1               5                   10                  15

Gly

<210> SEQ ID NO 180
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Glu Val Gly Gly Ser Gly Trp Leu Gly Asp Ala Phe Asp Ile
1               5                   10

<210> SEQ ID NO 181
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Arg Ala Ser Gln Gly Ile Ser Ser Ala Leu Ala
1               5                   10

<210> SEQ ID NO 182
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182
```

```
Asp Ala Ser Ser Leu Glu Ser
1               5

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gln Gln Phe His Thr Tyr Pro Phe Thr
1               5

<210> SEQ ID NO 184
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Thr Tyr Arg Met Val
1               5

<210> SEQ ID NO 185
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Tyr Ile Gly Ser Ser Gly Gly Gln Thr Ala Tyr Ala Asp Ser Val Lys
1               5                   10                  15

Gly

<210> SEQ ID NO 186
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

His Asn Arg Ala Ile Gly Thr Phe Asp Tyr
1               5                   10

<210> SEQ ID NO 187
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Lys Ser Ser Gln Ser Ile Leu Tyr Ser Ser Asn Asn Arg Asn Tyr Leu
1               5                   10                  15

Ala

<210> SEQ ID NO 188
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Trp Ala Ser Thr Arg Glu Ser
1               5

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gln His Tyr Tyr Thr Ala Pro Tyr Thr
1               5

<210> SEQ ID NO 190
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gly Tyr Ser Met His
1               5

<210> SEQ ID NO 191
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ser Ile Trp Pro Ser Gly Gly Tyr Thr Arg Tyr Ala Asp Ser Val Lys
1               5                   10                  15

Gly

<210> SEQ ID NO 192
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gly Asn Asp Ser Asp Ser Phe Ala Tyr Arg Phe
1               5                   10

<210> SEQ ID NO 193
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193
```

Arg Thr Ser Gln Ser Val Ser Asp Ser Leu Ala
1               5                   10

<210> SEQ ID NO 194
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Asp Ala Ser Asn Arg Ala Thr
1               5

<210> SEQ ID NO 195
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gln Gln Arg Gly Ser Trp Pro Ile Thr
1               5

<210> SEQ ID NO 196
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Asn Tyr Arg Met Met
1               5

<210> SEQ ID NO 197
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Tyr Ile Gly Ser Ser Gly Gly Met Thr Ser Tyr Ala Asp Ser Val Lys
1               5                   10                  15

Gly

<210> SEQ ID NO 198
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Glu Thr Asn Trp Asn Asp Leu Gly Arg Tyr Phe Asp Tyr
1               5                   10

<210> SEQ ID NO 199
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 199

Arg Ala Ser His Ser Val Gly Gly Gly Tyr Leu Ala
1               5                   10

<210> SEQ ID NO 200
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Asp Ala Phe Asn Arg Ala Thr
1               5

<210> SEQ ID NO 201
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gln Gln Arg Ser Glu Trp Pro Trp Thr
1               5

<210> SEQ ID NO 202
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Arg Tyr Lys Met Ser
1               5

<210> SEQ ID NO 203
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Tyr Ile Gly Ser Ser Gly Gly Met Thr Ser Tyr Ala Asp Ser Val Lys
1               5                   10                  15

Gly

<210> SEQ ID NO 204
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Asp Leu Thr Ala Thr Gly Tyr Phe Asp Tyr
1               5                   10
```

<210> SEQ ID NO 205
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Arg Ala Ser Gln Gly Ile Ser Ser Trp Leu Ala
1               5                   10

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Ala Ser Ser Leu Glu Ser
1               5

<210> SEQ ID NO 207
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Gln Gln Ala Asn Ser Phe Pro Pro Thr
1               5

<210> SEQ ID NO 208
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Asp Tyr Arg Met Thr
1               5

<210> SEQ ID NO 209
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Trp Ile Gly Ser Ser Gly Gly Gln Thr Ser Tyr Ala Asp Ser Val Lys
1               5                   10                  15

Gly

<210> SEQ ID NO 210
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 210

Gly Thr Pro Arg Val Ala Ser Tyr Phe Asp Tyr
1               5                   10

<210> SEQ ID NO 211
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Arg Ala Ser Gln Ser Val Gly Ser Asp Tyr Leu Ala
1               5                   10

<210> SEQ ID NO 212
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ala Ala Ser Thr Arg Ala Thr
1               5

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gln Gln Arg Ser Ser Trp Pro Pro Thr
1               5

<210> SEQ ID NO 214
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Lys Tyr Tyr Met Val
1               5

<210> SEQ ID NO 215
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Tyr Ile Ser Pro Ser Gly Gly Thr Tyr Tyr Ala Asp Ser Val Lys
1               5                   10                  15

Gly

```
<210> SEQ ID NO 216
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Asn Tyr Tyr Asp Ser Ser Gly Thr Arg Gly Ala Phe Asp Ile
1               5                   10

<210> SEQ ID NO 217
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Lys Ser Ser Gln Ser Val Leu Tyr Ser Ser Asn Asn Lys Asn Tyr Leu
1               5                   10                  15

Ala

<210> SEQ ID NO 218
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Trp Ala Ser Thr Arg Glu Ser
1               5

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Gln Gln Tyr Tyr Ser Thr Pro Leu Thr
1               5

<210> SEQ ID NO 220
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Glu Tyr Arg Met Thr
1               5

<210> SEQ ID NO 221
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 221

Tyr Ile Gly Ser Ser Gly Gly Met Thr Thr Tyr Ala Asp Ser Val Lys
1               5                   10                  15
Gly

<210> SEQ ID NO 222
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gly Ser Gly Ser Gly Tyr Asp Ser
1               5

<210> SEQ ID NO 223
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Arg Ala Ser Gln Gly Ile Arg Asn Asp Leu Gly
1               5                   10

<210> SEQ ID NO 224
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ala Ala Ser Ser Leu Gln Ser
1               5

<210> SEQ ID NO 225
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gln Gln Thr Ile Thr Phe Pro Leu Thr
1               5

<210> SEQ ID NO 226
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Ser Tyr Arg Met Met
1               5

<210> SEQ ID NO 227
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Trp Ile Ser Ser Ser Gly Gly Ser Thr Gly Tyr Ala Asp Ser Val Lys
1               5                   10                  15

Gly

<210> SEQ ID NO 228
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Thr Thr Val Thr Arg Val Gly Ser Phe Tyr Phe Asp Leu
1               5                   10

<210> SEQ ID NO 229
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Thr Gly Thr Ser Ser Asp Val Gly Tyr Tyr Asn Tyr Val Ser
1               5                   10

<210> SEQ ID NO 230
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Asp Val Ser Ala Arg Pro Ser
1               5

<210> SEQ ID NO 231
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Cys Ser Tyr Ala Gly Ser Tyr Thr Tyr Val
1               5                   10

<210> SEQ ID NO 232
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232
```

```
Met Tyr Tyr Met Gln
1               5

<210> SEQ ID NO 233
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ser Ile Arg Ser Ser Gly Gly Phe Thr Ser Tyr Ala Asp Ser Val Lys
1               5                   10                  15

Gly

<210> SEQ ID NO 234
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Gly Leu Arg Leu Asp Met
1               5

<210> SEQ ID NO 235
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Arg Ala Ser Gln Gly Ile Arg Asn Asp Leu Asp
1               5                   10

<210> SEQ ID NO 236
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ser Ala Ser Asn Leu Gln Ser
1               5

<210> SEQ ID NO 237
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Leu Gln His Asn Ser Phe Pro Leu Thr
1               5

<210> SEQ ID NO 238
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 238

Leu Tyr Arg Met Asn
1               5

<210> SEQ ID NO 239
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Tyr Ile Gly Ser Ser Gly Gly Ala Thr Ala Tyr Ala Asp Ser Val Lys
1               5                   10                  15
Gly

<210> SEQ ID NO 240
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gly Ala Trp Tyr Leu Asp Ser
1               5

<210> SEQ ID NO 241
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Arg Ala Ser Gln Ser Val Ser Thr Phe Leu Ala
1               5                   10

<210> SEQ ID NO 242
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Asp Ala Ser Asn Arg Ala Thr
1               5

<210> SEQ ID NO 243
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Gln Gln Tyr Ala Ser Pro Pro Arg Thr
1               5
```

```
<210> SEQ ID NO 244
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Gly Tyr Tyr Met Ser
1               5

<210> SEQ ID NO 245
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Ser Ile Ser Pro Ser Gly Gly Asn Thr Glu Tyr Ala Glu Ser Val Lys
1               5                   10                  15

Gly

<210> SEQ ID NO 246
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Asp Ser Gly Gln Thr Phe Tyr Tyr Ala Phe Asp Ile
1               5                   10

<210> SEQ ID NO 247
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Arg Ala Ser Gln Gly Ile Ser Arg Trp Leu Ala
1               5                   10

<210> SEQ ID NO 248
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Asp Ala Ser Asn Arg Ala Thr
1               5

<210> SEQ ID NO 249
<211> LENGTH: 11
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 249

Gln Gln Arg Ser Asn Trp Pro Pro Arg Leu Thr
1               5                   10

<210> SEQ ID NO 250
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Phe Tyr His Met Ser
1               5

<210> SEQ ID NO 251
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Ser Ile Gly Pro Ser Gly Gly Trp Thr Asn Tyr Ala Asp Ser Val Lys
1               5                   10                  15
Gly

<210> SEQ ID NO 252
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Asp Gly Gly Leu Glu Gly Met Asp Val
1               5

<210> SEQ ID NO 253
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Arg Ala Ser Gln Gly Val Ser Asn Tyr Leu Ala
1               5                   10

<210> SEQ ID NO 254
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Ala Ala Ser Thr Leu Gln Ser
1               5

```
<210> SEQ ID NO 255
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Gln Lys Tyr Asn Ser Ala Pro Tyr Thr
1               5

<210> SEQ ID NO 256
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Asn Tyr Ser Met Gly
1               5

<210> SEQ ID NO 257
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Gly Ile Tyr Ser Ser Gly Gly Tyr Thr Gln Tyr Ala Asp Ser Val Lys
1               5                   10                  15

Gly

<210> SEQ ID NO 258
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Gly His Tyr Val Trp Asp Ser Gly Trp Tyr Ser Ala Phe Asp Ile
1               5                   10                  15

<210> SEQ ID NO 259
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Arg Ala Ser Gln Ser Val Ser Ser Asp Leu Ala
1               5                   10

<210> SEQ ID NO 260
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 260

Gly Val Ser Thr Lys Ala Thr
1               5

<210> SEQ ID NO 261
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Gln Gln Tyr His Asn Trp Pro Pro Leu Thr
1               5                   10

<210> SEQ ID NO 262
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Ser Tyr Thr Met Glu
1               5

<210> SEQ ID NO 263
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Trp Ile Ser Pro Ser Gly Gly Tyr Thr Phe Tyr Ala Asp Ser Val Lys
1               5                   10                  15

Gly

<210> SEQ ID NO 264
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Gly Tyr Ser Tyr Gly Ser Ile Asp Leu
1               5

<210> SEQ ID NO 265
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Arg Ala Ser Gln Gly Ile Ser Ser Trp Leu Ala
1               5                   10

<210> SEQ ID NO 266
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ala Ala Ser Ser Leu Gln Ser
1               5

<210> SEQ ID NO 267
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Gln Gln Ala Asn Ser Phe Pro Tyr Leu Thr
1               5                   10

<210> SEQ ID NO 268
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Thr Tyr Met Met Met
1               5

<210> SEQ ID NO 269
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Ser Ile Trp Ser Ser Gly Gly Ser Thr Phe Tyr Ala Asp Ser Val Lys
1               5                   10                  15

Gly

<210> SEQ ID NO 270
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Gly Val Val Val Pro Ala Leu Asp Tyr
1               5

<210> SEQ ID NO 271
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271
```

```
Arg Ala Ser Glu Ser Ile Ser Arg Asn Leu Ala
1               5                   10

<210> SEQ ID NO 272
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Gly Ala Ala Thr Arg Val Ala
1               5

<210> SEQ ID NO 273
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Gln Gln Ala Asn Thr Phe Pro Phe Thr
1               5

<210> SEQ ID NO 274
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Met Tyr Arg Met Ser
1               5

<210> SEQ ID NO 275
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Tyr Ile Gly Ser Ser Gly Gly Pro Thr Ala Tyr Ala Asp Ser Val Lys
1               5                   10                  15

Gly

<210> SEQ ID NO 276
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Glu Gly Asp Ala Arg Val Pro Ala Ala Ile Gly Tyr
1               5                   10

<210> SEQ ID NO 277
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 277

Arg Ala Ser Gln Ser Ile Ser Ser Tyr Leu Asn
1               5                   10

<210> SEQ ID NO 278
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Ala Ala Ser Ser Leu Gln Ser
1               5

<210> SEQ ID NO 279
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Gln Gln Ser Tyr Ser Thr Pro Arg Thr
1               5

<210> SEQ ID NO 280
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

His Tyr Val Met Ser
1               5

<210> SEQ ID NO 281
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Ser Ile Gly Ser Ser Gly Gly Asp Thr His Tyr Ala Asp Ser Val Lys
1               5                   10                  15

Gly

<210> SEQ ID NO 282
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Val Trp Ile Ser Gly Ser Tyr Leu Asp Ala Phe Asp Ile
1               5                   10
```

<210> SEQ ID NO 283
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Arg Thr Ser His Asn Val Ala Asn Phe Leu Ala
1               5                   10

<210> SEQ ID NO 284
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Asp Ala Tyr Asn Arg Ala Thr
1               5

<210> SEQ ID NO 285
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Gln Gln Arg Ala Asn Trp Pro Leu Ser
1               5

<210> SEQ ID NO 286
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Arg Tyr Pro Met Glu
1               5

<210> SEQ ID NO 287
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Tyr Ile Ser Ser Ser Gly Gly Trp Thr Ser Tyr Ala Asp Ser Val Lys
1               5                   10                  15

Gly

<210> SEQ ID NO 288
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 288

Asp Gly Leu Glu Leu Phe Gly Gly Trp Leu Glu Ser
1               5                   10

<210> SEQ ID NO 289
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Arg Ala Ser Gln Ser Thr Ser Asn Ser Leu Ser
1               5                   10

<210> SEQ ID NO 290
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Ala Ala Ser Arg Leu Gln Ser
1               5

<210> SEQ ID NO 291
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Gln Gln Ser Trp Arg Thr Pro Leu Thr
1               5

<210> SEQ ID NO 292
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Gln Tyr Trp Met Thr
1               5

<210> SEQ ID NO 293
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Gly Ile Gly Pro Ser Gly Gly Pro Thr Thr Tyr Ala Asp Ser Val Lys
1               5                   10                  15

Gly

<210> SEQ ID NO 294
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

His Ser Thr Thr Val Thr Thr Asn Phe Asp Tyr
1               5                   10

<210> SEQ ID NO 295
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Arg Ala Ser Gln Ser Ile Ser Ser Tyr Leu Asn
1               5                   10

<210> SEQ ID NO 296
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Ala Ala Ser Ser Leu Gln Ser
1               5

<210> SEQ ID NO 297
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Gln Gln Ser Tyr Ser Thr Pro Arg Thr
1               5

<210> SEQ ID NO 298
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Met Tyr Tyr Met Tyr
1               5

<210> SEQ ID NO 299
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Ser Ile Arg Ser Ser Gly Gly Glu Thr Gln Tyr Ala Asp Ser Val Lys
1               5                   10                  15

Gly

<210> SEQ ID NO 300
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Val Trp Ile Ser Gly Ser Tyr Leu Asp Ala Phe Asp Ile
1               5                   10

<210> SEQ ID NO 301
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Arg Ala Thr Gln Tyr Ile Ser Asn Tyr Val Asn
1               5                   10

<210> SEQ ID NO 302
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Ala Ala Ser Ser Leu Gln Ser
1               5

<210> SEQ ID NO 303
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Gln Gln Ala Asn Ser Phe Pro Pro Thr
1               5

<210> SEQ ID NO 304
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Ala Tyr Ser Met His
1               5

<210> SEQ ID NO 305
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 305

Arg Leu Gly Ser Ser Gly Gly Pro Thr Ser Tyr Ala Asp Ser Val Lys
1               5                   10                  15

Gly

<210> SEQ ID NO 306
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Arg Ser Ser Tyr Gly Arg Gly Phe Asp Tyr
1               5                   10

<210> SEQ ID NO 307
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Arg Ala Ser Gln Ser Ile Ser Ser Tyr Leu Asn
1               5                   10

<210> SEQ ID NO 308
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Ala Ala Ser Ser Leu Gln Ser
1               5

<210> SEQ ID NO 309
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Gln Gln Ser Tyr Ser Thr Pro Arg Thr
1               5

<210> SEQ ID NO 310
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

His Tyr Pro Met Ser
1               5
```

<210> SEQ ID NO 311
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Tyr Ile Tyr Ser Ser Gly Gly Asp Thr Glu Tyr Ala Asp Ser Val Lys
1               5                   10                  15

Gly

<210> SEQ ID NO 312
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Tyr Gly Ser Gly Gly Trp Met Thr Tyr Gly Leu Asp Val
1               5                   10

<210> SEQ ID NO 313
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Arg Ala Ser Gln Ser Ile Asp Thr Tyr Leu Asn
1               5                   10

<210> SEQ ID NO 314
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Ala Ala Ser Lys Leu Glu Asp
1               5

<210> SEQ ID NO 315
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Gln Gln Ser Tyr Ser Ser Pro Gly Ile Thr
1               5                   10

<210> SEQ ID NO 316
<211> LENGTH: 5
<212> TYPE: PRT
<213> ORGANISM: Artificial Sequence
<220> FEATURE:
<223> OTHER INFORMATION: Description of Artificial Sequence: Synthetic -continued

```
        peptide

<400> SEQUENCE: 316

His Tyr Asp Met Ser
1               5

<210> SEQ ID NO 317
<211> LENGTH: 17
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 317

Ser Ile Trp Pro Ser Gly Gly Val Thr Trp Tyr Ala Asp Ser Val Lys
1               5                   10                  15

Gly

<210> SEQ ID NO 318
<211> LENGTH: 12
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 318

Gly Gly Tyr Asn Asn Tyr Tyr Ala Leu Asp Val
1               5                   10

<210> SEQ ID NO 319
<211> LENGTH: 11
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 319

Arg Ala Ser Gln Asn Ile Ala Gly Leu Leu Ala
1               5                   10

<210> SEQ ID NO 320
<211> LENGTH: 7
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 320

Lys Ala Ser Thr Leu Glu Ser
1               5

<210> SEQ ID NO 321
<211> LENGTH: 9
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 321

Gln Gln Tyr Ser Phe Asn Ser Gly Thr
1               5
```

```
<210> SEQ ID NO 322
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Lys Tyr His Met His
1               5

<210> SEQ ID NO 323
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Ser Ile Ser Pro Ser Gly Gly Val Thr Ser Tyr Ala Asp Ser Val Lys
1               5                   10                  15

Gly

<210> SEQ ID NO 324
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Asp Ala Cys Ser Gly Gly Thr Cys Gln Leu Asp Tyr
1               5                   10

<210> SEQ ID NO 325
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Arg Ala Ser Gln Ser Val Ser Ser Ser Tyr Leu Ala
1               5                   10

<210> SEQ ID NO 326
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Gly Ala Ser Ser Arg Ala Thr
1               5

<210> SEQ ID NO 327
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 327

Gln Gln Tyr Gly Ser Ser Pro Leu Thr
1               5

<210> SEQ ID NO 328
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Met Tyr Gly Met Pro
1               5

<210> SEQ ID NO 329
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Val Ile Ser Pro Ser Gly Gly Ser Thr Thr Tyr Ala Asp Ser Val Lys
1               5                   10                  15

Gly

<210> SEQ ID NO 330
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Gly Thr Pro Tyr Tyr Tyr Asp Ser Ser Tyr Asn Gly Gly Arg Ala Phe
1               5                   10                  15

Asp Ile

<210> SEQ ID NO 331
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Arg Ala Ser Gln Ser Ile Ser Ser Tyr Leu Asn
1               5                   10

<210> SEQ ID NO 332
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Ala Ala Ser Ser Leu Gln Ser
1               5
```

```
<210> SEQ ID NO 333
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Gln Gln Thr Tyr Ile Thr Pro Pro Ile Thr
1               5                   10

<210> SEQ ID NO 334
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Pro Tyr Leu Met His
1               5

<210> SEQ ID NO 335
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Tyr Ile Val Pro Ser Gly Gly Asn Thr Phe Tyr Ala Asp Ser Val Lys
1               5                   10                  15

Gly

<210> SEQ ID NO 336
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Gly Ile Gly Val Ala Ser Gly Leu Gly Ser Arg Tyr Leu Asp Tyr
1               5                   10                  15

<210> SEQ ID NO 337
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Lys Ser Ser Gln Ser Val Leu Tyr Ser Ser Asn Asn Lys Asn Tyr Leu
1               5                   10                  15

Ala

<210> SEQ ID NO 338
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 338

Trp Ala Ser Thr Arg Glu Ser
1               5

<210> SEQ ID NO 339
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Gln Gln Tyr Tyr Ser Thr Pro Pro Thr
1               5

<210> SEQ ID NO 340
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Pro Tyr Met Met Ala
1               5

<210> SEQ ID NO 341
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Arg Ile Gly Ser Trp Thr Asn Tyr Ala Asp Ser Val Lys Gly
1               5                   10

<210> SEQ ID NO 342
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Arg Ser Arg Asp Gly Tyr Lys Gly Gly Phe Asp Tyr
1               5                   10

<210> SEQ ID NO 343
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Gln Gly Asp Ser Leu Arg Ser Tyr Tyr Ala Ser
1               5                   10

<210> SEQ ID NO 344
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Gly Lys Asn Asn Arg Pro Ser
1               5

<210> SEQ ID NO 345
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Gln Ala Trp Asp Ser Ser Thr Val Val
1               5

<210> SEQ ID NO 346
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Ile Tyr Trp Met Met
1               5

<210> SEQ ID NO 347
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Tyr Ile Ser Pro Ser Gly Gly Met Thr Ser Tyr Ala Asp Ser Val Lys
1               5                   10                  15

Gly

<210> SEQ ID NO 348
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Gly Ile Tyr Cys Ser Ser Thr Ser Cys Tyr Asp Tyr Phe Asp Tyr
1               5                   10                  15

<210> SEQ ID NO 349
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349
```

```
Arg Ala Ser Gln Ser Val Ser Ser Tyr Leu Ala
1               5                   10

<210> SEQ ID NO 350
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Gly Ala Ser Ser Arg Ala Pro
1               5

<210> SEQ ID NO 351
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Gln Gln Tyr Gly Ser Ser Tyr Thr
1               5

<210> SEQ ID NO 352
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Val Tyr Met Met Pro
1               5

<210> SEQ ID NO 353
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Tyr Ile Ser Ser Ser Gly Gly Lys Thr Glu Tyr Ala Asp Ser Val Lys
1               5                   10                  15

Gly

<210> SEQ ID NO 354
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Asp Gly Ala Ala Ala Gly Pro Trp Asp Tyr Tyr Tyr Tyr Gly Leu Asp
1               5                   10                  15

Val

<210> SEQ ID NO 355
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Thr Gly Thr Ser Ser Asp Val Gly Gly Tyr Asn Tyr Val Ser
1               5                   10

<210> SEQ ID NO 356
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Glu Val Ser Lys Arg Pro Ser
1               5

<210> SEQ ID NO 357
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Ser Ser Tyr Ala Gly Thr Asn Asn Phe Val
1               5                   10

<210> SEQ ID NO 358
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

His Tyr Trp Met Lys
1               5

<210> SEQ ID NO 359
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Ser Ile Val Pro Ser Gly Gly Val Thr Tyr Tyr Ala Asp Ser Val Lys
1               5                   10                  15

Gly

<210> SEQ ID NO 360
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360
```

Asp Leu Thr Asn Met Ala Phe Asp Ile
1               5

<210> SEQ ID NO 361
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Ser Gly Ser Ser Ser Asn Ile Gly Ser Asn Thr Val Asn
1               5                   10

<210> SEQ ID NO 362
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Ser Asn Asn Gln Arg Pro Ser
1               5

<210> SEQ ID NO 363
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Ala Ala Trp Asp Asp Ser Val Ser Gly Val Val
1               5                   10

<210> SEQ ID NO 364
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Arg Tyr Lys Met Ser
1               5

<210> SEQ ID NO 365
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Tyr Ile Tyr Ser Ser Gly Gly Leu Thr Met Tyr Ala Asp Ser Val Lys
1               5                   10                  15
Gly

<210> SEQ ID NO 366
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 366

Asp Gly Gly Val Val Glu Ala Glu Asp Leu Phe Asp Tyr
1               5                   10

<210> SEQ ID NO 367
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Arg Ala Ser Gln Thr Ile Asn Asn Trp Leu Ala
1               5                   10

<210> SEQ ID NO 368
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Lys Ala Phe Asn Leu Glu Ser
1               5

<210> SEQ ID NO 369
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Gln Gln Tyr Asp Thr Tyr Ser Trp Thr
1               5

<210> SEQ ID NO 370
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Trp Tyr Gly Met Ser
1               5

<210> SEQ ID NO 371
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Ser Ile Trp Ser Ser Gly Gly Tyr Thr Gly Tyr Ala Asp Ser Val Lys
1               5                   10                  15

Gly
```

<210> SEQ ID NO 372
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Gly Ser Gly Ser Tyr Ile Ala Tyr
1               5

<210> SEQ ID NO 373
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Arg Ala Ser Gln Gly Ile Ser Ser Trp Leu Ala
1               5                   10

<210> SEQ ID NO 374
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Gly Ala Thr Ser Leu Glu Ser
1               5

<210> SEQ ID NO 375
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Gln Gln Ser Asn Ser Phe Pro Leu Thr
1               5

<210> SEQ ID NO 376
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Pro Tyr Ala Met Arg
1               5

<210> SEQ ID NO 377
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 377

Ser Ile Asp Pro Ser Gly Gly Pro Thr Tyr Tyr Ala Asp Ser Val Lys
1               5                   10                  15

Gly

<210> SEQ ID NO 378
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Arg Gly Arg Tyr Tyr Tyr Asp Ser Tyr Asp Ala Phe Asp Ile
1               5                   10

<210> SEQ ID NO 379
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Arg Ala Ser Gln Ser Val Thr Gly Asn Tyr Leu Ala
1               5                   10

<210> SEQ ID NO 380
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Gly Val Ser Ser Arg Ala Thr
1               5

<210> SEQ ID NO 381
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Gln Gln Tyr Gly Ser Ala Pro Phe Ala
1               5

<210> SEQ ID NO 382
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Tyr Tyr Tyr Met Tyr
1               5

<210> SEQ ID NO 383
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Tyr Ile Tyr Pro Ser Gly Gly Phe Thr Ser Tyr Ala Asp Ser Val Lys
1               5                   10                  15

Gly

<210> SEQ ID NO 384
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Leu Leu Gly Gly Thr Val Pro Pro Pro Asp Tyr
1               5                   10

<210> SEQ ID NO 385
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Arg Ala Ser Glu Asp Ile Arg Ser Ala Leu Ala
1               5                   10

<210> SEQ ID NO 386
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Gly Ala Ser Ser Leu Glu Ser
1               5

<210> SEQ ID NO 387
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Leu Gln His Ser Asn Tyr Pro Ala Thr
1               5

<210> SEQ ID NO 388
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388
```

```
Leu Tyr Leu Met Met
1               5

<210> SEQ ID NO 389
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Gly Ile Tyr Pro Ser Gly Gly Tyr Thr Gln Tyr Ala Asp Ser Val Lys
1               5                   10                  15

Gly

<210> SEQ ID NO 390
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Asp Lys Gly Arg Trp Asp Leu Leu Gly Trp Tyr Phe Asp Leu
1               5                   10

<210> SEQ ID NO 391
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Arg Ser Ser Gln Ser Leu Leu His Ser Asn Gly Tyr Asn Tyr Leu Asp
1               5                   10                  15

<210> SEQ ID NO 392
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Leu Gly Ser Asn Arg Ala Ser
1               5

<210> SEQ ID NO 393
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Met Gln Ala Arg Gln Thr Pro Trp Thr
1               5

<210> SEQ ID NO 394
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 394

Val Tyr Phe Met Pro
1               5

<210> SEQ ID NO 395
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Tyr Ile Tyr Pro Ser Gly Gly Arg Thr Phe Tyr Ala Asp Ser Val Lys
1               5                   10                  15

Gly

<210> SEQ ID NO 396
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Gln Asp Ser Ser Gly Trp Tyr Tyr Phe Asp Tyr
1               5                   10

<210> SEQ ID NO 397
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Thr Gly Thr Ser Ser Asp Val Gly Gly Tyr Asn Phe Val Ser
1               5                   10

<210> SEQ ID NO 398
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Asp Val Ser Asn Arg Pro Ser
1               5

<210> SEQ ID NO 399
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Ser Ser Tyr Thr Arg Ser Ser Thr Val Ile
1               5                   10
```

```
<210> SEQ ID NO 400
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Met Tyr Asn Met Tyr
1               5

<210> SEQ ID NO 401
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Tyr Ile Val Pro Ser Asp Gly Trp Thr Pro Tyr Ala Asp Ser Val Lys
1               5                   10                  15

Gly

<210> SEQ ID NO 402
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Glu Asp Pro Ser Ile Ser Gly Tyr Ile Asn Ala Phe Asp Ile
1               5                   10

<210> SEQ ID NO 403
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Arg Thr Ser Leu Ser Ile Ser Ser Asn Leu Ala
1               5                   10

<210> SEQ ID NO 404
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Asp Ala Ser Thr Arg Ala Thr
1               5

<210> SEQ ID NO 405
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                          peptide

<400> SEQUENCE: 405

Gln Gln Tyr Glu Thr Leu Pro Leu Thr
1               5

<210> SEQ ID NO 406
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Trp Tyr Glu Met Phe
1               5

<210> SEQ ID NO 407
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Ser Ile Tyr Pro Ser Gly Gly Leu Thr Pro Tyr Ala Asp Ser Val Lys
1               5                   10                  15

Gly

<210> SEQ ID NO 408
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Asp Ile His Ala Ile Phe Gly Pro Phe Tyr Tyr Tyr Tyr Gly Met Asp
1               5                   10                  15

Val

<210> SEQ ID NO 409
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Arg Ala Ser Gln Ala Ile Arg His Asp Leu Gly
1               5                   10

<210> SEQ ID NO 410
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Glu Val Ser Asn Leu Gln Ser
1               5
```

-continued

<210> SEQ ID NO 411
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Gln Gln Leu Asn Ser Tyr Pro Arg Thr
1               5

<210> SEQ ID NO 412
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Gln Tyr Leu Met Trp
1               5

<210> SEQ ID NO 413
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Tyr Ile Val Pro Ser Gly Gly Tyr Thr Leu Tyr Ala Asp Ser Val Lys
1               5                   10                  15

Gly

<210> SEQ ID NO 414
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Ser Gln Ala Leu Arg Phe Leu Glu Ser Pro Gly Ala Phe Asp Ile
1               5                   10                  15

<210> SEQ ID NO 415
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Lys Ser Ser Gln Ser Val Leu Tyr Ser Ser Asn Asn Lys Asn Tyr Leu
1               5                   10                  15

Ala

<210> SEQ ID NO 416
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Trp Ala Ser Thr Arg Glu Ser
1               5

<210> SEQ ID NO 417
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Gln Gln Tyr Tyr Ser Thr Pro Pro Thr
1               5

<210> SEQ ID NO 418
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Met Tyr Tyr Met Asp
1               5

<210> SEQ ID NO 419
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Gly Ile Ser Ser Gly Gly Phe Thr Ala Tyr Ala Asp Ser Val Lys Gly
1               5                   10                  15

<210> SEQ ID NO 420
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Glu Gly Gly Tyr Cys Ser Ser Thr Ser Cys Tyr Val Asp Tyr
1               5                   10

<210> SEQ ID NO 421
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Thr Gly Thr Thr Arg Asp Val Gly Gly Tyr Asp Tyr Val Ser
1               5                   10

```
<210> SEQ ID NO 422
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Glu Val Asn Asn Arg Pro Ser
1               5

<210> SEQ ID NO 423
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Asn Ser Tyr Ala Gly Ser Asn Lys Leu Ile
1               5                   10

<210> SEQ ID NO 424
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Val Tyr Pro Met Pro
1               5

<210> SEQ ID NO 425
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Val Ile Ser Pro Ser Gly Gly His Thr Thr Tyr Ala Asp Ser Val Lys
1               5                   10                  15

Gly

<210> SEQ ID NO 426
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Ser Val Pro Leu Tyr Tyr Phe Asp Tyr
1               5

<210> SEQ ID NO 427
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 427

Arg Ala Ser His Ile Ile Ile Arg Tyr Leu Asn
1               5                   10

<210> SEQ ID NO 428
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Ser Ala Ser Thr Leu Gln Gly
1               5

<210> SEQ ID NO 429
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Gln Gln Ser Tyr Ser Ser Pro Leu Thr
1               5

<210> SEQ ID NO 430
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Pro Tyr Ser Met Asn
1               5

<210> SEQ ID NO 431
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Arg Ile Val Pro Ser Gly Gly Phe Thr Leu Tyr Ala Asp Ser Val Lys
1               5                   10                  15

Gly

<210> SEQ ID NO 432
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Val Gly Ser Ser Ser Trp Tyr Leu Pro Tyr Phe Asp Tyr
1               5                   10

<210> SEQ ID NO 433
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Arg Ala Ser Gln Ser Val Ser Ser Ser Tyr Leu Ala
1               5                   10

<210> SEQ ID NO 434
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Gly Ala Ser Ser Arg Ala Thr
1               5

<210> SEQ ID NO 435
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Gln Gln Tyr Gly Ser Ser Val Thr
1               5

<210> SEQ ID NO 436
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Asn Tyr Pro Met Trp
1               5

<210> SEQ ID NO 437
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Tyr Ile Val Ser Ser Gly Gly Thr Met Tyr Ala Asp Ser Val Lys Gly
1               5                   10                  15

<210> SEQ ID NO 438
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Cys Ser Ser Gly Trp Tyr Val Asn Tyr Tyr Tyr Gly Met Asp Val
1               5                   10                  15
```

<210> SEQ ID NO 439
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Ser Gly Asp Glu Leu Gly Phe Gly Ser Val Cys
1               5                   10

<210> SEQ ID NO 440
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Tyr Glu Asp Asn Arg Arg Pro Ser
1               5

<210> SEQ ID NO 441
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Gln Ala Trp Ala Thr Thr Thr Val Ile
1               5

<210> SEQ ID NO 442
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Lys Tyr Met Met Gln
1               5

<210> SEQ ID NO 443
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Val Ile Val Ser Ser Gly Gly Phe Thr Trp Tyr Ala Asp Ser Val Lys
1               5                   10                  15

Gly

<210> SEQ ID NO 444
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 444

His Leu Trp Tyr Tyr Tyr Gly Met Asp Val
1               5                   10

<210> SEQ ID NO 445
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Thr Gly Thr Ser Ser Asp Val Gly Gly Tyr Asn Tyr Val Ser
1               5                   10

<210> SEQ ID NO 446
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Glu Val Ser Asn Arg Pro Ser
1               5

<210> SEQ ID NO 447
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Ser Ser Tyr Thr Ser Arg Ser Thr Pro Tyr Val
1               5                   10

<210> SEQ ID NO 448
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Ser Ile Tyr Pro Ser Gly Gly Pro Thr Gly Tyr Ala Asp Ser Val Lys
1               5                   10                  15

Gly

<210> SEQ ID NO 449
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Gly Tyr Ser Thr Gly Phe Tyr Asn Ser Gly Gly Tyr Phe Asp Tyr
1               5                   10                  15

```
<210> SEQ ID NO 450
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Ser Gly Gly Ser Ser Asn Ile Gly Ser Asn Tyr Val Ser
1               5                   10

<210> SEQ ID NO 451
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Asn Asn Asn Gln Arg Pro Ser
1               5

<210> SEQ ID NO 452
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Ala Ala Trp Asp Asp Ser Leu Ser Ser Ala Val
1               5                   10

<210> SEQ ID NO 453
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453

Thr Tyr Tyr Met Asn
1               5

<210> SEQ ID NO 454
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

Ser Ile Val Ser Ser Gly Gly Tyr Thr Glu Tyr Ala Asp Ser Val Lys
1               5                   10                  15
Gly

<210> SEQ ID NO 455
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 455

Asp Gly Leu Pro Val Ala Ala Thr Phe Asn Tyr Tyr Tyr Tyr Tyr
1               5                   10                  15

Met Asp Val

<210> SEQ ID NO 456
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

Arg Ala Ser Gln Ser Ile Ser Ser Tyr Leu Asn
1               5                   10

<210> SEQ ID NO 457
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

Ala Ala Ser Ser Leu Gln Ser
1               5

<210> SEQ ID NO 458
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 458

Gln Gln Ser Tyr Ser Thr Pro Leu Thr
1               5

<210> SEQ ID NO 459
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Lys Tyr Phe Met Gly
1               5

<210> SEQ ID NO 460
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Val Ile Ser Pro Ser Gly Gly Tyr Thr Tyr Tyr Ala Asp Ser Val Lys
1               5                   10                  15

Gly

```
<210> SEQ ID NO 461
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Trp Gly Ser Ser Trp Tyr Tyr Phe Asp Tyr
1               5                   10

<210> SEQ ID NO 462
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

Gln Ala Thr Gln Asp Ile Ser Asn Tyr Leu Asn
1               5                   10

<210> SEQ ID NO 463
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Asp Ala Ser Ile Leu Glu Thr
1               5

<210> SEQ ID NO 464
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Leu Gln His Asn Arg Tyr Pro Trp Thr
1               5

<210> SEQ ID NO 465
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Ser Tyr Gly Met Pro
1               5

<210> SEQ ID NO 466
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466
```

```
Val Ile Tyr Pro Ser Gly Gly Asn Thr Pro Tyr Ala Asp Ser Val Lys
1               5                   10                  15
Gly

<210> SEQ ID NO 467
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Gly Tyr Tyr Asp Ile Leu Thr Gly Tyr Tyr Gly Pro Asn Trp Phe Asp
1               5                   10                  15
Pro

<210> SEQ ID NO 468
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

Gly Gly Ile Asn Ile Gly Ser Lys Ser Val His
1               5                   10

<210> SEQ ID NO 469
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Tyr Phe Asp Ser Asp Arg Pro Ser
1               5

<210> SEQ ID NO 470
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Gln Val Trp Asp Ser Arg Ser Asp Gln Tyr Val
1               5                   10

<210> SEQ ID NO 471
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Asp Tyr Gln Met Glu
1               5

<210> SEQ ID NO 472
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Val Ile Arg Pro Ser Gly Gly Lys Thr Ala Tyr Ala Asp Ser Val Lys
1               5                   10                  15

Gly

<210> SEQ ID NO 473
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Ala Glu Leu Gly Tyr Cys Ser Gly Gly Ser Cys Tyr Phe Asp Gly Ala
1               5                   10                  15

Trp Phe Asp Pro
            20

<210> SEQ ID NO 474
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Arg Ala Ser Gln Ser Val Thr Ser Ser Tyr Val Ala
1               5                   10

<210> SEQ ID NO 475
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Gly Ala Ser Ser Arg Ala Thr
1               5

<210> SEQ ID NO 476
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Gln Gln Tyr Glu Asp Ser Thr His Ser
1               5

<210> SEQ ID NO 477
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 477

Thr Tyr Asn Met Pro
1               5

<210> SEQ ID NO 478
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Arg Ile Tyr Ser Ser Gly Gly Tyr Thr Pro Tyr Ala Asp Ser Val Asn
1               5                   10                  15

Gly

<210> SEQ ID NO 479
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Gln Gly Leu Asp Asp Asp Ile Trp Thr Asp Tyr Arg Asp Phe
1               5                   10

<210> SEQ ID NO 480
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Ser Gly Asp Lys Leu Gly Asp Lys Phe Ala Ser
1               5                   10

<210> SEQ ID NO 481
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

Gln Asp Arg Lys Arg Pro Ser
1               5

<210> SEQ ID NO 482
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Gln Val Trp Asp Ile Thr Ser Asp His Arg Gly Val
1               5                   10

<210> SEQ ID NO 483
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

Asp Tyr Ile Met Trp
1               5

<210> SEQ ID NO 484
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Arg Ile Tyr Ser Ser Gly Gly Phe Thr Asn Tyr Ala Asp Ser Val Lys
1               5                   10                  15
Gly

<210> SEQ ID NO 485
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Asp Leu Gly Gly Leu Ser Phe Ala Asp Tyr
1               5                   10

<210> SEQ ID NO 486
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Ser Gly Ser Ser Ser Asn Ile Gly Ser Asn Thr Val Thr
1               5                   10

<210> SEQ ID NO 487
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

Asn Asn Tyr Glu Arg Pro Ser
1               5

<210> SEQ ID NO 488
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488
```

```
Ala Thr Trp Asp Asp Ser Leu Ile Ala Asn Tyr Val
1               5                   10
```

<210> SEQ ID NO 489
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

```
Pro Tyr Leu Met Asn
1               5
```

<210> SEQ ID NO 490
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490

```
Ser Ile Tyr Ser Ser Gly Gly Thr Gly Tyr Ala Asp Ser Val Lys
1               5                   10                  15
Gly
```

<210> SEQ ID NO 491
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

```
Ile Tyr His Ser Ser Ser Gly Pro Phe Tyr Gly Met Asp Val
1               5                   10
```

<210> SEQ ID NO 492
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

```
Arg Ala Ser Gln Ser Val Ser Ser Gly Ser Leu Ala
1               5                   10
```

<210> SEQ ID NO 493
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 493

```
Ala Thr Ser Ser Arg Ala Ser
1               5
```

<210> SEQ ID NO 494
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 494

Gln Gln Cys Gly Asp Ser Pro Arg Thr
1               5

<210> SEQ ID NO 495
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Trp Tyr Arg Met Pro
1               5

<210> SEQ ID NO 496
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Tyr Ile Gly Pro Ser Gly Gly Asp Thr Val Tyr Ala Asp Ser Val Lys
1               5                   10                  15

Gly

<210> SEQ ID NO 497
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Arg Gly Gly Tyr Glu Phe Asp Phe
1               5

<210> SEQ ID NO 498
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Arg Ala Ser Gln Gly Ile Ser Asn Trp Leu Ala
1               5                   10

<210> SEQ ID NO 499
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 499

Gly Ala Ser Ser Leu Gln Ser
```

<210> SEQ ID NO 500
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 500

Gln Gln Asp Asn Ser Phe Pro Leu Thr
1               5

<210> SEQ ID NO 501
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 501

Pro Tyr Arg Met Pro
1               5

<210> SEQ ID NO 502
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 502

Tyr Ile Tyr Pro Ser Gly Gly Asn Thr Gly Tyr Ala Asp Ser Val Lys
1               5                   10                  15

Gly

<210> SEQ ID NO 503
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503

Ser Tyr Asp Phe Trp Ser Gly Tyr Trp Phe Asp Tyr
1               5                   10

<210> SEQ ID NO 504
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 504

Ser Gly Asn Asn Leu Gly Asn Lys Phe Val Tyr
1               5                   10

<210> SEQ ID NO 505
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 505

Gln Asp Thr Lys Arg Pro Ser
1               5

<210> SEQ ID NO 506
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

Gln Ala Trp Asp Ser Ser Thr Ala Val
1               5

<210> SEQ ID NO 507
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507

Asp Tyr Ile Met
1

<210> SEQ ID NO 508
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 508

Trp Ile Ser Ser Ser Gly Gly Gly Thr Thr Tyr Ala Asp Ser Val Lys
1               5                   10                  15

Gly

<210> SEQ ID NO 509
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 509

Val Ser Pro Tyr Ser Ser Gly Trp Tyr Pro Tyr Asn Trp Phe Asp Pro
1               5                   10                  15

<210> SEQ ID NO 510
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Ser Gly Ser Ser Tyr Asn Ile Gly Val Tyr Asp Val Tyr
1               5                   10

```
<210> SEQ ID NO 511
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 511

Thr Asn Asn Gln Arg Pro Ser
1               5

<210> SEQ ID NO 512
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Ala Ala Trp Asp Asp Ser Leu Ser Gly Ser Trp Met
1               5                   10

<210> SEQ ID NO 513
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 513

Asp Tyr Trp Met Tyr
1               5

<210> SEQ ID NO 514
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Tyr Ile Tyr Ser Ser Gly Gly Phe Thr Gly Tyr Ala Asp Ser Val Lys
1               5                   10                  15

Gly

<210> SEQ ID NO 515
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

Lys Val Ala Asp Ser Gly Met Asn Trp Phe Asp Pro
1               5                   10

<210> SEQ ID NO 516
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 516

Ser Gln Ser Val Ser Ser Ser Tyr Leu Ala
1               5                   10

<210> SEQ ID NO 517
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 517

Gly Ala Ser Ser Arg Ala Thr
1               5

<210> SEQ ID NO 518
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518

Gln Gln Tyr Gly Ser Ser Arg Thr
1               5

<210> SEQ ID NO 519
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 519

Phe Tyr Gly Met Asn
1               5

<210> SEQ ID NO 520
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 520

Gly Ile Gly Ser Ser Gly Tyr Thr Pro Tyr Ala Asp Ser Val Lys Gly
1               5                   10                  15

<210> SEQ ID NO 521
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

Ala Tyr Asp Phe Trp Ser Gly Tyr Gln Glu Leu Asp Tyr
1               5                   10

<210> SEQ ID NO 522
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 522

Thr Gly Thr Ser Ser Asp Val Gly Gly Tyr Asn Tyr Val Ser
1               5                   10

<210> SEQ ID NO 523
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

Glu Val Asn Asn Arg Pro Ser
1               5

<210> SEQ ID NO 524
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

Ser Ser Tyr Thr His Arg Asn Ser Phe Val
1               5                   10

<210> SEQ ID NO 525
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 525

Val Tyr Gly Met Pro
1               5

<210> SEQ ID NO 526
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Trp Ile Tyr Ser Ser Gly Gly Lys Thr Glu Tyr Val Asp Ser Val Lys
1               5                   10                  15

Gly

<210> SEQ ID NO 527
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 527

Asp Pro Val Arg Phe Leu Glu Trp Leu Trp Gly Ile Asp Tyr
```

```
1               5                   10
```

<210> SEQ ID NO 528
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 528

```
Thr Arg Ser Ser Gly Ser Ile Thr Ser Asn Phe Val Gln
1               5                   10
```

<210> SEQ ID NO 529
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 529

```
Glu Asp Lys Arg Arg Pro Ser
1               5
```

<210> SEQ ID NO 530
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530

```
Gln Ser Tyr Asp Phe Thr Asn Gln Ile
1               5
```

<210> SEQ ID NO 531
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 531

```
Gln Tyr Val Met Pro
1               5
```

<210> SEQ ID NO 532
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

```
Tyr Ile Val Pro Ser Gly Gly Glu Thr Asp Tyr Ala Asp Ser Val Lys
1               5                   10                  15

Gly
```

<210> SEQ ID NO 533
<211> LENGTH: 12
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 533

Leu Asp Asp Ser Ser Gly Trp Tyr Ser Phe Asp Tyr
1               5                   10

<210> SEQ ID NO 534
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 534

Ser Gly Asp Lys Leu Gly Asp Lys Tyr Ala Cys
1               5                   10

<210> SEQ ID NO 535
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 535

Gln Asp Ser Lys Arg Pro Ser
1               5

<210> SEQ ID NO 536
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 536

Gln Ala Trp Asp Ser Met Ser Val Val
1               5

<210> SEQ ID NO 537
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

Leu Tyr Tyr Met Trp
1               5

<210> SEQ ID NO 538
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Trp Ile Tyr Pro Ser Gly Gly Tyr Thr Pro Tyr Ala Asp Ser Val Lys
1               5                   10                  15

Gly

<210> SEQ ID NO 539
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 539

Gly Ile His Ser Gly Ser Tyr Ser Gly Gln Asp Tyr
1               5                   10

<210> SEQ ID NO 540
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 540

Arg Ala Ser Gln Ser Val Ser Ser Asn Leu Ala
1               5                   10

<210> SEQ ID NO 541
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 541

Gly Ala Ser Thr Arg Ala Thr
1               5

<210> SEQ ID NO 542
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 542

Gln His Tyr Asp Arg Tyr Pro Leu Thr
1               5

<210> SEQ ID NO 543
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 543

Phe Tyr Pro Met Val
1               5

<210> SEQ ID NO 544
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 544

```
Trp Ile Gly Pro Ser Gly Gly Thr Thr Lys Tyr Ala Asp Ser Val Lys
1               5                   10                  15

Gly

<210> SEQ ID NO 545
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 545

Asp Trp Gly Tyr Tyr Tyr Asp Ser Gly Ser Arg Leu Asp Tyr
1               5                   10

<210> SEQ ID NO 546
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 546

Gln Ala Ser Gln Asp Ile Asn Thr Tyr Leu Asn
1               5                   10

<210> SEQ ID NO 547
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 547

Asp Ala Ser Asn Leu Glu Thr
1               5

<210> SEQ ID NO 548
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 548

Gln Gln Tyr Asp Asn Leu Arg Thr
1               5

<210> SEQ ID NO 549
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Trp Tyr Tyr Met Arg
1               5

<210> SEQ ID NO 550
<211> LENGTH: 17
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 550

Arg Ile Val Ser Ser Gly Gly Asp Thr Pro Tyr Ala Asp Ser Val Lys
1               5                   10                  15

Gly

<210> SEQ ID NO 551
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 551

Glu Val Gly Pro Arg Ser Phe Asp Ser
1               5

<210> SEQ ID NO 552
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 552

Arg Ala Ser Gln Ser Val Thr Ser Thr Phe Leu Ala
1               5                   10

<210> SEQ ID NO 553
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 553

Gly Ala Ser Ser Arg Ala Thr
1               5

<210> SEQ ID NO 554
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 554

Gln Gln Cys Gly Ser Ser Pro Phe Ala
1               5

<210> SEQ ID NO 555
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 555

Phe Tyr Tyr Met Trp
```

<210> SEQ ID NO 556
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 556

Ser Ile Gly Ser Ser Gly Gly Phe Thr Glu Tyr Ala Asp Ser Val Lys
1               5                   10                  15

Gly

<210> SEQ ID NO 557
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 557

Glu Asp Tyr Asp Tyr Val Trp Gly Ser Tyr Arg Ser Pro Phe Phe Asp
1               5                   10                  15

Tyr

<210> SEQ ID NO 558
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 558

Arg Ala Ser Gln Ser Val Ser Ser Asn Leu Ala
1               5                   10

<210> SEQ ID NO 559
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 559

Gly Ala Ser Thr Arg Ala Thr
1               5

<210> SEQ ID NO 560
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560

Gln Gln Arg Ser Val Trp Pro Trp Thr
1               5

<210> SEQ ID NO 561
<211> LENGTH: 5
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 561

Asp Tyr Ser Met Asp
1               5

<210> SEQ ID NO 562
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 562

Ser Ile Ser Pro Ser Gly Gly Trp Thr Ile Tyr Ala Asp Ser Val Lys
1               5                   10                  15

Gly

<210> SEQ ID NO 563
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 563

Ser Ser Gly Asp Phe Trp Ser Gly Tyr Tyr Pro Tyr Tyr Met Asp Val
1               5                   10                  15

<210> SEQ ID NO 564
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Gln Ala Ser Gln Asp Ile Ser Asn Tyr Leu Asn
1               5                   10

<210> SEQ ID NO 565
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565

Asp Ala Ser Asn Leu Glu Thr
1               5

<210> SEQ ID NO 566
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

Gln Gln Tyr Asp Asn Leu Pro
```

```
1               5

<210> SEQ ID NO 567
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 567

Leu Thr Leu Trp Phe
1               5

<210> SEQ ID NO 568
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

Gly Ile Ser Pro Ser Gly Gly Lys Thr Ile Tyr Ala Asp Ser Val Lys
1               5                   10                  15

Gly

<210> SEQ ID NO 569
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 569

Asp Trp Tyr Cys Gly Gly Gly Ser Cys Phe Asp Trp Tyr Phe Asp Leu
1               5                   10                  15

<210> SEQ ID NO 570
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Arg Ala Ser Gln Ser Ile Ser Val Ser Leu His
1               5                   10

<210> SEQ ID NO 571
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571

Gly Ala Ser Ser Leu Gln Ser
1               5

<210> SEQ ID NO 572
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 572

Gln Gln Ser Tyr Arg Ile Pro Pro Thr
1               5

<210> SEQ ID NO 573
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 573

Lys Tyr Phe Met Glu
1               5

<210> SEQ ID NO 574
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

Ser Ile Trp Ser Ser Gly Gly Tyr Thr Ile Tyr Ala Asp Ser Val Lys
1               5                   10                  15

Gly

<210> SEQ ID NO 575
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 575

Ser Pro Ser Asp Asp Phe Trp Ser Gly Tyr His Gly Gly Ala Phe Asp
1               5                   10                  15

Ile

<210> SEQ ID NO 576
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 576

Gly Gly Asp Asn Ile Gly Gly Arg Ser Val Gln
1               5                   10

<210> SEQ ID NO 577
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 577

Asp Asp Gly Asp Arg Pro Leu
```

<210> SEQ ID NO 578
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 578

Gln Ala Trp Asp Ser Ser Arg Asp His Pro Val
1               5                   10

<210> SEQ ID NO 579
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 579

Gly Tyr Tyr Met Pro
1               5

<210> SEQ ID NO 580
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 580

Trp Ile Gly Pro Ser Gly Gly Asn Thr Leu Tyr Ala Asp Ser Val Lys
1               5                   10                  15

Gly

<210> SEQ ID NO 581
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 581

Ala Ser Tyr Ile Val Ala Thr Ile Pro Gln Tyr Phe Asp Tyr
1               5                   10

<210> SEQ ID NO 582
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 582

Arg Ala Ser Gln Ser Val Ser Ser Ser Tyr Leu Ala
1               5                   10

<210> SEQ ID NO 583
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 583

Gly Ala Ser Ser Arg Ala Thr
1               5

<210> SEQ ID NO 584
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 584

Gln Gln Tyr Gly Ser Ser Pro Leu Thr
1               5

<210> SEQ ID NO 585
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 585

Lys Tyr Asp Met Glu
1               5

<210> SEQ ID NO 586
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 586

Ser Ile Val Pro Ser Gly Gly Phe Thr Asp Tyr Ala Asp Ser Val Lys
1               5                   10                  15

Gly

<210> SEQ ID NO 587
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 587

Asp Ser Ser Ser Trp Tyr Lys Arg Phe Asp Pro
1               5                   10

<210> SEQ ID NO 588
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 588

Lys Thr Ser His Arg Ile Ser Ser Ser Tyr Leu Ala
1               5                   10

<210> SEQ ID NO 589
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 589

Gly Thr Ser His Arg Ala Thr
1               5

<210> SEQ ID NO 590
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 590

His Gln Arg Ser Asn Trp Pro Gln Thr
1               5

<210> SEQ ID NO 591
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 591

Val Tyr Asn Met Leu
1               5

<210> SEQ ID NO 592
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 592

Tyr Ile Tyr Ser Ser Gly Gly His Thr Ile Tyr Ala Asp Ser Val Lys
1               5                   10                  15

Gly

<210> SEQ ID NO 593
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 593

Gln Ala Gly Val Gly Trp Gln Leu Glu Pro Asp Asn Trp Phe Asp Pro
1               5                   10                  15

<210> SEQ ID NO 594
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 594

Thr Gly Thr Gly Ser Asp Val Gly Asp Tyr Asn Tyr Val Ser
1               5                   10

<210> SEQ ID NO 595
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 595

Asp Val Ser Asn Arg Pro Ser
1               5

<210> SEQ ID NO 596
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 596

Ser Ser Tyr Thr Asn Ser Ser Val Ile
1               5

<210> SEQ ID NO 597
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 597

Pro Tyr Met Met Ala
1               5

<210> SEQ ID NO 598
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 598

Arg Ile Tyr Pro Ser Gly Gly Glu Thr Thr Tyr Ala Asp Ser Val Lys
1               5                   10                  15

Gly

<210> SEQ ID NO 599
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 599

Gly Gln Ser Tyr Cys Ser Ser Thr Ser Cys Tyr Pro Tyr Tyr Tyr Tyr
1               5                   10                  15

Tyr Gly Met Asp Val
            20
```

<210> SEQ ID NO 600
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 600

Arg Ala Ser Gln Ser Ile Ser Ser Tyr Leu Asn
1               5                   10

<210> SEQ ID NO 601
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 601

Ala Ala Ser Ser Leu Gln Ser
1               5

<210> SEQ ID NO 602
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 602

Gln Gln Ser Tyr Ser Thr Pro Phe
1               5

<210> SEQ ID NO 603
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 603

Pro Tyr Val Met Pro
1               5

<210> SEQ ID NO 604
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 604

Tyr Ile Gly Pro Ser Gly Gly Asn Thr Arg Tyr Ala Asp Ser Val Lys
1               5                   10                  15

Gly

<210> SEQ ID NO 605
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 605

Asp Leu Leu Ser Gly Tyr Asp Tyr Tyr Tyr Tyr Pro Leu Asp Val
1               5                   10                  15

<210> SEQ ID NO 606
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 606

Thr Gly Ala Thr Ser Asp Ile Gly Thr Tyr Asp Leu Val Ser
1               5                   10

<210> SEQ ID NO 607
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 607

Glu Val Thr Asn Arg Pro Ser
1               5

<210> SEQ ID NO 608
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 608

Ser Ser Tyr Thr Arg Thr Asn Thr Val Ile
1               5                   10

<210> SEQ ID NO 609
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 609

Pro Tyr Lys Met Phe
1               5

<210> SEQ ID NO 610
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 610

Tyr Ile Arg Ser Ser Gly Gly Lys Thr His Tyr Ala Asp Ser Val Lys
1               5                   10                  15

Gly

```
<210> SEQ ID NO 611
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 611

Asp Ser Asn Ala Pro Tyr Tyr Tyr Asp Ser Ser Gly Tyr Asp Ala Phe
1               5                   10                  15

Asp Ile

<210> SEQ ID NO 612
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 612

Arg Ala Ser Gln Ser Ile Ser Ser Tyr Leu Asn
1               5                   10

<210> SEQ ID NO 613
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 613

Ala Ala Ser Ser Leu Gln Ser
1               5

<210> SEQ ID NO 614
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 614

Gln Gln Ser Tyr Ser Thr Pro Leu Thr
1               5

<210> SEQ ID NO 615
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 615

Thr Tyr Gly Met Thr
1               5

<210> SEQ ID NO 616
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 616

Ser Ile Ser Pro Ser Gly Gly Ala Thr Arg Tyr Val Asp Ser Val Lys
1               5                   10                  15

Gly

<210> SEQ ID NO 617
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 617

Arg Ala Ser Gln Ser Ile Ser Ser Tyr Leu Asn
1               5                   10

<210> SEQ ID NO 618
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 618

Ala Ala Ser Ser Leu Gln Ser
1               5

<210> SEQ ID NO 619
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 619

Gln Gln Ser Tyr Ser Thr Pro Leu Thr
1               5

<210> SEQ ID NO 620
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 620

Lys Tyr Phe Met Gly
1               5

<210> SEQ ID NO 621
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 621

Val Ile Ser Pro Ser Gly Gly Tyr Thr Tyr Tyr Ala Asp Ser Val Lys
1               5                   10                  15

Gly
```

```
<210> SEQ ID NO 622
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 622

Trp Gly Ser Ser Trp Tyr Tyr Phe Asp Tyr
1               5                   10

<210> SEQ ID NO 623
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 623

Arg Ala Ser Gln Ser Ile Ser Ser Tyr Leu Asn
1               5                   10

<210> SEQ ID NO 624
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 624

Ala Ala Ser Thr Leu Gln Ser
1               5

<210> SEQ ID NO 625
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 625

Gln His Leu Asn Thr Tyr Pro Ile Thr
1               5

<210> SEQ ID NO 626
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 626

Pro Tyr Met Met Glu
1               5

<210> SEQ ID NO 627
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 627
```

Ser Tyr Ile Gly Ser Ser Gly Gly Tyr Thr Lys Tyr Ala Asp Ser Val
1               5                   10                  15

Lys Gly

<210> SEQ ID NO 628
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 628

Ile Leu Gly Gly Asp Tyr Phe Asp Tyr
1               5

<210> SEQ ID NO 629
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 629

Lys Ser Ser Gln Asn Val Leu Leu Ser Ser Asn Ser Lys Asn Tyr Leu
1               5                   10                  15

Ala

<210> SEQ ID NO 630
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 630

Trp Ala Ser Thr Arg Glu Ser
1               5

<210> SEQ ID NO 631
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 631

Gln Gln Tyr Tyr Ser Ile Pro Trp Ser
1               5

<210> SEQ ID NO 632
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 632

Asn Tyr Arg Met Ser
1               5

<210> SEQ ID NO 633
<211> LENGTH: 17

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 633

Ser Ile Gly Ser Ser Gly Gly Gln Thr Met Tyr Ala Asp Ser Val Lys
1               5                   10                  15

Gly

<210> SEQ ID NO 634
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 634

Ser His Pro Val Ser Gly Gly Val Phe Asp Phe
1               5                   10

<210> SEQ ID NO 635
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 635

Arg Ala Ser Gln Ser Ile Ser Ser Trp Leu Ala
1               5                   10

<210> SEQ ID NO 636
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 636

Lys Ala Ser Ser Leu Glu Ser
1               5

<210> SEQ ID NO 637
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 637

Gln Gln Tyr Asp Thr Tyr Pro Leu Thr
1               5

<210> SEQ ID NO 638
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 638
```

```
Ser Tyr Trp Met His
1               5

<210> SEQ ID NO 639
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 639

Gly Ile Tyr Pro Ser Gly Gly Asn Thr Asn Tyr Ala Asp Ser Val Lys
1               5                   10                  15

Gly

<210> SEQ ID NO 640
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 640

Val Ile Tyr Asp Phe Trp Ser Gly Tyr Tyr Phe Asp Tyr
1               5                   10

<210> SEQ ID NO 641
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 641

Arg Ala Ser Glu Ser Ile Ser Ser Tyr Val Ala
1               5                   10

<210> SEQ ID NO 642
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 642

Gly Ala Ser Asn Arg Ala Thr
1               5

<210> SEQ ID NO 643
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 643

Gln Gln Tyr Gly Ser Ser Pro Pro Leu Thr
1               5                   10

<210> SEQ ID NO 644
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 644

Arg Tyr Thr Met Met
1               5

<210> SEQ ID NO 645
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 645

Tyr Ile Gly Ser Ser Gly Gly Val Thr Ser Tyr Ala Asp Ser Val Lys
1               5                   10                  15
Gly

<210> SEQ ID NO 646
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 646

Asp Pro Arg Asp Tyr Ser Asp Tyr Arg Gly Gly Tyr Trp Tyr Phe Asp
1               5                   10                  15
Leu

<210> SEQ ID NO 647
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 647

Thr Leu Ser Ser Gly His Ser Asn Tyr Ala Ile Ala
1               5                   10

<210> SEQ ID NO 648
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 648

Lys Leu Phe Ser Asp Gly Arg His Asn Lys Gly Asp
1               5                   10

<210> SEQ ID NO 649
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 649
```

```
Gln Thr Trp Val Ala Gly Ile Val Val
1               5

<210> SEQ ID NO 650
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 650

Arg Tyr Leu Met Met
1               5

<210> SEQ ID NO 651
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 651

Tyr Ile Tyr Pro Ser Gly Gly Ser Thr Thr Tyr Ala Asp Ser Val Lys
1               5                   10                  15

Gly

<210> SEQ ID NO 652
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 652

Asp Arg Val Val Val Ala Ala Thr Pro Leu Thr Gly Phe Asp Tyr
1               5                   10                  15

<210> SEQ ID NO 653
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 653

Arg Ala Ser Gln Ser Ile Ser Ser Trp Leu Ala
1               5                   10

<210> SEQ ID NO 654
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 654

Lys Ala Ser Ser Leu Glu Ser
1               5

<210> SEQ ID NO 655
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 655

Gln Gln Tyr Asp Thr Tyr Pro Leu Thr
1               5

<210> SEQ ID NO 656
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 656

Ser Tyr Trp Met His
1               5

<210> SEQ ID NO 657
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 657

Gly Ile Tyr Pro Ser Gly Gly Asn Thr Asn Tyr Ala Asp Ser Val Lys
1               5                   10                  15

Gly

<210> SEQ ID NO 658
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 658

Val Ile Tyr Asp Phe Trp Ser Gly Tyr Tyr Phe Asp Tyr
1               5                   10

<210> SEQ ID NO 659
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 659

Arg Ala Ser Gln Pro Val Ser Ser Thr Tyr Leu Ala
1               5                   10

<210> SEQ ID NO 660
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 660

Asp Thr Ser Lys Arg Ala Thr
1               5
```

```
<210> SEQ ID NO 661
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 661

Gln Gln Tyr Gly Arg Ser Pro Tyr Thr
1               5

<210> SEQ ID NO 662
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 662

Pro Tyr Ile Met Lys
1               5

<210> SEQ ID NO 663
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 663

Ser Ile Ser Ser Ser Gly Gly Pro Thr Asn Tyr Ala Asp Ser Val Lys
1               5                   10                  15

Gly

<210> SEQ ID NO 664
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 664

Ser Tyr Ser Asn Tyr Pro Arg Arg Phe Phe Asp Tyr
1               5                   10

<210> SEQ ID NO 665
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 665

Arg Ala Ser Gln Ser Ile Ala Thr Tyr Leu Asn
1               5                   10

<210> SEQ ID NO 666
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 666

Ala Ala Thr Ser Leu Gln Ser
1               5

<210> SEQ ID NO 667
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 667

Gln Gln Thr Lys Ile Phe Pro Thr Trp Thr
1               5                   10

<210> SEQ ID NO 668
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 668

Ala Tyr Leu Met Asp
1               5

<210> SEQ ID NO 669
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 669

Val Ile Tyr Ser Ser Gly Gly Pro Thr Met Tyr Ala Asp Ser Val Lys
1               5                   10                  15

Gly

<210> SEQ ID NO 670
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 670

Trp Cys Ser Ser Gly Trp Tyr Pro Gln Cys His Asn
1               5                   10

<210> SEQ ID NO 671
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 671

Arg Ala Ser His Arg Val Thr Gly Tyr Leu Asn
1               5                   10

```
<210> SEQ ID NO 672
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 672

Ala Thr Ser Thr Val Gln Ser
1               5

<210> SEQ ID NO 673
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 673

Gln Gln Ser Tyr Ser Ala Phe Arg
1               5

<210> SEQ ID NO 674
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 674

Asp Tyr Ile Met Pro
1               5

<210> SEQ ID NO 675
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 675

Arg Ile Tyr Pro Ser Gly Gly Pro Thr Trp Tyr Ala Asp Ser Val Lys
1               5                   10                  15

Gly

<210> SEQ ID NO 676
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 676

Asp Thr Thr Ser Gly Asp Tyr Phe Asp Leu
1               5                   10

<210> SEQ ID NO 677
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 677

Thr Gly Thr Ser Ser Asp Val Gly Ala Tyr Asn Tyr Val Ser
1               5                   10

<210> SEQ ID NO 678
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 678

Asp Val Ser Asn Arg Pro Ser
1               5

<210> SEQ ID NO 679
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 679

Ser Ser Tyr Thr Ser Ser Ser Thr Arg Val
1               5                   10

<210> SEQ ID NO 680
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 680

Leu Tyr Val Met Phe
1               5

<210> SEQ ID NO 681
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 681

Arg Ile Arg Pro Ser Gly Gly Val Thr Asp Tyr Ala Asp Ser Val Lys
1               5                   10                  15

Gly

<210> SEQ ID NO 682
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 682

Asp Thr Arg Tyr Asp Tyr Asp Phe Trp Ser Gly Tyr Tyr Thr Gly Phe
1               5                   10                  15

Phe Asp Ile
```

```
<210> SEQ ID NO 683
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 683

Ser Gly Glu Thr Leu Gly Gly Gln Phe Ala Ser
1               5                   10

<210> SEQ ID NO 684
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 684

Gln Asn Thr Lys Arg Pro Ser
1               5

<210> SEQ ID NO 685
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 685

Gln Ala Trp Asp Thr Asn Thr Val Val
1               5

<210> SEQ ID NO 686
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 686

Lys Tyr Trp Met Gln
1               5

<210> SEQ ID NO 687
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 687

Trp Ile Tyr Pro Ser Gly Gly Asn Thr Pro Tyr Ala Asp Ser Val Lys
1               5                   10                  15

Gly

<210> SEQ ID NO 688
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 688

Ser Gly Ser Arg Pro Ser Tyr Tyr Tyr Tyr Gly Met Asp Val
1               5                   10                  15

<210> SEQ ID NO 689
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 689

Thr Gly Thr Ser Ser Asp Val Gly Ala Tyr Asn Tyr Val Ser
1               5                   10

<210> SEQ ID NO 690
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 690

Glu Val Ser Asn Arg Pro Ser
1               5

<210> SEQ ID NO 691
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 691

Asn Ser Tyr Thr Thr Ser Ala Thr Leu Val
1               5                   10

<210> SEQ ID NO 692
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 692

Leu Tyr Tyr Met Tyr
1               5

<210> SEQ ID NO 693
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 693

Gly Ile Val Pro Ser Gly Gly Arg Thr Asp Tyr Ala Asp Ser Val Lys
1               5                   10                  15

Gly

<210> SEQ ID NO 694
<211> LENGTH: 15
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 694

Gly Leu Leu Arg Phe Leu Glu Trp Leu Leu Tyr Pro Phe Asp Tyr
1               5                   10                  15

<210> SEQ ID NO 695
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 695

Ser Gly Ser Ser Ser Asn Ile Gly Thr Asn Thr Leu Asn
1               5                   10

<210> SEQ ID NO 696
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 696

Gly Asn Asn Gln Arg Pro Ser
1               5

<210> SEQ ID NO 697
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 697

Ala Thr Trp Asp Asp Ser Leu Ile Gly Pro Val
1               5                   10

<210> SEQ ID NO 698
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 698

Pro Tyr Ser Met Glu
1               5

<210> SEQ ID NO 699
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 699

Ser Ile Arg Pro Ser Gly Gly Leu Thr Ala Tyr Ala Asp Ser Val Lys
1               5                   10                  15

Gly

<210> SEQ ID NO 700
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 700

Trp Leu Gly Phe Asp Ile Leu Thr Gly Tyr Phe Asp Tyr
1               5                   10

<210> SEQ ID NO 701
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 701

Ser Gly Asp Lys Leu Gly Asp Lys Phe Val Ser
1               5                   10

<210> SEQ ID NO 702
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 702

Gln Asp Ser Lys Arg Pro Ser
1               5

<210> SEQ ID NO 703
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 703

Gln Ala Trp Asp Ser Ser Thr Phe Tyr Val
1               5                   10

<210> SEQ ID NO 704
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 704

Gly Ile Tyr Ser Ser Gly Gly Leu Thr Trp Tyr Ala Asp Ser Val Lys
1               5                   10                  15

Gly

<210> SEQ ID NO 705
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 705

Asp Gly Val Leu Tyr Tyr Ser Tyr Tyr Gly Met Glu Val
1               5                   10

<210> SEQ ID NO 706
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 706

Arg Ala Ser Gln Asn Ile Arg Ser Phe Leu Ala
1               5                   10

<210> SEQ ID NO 707
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 707

Lys Thr Ser Asn Leu Gln Ser
1               5

<210> SEQ ID NO 708
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 708

Gln Gln Tyr Tyr Thr Tyr Ser Trp Thr
1               5

<210> SEQ ID NO 709
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 709

Gly Tyr Trp Met Lys
1               5

<210> SEQ ID NO 710
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 710

Ser Ile Tyr Pro Ser Gly Gly Lys Thr Pro Tyr Ala Asp Ser Val Lys
1               5                   10                  15

Gly
```

```
<210> SEQ ID NO 711
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 711

Trp Pro Thr Ser Asp Tyr Gly Gly Lys Tyr Trp Phe Asp Pro
1               5                   10

<210> SEQ ID NO 712
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 712

Ser Ser Gln Ser Leu Leu His Ser Asp Gly Lys Thr Tyr Leu Tyr
1               5                   10                  15

<210> SEQ ID NO 713
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 713

Glu Ala Ser Asn Arg Phe Ser
1               5

<210> SEQ ID NO 714
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 714

Met Gln Ser Ile Glu Leu Pro Arg Thr
1               5

<210> SEQ ID NO 715
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 715

Pro Tyr Tyr Met Gln
1               5

<210> SEQ ID NO 716
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
-continued

<400> SEQUENCE: 716

Arg Ile Ser Ser Ser Gly Gly Pro Thr Asn Tyr Ala Asp Ser Val Lys
1               5                   10                  15

Gly

<210> SEQ ID NO 717
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 717

Gly Tyr Gly His Gly Leu Asp Tyr
1               5

<210> SEQ ID NO 718
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 718

Thr Leu Ser Ser Gly Tyr Ser Asn Tyr Ala Ile Ala
1               5                   10

<210> SEQ ID NO 719
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 719

Arg Val Asn Ser Asp Gly Ser His Ser Lys Gly Asp
1               5                   10

<210> SEQ ID NO 720
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 720

Gln Thr Trp Gly Met Gly Ile Leu Val Val
1               5                   10

<210> SEQ ID NO 721
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 721

Gln Tyr Arg Met Pro
1               5

<210> SEQ ID NO 722
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 722

Trp Ile Trp Pro Ser Gly Gly Trp Thr Gln Tyr Ala Asp Ser Val Lys
1               5                   10                  15
Gly

<210> SEQ ID NO 723
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 723

Gly Asp Ser Ser Gly Tyr Pro Tyr Tyr Phe Asp Tyr
1               5                   10

<210> SEQ ID NO 724
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 724

Ser Gly Ser Ser Ser Asn Ile Gly Thr Asn Thr Leu Asn
1               5                   10

<210> SEQ ID NO 725
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 725

Ala Asn Asn Gln Arg Pro Ser
1               5

<210> SEQ ID NO 726
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 726

Ala Ala Trp Asp Asp Ser Leu Ser Gly Leu
1               5                   10

<210> SEQ ID NO 727
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 727
```

```
Phe Tyr Thr Met Arg
1               5

<210> SEQ ID NO 728
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 728

Ser Ile Gly Ser Ser Gly Gly Tyr Thr Gly Tyr Ala Asp Ser Val Lys
1               5                   10                  15

Gly

<210> SEQ ID NO 729
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 729

Arg His Tyr Gly Gly Asn Ser Pro Tyr Tyr Phe Asp Tyr
1               5                   10

<210> SEQ ID NO 730
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 730

Thr Gly Thr Ser Asn Asp Val Gly Gly Tyr Asn Tyr Val Ser
1               5                   10

<210> SEQ ID NO 731
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 731

Glu Val Ser Asn Arg Pro Ser
1               5

<210> SEQ ID NO 732
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 732

Asn Ser Tyr Thr Ser Ser Arg Thr Trp Val
1               5                   10

<210> SEQ ID NO 733
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 733

Pro Tyr Glu Met Asn
1               5

<210> SEQ ID NO 734
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 734

Gly Ile Val Pro Ser Gly Gly Ile Thr Met Tyr Ala Asp Ser Val Lys
1               5                   10                  15

Gly

<210> SEQ ID NO 735
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 735

Asp Asn Arg Asn Pro Val Met Val Met Ile Asp Tyr
1               5                   10

<210> SEQ ID NO 736
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 736

Arg Ala Ser Gln Gly Ile Ser Asn Tyr Leu Ala
1               5                   10

<210> SEQ ID NO 737
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 737

Asp Ala Ser Ser Leu Glu Ser
1               5

<210> SEQ ID NO 738
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 738

Gln Gln Phe Asn Ser Tyr Pro Leu Thr
1               5
```

<210> SEQ ID NO 739
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 739

His Tyr Tyr Met Pro
1               5

<210> SEQ ID NO 740
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 740

Ser Ile Tyr Ser Ser Gly Gly Val Thr Trp Tyr Ala Asp Ser Val Lys
1               5                   10                  15

Gly

<210> SEQ ID NO 741
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 741

Val Ser Tyr Asp Ser Ser Gly Tyr Tyr Pro Phe Asp Tyr
1               5                   10

<210> SEQ ID NO 742
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 742

Thr Gly Thr Ser Ser Asp Val Gly Gly Tyr Asn Tyr Val Ser
1               5                   10

<210> SEQ ID NO 743
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 743

Glu Val Ser Lys Arg Pro Ser
1               5

<210> SEQ ID NO 744
<211> LENGTH: 11
<212> TYPE: PRT
<213> ORGANISM: Artificial Sequence
<220> FEATURE:
<223> OTHER INFORMATION: Description of Artificial Sequence: Synthetic

```
                                peptide

<400> SEQUENCE: 744

Ser Ser Tyr Ala Gly Ser Asn Asn Leu Gly Val
1               5                   10

<210> SEQ ID NO 745
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 745

Met Tyr Tyr Met Leu
1               5

<210> SEQ ID NO 746
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 746

Ser Ile Tyr Ser Ser Gly Gly Met Thr Met Tyr Ala Asp Ser Val Lys
1               5                   10                  15

Gly

<210> SEQ ID NO 747
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 747

Val Gly Ile Ala Val Ala Gly Arg Ala Leu Asp Tyr
1               5                   10

<210> SEQ ID NO 748
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 748

Arg Ala Ser Gln Val Ile Ser Ser Trp Leu Ala
1               5                   10

<210> SEQ ID NO 749
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 749

Ala Ala Ser Ser Leu Gln Ser
1               5
```

```
<210> SEQ ID NO 750
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 750

Gln Gln Tyr Asn Ser Tyr Pro Trp Ala
1               5

<210> SEQ ID NO 751
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 751

Lys Tyr Ile Met Met
1               5

<210> SEQ ID NO 752
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 752

Trp Ile Tyr Ser Ser Gly Gly Asn Thr Asn Tyr Ala Asp Ser Val Lys
1               5                   10                  15

Gly

<210> SEQ ID NO 753
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 753

Glu Gly Ala Tyr Ser Gly Ser Tyr Gly Gly Asp Ala Phe Asp Ile
1               5                   10                  15

<210> SEQ ID NO 754
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 754

Thr Gly Thr Asn Thr Asp Val Gly Gly Tyr Asn Tyr Val Ala
1               5                   10

<210> SEQ ID NO 755
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 755

Asp Val Ser Asn Arg Pro Ser
1               5

<210> SEQ ID NO 756
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 756

Ser Ser Phe Thr Ser Arg Ser Thr His Val
1               5                   10

<210> SEQ ID NO 757
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 757

His Tyr Pro Met Pro
1               5

<210> SEQ ID NO 758
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 758

Tyr Ile Tyr Pro Ser Gly Gly Val Thr Pro Tyr Ala Asp Ser Val Lys
1               5                   10                  15

Gly

<210> SEQ ID NO 759
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 759

Asp Pro Pro Tyr Tyr Asp Phe Trp Ser Gly Tyr Tyr Thr Ser
1               5                   10

<210> SEQ ID NO 760
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 760

Arg Thr Ser Gln Asp Val Arg Asn Trp Val Ala
1               5                   10

<210> SEQ ID NO 761
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 761

Met Ala Ser Thr Leu Gln Ser
1               5

<210> SEQ ID NO 762
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 762

Gln Gln Ala Asp Thr Phe Pro Trp Thr
1               5

<210> SEQ ID NO 763
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 763

Met Tyr Ser Met Asn
1               5

<210> SEQ ID NO 764
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 764

Ser Ile Val Ser Ser Gly Gly Asp Thr Arg Tyr Ala Asp Ser Val Lys
1               5                   10                  15

Gly

<210> SEQ ID NO 765
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 765

Asp Ile Ser Gly Tyr Tyr Pro Pro Tyr Phe Asp Tyr
1               5                   10

<210> SEQ ID NO 766
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 766
```

```
Arg Ala Ser Gln Asn Ile His Ser Tyr Leu His
1               5                   10
```

<210> SEQ ID NO 767
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 767

```
Ala Ala Ser Thr Leu Gln Arg
1               5
```

<210> SEQ ID NO 768
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 768

```
His Gln Ser Tyr Met Ser Pro Pro Thr
1               5
```

<210> SEQ ID NO 769
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 769

```
Trp Tyr Met Met Gly
1               5
```

<210> SEQ ID NO 770
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 770

```
Val Ile Tyr Pro Ser Gly Gly His Thr Pro Tyr Ala Asp Ser Val Lys
1               5                   10                  15
Gly
```

<210> SEQ ID NO 771
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 771

```
Asp His Ile Arg Thr Ala Ser Gly Ala Phe Trp Phe Asp Pro
1               5                   10
```

<210> SEQ ID NO 772
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 772

Arg Ala Ser Gln Ser Val Ser Ser Asn Tyr Leu Ala
1               5                   10

<210> SEQ ID NO 773
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 773

His Ala Asp Asn Arg
1               5

<210> SEQ ID NO 774
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 774

Gln Gln Tyr Gly Thr Ser Pro Gly Val Thr
1               5                   10

<210> SEQ ID NO 775
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 775

Ile Tyr Thr Met Glu
1               5

<210> SEQ ID NO 776
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 776

Arg Ile Ser Pro Ser Gly Gly Asp Thr Ile Tyr Ala Asp Ser Val Lys
1               5                   10                  15

Gly

<210> SEQ ID NO 777
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 777

Thr Lys Gly Val Asp Cys Ser Gly Gly Ser Cys Tyr Arg Ala Gly Ile
1               5                   10                  15
```

Asp Tyr

<210> SEQ ID NO 778
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 778

Thr Gly Thr Ser Ser Asp Val Gly Ala Tyr Asn Tyr Val Ser
1               5                   10

<210> SEQ ID NO 779
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 779

Asp Val Ser Asp Arg Pro Ser
1               5

<210> SEQ ID NO 780
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 780

Cys Ser Tyr Ala Arg Ala Ser Thr Phe Ser Tyr Val
1               5                   10

<210> SEQ ID NO 781
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 781

Met Tyr Trp Met Gly
1               5

<210> SEQ ID NO 782
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 782

Ser Ile Val Ser Ser Gly Gly Trp Thr Gln Tyr Ala Asp Ser Val Lys
1               5                   10                  15

Gly

<210> SEQ ID NO 783
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 783

Asp His Asp Ser Ser Gly Tyr Trp Phe Asp Asp
1               5                   10

<210> SEQ ID NO 784
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 784

Gln Ala Ser Gln Asp Ile Asn Ile Tyr Leu Asn
1               5                   10

<210> SEQ ID NO 785
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 785

Asp Ala Ser Asn Leu Glu Pro
1               5

<210> SEQ ID NO 786
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 786

Gln Arg Phe Asp Asp Leu Tyr Thr
1               5

<210> SEQ ID NO 787
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 787

Val Tyr Gly Met Tyr
1               5

<210> SEQ ID NO 788
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 788

Arg Ile Gly Pro Ser Gly Gly Met Thr Tyr Tyr Ala Asp Ser Val Lys
1               5                   10                  15

Gly
```

```
<210> SEQ ID NO 789
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 789

Glu Arg Leu Pro Tyr Gly Asp His Gln His Tyr Phe Asp Tyr
1               5                   10

<210> SEQ ID NO 790
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 790

Gln Ala Ser Gln Asp Ile Asp Asn Tyr Leu Asn
1               5                   10

<210> SEQ ID NO 791
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 791

Asp Ala Ser Asn Leu Glu Thr
1               5

<210> SEQ ID NO 792
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 792

Gln Gln Tyr Asp Asp Leu Pro Arg Asp Thr
1               5                   10

<210> SEQ ID NO 793
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 793

Val Tyr Trp Met Leu
1               5

<210> SEQ ID NO 794
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 794

Tyr Ile Tyr Ser Ser Gly Gly Trp Thr Val Tyr Ala Asp Ser Val Lys
1               5                   10                  15
Gly

<210> SEQ ID NO 795
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 795

Val Val Phe Glu Ser Gly Asp Phe Trp Ser Gly Tyr Pro Tyr Tyr Phe
1               5                   10                  15
Asp Tyr

<210> SEQ ID NO 796
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 796

Ser Gly Gly Ser Ser Asn Ile Glu Asn Asn Thr Val Asn
1               5                   10

<210> SEQ ID NO 797
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 797

Gly Asp Thr Glu Arg Pro Ser
1               5

<210> SEQ ID NO 798
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 798

Ala Thr Trp Asp Asp Thr Leu Asp Gly Tyr Val
1               5                   10

<210> SEQ ID NO 799
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 799

Val Tyr Ile Met Gly
1               5
```

```
<210> SEQ ID NO 800
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 800

Ser Ile Tyr Ser Ser Gly Gly Ser Thr Asn Tyr Ala Asp Ser Val Lys
1               5                   10                  15

Gly

<210> SEQ ID NO 801
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 801

Arg Gly Asp Trp Gly Ser Val Gly Phe Asp Pro
1               5                   10

<210> SEQ ID NO 802
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 802

Arg Ala Ser Gln Ser Ile Ser Gly Trp Leu Ala
1               5                   10

<210> SEQ ID NO 803
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 803

Lys Ala Ser Thr Leu Glu Ser
1               5

<210> SEQ ID NO 804
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 804

Gln Gln Tyr Asp Ser Tyr Pro Tyr Thr
1               5

<210> SEQ ID NO 805
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 805

Val Ile Ser Pro Ser Gly Gly Thr Thr Asn Tyr Ala Asp Ser Val Lys
1               5                   10                  15
Gly

<210> SEQ ID NO 806
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 806

Gly Ser Ser Ile Ala Ala Arg Pro Leu Asp Tyr
1               5                   10

<210> SEQ ID NO 807
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 807

Arg Ala Ser Gln Ser Ile Gly Ser Tyr Leu Asn
1               5                   10

<210> SEQ ID NO 808
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 808

Ala Val Ser Ser Leu Gln Ser
1               5

<210> SEQ ID NO 809
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 809

Gln Gln Ser Tyr Ser Asn Pro Ile Ser
1               5

<210> SEQ ID NO 810
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 810

Asp Tyr Thr Met Glu
1               5

<210> SEQ ID NO 811
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 811

Gly Ile Ser Pro Ser Gly Gly Tyr Thr Asp Tyr Ala Asp Ser Val Lys
1               5                   10                  15
Gly

<210> SEQ ID NO 812
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 812

Asn Leu Ile Thr Met Ile Val Val Gly Glu Phe Asp Tyr
1               5                   10

<210> SEQ ID NO 813
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 813

Ser Gly Ser Ser Ser Asn Ile Gly Gly Asn Arg Val Asn
1               5                   10

<210> SEQ ID NO 814
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 814

Ser Thr Asn Gln Arg Pro Ser
1               5

<210> SEQ ID NO 815
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 815

Ala Ala Trp Asp Asp Thr Leu Asn Gly Pro Val
1               5                   10

<210> SEQ ID NO 816
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 816
```

```
Asn Tyr Asp Met Met
1               5

<210> SEQ ID NO 817
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 817

Ser Ile Gly Ser Ser Gly Gly Ile Thr Phe Tyr Ala Asp Ser Val Lys
1               5                   10                  15

Gly

<210> SEQ ID NO 818
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 818

Glu Tyr Ser Ser Gly Trp Pro Leu Asp Tyr
1               5                   10

<210> SEQ ID NO 819
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 819

Arg Ala Ser Gln Ser Ile Ser Thr Phe Leu Asn
1               5                   10

<210> SEQ ID NO 820
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 820

Ala Ala Ser Ser Leu Gln Ser
1               5

<210> SEQ ID NO 821
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 821

Gln Gln Ser Tyr Ser Thr Pro Pro Ile Thr
1               5                   10

<210> SEQ ID NO 822
<211> LENGTH: 5
<212> TYPE: PRT
<213> ORGANISM: Artificial Sequence
```

```
-continued

<220> FEATURE:
<223> OTHER INFORMATION: Description of Artificial Sequence: Synthetic
      peptide

<400> SEQUENCE: 822

Arg Tyr Asp Met Leu
1               5

<210> SEQ ID NO 823
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 823

Gly Ile Ser Pro Ser Gly Gly Phe Thr Thr Tyr Ala Asp Ser Val Lys
1               5                   10                  15
Gly

<210> SEQ ID NO 824
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 824

Pro Ala Leu Tyr Tyr Tyr Gly Ser Gly Arg Leu Lys Ala Phe Asp Ile
1               5                   10                  15

<210> SEQ ID NO 825
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 825

Arg Ser Ser Gln Ser Leu Leu His Ser Asn Gly Tyr Asn Tyr Leu Asp
1               5                   10                  15

<210> SEQ ID NO 826
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 826

Leu Gly Ser Tyr Arg Ala Ser
1               5

<210> SEQ ID NO 827
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 827

Met Gln Ala Leu Gln Thr Pro Ile Thr
1               5
```

```
<210> SEQ ID NO 828
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 828

Arg Tyr Gln Met Gly
1               5

<210> SEQ ID NO 829
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 829

Ser Ile Ser Pro Ser Gly Gly Gly Thr Val Tyr Ala Asp Ser Val Lys
1               5                   10                  15

Gly

<210> SEQ ID NO 830
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 830

Asn Tyr Tyr Tyr Met Asp Val
1               5

<210> SEQ ID NO 831
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 831

Arg Ala Ser Gln Gly Ile Arg Asn Asp Leu Gly
1               5                   10

<210> SEQ ID NO 832
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 832

Ala Ala Ser Ser Leu Gln Ser
1               5

<210> SEQ ID NO 833
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 833

Leu Gln His Asn Ser Tyr Pro Phe Thr
1               5

<210> SEQ ID NO 834
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 834

Ala Tyr Arg Met Gln
1               5

<210> SEQ ID NO 835
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 835

Tyr Ile Gly Ser Ser Gly Gly Gln Thr Ser Tyr Ala Asp Ser Val Lys
1               5                   10                  15

Gly

<210> SEQ ID NO 836
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 836

Ala Lys Pro Gly Arg Pro Phe Asp Phe
1               5

<210> SEQ ID NO 837
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 837

Arg Ala Ser Gln Ser Ile Ser Ser Tyr Leu Asn
1               5                   10

<210> SEQ ID NO 838
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 838

Ala Ala Ser Ser Leu Gln Ser
1               5

```
<210> SEQ ID NO 839
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 839

Gln Gln Ser Tyr Ser Thr Pro His Thr
1               5

<210> SEQ ID NO 840
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 840

His Tyr Val Met Ser
1               5

<210> SEQ ID NO 841
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 841

Ser Ile Gly Ser Ser Gly Gly Asp Thr His Tyr Ala Asp Ser Val Lys
1               5                   10                  15

Gly

<210> SEQ ID NO 842
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 842

Val Trp Ile Ser Gly Ser Tyr Leu Asp Ala Phe Asp Ile
1               5                   10

<210> SEQ ID NO 843
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 843

Arg Ser Ser Gln Ser Leu Leu Leu Ser Asn Gly Tyr Asn Tyr Leu Asp
1               5                   10                  15

<210> SEQ ID NO 844
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 844

Leu Gly Ser His Arg Ala Ser
1               5

<210> SEQ ID NO 845
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 845

Met Gln Ala Leu Gln Thr Pro Val Ile Thr
1               5                   10

<210> SEQ ID NO 846
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 846

Lys Tyr Met Met Phe
1               5

<210> SEQ ID NO 847
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 847

Ser Ile Tyr Pro Ser Gly Gly Trp Thr Tyr Tyr Ala Asp Ser Val Lys
1               5                   10                  15

Gly

<210> SEQ ID NO 848
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 848

Leu Gly Tyr Pro Pro Tyr
1               5

<210> SEQ ID NO 849
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 849

Arg Ala Ser Gln Ser Ile Ser Ser Trp Leu Ala
1               5                   10

<210> SEQ ID NO 850
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 850

Lys Ala Ser Phe Leu Lys Ser
1               5

<210> SEQ ID NO 851
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 851

Gln Gln Tyr Asn Ser Tyr Pro Phe Thr
1               5

<210> SEQ ID NO 852
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 852

His Tyr Ile Met Phe
1               5

<210> SEQ ID NO 853
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 853

Gly Ile Tyr Pro Ser Gly Gly Phe Thr Tyr Tyr Ala Asp Ser Val Lys
1               5                   10                  15

Gly

<210> SEQ ID NO 854
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 854

Gly His Asp Ala Phe Asp Ile
1               5

<210> SEQ ID NO 855
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 855
```

```
Arg Ala Ser Gln Ser Val Gly Ser Gln Leu Ala
1               5                   10
```

<210> SEQ ID NO 856
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 856

```
Asp Ala Ser Thr Arg Ala Thr
1               5
```

<210> SEQ ID NO 857
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 857

```
His Gln Tyr Asp Asn Trp Pro His Thr
1               5
```

<210> SEQ ID NO 858
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 858

```
Phe Tyr Arg Met Ser
1               5
```

<210> SEQ ID NO 859
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 859

```
Trp Ile Gly Ser Ser Gly Gly Pro Thr Ser Tyr Ala Asp Ser Val Lys
1               5                   10                  15

Gly
```

<210> SEQ ID NO 860
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 860

```
Ser Gly Gly Val Ala Gly Thr Phe Gly Tyr
1               5                   10
```

<210> SEQ ID NO 861
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 861

Arg Ala Ser Gln Ser Ile Ser His Trp Leu Ala
1               5                   10

<210> SEQ ID NO 862
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 862

Lys Ala Ser Ser Leu Gln Ser
1               5

<210> SEQ ID NO 863
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 863

Gln Gln Tyr Asp Ser Tyr Pro Phe Thr
1               5

<210> SEQ ID NO 864
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 864

Pro Tyr Tyr Met Ser
1               5

<210> SEQ ID NO 865
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 865

Val Ile Ser Pro Ser Gly Gly Val Thr His Tyr Ala Asp Ser Val Lys
1               5                   10                  15

Gly

<210> SEQ ID NO 866
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 866

Ser Ser Ser Ser Ser Trp Tyr Ala Phe Asp Tyr
1               5                   10
```

<210> SEQ ID NO 867
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 867

Arg Ala Ser Gln Phe Ile Ser His Trp Leu Ala
1               5                   10

<210> SEQ ID NO 868
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 868

Lys Ser Ser Thr Leu Lys Ser
1               5

<210> SEQ ID NO 869
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 869

Gln Gln Tyr Asp Ser Val Pro Tyr Thr
1               5

<210> SEQ ID NO 870
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 870

Tyr Tyr Gly Met Leu
1               5

<210> SEQ ID NO 871
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 871

Tyr Ile Ser Pro Ser Gly Gly Phe Thr Lys Tyr Ala Asp Ser Val Lys
1               5                   10                  15

Gly

<210> SEQ ID NO 872
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 872

Asp Leu Ser Ser Gly Gly Phe Asp Tyr
1               5

<210> SEQ ID NO 873
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 873

Arg Ala Ser Gln Thr Ile Ser Ser Trp Leu Ala
1               5                   10

<210> SEQ ID NO 874
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 874

Arg Ala Ser Thr Leu Lys Ser
1               5

<210> SEQ ID NO 875
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 875

Gln Gln Tyr Asp Ser Tyr Arg Tyr Thr
1               5

<210> SEQ ID NO 876
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 876

Lys Tyr Tyr Met Gly
1               5

<210> SEQ ID NO 877
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 877

Tyr Ile Gly Ser Ser Gly Gly Tyr Thr Asn Tyr Ala Asp Ser Val Lys
1               5                   10                  15

Gly

```
<210> SEQ ID NO 878
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 878

Pro Gln Leu Ala Phe Asp Ile
1               5

<210> SEQ ID NO 879
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 879

Ala Gly Ser Ser Ser Asn Ile Gly Ser Asn Ser Val Tyr
1               5                   10

<210> SEQ ID NO 880
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 880

Ser Asn Asn Lys Arg Pro Ser
1               5

<210> SEQ ID NO 881
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 881

Ala Ala Trp Asp Asp Ser Leu Arg Ser Val Val
1               5                   10

<210> SEQ ID NO 882
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 882

Arg Tyr Gly Met Leu
1               5

<210> SEQ ID NO 883
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 883
```

```
Val Ile Tyr Pro Ser Gly Gly Val Thr Trp Tyr Ala Asp Ser Val Lys
1               5                   10                  15

Gly
```

<210> SEQ ID NO 884
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 884

```
Pro Ala Thr Met Val Arg Tyr
1               5
```

<210> SEQ ID NO 885
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 885

```
Arg Val Ser Gln Ser Val Ser Ser Ser Tyr Leu Ala
1               5                   10
```

<210> SEQ ID NO 886
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 886

```
Gly Ala Ser Ser Arg Ala Thr
1               5
```

<210> SEQ ID NO 887
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 887

```
Gln Gln Arg Ser Asn Trp Pro Pro Ile Thr
1               5                   10
```

<210> SEQ ID NO 888
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 888

```
Val Tyr Ala Met His
1               5
```

<210> SEQ ID NO 889
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 889

Ser Ile Val Pro Ser Gly Gly Val Thr Leu Tyr Ala Asp Ser Val Lys
1               5                   10                  15

Gly

<210> SEQ ID NO 890
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 890

Ser Ser Ser Ser Phe Leu Tyr Tyr Tyr Gly Met Asp Val
1               5                   10

<210> SEQ ID NO 891
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 891

Thr Gly Thr Ser Ser Asp Val Gly Gly Tyr Asn Tyr Val Ser
1               5                   10

<210> SEQ ID NO 892
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 892

Glu Val Gly Asn Arg Pro Ser
1               5

<210> SEQ ID NO 893
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 893

Ser Ser Tyr Thr Ser Ser Ser Thr Trp Val
1               5                   10

<210> SEQ ID NO 894
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 894

Leu Tyr Val Met Gln
1               5
```

<210> SEQ ID NO 895
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 895

Val Ile Val Pro Ser Gly Gly Asp Thr Tyr Tyr Ala Asp Ser Val Lys
1               5                   10                  15
Gly

<210> SEQ ID NO 896
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 896

Gly Tyr Cys Thr Gly Gly Val Cys Tyr Leu Gly Phe Asp Cys
1               5                   10

<210> SEQ ID NO 897
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 897

Arg Ser Ser Gln Ser Leu Leu His Ser Asp Gly Tyr Asn Tyr Leu Asp
1               5                   10                  15

<210> SEQ ID NO 898
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 898

Leu Gly Ser Asn Arg Ala Ser
1               5

<210> SEQ ID NO 899
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 899

Met Gln Ala Leu Gln Thr Pro Leu Thr
1               5

<210> SEQ ID NO 900
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 900

Trp Tyr Thr Met Ala
1               5

<210> SEQ ID NO 901
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 901

Ser Ile Trp Ser Ser Gly Gly Gln Thr Gln Tyr Ala Asp Ser Val Lys
1               5                   10                  15

Gly

<210> SEQ ID NO 902
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 902

Pro Gly Leu Pro Ile Ala Gly Ser Phe His Gly Asp Phe Asp Leu
1               5                   10                  15

<210> SEQ ID NO 903
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 903

Arg Ala Asn Gln Val Ile Ser Thr Trp Leu Ser
1               5                   10

<210> SEQ ID NO 904
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 904

Thr Ala Ser Thr Leu Gln Ser
1               5

<210> SEQ ID NO 905
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 905

Gln Gln Ala Asn Ser Phe Pro Ile Thr
1               5

```
<210> SEQ ID NO 906
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 906

His Tyr Pro Met Ile
1               5

<210> SEQ ID NO 907
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 907

Ser Ile Arg Pro Ser Gly Gly Asp Thr Lys Tyr Ala Asp Ser Val Lys
1               5                   10                  15

Gly

<210> SEQ ID NO 908
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 908

Met Glu Thr Gly Tyr Asp Ile Leu Thr Gly Tyr Tyr Ile Arg Trp Arg
1               5                   10                  15

Tyr Phe Asp Tyr
            20

<210> SEQ ID NO 909
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 909

Ser Gly Ser Ser Ser Asn Ile Gly Ser Asn Tyr Val Tyr
1               5                   10

<210> SEQ ID NO 910
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 910

Ile Asn Asp His Arg Pro Ser
1               5

<210> SEQ ID NO 911
<211> LENGTH: 11
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 911

Ala Val Trp Asp Asp Ser Leu Ser Gly Trp Val
1               5                   10

<210> SEQ ID NO 912
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 912

Asp Tyr Phe Met Tyr
1               5

<210> SEQ ID NO 913
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 913

Ser Ile Gly Pro Ser Gly Gly Trp Thr Trp Tyr Ala Asp Ser Val Lys
1               5                   10                  15

Gly

<210> SEQ ID NO 914
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 914

Gly Thr Gly Ser Phe Asp Tyr
1               5

<210> SEQ ID NO 915
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 915

Ser Gly Ser Ser Ser Asn Ile Gly Ser Asn Tyr Val Tyr
1               5                   10

<210> SEQ ID NO 916
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 916

Thr Asn Asn Gln Arg Pro Ser
1               5

```
<210> SEQ ID NO 917
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 917

Ala Thr Trp Asp Asp Asp Leu Ser Gly Pro Val
1               5                   10

<210> SEQ ID NO 918
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 918

Lys Tyr Ala Met Tyr
1               5

<210> SEQ ID NO 919
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 919

Ser Ile Val Ser Ser Gly Gly Glu Thr His Tyr Ala Asp Ser Val Lys
1               5                   10                  15

Gly

<210> SEQ ID NO 920
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 920

Gly Gly Gln Trp Leu Pro Tyr Tyr Phe Asp Ser
1               5                   10

<210> SEQ ID NO 921
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 921

Arg Ala Ser Gln Ser Val Ser Thr Asn Leu Ala
1               5                   10

<210> SEQ ID NO 922
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 922

Gly Ala Ser Thr Arg Ala Thr
1               5

<210> SEQ ID NO 923
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 923

Gln Gln Tyr Gly Ser Ser Gln Leu Thr
1               5

<210> SEQ ID NO 924
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 924

Asn Tyr Arg Met Ile
1               5

<210> SEQ ID NO 925
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 925

Arg Ile Ser Ser Ser Gly Gly Asn Thr Gln Tyr Ala Asp Ser Val Lys
1               5                   10                  15

Gly

<210> SEQ ID NO 926
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 926

Ala Gly Gly Tyr Ser Tyr Gly Pro Pro Thr Tyr Tyr Tyr Gly Met
1               5                   10                  15

Asp Val

<210> SEQ ID NO 927
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 927

Gln Tyr Glu Leu Thr Gln Pro Arg Ser Val Ser Gly Ser Pro Gly Gln
1               5                   10                  15
```

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Tyr Thr Leu Val Phe Gly Gly Gly Thr Lys Leu Thr Val Leu
            100                 105                 110

<210> SEQ ID NO 928
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 928

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
            20                  25                  30

Gln Met Val Trp Val Arg Gln Ala Pro Gly Lys Gly Leu Glu Trp Val
        35                  40                  45

Ser Val Ile Tyr Pro Ser Gly Gly Pro Thr Val Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Glu Asp Tyr Tyr Asp Ser Ser Gly Pro Gly Ala Phe Asp
            100                 105                 110

Ile Trp Gly Gln Gly Thr Met Val Thr Val Ser Ser
        115                 120

<210> SEQ ID NO 929
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(330)

<400> SEQUENCE: 929 cag tac gaa ttg act cag cct cgc tca gtg tcc ggg tct cct gga cag      48
Gln Tyr Glu Leu Thr Gln Pro Arg Ser Val Ser Gly Ser Pro Gly Gln
 1               5                  10                  15 tca gtc acc atc tcc tgc act gga acc agc agt gat gtt ggt ggt tat     96
Ser Val Thr Ile Ser Cys Thr Gly Thr Ser Ser Asp Val Gly Gly Tyr
            20                  25                  30 aac tat gtc tcc tgg tac caa cag cac cca ggc aaa gcc ccc aaa ctc    144
Asn Tyr Val Ser Trp Tyr Gln Gln His Pro Gly Lys Ala Pro Lys Leu
        35                  40                  45 atg att tat gat gtc agt aag cgg ccc tca ggg gtc cct gat cgc ttc    192

```
Met Ile Tyr Asp Val Ser Lys Arg Pro Ser Gly Val Pro Asp Arg Phe
    50                  55                  60 tct ggc tcc aag tct ggc aac acg gcc tcc ctg acc atc tct ggg ctc        240
Ser Gly Ser Lys Ser Gly Asn Thr Ala Ser Leu Thr Ile Ser Gly Leu
65                  70                  75                  80 cag gct gag gat gag gct gat tat tac tgc tgc tca tat gca ggc agc        288
Gln Ala Glu Asp Glu Ala Asp Tyr Tyr Cys Cys Ser Tyr Ala Gly Ser
                85                  90                  95 tac act ttg gtg ttc ggc gga ggg acc aag ctg acc gtc cta                330
Tyr Thr Leu Val Phe Gly Gly Gly Thr Lys Leu Thr Val Leu
            100                 105                 110

<210> SEQ ID NO 930
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 930

Gln Tyr Glu Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Leu Val Phe Gly Gly Gly Thr Lys Leu Thr Val Leu
            100                 105                 110

<210> SEQ ID NO 931
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(372)

<400> SEQUENCE: 931 gaa gtt caa ttg tta gag tct ggt ggc ggt ctt gtt cag cct ggt ggt        48
Glu Val Gln Leu Leu Glu Ser Gly Gly Gly Leu Val Gln Pro Gly Gly
1               5                   10                  15 tct tta cgt ctt tct tgc gct gct tcc gga ttc act ttc tct act tac        96
Ser Leu Arg Leu Ser Cys Ala Ala Ser Gly Phe Thr Phe Ser Thr Tyr
                20                  25                  30 cag atg gtt tgg gtt cgc caa gct cct ggt aaa ggt ttg gag tgg gtt        144
Gln Met Val Trp Val Arg Gln Ala Pro Gly Lys Gly Leu Glu Trp Val
            35                  40                  45 tct gtt atc tat cct tct ggt ggc cct act gtt tat gct gac tcc gtt        192
Ser Val Ile Tyr Pro Ser Gly Gly Pro Thr Val Tyr Ala Asp Ser Val
    50                  55                  60 aaa ggt cgc ttc act atc tct aga gac aac tct aag aat act ctc tac        240
Lys Gly Arg Phe Thr Ile Ser Arg Asp Asn Ser Lys Asn Thr Leu Tyr
65                  70                  75                  80
```

```
ttg cag atg aac agc tta agg gct gag gac acg gcc gtg tat tac tgt      288
Leu Gln Met Asn Ser Leu Arg Ala Glu Asp Thr Ala Val Tyr Tyr Cys
            85                  90                  95 gcg aga ggg gag gac tac tat gat agt agt ggc ccg ggg gct ttt gat      336
Ala Arg Gly Glu Asp Tyr Tyr Asp Ser Ser Gly Pro Gly Ala Phe Asp
100                 105                 110 atc tgg ggc caa ggg aca atg gtc acc gtc tca agc                      372
Ile Trp Gly Gln Gly Thr Met Val Thr Val Ser Ser
        115                 120

<210> SEQ ID NO 932
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 932

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gln Met Val Trp Val Arg Gln Ala Pro Gly Lys Gly Leu Glu Trp Val
        35                  40                  45

Ser Val Ile Tyr Pro Ser Gly Gly Pro Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Glu Asp Tyr Tyr Asp Ser Ser Gly Pro Gly Ala Phe Asp
        100                 105                 110

Ile Trp Gly Gln Gly Thr Met Val Thr Val Ser Ser
        115                 120

<210> SEQ ID NO 933
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 933

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
            85                  90                  95

Tyr Thr Leu Val Phe Gly Gly Gly Thr Lys Leu Thr Val Leu
        100                 105                 110
```

<210> SEQ ID NO 934
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 934

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gln Met Val Trp Val Arg Gln Ala Pro Gly Lys Gly Leu Glu Trp Val
        35                  40                  45

Ser Val Ile Tyr Pro Ser Gly Gly Pro Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Glu Asp Tyr Tyr Asp Ser Ser Gly Pro Gly Ala Phe Asp
            100                 105                 110

Ile Trp Gly Gln Gly Thr Met Val Thr Val Ser Ser
        115                 120

<210> SEQ ID NO 935
<211> LENGTH: 330
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(330)

<400> SEQUENCE: 935 cag agc gcc ctg acc cag ccc aga agc gtg tcc ggc agc cca ggc cag     48
Gln Ser Ala Leu Thr Gln Pro Arg Ser Val Ser Gly Ser Pro Gly Gln
1               5                   10                  15 agc gtg acc atc agc tgc acc ggc acc agc agc gac gtg ggc ggc tac     96
Ser Val Thr Ile Ser Cys Thr Gly Thr Ser Ser Asp Val Gly Gly Tyr
            20                  25                  30 aac tac gtg tcc tgg tat cag cag cac ccc ggc aag gcc ccc aag ctg    144
Asn Tyr Val Ser Trp Tyr Gln Gln His Pro Gly Lys Ala Pro Lys Leu
        35                  40                  45 atg atc tac gac gtg tcc aag agg ccc agc ggc gtg ccc gac agg ttc    192
Met Ile Tyr Asp Val Ser Lys Arg Pro Ser Gly Val Pro Asp Arg Phe
    50                  55                  60 agc ggc agc aag agc ggc aac acc gcc agc ctg acc atc tcc gga ctg    240
Ser Gly Ser Lys Ser Gly Asn Thr Ala Ser Leu Thr Ile Ser Gly Leu
65                  70                  75                  80 cag gcc gag gac gag gcc gac tac tac tgc tgc agc tac gcc ggc agc    288
Gln Ala Glu Asp Glu Ala Asp Tyr Tyr Cys Cys Ser Tyr Ala Gly Ser
                85                  90                  95 tac acc ctg gtg ttc ggc gga ggg acc aag ctg acc gtg ctg              330
Tyr Thr Leu Val Phe Gly Gly Gly Thr Lys Leu Thr Val Leu
            100                 105                 110

<210> SEQ ID NO 936
<211> LENGTH: 110

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 936

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Leu Val Phe Gly Gly Gly Thr Lys Leu Thr Val Leu
            100                 105                 110

<210> SEQ ID NO 937
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(372)

<400> SEQUENCE: 937 gag gtg caa ttg ctg gaa agc ggc gga gga ctg gtg cag cca ggc ggc    48
Glu Val Gln Leu Leu Glu Ser Gly Gly Gly Leu Val Gln Pro Gly Gly
1               5                   10                  15 agc ctg agg ctg tcc tgc gcc gcc agc ggc ttc acc ttc agc acc tac    96
Ser Leu Arg Leu Ser Cys Ala Ala Ser Gly Phe Thr Phe Ser Thr Tyr
            20                  25                  30 cag atg gtg tgg gtg cgc cag gcc cca ggc aag ggc ctg gaa tgg gtg   144
Gln Met Val Trp Val Arg Gln Ala Pro Gly Lys Gly Leu Glu Trp Val
        35                  40                  45 tcc gtg atc tac ccc agc ggc gga ccc acc gtg tac gcc gac agc gtg   192
Ser Val Ile Tyr Pro Ser Gly Gly Pro Thr Val Tyr Ala Asp Ser Val
    50                  55                  60 aag ggc agg ttc acc atc agc agg gac aac agc aag aac acc ctg tac   240
Lys Gly Arg Phe Thr Ile Ser Arg Asp Asn Ser Lys Asn Thr Leu Tyr
65                  70                  75                  80 ctg cag atg aac agc ctg agg gcc gag gac acc gcc gtg tac tac tgc   288
Leu Gln Met Asn Ser Leu Arg Ala Glu Asp Thr Ala Val Tyr Tyr Cys
                85                  90                  95 gcc agg ggc gag gac tac tac gac agc agc ggc cca ggc gcc ttc gac   336
Ala Arg Gly Glu Asp Tyr Tyr Asp Ser Ser Gly Pro Gly Ala Phe Asp
            100                 105                 110 atc tgg ggc cag ggc aca atg gtg acc gtg tcc agc                    372
Ile Trp Gly Gln Gly Thr Met Val Thr Val Ser Ser
        115                 120

<210> SEQ ID NO 938
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 938

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gln Met Val Trp Val Arg Gln Ala Pro Gly Lys Gly Leu Glu Trp Val
        35                  40                  45

Ser Val Ile Tyr Pro Ser Gly Gly Pro Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Glu Asp Tyr Tyr Asp Ser Ser Gly Pro Gly Ala Phe Asp
            100                 105                 110

Ile Trp Gly Gln Gly Thr Met Val Thr Val Ser Ser
        115                 120

<210> SEQ ID NO 939
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 939
cagagcgccc tgacccagcc cagaagcgtg tccggcagcc caggccagag cgtgaccatc      60
agctgcaccg gcaccagcag cgacgtgggc ggctacaact acgtgtcctg gtatcagcag     120
caccccggca aggccccaa gctgatgatc tacgacgtgt ccaagaggcc cagcggcgtg     180
cccgacaggt tcagcggcag caagagcggc aacaccgcca gcctgaccat ctccggactg    240
caggccgagg acgaggccga ctactactgc tgcagctacg ccggcagcta caccctggtg    300
ttcggcggag ggaccaagct gaccgtgctg ggccagccca ggctgccccc agcgtgacc    360 ctgttccccc cagcagcga ggaactgcag gccaacaagg ccacactggt gtgcctgatc    420
agcgacttct acccaggcgc cgtgaccgtg cctggaagg ccgacagcag ccccgtgaag    480
gccggcgtgg agacaaccac ccccagcaag cagagcaaca caagtacgc cgccagcagc    540 tacctgagcc tgacccccga gcagtggaag tcccacaggt cctacagctg ccaggtgacc    600
cacgagggca gcaccgtgga gaaaaccgtg gcccccaccg agtgtagctg atga          654

<210> SEQ ID NO 940
<211> LENGTH: 1365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 940
gaggtgcaat tgctggaaag cggcggagga ctggtgcagc aggcggcag cctgaggctg       60 tcctgcgccg ccagcggctt caccttcagc acctaccaga tggtgtgggt gcgccaggcc     120
ccaggcaagg gcctggaatg ggtgtccgtg atctacccca gcggcggacc caccgtgtac    180

```
gccgacagcg tgaagggcag gttcaccatc agcagggaca cagcaagaa caccctgtac    240 ctgcagatga acagcctgag ggccgaggac accgccgtgt actactgcgc caggggcgag    300
gactactacg acagcagcgg cccaggcgcc ttcgacatct ggggccaggg cacaatggtg    360
accgtgtcca gcgccagcac caagggcccc agcgtgttcc cgctagcacc ttcctccaag    420
tccacctctg gcggcaccgc cgctctgggc tgcctggtga aggactactt ccctgagcct    480
gtgaccgtga gctggaactc tggcgccctg acctccggcg tgcataacctt ccctgccgtg    540 ctgcagtcct ccggcctgta ctccctgtcc tccgtggtga cagtgccttc ctcctccctg    600
ggcacccaga cctacatctg caacgtgaac cacaagcctt ccaacaccaa ggtggacaag    660
cgggtggagc ctaagtcctg cgacaagacc cacacctgcc ctccctgccc tgcccctgag    720
ctgctgggcg gaccctccgt gttcctgttc cctcctaagc ctaaggacac cctgatgatc    780
tcccggaccc ctgaggtgac ctgcgtggtg gtggacgtgt cccacgagga cccagaggtg    840
aagtttaatt ggtatgtgga cggcgtggag gtccacaacg ccaagaccaa gcctcgggag    900
gaacagtaca actccaccta ccgggtggtg tccgtgctga ccgtgctgca ccaggactgg    960
ctgaacggca aggaatacaa gtgcaaagtc tccaacaagg ccctgcctgc ccccatcgag   1020
aaaaccatct ccaaggccaa gggccagcct cgcgagcctc aggtgtacac cctgcctcct   1080
agccgggagg aaatgaccaa gaaccaggtg tccctgacct gtctggtgaa gggcttctac   1140
ccttccgata tcgccgtgga gtgggagtcc aacggccagc tgagaacaa ctacaagacc   1200 acccctcctg tgctggactc cgacggctcc ttcttcctgt actccaagct gaccgtggac   1260
aagtcccggt ggcagcaggg caacgtgttc tcctgctccg tgatgcacga ggcccctgcac   1320 aaccactaca cccagaagtc cctgtccctg agccctggca agtga                   1365
```

<210> SEQ ID NO 941
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 941

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Leu Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160
```

```
Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser Ser Ser
    210                 215

<210> SEQ ID NO 942
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 942

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gln Met Val Trp Val Arg Gln Ala Pro Gly Lys Gly Leu Glu Trp Val
        35                  40                  45

Ser Val Ile Tyr Pro Ser Gly Gly Pro Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Glu Asp Tyr Tyr Asp Ser Ser Gly Pro Gly Ala Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300
```

```
Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys Ser
    450                 455

<210> SEQ ID NO 943
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 943

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Ser Met Asn Trp Val Arg Gln Ala Pro Gly Lys Gly Leu Glu Trp Val
        35                  40                  45

Ser Ser Ile Tyr Ser Ser Gly Gly Ser Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ala Phe Asp Ile Trp Gly Gln Gly Thr Met Val Thr
            100                 105                 110

Val Ser Ser
        115

<210> SEQ ID NO 944
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 944

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Ser Val Gly Thr Tyr
             20                  25                  30

Leu Asn Trp Tyr Gln Gln Lys Pro Gly Lys Ala Pro Lys Leu Leu Ile
         35                  40                  45

Tyr Ala Thr Ser Asn Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Ile Pro Arg
                 85                  90                  95

Phe Thr Phe Gly Pro Gly Thr Lys Val Asp Ile Lys
            100                 105
```

```
<210> SEQ ID NO 945
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 945
```

```
Met Lys Lys Leu Leu Phe Ala Ile Pro Leu Val Val Pro Phe Val Ala
 1               5                  10                  15

Gln Pro Ala Met Ala Glu Val Gln Leu Leu Ser Gly Gly Gly Leu
             20                  25                  30

Val Gln Pro Gly Gly Ser Leu Arg Leu Ser Cys Ala Ala Ser Gly Phe
         35                  40                  45

Thr Phe Ser Gln Tyr Pro Met Trp Trp Val Arg Gln Ala Pro Gly Lys
 50                  55                  60

Gly Leu Glu Trp Val Ser Tyr Ile Val Pro Ser Gly Gly Arg Thr Tyr
 65                  70                  75                  80

Tyr Ala Asp Ser Val Lys Gly Arg Phe Thr Ile Ser Arg Asp Asn Ser
                 85                  90                  95

Lys Asn Thr Leu Tyr Leu Gln Met Asn Ser Leu Arg Ala Glu Asp Thr
            100                 105                 110

Ala Val Tyr Tyr Cys Ala Lys Asp Arg Ala Tyr Gly Asp Tyr Val Gly
        115                 120                 125

Trp Asn Gly Phe Asp Tyr Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser
```

```
<210> SEQ ID NO 946
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 946
```

```
Phe Tyr Ser His Ser Ala Gln Asp Ile Gln Met Thr Gln Ser Pro Ala
 1               5                  10                  15

Thr Leu Ser Leu Ser Pro Gly Glu Arg Ala Thr Leu Ser Cys Arg Ala
             20                  25                  30

Ser Gln Ser Ile Ser Ser Phe Leu Ala Trp Tyr Gln Gln Lys Pro Gly
         35                  40                  45
```

-continued

```
Gln Ala Pro Arg Leu Leu Ile Tyr Asp Ala Ser Tyr Arg Ala Thr Gly
    50                  55                  60

Ile Pro Ala Arg Phe Ser Gly Ser Gly Ser Gly Thr Asp Phe Thr Leu
65                  70                  75                  80

Thr Ile Ser Ser Leu Glu Pro Glu Asp Tyr Ala Val Tyr Tyr Cys Gln
                85                  90                  95

Gln Arg Gly Asn Trp Pro Ile Thr Phe Gly Gln Gly Thr Arg Leu Glu
            100                 105                 110

Ile Lys Arg Thr Val Ala Ala Pro Ser
        115                 120

<210> SEQ ID NO 947
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 947
gacuugccgc gagacaugat t                                                 21

<210> SEQ ID NO 948
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 948
ucaugucucg cggcaaguct t                                                 21

<210> SEQ ID NO 949
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 949
gacuucgcgg gacacaugat t                                                 21

<210> SEQ ID NO 950
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 950
ucaugugucc cgcgaaguct t                                                 21
```

<210> SEQ ID NO 951
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<221> NAME/KEY: MOD_RES
<222> LOCATION: (1)..(1)
<223> OTHER INFORMATION: (7-methoxycoumarin-4-yl)acetic acid-Pro
<220> FEATURE:
<221> NAME/KEY: MOD_RES
<222> LOCATION: (7)..(7)
<223> OTHER INFORMATION: 2,3-diaminopropionic acid(2,4-dinitrophenyl)
<220> FEATURE:
<223> OTHER INFORMATION: C-term amidated

<400> SEQUENCE: 951

Pro Lys Pro Leu Ala Leu Xaa Ala Arg
1               5

<210> SEQ ID NO 952
<211> LENGTH: 8
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<221> NAME/KEY: MOD_RES
<222> LOCATION: (1)..(1)
<223> OTHER INFORMATION: (7-methoxycoumarin-4-yl)acetic acid-Lys
<220> FEATURE:
<221> NAME/KEY: MOD_RES
<222> LOCATION: (6)..(6)
<223> OTHER INFORMATION: 2,3-diaminopropionic acid(2,4-dinitrophenyl)
<220> FEATURE:
<223> OTHER INFORMATION: C-term amidated

<400> SEQUENCE: 952

Lys Pro Leu Gly Leu Xaa Ala Arg
1               5

<210> SEQ ID NO 953
<211> LENGTH: 14
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 953

Thr Gly Thr Ser Ser Asp Val Gly Gly Tyr Asn Tyr Val Ser
1               5                   10

<210> SEQ ID NO 954
<211> LENGTH: 7
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 954

Asp Val Ser Lys Arg Pro Ser
1               5

<210> SEQ ID NO 955
<211> LENGTH: 10
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 955

Cys Ser Tyr Ala Gly Ser Tyr Thr Leu Val
1               5                   10

<210> SEQ ID NO 956
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 956

Thr Tyr Gln Met Val
1               5

<210> SEQ ID NO 957
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 957

Val Ile Tyr Pro Ser Gly Gly Pro Thr Val Tyr Ala Asp Ser Val Lys
1               5                   10                  15

Gly

<210> SEQ ID NO 958
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 958

Gly Glu Asp Tyr Tyr Asp Ser Ser Gly Pro Gly Ala Phe Asp Ile
1               5                   10                  15

<210> SEQ ID NO 959
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 959

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

```
Gln Ala Glu Asp Glu Ala Asp Tyr Tyr Cys Cys Ser Tyr Ala Gly Ser
                85                  90                  95

Tyr Thr Leu Val Phe Gly Gly Thr Lys Leu Thr Val Leu
            100                 105                 110

<210> SEQ ID NO 960
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 960

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
                100                 105
```

METALLOPROTEINASE 9 BINDING PROTEINS

CROSS REFERENCE TO RELATED APPLICATIONS

This application claims priority to U.S. Application Ser. No. 61/033,075, filed on Mar. 3, 2008, U.S. Application Ser. No. 61/054,938, filed on May 21, 2008, and U.S. Application Ser. No. 61/138,297, filed on Dec. 17, 2008. The disclosures of the prior applications are considered part of (and are incorporated by reference in) the disclosure of this application.

BACKGROUND

Matrix Metalloproteinases (MMPs) are a family of zinc metalloendopeptidases secreted by cells, and are responsible for much of the turnover of matrix components. The MMP family consists of at least 26 members, all of which share a common catalytic core with a zinc molecule in the active site.

SUMMARY

This disclosure relates, inter alia, to proteins that bind MMP-9, herein referred to as "MMP-9 binding proteins," and methods of identifying and using such proteins. These proteins include antibodies and antibody fragments (e.g., primate antibodies and Fabs, especially human antibodies and Fabs) that bind to MMP-9 (e.g., human MMP-9). In some embodiments, these proteins include antibodies and antibody fragments (e.g., primate antibodies and Fabs, especially human antibodies and Fabs) that inhibit MMP-9 (e.g., human MMP-9) (e.g., inhibit the catalytic activity of MMP-9). The MMP-9 binding proteins can be used in the treatment of diseases, particularly human disease, such as cancer, inflammation, heart failure, septic shock, neuropathic pain, inflammatory pain, or macular degeneration, in which excess or inappropriate activity of MMP-9 features. In many cases, the proteins have tolerable low or no toxicity.

In some aspects, the disclosure relates to proteins (e.g., antibodies, peptides and Kunitz domain proteins) that bind MMP-9, in particular, proteins (e.g., antibodies (e.g., human antibodies), peptides and Kunitz domain proteins) that bind and inhibit MMP-9.

In one embodiment, the disclosure provides an antibody (e.g., a human antibody) that binds to human MMP-9. In one embodiment, the human antibody is an inhibitor of the catalytic activity of MMP-9. The antibody can be, e.g., an IgG1, IgG2, IgG3, IgG4, Fab, Fab2', scFv, minibody, scFv::Fc fusion, Fab::HSA fusion, HSA::Fab fusion, Fab::HSA::Fab fusion, or other molecule that comprises the antigen combining site of one of the antibodies herein listed. In one embodiment, the antibody is used to guide a nano-particle or toxin to a cell expressing MMP-9 on the cell surface. In one embodiment, the antibody causes effector functions (CDC or ADCC) to kill the cell which expresses MMP-9.

In some embodiments, the VH and VL regions of the binding proteins (e.g., Fabs) can be provided as IgG, Fab, Fab2, Fab2', scFv, PEGylated Fab, PEGylated scFv, PEGylated Fab2, VH::CH1::HSA+LC, HSA::VH::CH1+LC, LC:: HSA+VH::CH1, HSA::LC+VH::CH1, or other appropriate construct.

In another embodiment, the binding protein comprises a Kunitz domain protein or modified version (e.g., HSA fusion) or peptide-based MMP-9 binding protein that can inhibit MMP-9 activity.

In one aspect, the disclosure features a protein (e.g., an isolated protein) that binds to MMP-9 (e.g., human MMP-9) and includes at least one immunoglobulin variable region. For example, the protein includes a heavy chain (HC) immunoglobulin variable domain sequence and a light chain (LC) immunoglobulin variable domain sequence. In one embodiment, the protein binds to and inhibits MMP-9 (e.g., inhibits MMP-9 catalytic activity), e.g., human MMP-9.

In some embodiments, the protein binds to human MMP-9 specifically, and not to MMP-9 from another species (e.g., the protein does not bind to MMP-9 from another species with greater than background levels of binding).

In some embodiments, the protein binds MMP-9 specifically, and not to another matrix metalloproteinase (e.g., the protein does not bind to any other matrix metalloproteinase with greater than background levels of binding).

Such binding proteins can be conjugated to a drug (e.g., to form a MMP-9 binding protein-drug conjugate) and used therapeutically. This disclosure relates, in part, to MMP-9 binding protein-drug conjugates, the preparation of these conjugates, and uses thereof. The conjugates can be used, e.g., in the treatment of disorders, e.g., for the treatment of cancer, inflammation, heart failure, septic shock, neuropathic pain, inflammatory pain, or macular degeneration. Targeting (e.g., an killing) of the MMP-9 expressing cells and/or tumors, e.g., with high affinity binding protein-drug conjugates can be a potent therapy in the treatment of diseases, e.g., cancer, inflammation, heart failure, septic shock, neuropathic pain, inflammatory pain, or macular degeneration.

The protein can include one or more of the following characteristics: (a) a human CDR or human framework region; (b) the HC immunoglobulin variable domain sequence comprises one or more (e.g., 1, 2, or 3) CDRs that are at least 85, 88, 90, 91, 92, 93, 94, 95, 96, 97, 98, 99, or 100% identical to a CDR of a HC variable domain described herein; (c) the LC immunoglobulin variable domain sequence comprises one or more (e.g., 1, 2, or 3) CDRs that are at least 85, 88, 90, 91, 92, 93, 94, 95, 96, 97, 98, 99, or 100% identical to a CDR of a LC variable domain described herein; (d) the LC immunoglobulin variable domain sequence is at least 85, 88, 90, 91, 92, 93, 94, 95, 96, 97, 98, 99, or 100% identical to a LC variable domain described herein; (e) the HC immunoglobulin variable domain sequence is at least 85, 88, 90, 91, 92, 93, 94, 95, 96, 97, 98, 99, or 100% identical to a HC variable domain described herein; (f) the protein binds an epitope bound by a protein described herein, or an epitope that overlaps with such epitope; and (g) a primate CDR or primate framework region.

The protein can bind to MMP-9, e.g., human MMP-9, with a binding affinity of at least $10^5$, $10^6$, $10^7$, $10^8$, $10^9$, $10^{10}$ and $10^{11}$ $M^{-1}$. In one embodiment, the protein binds to MMP-9 with a $K_{off}$ slower than $1\times10^{-3}$, $5\times10^{-4}$ $s^{-1}$, or $1\times10^{-4}$ $s^{-1}$. In one embodiment, the protein binds to MMP-9 with a $K_{on}$ faster than $1\times10^2$, $1\times10^3$, or $5\times10^3$ $M^{-1}s^{-1}$. In one embodiment, the protein inhibits human MMP-9 activity, e.g., with a Ki of less than $10^{-5}$, $10^{-6}$, $10^{-7}$, $10^{-8}$, $10^{-9}$, and $10^{-10}$ M. The protein can have, for example, an IC50 of less than 100 nM, 10 nM or 1 nM. In some embodiments, the protein has an IC50 of about 1.8 nM. The affinity of the protein for MMP-9 can be characterized by a $K_D$ of less than 100 nm, less than 10 nM, or about 3 nM (e.g., 3.1 nM), about 5 nM (e.g., 5 nM), about 6 nm (e.g., 5.9 nM), about 7 nM (e.g., 7.1 nM), or about 10 nM (e.g., 9.6 nM).

In some embodiments, the protein has a $K_D$<200 nM.

In some embodiments, the protein has a t1/2 of at least about 10 minutes (e.g., 11 minutes), at least about 20 minutes (e.g., 18 minutes), at least about 25 minutes (e.g., 23 minutes), at least about 35 minutes (e.g., 33 minutes), or at least about 60 minutes (e.g., 57 minutes).

In one embodiment, the protein binds the catalytic domain of human MMP-9, e.g., the protein contacts residues in or near the active site of MMP-9.

In some embodiments, the protein does not contact residues in or near the active site of MMP-9 but instead binds elsewhere on MMP-9 and causes a steric change in MMP-9 that affects (e.g., inhibits) its activity.

In one embodiment, the protein also binds to MMP-16 and/or MMP-24, e.g., with a binding affinity of at least $10^5$, $10^6$, $10^7$, $10^{10}$, $10^9$, $10^{10}$ and $10^{11}$ M$^{-1}$. For example, the protein binds to both MMP-9 and to MMP-16 or MMP-24 with a binding affinity of at least $10^5$, $10^6$, $10^7$, $10^8$, $10^9$, $10^{10}$ and $10^{11}$ M$^{-1}$.

In a preferred embodiment, the protein is a human antibody having the light and heavy chains of antibodies picked from the list comprising 539A-M0240-B03, 539A-X0034-C02, M0078-G07, M0081-D05, M0076-D03, M0072-H07, M0075-D12, and M0166-F10. In a preferred embodiment, the protein is a human antibody having its heavy chain picked from the list comprising 539A-M0240-B03, 539A-X0034-C02, M0078-G07, M0081-D05, M0076-D03, M0072-H07, M0075-D12, and M0166-F10. In a preferred embodiment, the protein is a human antibody having its light chain picked from the list comprising 539A-M0240-B03, 539A-X0034-C02, M0078-G07, M0081-D05, M0076-D03, M0072-H07, M0075-D12, and M0166-F10. In a preferred embodiment, the protein is a human antibody having one or more (e.g., 1, 2, or 3) heavy chain CDRs picked from the corresponding CDRs of the list of heavy chains comprising 539A-M0240-B03, 539A-X0034-C02, M0078-G07, M0081-D05, M0076-D03, M0072-H07, M0075-D12, and M0166-F10. In a preferred embodiment, the protein is a human antibody having one or more (e.g., 1, 2, or 3) light chain CDRs picked from the corresponding CDRs of the list of light chains comprising 539A-M0240-B03, 539A-X0034-C02, M0078-G07, M0081-D05, M0076-D03, M0072-H07, M0075-D12, and M0166-F10.

In a more preferred embodiment, the protein is a human antibody having the light and heavy chains of antibodies from M0166-F10. In another preferred embodiment, the protein is a human antibody having its heavy chain from M0166-F10. In yet another preferred embodiment, the protein is a human antibody having its light chain from M0166-F10. In an even more preferred embodiment, the protein is a human antibody having one or more (e.g., 1, 2, or 3) heavy chain CDRs from the corresponding CDRs of the heavy chain comprising M0166-F10. In another even more preferred embodiment, the protein is a human antibody having one or more (e.g., 1, 2, or 3) light chain CDRs from the corresponding CDRs of the light chains comprising M0166-F10.

In a more preferred embodiment, the protein is a human antibody having one or more heavy chain CDRs from the corresponding CDRs of the heavy chain comprising 539A-M0240-B03. In another more preferred embodiment, the protein is a human antibody having one or more (e.g., 1, 2, or 3) light chain CDRs from the corresponding CDRs of the light chain comprising 539A-M0240-B03. In another even more preferred embodiment, the protein is a human antibody having one or more (e.g., 1, 2, or 3) light chain CDRs from the corresponding CDRs of the light chains of 539A-M0240-B03, and/or one or more heavy chain CDRs from the corresponding CDRs of the heavy chain of 539A-M0240-B03.

In a more preferred embodiment, the protein is a human antibody having one or more heavy chain CDRs from the corresponding CDRs of the heavy chain comprising 539A-X0034-C02. In another more preferred embodiment, the protein is a human antibody having one or more (e.g., 1, 2, or 3) light chain CDRs from the corresponding CDRs of the light chain comprising 539A-X0034-C02. In another even more preferred embodiment, the protein is a human antibody having one or more (e.g., 1, 2, or 3) light chain CDRs from the corresponding CDRs of the light chains of 539A-X0034-C02, and/or one or more heavy chain CDRs from the corresponding CDRs of the heavy chain of 539A-X0034-C02.

In one embodiment, the HC and LC variable domain sequences are components of the same polypeptide chain. In another, the HC and LC variable domain sequences are components of different polypeptide chains. For example, the protein is an IgG, e.g., IgG1, IgG2, IgG3, or IgG4. The protein can be a soluble Fab (sFab). In other implementations the protein includes a Fab2', scFv, minibody, scFv::Fc fusion, Fab::HSA fusion, HSA::Fab fusion, Fab::HSA::Fab fusion, or other molecule that comprises the antigen combining site of one of the binding proteins herein. The VH and VL regions of these Fabs can be provided as IgG, Fab, Fab2, Fab2', scFv, PEGylated Fab, PEGylated scFv, PEGylated Fab2, VH::CH1::HSA+LC, HSA::VH::CH1+LC, LC::HSA+VH::CH1, HSA::LC+VH::CH1, or other appropriate construction.

In one embodiment, the protein is a human or humanized antibody or is non-immunogenic in a human. For example, the protein includes one or more human antibody framework regions, e.g., all human framework regions. In one embodiment, the protein includes a human Fc domain, or an Fc domain that is at least 95, 96, 97, 98, or 99% identical to a human Fc domain.

In one embodiment, the protein is a primate or primatized antibody or is non-immunogenic in a human. For example, the protein includes one or more primate antibody framework regions, e.g., all primate framework regions. In one embodiment, the protein includes a primate Fc domain, or an Fc domain that is at least 95, 96, 97, 98, or 99% identical to a primate Fc domain. "Primate" includes humans (*Homo sapiens*), chimpanzees (*Pan troglodytes* and *Pan paniscus* (bonobos)), gorillas (*Gorilla gorilla*), gibons, monkeys, lemurs, aye-ayes (*Daubentonia madagascariensis*), and tarsiers.

In certain embodiments, the protein includes no sequences from mice or rabbits (e.g., is not a murine or rabbit antibody).

In one embodiment, the protein is capable of binding to tumor cells expressing MMP-9, e.g., to Colo205 (a human colorectal carcinoma cell line), or MCF-7 (a human breast adenocarcinoma cell line) cells.

In one embodiment, protein is physically associated with a nanoparticle, and can be used to guide a nanoparticle to a cell expressing MMP-9 on the cell surface. In one embodiment, the protein causes effector cells (CDC or ADCC) to kill a cell which expresses MMP-9.

In another aspect, the disclosure features a MMP-9 binding protein that is a competitive inhibitor of MMP-9. In some embodiments, the binding protein competes with an MMP-9 substrate (e.g., collagen), e.g., binds to the same epitope as the substrate, e.g., and prevents substrate binding.

In some aspects, the disclosure features a method of inhibiting an interaction between MMP-9 and an MMP-9 substrate (e.g., collagen). The method includes contacting an MMP-9 binding protein described herein with MMP-9 (e.g., in vitro or in vivo), wherein the binding protein binds to MMP-9 and thereby prevents the binding of an MMP-9 substrate to MMP-9. In some embodiments, the binding protein binds to the same epitope on MMP-9 as the substrate, e.g., the binding protein is a competitive inhibitor. In some embodiments, the binding protein does not bind the same epitope as the substrate but causes a steric change in MMP-9 that decreases or inhibits the ability of the substrate to bind.

In one aspect, the disclosure features a MMP-9 binding protein-drug conjugate that includes a MMP-9 binding protein and a drug.

In one embodiment, the binding protein comprises at least one immunoglobulin variable region, and/or the protein binds to and/or inhibits MMP-9, e.g., inhibits MMP-9 catalytic activity.

In one embodiment, the drug is a cytotoxic or cytostatic agent. The cytotoxic agent can be, e.g., selected from the group consisting of an auristatin, a DNA minor groove binding agent, a DNA minor groove alkylating agent, an enediyne, a lexitropsin, a duocarmycin, a taxane, a puromycin, a dolastatin, a podophyllotoxin, a baccatin derivative, a cryptophysin, a combretastatin, a maytansinoid, and a vinca alkaloid. In one embodiment, the cytotoxic agent is an auristatin and, e.g., the auristatin is selected from AFP, MMAF, MMAE, AEB, AEVB and auristatin E. In one embodiment, the auristatin is AFP or MMAF. In another embodiment, the cytotoxic agent is a maytansinoid and, e.g., the maytansinoid is selected from a maytansinol, maytansine, DM1, DM2, DM3 and DM4. In one embodiment, the maytansinoid is DM1. In another embodiment, the cytotoxic agent is selected from paclitaxel, docetaxel, CC-1065, SN-38, topotecan, morpholino-doxorubicin, rhizoxin, cyanomorpholino-doxorubicin, dolastatin-10, echinomycin, combretatstatin, calicheamicin, and netropsin. In one embodiment, the cytotoxin is an auristatin, a maytansinoid, or calicheamicin.

In one embodiment, the cytotoxic agent is an antitubulin agent and, e.g., the antitubulin agent is selected from AFP, MMAP, MMAE, AEB, AEVB, auristatin E, vincristine, vinblastine, vindesine, vinorelbine, VP-16, camptothecin, paclitaxel, docetaxel, epothilone A, epothilone B, nocodazole, colchicines, colcimid, estramustine, cemadotin, discodermolide, maytansinol, maytansine, DM1, DM2, DM3, DM4 and eleutherobin.

In one embodiment, the MMP-9 binding protein (e.g., antibody) is conjugated to the drug (e.g., cytotoxic agent) via a linker. In one embodiment, the linker is cleavable under intracellular conditions, e.g., the cleavable linker is a peptide linker cleavable by an intracellular protease. In one embodiment, the linker is a peptide linker, e.g., a dipeptide linker, e.g., a val-cit linker or a phe-lys linker. In one embodiment, the cleavable linker is hydrolyzable at a pH of less than 5.5, e.g., the hydrolyzable linker is a hydrazone linker. In another embodiment, the cleavable linker is a disulfide linker.

A binding protein described herein can be provided as a pharmaceutical composition, e.g., including a pharmaceutically acceptable carrier. The composition can be at least 10, 20, 30, 50, 75, 85, 90, 95, 98, 99, or 99.9% free of other protein species. In some embodiments, the binding protein can be produced under GMP (good manufacturing practices). In some embodiments, the binding protein is provided in pharmaceutically acceptable carriers, e.g., suitable buffers or excipients.

The dose of a binding protein (e.g., a pharmaceutical composition containing a binding protein described herein) is sufficient to block about 20%, about 30%, about 40%, about 50%, about 60%, about 70%, about 80%, about 85%, about 90%, about 95%, about 99%, or about 100% of the activity of MMP-9 in the patient, e.g., at the site of disease. Depending on the disease, this may require a dose, e.g., of between about 0.01 mg/Kg to about 100 mg/Kg, e.g., between about 0.1 and about 10 mg/Kg. For example, the dose can be a dose of about 0.1, about 1, about 3, about 6, or about 10 mg/Kg. For example, for an IgG having a molecular mass of 150,000 g/mole (2 binding sites), these doses correspond to approximately 18 nM, 180 nM, 540 nM, 1.08 microM, and 1.8 microM, respectively, of binding sites for a 5 L blood volume. Medicine being partly an art, the optimal dose will be established by clinical trials, but will most likely lie in this range.

In another aspect, the disclosure features a method of detecting an MMP-9 in a sample, e.g., a sample from a patient (e.g., tissue biopsy or blood sample). The method includes: contacting the sample with an MMP-9 binding protein; and detecting an interaction between the protein and the MMP-9, if present. In some embodiments, the protein includes a detectable label. An MMP-9 binding protein can be used to detect MMP-9 in a subject. The method includes: administering an MMP-9 binding protein to a subject; and detecting the protein in the subject. In some embodiments, the protein further includes a detectable label. For example, the detecting comprises imaging the subject. For example, MMP-9 activity can be a marker of joint pathogenesis and/or disease progression in subjects with, or suspected of having, arthritis.

In another aspect, the disclosure features a method of modulating MMP-9 activity. The method includes: contacting an MMP-9 with an MMP-9 binding protein (e.g., in a human subject), thereby modulating MMP-9 activity. In some embodiments, the binding protein inhibits MMP-9 activity (e.g., inhibits MMP-9 catalytic activity).

In another aspect, the disclosure features a method of treating cancer (e.g., metastatic cancer) (e.g., in a subject that has cancer or is suspected of having cancer). The method includes: administering, to a subject, an MMP-9 binding protein in an amount sufficient to treat a cancer in the subject. For example, the cancer is head and neck cancer, oral cavity cancer, laryngeal cancer, chondrosarcoma, breast cancer (which may be estrogen receptor positive (ER+), estrogen receptor negative (ER−), Her2 positive (Her2+), Her2 negative (Her2−), or a combination thereof, e.g., ER+/Her2+, ER+/Her2−, ER−/Her2+, or ER−/Her2−), laryngeal cancer, ovarian cancer, lung cancer, prostate cancer, colon cancer (e.g., primary or metastatic colon cancer), testicular carcinoma, melanoma, leukemia, B cell lymphoma, multiple myeloma, or a brain tumor (e.g., astrocytomas, glioblastomas, gliomas).

MMP-9 binding proteins can be useful for modulating metastatic activity in a subject (e.g., in a subject that has a metastatic cancer or is suspected of having a metastatic cancer). The protein can be administered, to the subject, in an amount effective to modulate metastatic activity. For example, the protein inhibits one or more of: tumor growth, tumor embolism, tumor mobility, tumor invasiveness, and cancer cell proliferation.

The methods disclosed herein relating to the treatment cancer (e.g., treating cancer and/or modulation of metastatic activity) can further include providing (e.g., administering) to the subject a second therapy that is an anti-cancer therapy, e.g., administration of a chemotherapeutic, e.g., an agent that antagonizes signaling through a VEGF pathway, e.g., bevacizumab (AVASTIN®). In one embodiment, the second therapy includes administering 5-FU, leucovorin, and/or irinotecan. In one embodiment, the second therapy includes administering a Tie1 inhibitor (e.g., an anti-Tie1 antibody). As another example, the second agent can be an anti-MMP14 binding protein (e.g., IgG or Fab, e.g., DX-2400, or a protein described in U.S. Pub. App. No. 2007-0217997). In one embodiment, the second therapy is an inhibitor of plasmin (e.g., a kunitz domain disclosed in U.S. Pat. No. 6,010,880, such as a protein or polypeptide comprising the amino acid sequence MHSFCAFKAETGPCRARFDRWFFNIF-TRQCEEFIYGGCEGNQNRFESLEECKKMCTRD (SEQ ID NO: 1).

In another aspect, the disclosure features a method of treating heart failure (e.g., in a subject that has heart failure or is suspected of having heart failure). The method includes: administering, to a subject, an MMP-9 binding protein in an amount sufficient to treat heart failure in the subject. The method can further include providing to the subject a second therapy that is a heart failure therapy.

In another aspect, the disclosure features a method of treating septic shock (e.g., in a subject that has septic shock or is suspected of having septic shock). The method includes: administering, to a subject, an MMP-9 binding protein in an amount sufficient to treat septic shock in the subject. The method can further include providing to the subject a second therapy that is a therapy for septic shock.

In another aspect, the disclosure features a method of treating neuropathic pain (e.g., in a subject that has neuropathic pain or is suspected of having neuropathic pain). The method includes: administering, to a subject, an MMP-9 binding protein in an amount sufficient to treat neuropathic pain in the subject. The method can further include providing to the subject a second therapy that is a therapy for neuropathic pain.

In another aspect, the disclosure features a method of treating inflammatory pain (e.g., in a subject that has inflammatory pain or is suspected of having inflammatory pain). The method includes: administering, to a subject, an MMP-9 binding protein in an amount sufficient to treat inflammatory pain in the subject. The method can further include providing to the subject a second therapy that is a therapy for inflammatory pain.

In another aspect, the disclosure features a method of treating an ocular condition (e.g., macular degeneration) (e.g., in a subject that has an ocular condition or is suspected of having an ocular condition). The method includes: administering, to a subject, an MMP-9 binding protein in an amount sufficient to treat the ocular condition in the subject. In one embodiment, the method further includes administering a second agent an agent that antagonizes signaling through a VEGF pathway, e.g., bevacizumab or ranibizumab. In one embodiment where the second agent is a VEGF pathway inhibitor (e.g., bevacizumab or ranibizumab), the ocular condition is macular degeneration, e.g., age-related macular degeneration, such as wet age-related macular degeneration.

In another aspect, the disclosure features a method of treating an inflammatory disease (e.g., chronic obstructive pulmonary disease (COPD), asthma, rhinitis, inflammatory bowel disease, synovitis, rheumatoid arthritis) (e.g., in a subject that has an inflammatory disease or is suspected of having an inflammatory disease). The method includes: administering, to a subject, an MMP-9 binding protein in an amount sufficient to treat the inflammatory disease in the subject. The method can further include providing to the subject a second therapy that is an anti-inflammatory therapy. For example, particularly for rheumatoid arthritis, the second therapy comprises administering one or more of the following agents: aspirin, naproxen, ibuprofen, etodolac, cortisone (corticosteroids), antacids, sucralfate, proton-pump inhibitors, misoprostol, gold (e.g., gold salts, gold thioglucose, gold thiomalate, oral gold), methotrexate, sulfasalazine, D-penicillamine, azathioprine, cyclophosphamide, chlorambucil, cyclosporine, leflunomide, etanercept, infliximab, anakinra, adalimumab, and/or hydroxychloroquine.

Other exemplary therapeutic methods that include administering an MMP-9 binding protein are described below. An MMP-9 binding protein described herein can be administered in combination with one or more other MMP inhibitors, e.g., small molecule inhibitors, e.g., broad specificity inhibitors. In one embodiment, the small molecule inhibitors are one or more of neovastat, marimastat, BAY 12-9566, or prinomastat. In another embodiment, the one or more MMP inhibitors include another MMP-9 binding protein.

MMP-9 binding proteins are useful for targeted delivery of an agent to a subject (e.g., a subject who has or is suspected of having a tumor), e.g., to direct the agent to a tumor in the subject. For example, an MMP-9 binding protein that is coupled to an anti-tumor agent (such as a chemotherapeutic, toxin, drug, or a radionuclide (e.g., $^{131}$I, $^{90}$Y, $^{177}$Lu)) can be administered to a subject who has or is suspected of having a tumor.

In another aspect, the disclosure features a method of imaging a subject. The method includes administering an MMP-9 binding protein to the subject. In some embodiments, the protein is one that does not substantially inhibit MMP-9 catalytic activity. The MMP-9 binding protein may include a detectable label (e.g., a radionuclide or an MRI-detectable label). In one embodiment, the subject has or is suspected of having a tumor. The method is useful for cancer diagnosis, intraoperative tumor detection, post-operative tumor detection, or monitoring tumor invasive activity.

In one aspect, the disclosure features the use of an MMP-9 binding protein described herein for the manufacture of a medicament for the treatment of a disorder described herein, e.g., cancer, inflammation, heart failure, septic shock, neuropathic pain, inflammatory pain, or macular degeneration.

The details of one or more embodiments of the invention are set forth in the accompanying drawings and the description below. Other features, objects, and advantages of the invention will be apparent from the description and drawings, and from the claims.

The contents of all cited references including literature references, issued patents, published or non-published patent applications cited throughout this application as well as those listed below are hereby expressly incorporated by reference in their entireties. In case of conflict, the present application, including any definitions herein, will control.

DESCRIPTION OF DRAWINGS

FIG. 1A is a line graph showing human MMP-9 activity (Fluo/sec) in the presence of increasing concentrations (nM) of an MMP-9 binding protein (539A-M0166-F10). FIG. 1B is a table showing that an MMP-9 binding protein (539A-M0166-F10) is specific for human MMP-9.

FIG. 5 is a table showing that an MMP-9 binding protein (539A-M0240-B03) inhibits human and mouse MMP-9 but not human MMP-1, -2, -3, -7, -8, -10, -12, and -14.

In FIG. 6A, the substrate is human MMP-9. In FIG. 6B, the substrate is mouse MMP-9.

DETAILED DESCRIPTION

Figures 1A, 1B:
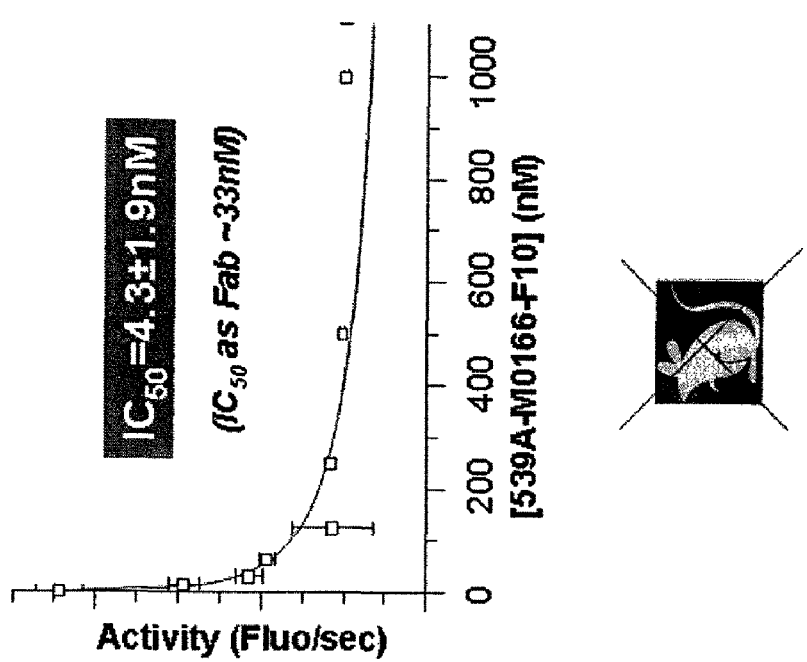
FIGS. 1A and 1B.

Matrix metalloproteinase-2 (MMP-2) and matrix metalloproteinase-9 (MMP-9) are 72- and 92-kD, respectively, type IV collagenases that are members of a group of secreted zinc metalloproteases which, in mammals, degrade the collagens of the extracellular matrix. Other members of this group include interstitial collagenase (MMP-1) and stromelysin (MMP-3). MMP-2, the 72-kD type IV collagenase (also known as CLG4A), is secreted from normal skin fibroblasts, whereas MMP-9, the 92-kD collagenase (also known as CLG4B), is produced by normal alveolar macrophages and granulocytes. The present disclosure provides proteins that bind to MMP-9 and, in some instances, inhibit MMP-9 activity.

The term "binding protein" refers to a protein that can interact with a target molecule. This term is used interchangeably with "ligand." An "MMP-9 binding protein" refers to a protein that can interact with MMP-9, and includes, in particular, proteins that preferentially interact with and/or inhibit MMP-9. For example, the MMP-9 binding protein is an antibody.

The term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')$_2$, Fd fragments, Fv fragments, scFv, and domain antibodies (dAb) fragments (de Wildt et al., Eur J Immunol. 1996; 26(3):629-39.)) as well as complete antibodies. An antibody can have the structural features of IgA, IgG, IgE, IgD, IgM (as well as subtypes thereof). Antibodies may be from any source, but primate (human and non-human primate) and primatized are preferred The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901-917. Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

As used herein, an "immunoglobulin variable domain sequence" refers to an amino acid sequence which can form the structure of an immunoglobulin variable domain such that one or more CDR regions are positioned in a conformation suitable for an antigen binding site. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes immunoglobulin variable domain sequence can associate with another immunoglobulin variable domain sequence to form an antigen binding site, e.g., a structure that preferentially interacts with an MMP-9 protein, e.g., the MMP-9 catalytic domain.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. In IgGs, the heavy chain constant region includes three immunoglobulin domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system. The light chains of the immunoglobulin may be of types kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. For example, the Fc region can be human. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. In one embodiment, the framework (FR) residues of a selected Fab can be converterted to the amino-acid type of the corresponding residue in the most similar primate germline gene, especially the human germline gene. One or more of the constant regions can be human or effectively human. For example, at least 70, 75, 80, 85, 90, 91, 92, 93, 94, 95, 96, 97, 98, 99, or 100% of an immunoglobulin variable domain, the constant region, the constant domains (CH1, CH2, CH3, CL1), or the entire antibody can be human or effectively human.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the many immunoglobulin variable region genes. Full-length immunoglobulin "light chains" (about 25 KDa or about 214 amino acids) are encoded by a variable region gene at the NH2-terminus (about 110 amino acids) and a kappa or lambda constant region gene at the COOH—-terminus. Full-length immunoglobulin "heavy chains" (about 50 KDa or about 446 amino acids), are similarly encoded by a variable region gene (about 116 amino acids) and one of the other aforementioned constant region genes, e.g., gamma (encoding about 330 amino acids). The length of human HC varies considerably because HC CDR3 varies from about 3 amino-acid residues to over 35 amino-acid residues.

The term "antigen-binding fragment" of a full length antibody refers to one or more fragments of a full-length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')$_2$ fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and 4,881,175; Bird et al. (1988) *Science* 242:423-426; and Huston et al. (1988) *Proc. Natl. Acad. Sci. USA* 85:5879-5883.

Antibody fragments can be obtained using any appropriate technique including conventional techniques known to those with skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition, irrespective of how the antibody was generated.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified to include a sufficient number of human framework amino acid positions such that the immunoglobulin variable region does not elicit an immunogenic response in a normal human. Descriptions of "humanized" immunoglobulins include, for example, U.S. Pat. No. 6,407,213 and U.S. Pat. No. 5,693,762.

As used herein, "binding affinity" refers to the apparent association constant or $K_a$. The $K_a$ is the reciprocal of the dissociation constant ($K_d$). A binding protein may, for example, have a binding affinity of at least $10^5$, $10^6$, $10^7$, $10^8$, $10^9$, $10^{10}$ and $10^{11}$ M$^{-1}$ for a particular target molecule, e.g., MMP-9, MMP-16, or MMP-24. Higher affinity binding of a binding protein to a first target relative to a second target can be indicated by a higher $K_a$ (or a smaller numerical value $K_d$) for binding the first target than the $K_a$ (or numerical value $K_d$) for binding the second target. In such cases, the binding protein has specificity for the first target (e.g., a protein in a first conformation or mimic thereof) relative to the second target (e.g., the same protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 91, 100, 500, 1000, or 105 fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in TRIS-buffer (50 mM TRIS, 150 mM NaCl, 5 mM CaCl$_2$ at pH7.5). These techniques can be used to measure the concentration of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation:

$$[Bound]=N \cdot [Free]/((1/Ka)+[Free]).$$

It is not always necessary to make an exact determination of $K_a$, though, since sometimes it is sufficient to obtain a quantitative measurement of affinity, e.g., determined using a method such as ELISA or FACS analysis, is proportional to $K_a$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

An "isolated composition" refers to a composition (e.g., protein) that is removed from at least 90% of at least one component of a natural sample from which the isolated composition can be obtained. Compositions produced artificially or naturally can be "compositions of at least" a certain degree of purity if the species or population of species of interests is at least 5, 10, 25, 50, 75, 80, 90, 92, 95, 98, or 99% pure on a weight-weight basis.

An "epitope" refers to the site on a target compound that is bound by a binding protein (e.g., an antibody such as a Fab or full length antibody). In the case where the target compound is a protein, the site can be entirely composed of amino acid components, entirely composed of chemical modifications of amino acids of the protein (e.g., glycosyl moieties), or composed of combinations thereof. Overlapping epitopes include at least one common amino acid residue, glycosyl group, phosphate group, sulfate group, or other molecular feature.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

In a preferred embodiment, the length of a reference sequence aligned for comparison purposes is at least 30%, preferably at least 40%, more preferably at least 50%, even more preferably at least 60%, and even more preferably at least 70%, 80%, 85%, 90%, 91%, 92%, 93%, 94%, 95%, 96%, 97%, 98%, 99%, or 100% of the length of the reference sequence. For example, the reference sequence may be the length of the immunoglobulin variable domain sequence.

As used herein, the term "substantially identical" (or "substantially homologous") is used herein to refer to a first amino acid or nucleic acid sequence that contains a sufficient number of identical or equivalent (e.g., with a similar side chain, e.g., conserved amino acid substitutions) amino acid residues or nucleotides to a second amino acid or nucleic acid sequence such that the first and second amino acid or nucleic acid sequences have (or encode proteins having) similar activities, e.g., a binding activity, a binding preference, or a biological activity. In the case of antibodies, the second antibody has the same specificity and has at least 50%, at least 25%, or at least 10% of the affinity relative to the same antigen.

Sequences similar or homologous (e.g., at least about 85% sequence identity) to the sequences disclosed herein are also part of this application. In some embodiments, the sequence identity can be about 85%, 90%, 91%, 92%, 93%, 94%, 95%, 96%, 97%, 98%, 99% or higher. In addition, substantial identity exists when the nucleic acid segments hybridize under selective hybridization conditions (e.g., highly stringent hybridization conditions), to the complement of the strand. The nucleic acids may be present in whole cells, in a cell lysate, or in a partially purified or substantially pure form.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6. Aqueous and nonaqueous methods are described in that reference and either can be used. Specific hybridization conditions referred to herein are as follows: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified. The disclosure includes nucleic acids that hybridize with low, medium, high, or very high stringency to a nucleic acid described herein or to a complement thereof, e.g., nucleic acids encoding a binding protein described herein. The nucleic acids can be the same length or within 30, 20, or 10% of the length of the reference nucleic acid. The nucleic acid can correspond to a region encoding an immunoglobulin variable domain sequence described herein.

An MMP-9 binding protein may have mutations (e.g., at least one, two, or four, and/or less than 15, 10, 5, or 3) relative to a binding protein described herein (e.g., conservative or non-essential amino acid substitutions), which do not have a substantial effect on protein function. Whether or not a particular substitution will be tolerated, i.e., will not adversely affect biological properties, such as binding activity can be predicted, e.g., by evaluating whether the mutation is conservative or by the method of Bowie, et al. (1990) *Science* 247:1306-1310.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). It is possible for many framework and CDR amino acid residues to include one or more conservative substitutions.

Motif sequences for biopolymers can include positions which can be varied amino acids. For example, the symbol "X" in such a context generally refers to any amino acid (e.g., any of the twenty natural amino acids or any of the nineteen non-cysteine amino acids). Other allowed amino acids can also be indicated for example, using parentheses and slashes. For example, "(A/W/F/N/Q)" means that alanine, tryptophan, phenylalanine, asparagine, and glutamine are allowed at that particular position.

A "non-essential" amino acid residue is a residue that can be altered from the wild-type sequence of the binding agent, e.g., the antibody, without abolishing or more preferably, without substantially altering a biological activity, whereas changing an "essential" amino acid residue results in a substantial loss of activity.

The term "cognate ligand" refers to a naturally occurring ligand of an MMP-9, including naturally occurring variants thereof (e.g., splice variants, naturally occurring mutants, and isoforms).

Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02. Particular binding proteins may show a difference, e.g., in specificity or binding, that are statistically significant (e.g., P value<0.05 or 0.02). The terms "induce", "inhibit", "potentiate", "elevate", "increase", "decrease" or the like, e.g., which denote distinguishable qualitative or quantitative differences between two states, and may refer to a difference, e.g., a statistically significant difference, between the two states.

MMP-9 Binding Proteins

The disclosure provides proteins that bind to MMP-9 (e.g., human MMP-9) and include at least one immunoglobin variable region. For example, the MMP-9 binding protein includes a heavy chain (HC) immunoglobulin variable domain sequence and a light chain (LC) immunoglobulin variable domain sequence. A number of exemplary MMP-9 binding proteins are described herein.

The MMP-9 binding protein may be an isolated protein (e.g., at least 70, 80, 85, 90, 91, 92, 93, 94, 95, 96, 97, 98, or 99% free of other proteins).

The MMP-9 binding protein may additionally inhibit MMP-9, e.g., human MMP-9. The binding protein can inhibit the catalytic activity of MMP-9 (e.g., human MMP-9). In one embodiment, the protein binds the catalytic domain of human MMP-9, e.g., the protein contacts residues in or near the active site of MMP-9. In some embodiments, the protein does not contact residues in or near the active site of MMP-9 but instead binds elsewhere on MMP-9 and causes a steric change in MMP-9 that affects (e.g., inhibits) its activity.

Exemplary MMP-9 binding proteins include 539A-M0240-B03, 539A-X0034-C02, M0078-G07, M0081-D05, M0076-D03, M0072-H07, M0075-D12, and M0166-F10, or proteins that comprise the HC and/or LC CDRs of 539A-M0240-B03, 539A-X0034-C02, M0078-G07, M0081-D05, M0076-D03, M0072-H07, M0075-D12, and M0166-F10.

MMP-9 binding proteins may be antibodies. MMP-9 binding antibodies may have their HC and LC variable domain sequences included in a single polypeptide (e.g., scFv), or on different polypeptides (e.g., IgG or Fab).

Matrix Metalloproteinase 9 (MMP-9)

MMP-9 Sequences. MMP-9 is encoded by a gene designated as MMP9 with full name Matrix metalloproteinase-9 precursor. Synonyms for MMP-9 include matrix metalloproteinase 9, gelatinase B (GELB), 92 kDa gelatinase (CLG4B), 92 kDa type IV collagenase (EC 3.4.24.35). The DNA sequence is known for *Homo sapiens* and *Mus musculus*. An exemplary cDNA sequence encoding human MMP9 and the amino acid sequence are shown below. Exemplary cDNA sequences encoding murine MMP9 and amino acid sequences are also shown below. An exemplary MMP-9 protein can include the human or mouse MMP-9 amino acid sequence, a sequence that is 80%, 85%, 90%, 95%, 96%, 97%, 98%, or 99% identical to one of these sequences, or a fragment thereof, e.g., a fragment without the signal sequence or prodomain.

Table 1 shows the similar genes in other organisms and the percentage of similarity with human MMP-9. No similarity-to-human data found for MMP9 for: chimpanzee (Pan troglodytes), pig (*Sus scrofa*), cow (*Bos taurus*), fruit fly (*Drosophila melanogaster*), worm (*Caenorhabditis elegans*), baker's yeast (*Saccharomyces cerevisiae*), tropical clawed frog (*Silurana tropicalis*), African malaria mosquito (*Anopheles gambiae*), green algae (*Chlamydomonas reinhardtii*), soybean (*Glycine max*), barley (*Hordeum vulgare*), tomato (*Lycopersicon esculentum*), rice blast fungus (*Magnaporthe grisea*), sugarcane (*Saccharum officinarum*), loblolly pine (*Pinus taeda*), corn (*Zea mays*), wheat (*Triticum aestivum*), Alicante grape (*Vitis vinifera*), bread mold (*Neurospora crassa*), fission yeast (*Schizosaccharomyces pombe*), sea squirt (*Ciona intestinalis*), amoeba (*Dictyostelium discoideum*), *A. gosspyii* yeast (*Ashbya gossypii*), *K. lactis* yeast (*Kluyveromyces lactis*), medicago trunc (*Medicago truncatula*), malaria parasite (*Plasmodium falciparum*), schistosome parasite (*Schistosoma mansoni*), sorghum (*Sorghum bicolor*), toxoplasmosis (*Toxoplasma gondii*).

```
cDNA and amino acid sequences of human MMP9
ACCESSION AK123156
VERSION AK123156.1 GI: 34528630 translation = "MARKGARRPRQGPGSHKWLQPGSRREKERIPQPPPPARPPRDAA

PRRVLVPAVRRVPESGHFAGRPWAPQCHPKGLRRPSAESHSVAQAGVQCHDLGSLQPP

PPSSGDSPASASRVAGITSTVPGTLSALDDCCLITELPYKPPAVLY" (SEQ ID NO: 6)

1 acactttgcg ttccgcggcc ccggcccctt ggtttcctag tcctggctcc attccctct 61 caggcctagg gctgggaccc ctccccgccc ccggtcttgg ccctgccccc ttcaacagac 121 ggtccgcccc ggccctccc cctcgtcccg cccggccctg gcaggccccg ccccctgcgg 181 cctctacctt tgacgtcttc ccccgggagg tggcggggt ctgcgaccga atgccggcgg 241 gactctgggt cagggcttct ggcgggccct gcgggggca gcgaggtgac cgtgaacctg 301 cggctcatgg cgcggaaagg agccaggcgg ccgcggcaag gtccgggatc gcacaagtgg 361 ctgcaaccag gctctaggag ggagaaagag cggatccccc aaccccctcc gcccgcccgc 421 ccccgcgag acgcggcgcc gcgcagggtc ctagtgcccg ctgtgcgaag ggttcctgaa 481 tctggccact tcgctgggag gccctgggct cccagtgcc acccgaaggg cctgaggagg 541 ccatctgcag aatctcactc tgtcgcccag gccggagtgc agtgtcatga tcttggctca 601 ctgcaacctc cgcctcccag ttcaggagat tctcctgcct cagcctcccg ggtggctggg 661 attacaagca cagtgcctgg cacattatcg gcacttgatg actgttgtct aataactgag 721 cttccataca aaccacctgc cgtcctgtac tgaaggagaa agagcttcca gccggggagg 781 caggaaatct gggtcctggt cttggttgca tccctgactt cctaaatgac ctggagaagg 841 cctctgcctc tgctgggatc ttgtctgtgc tggggcattt gtttccattt ccaagggctt 901 tttcttcctc gctcagaatt tgaccactca ctaagaggag cttagtgtgg tgtctcacga 961 agggatcctc ctcagccctc acctcggtac tggaagacgt cgtgcgtgtc caaaggcacc 1021 ccggggaaca tccggtccac ctcgctggcg ctccggggat ccaccatctg cgccttcacg 1081 tcgaacctgc gggcaggcgc ggaggagaca ggtgctgagc cggctagcgg acggaccgac 1141 ggcgcccggg ctccccctgc cggcggccgc ggcggcgctc acctccagag gcgccgcccg
```

-continued

```
1201 ctgaacagca gcatcttccc cctgccactc cggagggccc cggtcacctg ggccacgtcg 1261 gcgcccaggc ccagcttgtc cagacgcctc gggcccagca ccgacgcgcc tgtgtacacc 1321 cacacctggc gccctgcagg ggaggagggt cacgtcggtt tggggcgca gagggagcac 1381 gtactcctag aacgcgagga gggagattcc ggcgaggcct tcctagccc gcgtgcccgc 1441 agtccctgca acccagggc agaggcgctg ggtagagcga cgcgagggcg tggagaggag 1501 ggggcagaaa ctcagccgcc cctacgtttg ctaaactgcg tccgccaggg ggcgtatttt 1561 tctaaaacgc acaagacgtt tcgtgggtta tcgatggtct cttgagcctc cttgactgat 1621 ggggattgac cgggcggggg agggaaagta ggtaactaac cagagaagaa gaaaagcttc 1681 ttggagagcg gctcctcaaa gaccgagtcc agcttgcggg gcagcgcggg ccacttgtcg 1741 gcgataagga aggggccctg cggccggctc ccctgccct cagagaatcg ccagtacttc 1801 ctgagaaagc gaggagggaa aggacgggct ctaagccttg gacacagggc cagtgggcgg 1861 gaagggacgg gcagccctc cgcaaagccc cctcccgcat ccacacaacc ccgcctcctc 1921 acccatcctt gaacaaatac agctggttcc caatc (SEQ ID NO: 7)
``` cDNA and amno acid sequences of mouse MMP9
ACCESSION NM_013599
VERSION NM_013599.2 GI: 31560795
translation = "MSPWQPLLLALLAFGCSSAAPYQRQPTFVVFPKDLKTSNLTDTQ
LAEAYLYRYGYTRAAQMMGEKQSLRPALLMLQKQLSLPQTGELDSQTLKAIRTPRCGV
PDVGRFQTFKGLKWDHHNITYWIQNYSEDLPRDMIDDAFARAFAVWGEVAPLTFTRVY
GPEADIVIQFGVAEHGDGYPFDGKDGLLAHAFPPGAGVQGDAHFDDDELWSLGKGVVI
PTYYGNSNGAPCHFPFTFEGRSYSACTTDGRNDGTPWCSTTADYDKDGKFGFCPSERL
YTEHGNGEGKPCVFPFIFEGRSYSACTTKGRSDGYRWCATTANYDQDKLYGFCPTRVD
ATVVGGNSAGELCVFPFVFLGKQYSSCTSDGRRDGRLWCATTSNFDTDKKWGFCPDQG
YSLFLVAAHEFGHALGLDHSSVPEALMYPLYSYLEGFPLNKDDIDGIQYLYGRGSKPD
PRPPATTTTEPQPTAPPTMCPTIPPTAYPTVGPTVGPTGAPSPGPTSSPSPGPTGAPS
PGPTAPPTAGSSEASTESLSPADNPCNVDVFDAIAEIQGALHFFKDGWYWKFLNHRGS
PLQGPFLTARTWPALPATLDSAFEDPQTKRVFFFSGRQMWVYTGKTVLGPRSLDKLGL
GPEVTHVSGLLPRRLGKALLFSKGRVWRFDLKSQKVDPQSVIRVDKEFSGVPWNSHDI
FQYQDKAYFCHGKFFWRVSFQNEVNKVDHEVNQVDDVGYVTYDLLQCP" (SEQ ID NO: 8)

```
  1 ctcaccatga gtccctggca gcccctgctc ctggctctcc tggctttcgg ctgcagctct 61 gctgcccctt accagcgcca gccgactttt gtggtcttcc ccaaagacct gaaaacctcc 121 aacctcacgg acacccagct ggcagaggca tacttgtacc gctatggtta cacccgggcc 181 gcccagatga tgggagagaa gcagtctcta cggccggctt tgctgatgct tcagaagcag 241 ctctccctgc ccagactgg tgagctggac agccagacac taaaggccat cgaacacca 301 cgctgtggtg tcccagacgt gggtcgattc caaaccttca aaggcctcaa gtgggaccat 361 cataacatca catactggat ccaaaactac tctgaagact gccgcgaga catgatcgat 421 gacgccttcg cgcgcgcctt cgcggtgtgg gcgaggtgg caccctcac cttcacccgc 481 gtgtacggac ccgaagcgga cattgtcatc cagtttggtg tcgcggagca cggagacggg 541 tatcccttcg acggcaagga cggccttctg gcacacgcct tccccctgg cgccggcgtt 601 cagggagatg cccatttcga cgacgacgag ttgtggtcgc tgggcaaagg cgtcgtgatc 661 cccacttact atggaaactc aaatggtgcc ccatgtcact ttcccttcac cttcgaggga 721 cgctcctatt cggcctgcac cacagacggc cgcaacgacg gcacgccttg gtgtagcaca
```

-continued

```
 781 acagctgact acgataagga cggcaaattt ggtttctgcc ctagtgagag actctacacg
 841 gagcacggca acggagaagg caaaccctgt gtgttcccgt tcatctttga gggccgctcc
 901 tactctgcct gcaccactaa aggccgctcg gatggttacc gctggtgcgc caccacagcc
 961 aactatgacc aggataaact gtatggcttc tgccctaccc gagtggacgc gaccgtagtt
1021 gggggcaact cggcaggaga gctgtgcgtc ttccccttcg tcttcctggg caagcagtac
1081 tcttcctgta ccagcgacgg ccgcagggat gggcgcctct ggtgtgcgac cacatcgaac
1141 ttcgacactg acaagaagtg gggtttctgt ccagaccaag ggtacagcct gttcctggtg
1201 gcagcgcacg agttcggcca tgcactgggc ttagatcatt ccagcgtgcc ggaagcgctc
1261 atgtacccgc tgtatagcta cctcgagggc ttccctctga ataaagacga catagacggc
1321 atccagtatc tgtatggtcg tggctctaag cctgacccaa ggcctccagc caccaccaca
1381 actgaaccac agccgacagc acctcccact atgtgtccca ctatacctcc cacggcctat
1441 cccacagtgg gccccacggt tggccctaca ggcgcccct cacctggccc cacaagcagc
1501 ccgtcacctg gccctacagg cgcccctca cctggcccta cagcgccccc tactgcgggc
1561 tcttctgagg cctctacaga gtctttgagt ccggcagaca atccttgcaa tgtggatgtt
1621 tttgatgcta ttgctgagat ccagggcgct ctgcatttct tcaaggacgg ttggtactgg
1681 aagttcctga atcatagagg aagcccatta cagggcccct ccttactgc ccgcacgtgg
1741 ccagccctgc ctgcaacgct ggactccgcc tttgaggatc cgcagaccaa gagggttttc
1801 ttcttctctg gacgtcaaat gtgggtgtac acaggcaaga ccgtgctggg ccccaggagt
1861 ctggataagt tgggtctagg cccagaggta acccacgtca gcgggcttct cccgcgtcgt
1921 ctcgggaagg ctctgctgtt cagcaagggg cgtgtctgga gattcgactt gaagtctcag
1981 aaggtggatc cccagagcgt cattcgcgtg gataaggagt ctctggtgt gccctggaac
2041 tcacacgaca tcttccagta ccaagacaaa gcctatttct gccatggcaa attcttctgg
2101 cgtgtgagtt tccaaaatga ggtgaacaag gtggaccatg aggtgaacca ggtggacgac
2161 gtgggctacg tgacctacga cctcctgcag tgcccttgaa ctagggctcc ttctttgctt
2221 caaccgtgca gtgcaagtct ctagagacca ccaccaccac caccacacac aaacccatc
2281 cgagggaaag gtgctagctg gccaggtaca gactggtgat ctcttctaga gactgggaag
2341 gagtggaggc aggcagggct ctctctgccc accgtccttt cttgttggac tgtttctaat
2401 aaacacggat ccccaacctt ttccagctac tttagtcaat cagcttatct gtagttgcag
2461 atgcatccga gcaagaagac aacttttgtag ggtggattct gaccttttat ttttgtgtgg
2521 cgtctgagaa ttgaatcagc tggcttttgt gacaggcact tcaccggcta aaccacctct
2581 cccgactcca gcccttttat ttattatgta tgaggttatg ttcacatgca tgtatttaac
2641 ccacagaatg cttactgtgt gtcgggcgcg gctccaaccg ctgcataaat attaaggtat
2701 tcagttgccc ctactggaag gtattatgta actatttctc tcttacattg gagaacacca
2761 ccgagctatc cactcatcaa acatttattg agagcatccc tagggagcca ggctctctac
2821 tgggcgttag ggacagaaat gttggttctt ccttcaagga ttgctcagag attctccgtg
2881 tcctgtaaat ctgctgaaac cagaccccag actcctctct ctcccgagag tccaactcac
2941 tcactgtggt tgctggcagc tgcagcatgc gtatacagca tgtgtgctag agaggtagag
3001 ggggtctgtg cgttatggtt caggtcagac tgtgtcctcc aggtgagatg accccctcagc
3061 tggaactgat ccaggaagga taaccaagtg tcttcctggc agtctttttt aaataaatga
3121 ataaatgaat atttacttaa aaaaaaaaaa aaaaaaaaaa aaaaaaaaaa aaaaaaaaaa
3181 aaaaa (SEQ ID NO: 9)
```

```
//
ACCESSION NP_038627
VERSION NP_038627.1 GI: 7305277
    1 mspwqpllla llafgcssaa pyqrqptfvv fpkdlktsnl tdtqlaeayl yrygytraaq 61 mmgekqslrp allmlqkqls lpqtgeldsq tlkairtprc gvpdvgrfqt fkglkwdhhn 121 itywiqnyse dlprdmidda farafavwge vapltftrvy gpeadiviqf gvaehgdgyp 181 fdgkdgllah afppgagvqg dahfdddelw slgkgvvipt yygnsngapc hfpftfegrs 241 ysacttdgrn dgtpwcstta dydkdgkfgf cpserlyteh gngegkpcvf pfifegrsys 301 acttkgrsdg yrwcattany dqdklygfcp trvdatvvgg nsagelcvfp fvflgkqyss 361 ctsdgrrdgr lwcattsnfd tdkkwgfcpd qgyslflvaa hefghalgld hssvpealmy 421 plysylegfp lnkddidgiq ylygrgskpd prppatttte pqptapptmc ptipptaypt 481 vgptvgptga pspgptssps pgptgapspg ptapptagss easteslspa dnpcnvdvfd 541 aiaeiqgalh ffkdgwywkf lnhrgsplqg pfltartwpa lpatldsafe dpqtkrvfff 601 sgrqmwvytg ktvlgprsld klglgpevth vsgllprrlg kallfskgrv wrfdlksqkv 661 dpqsvirvdk efsgvpwnsh difqyqdkay fchgkffwrv sfqnevnkvd hevnqvddvg 721 yvtydllqcp (SEQ ID NO: 10)
//
```

TABLE 1

MMP-9 orthologs from nine species

| Organism | Gene | Locus | Description | Human Similarity | s |
|---|---|---|---|---|---|
| dog (Canis familiaris) | MMP9[1] | — | matrix metallopeptidase 9 (gelatinase B, 92 kDa gelatinase | 85.46(n) 80.97(a) | 403885 NM 001003219.1 NP 001003219.1 |
| rat (Rattus norvegicus) | Mmp9[1] | — | matrix metallopeptidase 9 | 79.15(n) 74.89(a) | 81687 NM 031055.1 NP 112317.1 |
| mouse (Mus musculus) | Mmp9[1,4] | 2 (96.00 cM)[4] | matrix metallopeptidase 9[1,4] | 78.69(n)[1] 75(a)[1] | 17395[1] NM 013599.2[1] NP 038627.1[1] AK004651[4] AK142787[4] see all 16) |
| chicken Gallus gallus | LOC3953871 | — | matrix metallopeptidase 9 (gelatinase B, 92 kDa gelatinase | 66.96(n) 62.54(a) | 395387 NM 204667.1 67.1 NP 989998.1 |
| zebrafish (Danio rerio) | wufb02g06[1]~ | — | Danio rerio cDNA clone MGC64165 IMAGE6797338, complete | 70.96(n) | BC053292.1 |
| African clawed frog (Xenopus laevis) | MGC69080[1]~ | — | hypothetical protein MGC69080 | 72.25(n) | BC057745.1 |
| rainbow trout (Oncorhynchus mykiss) | Omy.10476[1]~ | — | Oncorhynchus mykiss mRNA for matrix metalloproteinase | 74.67(n) | AJ320533.1 |
| thale cress (Arabidopsis thaliana) | MMP[1] | — | MMP (MATRIX METALLOPROTEINASE); metalloendopeptidase/ | 53(n) 46.85(a) | 843353 NM 105685.3 NP 177174.1 |
| rice (Oryza sativa) | P0516G10.18[1] | — | putative zinc metalloproteinase | 51.98(n) 41.81(a) | 3063368 XM 467714.1 XP 467714.1 |

Domains of MMP-9. MMP-9 belongs to the peptidase M10A family. MMP-9 consists of five domains; the amino-terminal and zinc-binding domains shared by all members of the secreted metalloprotease gene family, the collagen-binding fibronectin-like domain also present in the 72-kDa type IV collagenase, a carboxyl-terminal hemopexin-like domain shared by all known enzymes of this family with the exception of PUMP-1, and a unique 54-amino-acid-long proline-rich domain homologous to the alpha 2 chain of type V collagen (Wilhelm et al. (1989) *J. Biol. Chem.* 264, 17213-17221) (Table 2).

TABLE 2

MMP-9 domains

| | | | | |
|---|---|---|---|---|
| FT | SIGNAL | 1 | 19 | |
| FT | PROPEP | 20 | 93 | Activation peptide. |
| FT | CHAIN | 94 | ? | 67 kDa matrix metalloproteinase-9. |
| FT | CHAIN | 107 | 707 | 82 kDa matrix metalloproteinase-9. |
| FT | PROPEP | ? | 707 | Removed in 64 kDa matrix |
| FT | | | | metalloproteinase-9 and 67 kDa |
| FT | | | | matrix metalloproteinase-9. |
| FT | DOMAIN | 225 | 273 | Fibronectin type-II 1. |
| FT | DOMAIN | 283 | 331 | Fibronectin type-II 2. |
| FT | DOMAIN | 342 | 390 | Fibronectin type-II 3. |
| FT | DOMAIN | 513 | 707 | Hemopexin-like. |
| FT | ACT_SITE | 402 | 402 | |
| FT | METAL | 131 | 131 | Calcium 1. |
| FT | METAL | 165 | 165 | Calcium 2 (via carbonyl oxygen). |
| FT | METAL | 175 | 175 | Zinc 1 (structural). |
| FT | METAL | 177 | 177 | Zinc 1 (structural). |
| FT | METAL | 182 | 182 | Calcium 3. |
| FT | METAL | 183 | 183 | Calcium 3 (via carbonyl oxygen). |
| FT | METAL | 185 | 185 | Calcium 3 (via carbonyl oxygen). |
| FT | METAL | 187 | 187 | Calcium 3 (via carbonyl oxygen). |
| FT | METAL | 190 | 190 | Zinc 1 (structural). |
| FT | METAL | 197 | 197 | Calcium 2 (via carbonyl oxygen). |
| FT | METAL | 199 | 199 | Calcium 2 (via carbonyl oxygen). |
| FT | METAL | 201 | 201 | Calcium 2. |
| FT | METAL | 203 | 203 | Zinc 1 (structural). |
| FT | METAL | 205 | 205 | Calcium 3. |
| FT | METAL | 206 | 206 | Calcium 1. |
| FT | METAL | 208 | 208 | Calcium 1. |
| FT | METAL | 208 | 208 | Calcium 3. |
| FT | METAL | 401 | 401 | Zinc 2 (catalytic). |
| FT | METAL | 405 | 405 | Zinc 2 (catalytic). |
| FT | METAL | 411 | 411 | Zinc 2 (catalytic). |
| FT | SITE | 59 | 60 | Cleavage (by MMP3). |
| FT | SITE | 99 | 99 | Cysteine switch (By similarity). |
| FT | SITE | 106 | 107 | Cleavage (by MMP3). |
| FT | CARBOHYD | 38 | 38 | N-linked (GlcNAc . . . ) (Potential). |
| FT | CARBOHYD | 120 | 120 | N-linked (GlcNAc . . . ) (Potential). |
| FT | CARBOHYD | 127 | 127 | N-linked (GlcNAc . . . ) (Potential). |
| FT | DISULFID | 230 | 256 | By similarity. |
| FT | DISULFID | 244 | 271 | By similarity. |
| FT | DISULFID | 288 | 314 | By similarity. |
| FT | DISULFID | 302 | 329 | By similarity. |
| FT | DISULFID | 347 | 373 | By similarity. |
| FT | DISULFID | 361 | 388 | By similarity. |
| FT | DISULFID | 516 | 704 | |
| FT | VARIANT | 20 | 20 | A -> V (in dbSNP: rs1805088). |
| FT | VARIANT | 82 | 82 | E -> K (in dbSNP: rs1805089). |
| FT | VARIANT | 127 | 127 | N -> K (in dbSNP: rs3918252). |
| FT | VARIANT | 239 | 239 | R -> H. |
| FT | VARIANT | 279 | 279 | R -> Q (common polymorphism; dbSNP: rs17576). |
| FT | VARIANT | 571 | 571 | F -> V. |
| FT | VARIANT | 574 | 574 | P -> R (in dbSNP: rs2250889). |
| FT | VARIANT | 668 | 668 | R -> Q (in dbSNP: rs17577). |
| FT | TURN | 32 | 33 | |
| FT | HELIX | 41 | 51 | |
| FT | TURN | 52 | 53 | |
| FT | HELIX | 68 | 78 | |
| FT | TURN | 79 | 79 | |
| FT | HELIX | 88 | 94 | |

TABLE 2-continued

MMP-9 domains

| | | | |
|---|---|---|---|
| FT | TURN | 95 | 95 |
| FT | STRAND | 103 | 105 |
| FT | STRAND | 119 | 125 |
| FT | STRAND | 130 | 132 |
| FT | HELIX | 134 | 149 |
| FT | TURN | 150 | 150 |
| FT | STRAND | 151 | 153 |
| FT | STRAND | 155 | 158 |
| FT | TURN | 162 | 163 |
| FT | STRAND | 164 | 171 |
| FT | STRAND | 176 | 178 |
| FT | STRAND | 183 | 186 |
| FT | STRAND | 189 | 191 |
| FT | STRAND | 194 | 196 |
| FT | TURN | 197 | 200 |
| FT | STRAND | 202 | 205 |
| FT | TURN | 206 | 207 |
| FT | STRAND | 213 | 219 |
| FT | HELIX | 220 | 231 |
| FT | TURN | 232 | 233 |
| FT | TURN | 240 | 241 |
| FT | TURN | 243 | 244 |
| FT | STRAND | 245 | 247 |
| FT | STRAND | 255 | 261 |
| FT | HELIX | 262 | 265 |
| FT | STRAND | 268 | 270 |
| FT | TURN | 274 | 276 |
| FT | STRAND | 279 | 283 |
| FT | TURN | 284 | 285 |
| FT | STRAND | 290 | 294 |
| FT | TURN | 295 | 296 |
| FT | STRAND | 297 | 301 |
| FT | TURN | 305 | 306 |
| FT | STRAND | 313 | 319 |
| FT | HELIX | 320 | 323 |
| FT | STRAND | 326 | 328 |
| FT | HELIX | 333 | 335 |
| FT | TURN | 340 | 344 |
| FT | STRAND | 349 | 353 |
| FT | TURN | 354 | 355 |
| FT | STRAND | 356 | 358 |
| FT | TURN | 364 | 365 |
| FT | STRAND | 372 | 378 |
| FT | HELIX | 379 | 382 |
| FT | STRAND | 385 | 387 |
| FT | HELIX | 395 | 406 |
| FT | TURN | 407 | 408 |
| FT | TURN | 415 | 416 |
| FT | TURN | 418 | 419 |
| FT | HELIX | 433 | 442 |
| FT | STRAND | 512 | 517 |
| FT | HELIX | 515 | 517 |
| FT | STRAND | 522 | 527 |
| FT | TURN | 528 | 529 |
| FT | STRAND | 530 | 535 |
| FT | TURN | 536 | 537 |
| FT | STRAND | 538 | 542 |
| FT | STRAND | 545 | 547 |
| FT | STRAND | 551 | 555 |
| FT | HELIX | 556 | 559 |
| FT | TURN | 561 | 562 |
| FT | STRAND | 568 | 572 |
| FT | TURN | 574 | 576 |
| FT | STRAND | 579 | 583 |
| FT | TURN | 584 | 585 |
| FT | STRAND | 586 | 591 |
| FT | TURN | 592 | 593 |
| FT | STRAND | 594 | 600 |
| FT | HELIX | 601 | 604 |
| FT | TURN | 605 | 605 |
| FT | TURN | 608 | 609 |
| FT | STRAND | 615 | 618 |
| FT | TURN | 621 | 622 |
| FT | STRAND | 623 | 628 |
| FT | TURN | 629 | 630 |
| FT | STRAND | 631 | 636 |
| FT | TURN | 637 | 640 |
| FT | HELIX | 644 | 646 |

TABLE 2-continued

| | MMP-9 domains | | |
|---|---|---|---|
| FT | HELIX | 650 | 653 |
| FT | TURN | 655 | 656 |
| FT | STRAND | 662 | 667 |
| FT | TURN | 668 | 669 |
| FT | STRAND | 670 | 675 |
| FT | TURN | 676 | 677 |
| FT | STRAND | 678 | 683 |
| FT | TURN | 686 | 687 |
| FT | STRAND | 690 | 696 |
| FT | TURN | 697 | 700 |
| FT | TURN | 702 | 703 |

Factors that regulate MMP-9. The catalytic activity of MMP-9 is inhibited by histatin-3 $^1/_{24}$ (histatin-5). MMP-9 is activated by urokinase-type plasminogen activator; plasminogen; IL-1beta, 4-aminophenylmercuric acetate and phorbol ester. MMP-9 exists as monomer, disulfide-linked homodimer, and as a heterodimer with a 25 kDa protein. Macrophages and transformed cell lines produce only the monomeric MMP-9, the hetrodimeric form is produced by normal alveolar macrophages and granulocytes. The processing of the precursor yields different active forms of 64, 67 and 82 kDa. Sequentially processing by MMP-3 yields the 82 kDa matrix metalloproteinase-9. In arthritis patients, this enzyme can contribute to the pathogenesis of joint destruction and can be a useful marker of disease status.

Endogenous inhibitors of MMP-9. MMP-9 has a number of endogenous inhibitors. Like other MMPs, MMP-9 is inhibited by TIMPs (Murphy, G., and Willenbrock, F. (1995) *Methods Enzymol.* 248, 496-510). A characteristic of MMP-9 (and MMP-2) is the ability of their zymogens to form tight non-covalent and stable complexes with TIMPs. It has been shown that pro-MMP-2 binds TIMP-2 (Goldberg et al. (1989) *Proc. Natl. Acad. Sci. U.S.A.* 86, 8207-8211), whereas pro-MMP-9 binds TIMP-1 (Wilhelm et al. (1989) *J. Biol. Chem.* 264, 17213-17221). TIMPs typically are slow, tight binding inhibitors. A MMP-9 binding protein (e.g., antibody) selected from a library of phage-displayed proteins can be selected have more rapid kinetics. For example, recombinant TIMP-1 can be administered to inhibit MMP-9, e.g., in combination with a MMP-9 binding protein described herein.

Small molecule inhibitors of MMP-9. Skiles et al. (2004, Curr Med Chem, 11:2911-77) reported that first generation small-molecule MMP inhibitors had poor bioavailability and the second generation had caused musculoskeletal pain and inflammation. Most small-molecule MMP inhibitors interact with the catalytic zinc but have fairly low affinity. Thus, a higher concentration is needed to have effect. The interaction with the catalytic zinc leads to inhibition of other MMPs and toxic side effects. A MMP-9 binding protein described herein can be used in combination with a small molecule inhibitor. For example, because the inhibitors are used in combination, the dose of the small molecule used can be decreased and therefore result in fewer side effects. Examples of small molecule MMP-9 inhibitors include small synthetic anthranilic acid-based inhibitors (see, e.g., Calbiochem Inhibitor-I, catalogue #444278 and Levin et al., 2001, *Bioorg. Med. Chem. Lett.* 11:2975-2978).

Small interfering RNA inhibitors of MMP-9. MMP-9 can be inhibited by small interfering RNA (siRNA). Examples of siRNA that can be used include:

```
MMP-9 siRNA
5'-GACUUGCCGCGAGACAUGAtt-3'    (SEQ ID NO: 947)

3'-ttCUGAACGGCGCUCUGUACU-5'    (SEQ ID NO: 948)

Control RNA (mismatch)
5'-GACUUCGCGGGACACAUGAtt-3'    (SEQ ID NO: 949)

3'-ttCUGAAGCGCCCUGUGUACU-5'    (SEQ ID NO: 950)
```

See also Kawasaki et al., Feb. 10, 2008, *Nat. Med.* advance on-line publication doi:10.1038/nm1723. The siRNA can be administered to inhibit MMP-9, e.g., in combination with a MMP-9 binding protein described herein.

Drug Conjugates

The MMP-9 binding proteins described herein can be conjugated to a drug (e.g., a cytotoxic, cytostatic, or immunomodulatory agent). The conjugates can be used therapeutically or prophylactically, e.g., the binding protein can target the drug, e.g., in vivo, e.g., to a site of disease (e.g., a tumor or site of inflammation), e.g., such that the drug affects the site of disease (e.g., causes a cytostatic or cytotoxic effect on targeted cells).

In some embodiments, the binding protein itself has therapeutic or prophylactic efficacy (e.g., the protein can modulate (e.g., antagonize) MMP-9, or cause a cytostatic or cytotoxic effect on a cell that expresses MMP-9 (e.g., an endothelial cell or tumor cell)). The binding protein-drug conjugate can be used such that the binding protein and drug both contribute (e.g., additively or synergistically) to an effect on MMP-9 (e.g., a therapeutic effect, e.g., in vivo, e.g., to a site of disease (e.g., a tumor or site of undesired angiogenesis or vascularization). The drug and/or binding protein can be, for example, cytotoxic, cytostatic or otherwise prevent or reduce the ability of a targeted cell to divide and/or survive (e.g., when the drug is taken up or internalized by the targeted cell and/or upon binding of the binding protein to MMP-9). For example, if the targeted cell is a cancer cell, the drug and/or binding protein can prevent or reduce the ability of the cell to divide and/or metastasize.

Useful classes of drugs that can be used in the binding protein-drug conjugates described herein include cytotoxic or immunomodulatory agents such as, for example, antitubulin agents, auristatins, DNA minor groove binders, DNA replication inhibitors, alkylating agents (e.g., platinum complexes such as cis-platin, mono(platinum), bis(platinum) and trinuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like.

Individual cytotoxic or immunomodulatory agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (actinomycin), daunorubicin, decarbazine, docetaxel, doxorubicin, an estrogen, 5-fluorodeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbazine, rapamycin (Sirolimus), streptozotocin, tenoposide, 6-thioguanine, thioTEPA, topotecan, vinblastine, vincristine, vinorelbine, VP-16 and VM-26.

In some typical embodiments, the drug comprises a cytotoxic agent. Suitable cytotoxic agents include, for example, dolastatins (e.g., auristatin E, AFP, MMAF, MMAE), DNA minor groove binders (e.g., enediynes and lexitropsins), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In some embodiments, the drug is a cytotoxic agent such as AFP, MMAF, MMAE, AEB, AEVB, auristatin E, paclitaxel, docetaxel, CC-1065, SN-38, topotecan, morpholino-doxorubicin, rhizoxin, cyanomorpholino-doxorubicin, dolastatin-10, echinomycin, combretatstatin, chalicheamicin, maytansine, DM-1, or netropsin.

In some embodiments, the drug is a cytotoxic agent that comprises a conventional chemotherapeutic such as, for example, doxorubicin, paclitaxel, melphalan, vinca alkaloids, methotrexate, mitomycin C or etoposide. In some embodiments, the drug can be a combined therapy, such as CHOP (Cyclophosphamide, Doxorubicin, Prednisolone and Vincristine), CHOP-R (Cyclophosphamide, Doxorubicin Vincristine, Prednisolone, and rituximab) or ABVD (Doxorubicin, Bleomycin, Vinblastine and Dacarbazine). Agents such as CC-1065 analogues (e.g., DC1), calicheamicin, maytansine, analogues of dolastatin 10, rhizoxin, and palytoxin can also be used.

In specific embodiments, the drug can be a cytotoxic or cytostatic agent that comprises auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other auristatin derivatives include AFP, MMAF, and MMAE. The synthesis and structure of auristatin E and its derivatives are described in US 20030083263 and US 20050009751, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414. In some preferred embodiments, MMAF or AFP is used.

In specific embodiments, the drug is a cytotoxic agent that comprises a DNA minor groove binding agent. See, e.g., U.S. Pat. No. 6,130,237. For example, in some embodiments, the minor groove binding agent is a CBI compound. In other embodiments, the minor groove binding agent is an enediyne (e.g., calicheamicin).

Examples of anti-tubulin agents that can be used in the MMP-9 binding protein-drug conjugates include, but are not limited to, taxanes (e.g., TAXOL® (paclitaxel), TAXOTERE® (docetaxel)), T67 (Tularik), vinca alkyloids (e.g., vincristine, vinblastine, vindesine, and vinorelbine), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, eleutherobin, rhizoxin/maytansine, auristatin dolastatin 10 MMAE, and peloruside A.

In some embodiments, the drug is a cytotoxic agent such as an anti-tubulin agent. In some embodiments, the anti-tubulin agent is an auristatin, a vinca alkaloid, a podophyllotoxin, a taxane, a baccatin derivative, a cryptophysin, a maytansinoid, a combretastatin, or a dolastatin. In some embodiments, the antitubulin agent is AFP, MMAP, MMAE, AEB, AEVB, auristatin E, vincristine, vinblastine, vindesine, vinorelbine, VP-16, camptothecin, paclitaxel, docetaxel, epothilone A, epothilone B, nocodazole, colchicines, colcimid, estramustine, cemadotin, discodermolide, maytansine, DM1, DM2, DM3, DM4, or eleutherobin.

In some embodiments, the cytotoxic agent comprises a maytansinoid, another group of anti-tubulin agents. For example, in specific embodiments, the maytansinoid is maytansine or DM-1 (ImmunoGen, Inc.; see also Chari et al. *Cancer Res.* 52:127-131 (1992)). In some embodiments, sterically hindered thiol and disulfide-containing maytansinoids in which the alpha-carbon atom bearing the sulfur atom bears one or two alkyl substituents are used in the binding protein-drug conjugate, e.g., US 2007-0292422; US 2007-0264266.

In some embodiments, the drug comprises an agent that acts to disrupt DNA. The drug may be selected from enediynes (e.g., calicheamicin and esperamicin) and non-enediyne small molecule agents (e.g., bleomycin, methidiumpropyl-EDTA-Fe(II)). Other useful drugs include daunorubicin, doxorubicin, distamycin A, cisplatin, mitomycin C, ecteinascidins, duocarmycin/CC-1065, and bleomycin/pepleomycin.

In other embodiments, the drug can comprise an alkylating agent such as Asaley NSC 167780, AZQ NSC 182986, BCNU NSC 409962, Busulfan NSC 750, carboxyphthalatoplatinum NSC 271674, CBDCA NSC 241240, CCNU NSC 79037, CHIP NSC 256927, chlorambucil NSC 3088, chlorozotocin NSC 178248, cis-platinum NSC 119875, clomesone NSC 338947, cyanomorpholinodoxorubicin NSC 357704, cyclodisone NSC 348948, dianhydrogalactitol NSC 132313, fluorodopan NSC 73754, hepsulfam NSC 329680, hycanthone NSC 142982, melphalan NSC 8806, methyl CCNU NSC 95441, mitomycin C NSC 26980, mitozolamide NSC 353451, nitrogen mustard NSC 762, PCNU NSC 95466, piperazine NSC 344007, piperazinedione NSC 135758, pipobroman NSC 25154, porfiromycin NSC 56410, spirohydantoin mustard NSC 172112, teroxirone NSC 296934, tetraplatin NSC 363812, thio-tepa NSC 6396, triethylenemelamine NSC 9706, uracil nitrogen mustard NSC 34462, or Yoshi-864 NSC 102627.

In some embodiments, the drug can comprise an antimitotic agent such as allocolchicine NSC 406042, Halichondrin B NSC 609395, colchicine NSC 757, colchicine derivative NSC 33410, dolastatin 10 NSC 376128 (NG—auristatin derived), maytansine NSC 153858, rhizoxin NSC 332598, taxol NSC 125973, taxol derivative NSC 608832, thiocolchicine NSC 361792, trityl cysteine NSC 83265, vinblastine sulfate NSC 49842, or vincristine sulfate NSC 67574.

In other embodiments, the drug can comprise an topoisomerase I inhibitor such as camptothecin NSC 94600, camptothecin, Na salt NSC 100880, aminocamptothecin NSC 603071, camptothecin derivative NSC 95382, camptothecin derivative NSC 107124, camptothecin derivative NSC 643833, camptothecin derivative NSC 629971, camptothecin derivative NSC 295500, camptothecin derivative NSC 249910, camptothecin derivative NSC 606985, camptothecin derivative NSC 374028, camptothecin derivative NSC 176323, camptothecin derivative NSC 295501, camptothecin derivative NSC 606172, camptothecin derivative NSC 606173, camptothecin derivative NSC 610458, camptothecin derivative NSC 618939, camptothecin derivative NSC 610457, camptothecin derivative NSC 610459, camptothecin derivative NSC 606499, camptothecin derivative NSC 610456, camptothecin derivative NSC 364830, camptothecin derivative NSC 606497, or morpholinodoxorubicin NSC 354646.

In other embodiments, the drug can comprise an topoisomerase II inhibitor such as doxorubicin NSC 123127, amonafide NSC 308847, m-AMSA NSC 249992, anthrapyrazole derivative NSC 355644, pyrazoloacridine NSC 366140, bisantrene HCL NSC 337766, daunorubicin NSC 82151, deoxydoxorubicin NSC 267469, mitoxantrone NSC 301739, menogaril NSC 269148, N,N-dibenzyl daunomycin NSC 268242, oxanthrazole NSC 349174, rubidazone NSC 164011, VM-26 NSC 122819, or VP-16 NSC 141540.

In other embodiments, the drug can comprise an RNA or DNA antimetabolite such as L-alanosine NSC 153353, 5-azacytidine NSC 102816, 5-fluorouracil NSC 19893, acivicin NSC 163501, aminopterin derivative NSC 132483, aminopterin derivative NSC 184692, aminopterin derivative NSC 134033, an antifol NSC 633713, an antifol NSC 623017, Baker's soluble antifol NSC 139105, dichlorallyl lawsone NSC 126771, brequinar NSC 368390, ftorafur (pro-drug) NSC 148958, 5,6-dihydro-5-azacytidine NSC 264880, methotrexate NSC 740, methotrexate derivative NSC 174121, N-(phosphonoacetyl)-L-aspartate (PALA) NSC 224131, pyrazofurin NSC 143095, trimetrexate NSC 352122, 3-HP NSC 95678, 2'-deoxy-5-fluorouridine NSC 27640, 5-HP NSC 107392, alpha-TGDR NSC 71851, aphidicolin glycinate NSC 303812, ara-C NSC 63878, 5-aza-2'-deoxycytidine NSC 127716, beta-TGDR NSC 71261, cyclocytidine NSC 145668, guanazole NSC 1895, hydroxyurea NSC 32065, inosine glycodialdehyde NSC 118994, macbecin 11 NSC 330500, pyrazoloimidazole NSC 51143, thioguanine NSC 752, or thiopurine NSC 755. See also US 2007-0292441.

The abbreviation "AFP" refers to dimethylvaline-valine-dolaisoleuine-dolaproine-phenylalanine-p-phenylenediamine (e.g., see Formula XVI in US 2006-0233794).

The abbreviation "MAE" refers to monomethyl auristatin E (see Formula XI in US 2006-0233794).

The abbreviation "AEB" refers to an ester produced by reacting auristatin E with paraacetyl benzoic acid (e.g., see Formula XX in US 2006-0233794)

The abbreviation "AEVB" refers to an ester produced by reacting auristatin E with benzoylvaleric acid (e.g., see Formula XXI in US 2006-0233794).

The abbreviation "MMAF" refers to dovaline-valine-dolaisoleunine-dolaproine-phenylalanine (e.g., see Formula IVIV in US 2006-0233794).

The abbreviations "fk" and "phe-lys" refer to the linker phenylalanine-lysine.

The abbreviations "vc" and "val-cit" refer to the linker valine-citrulline.

In some embodiments, the drug is a cytotoxic agent selected from the group consisting of an auristatin, a DNA minor groove binding agent, a DNA minor groove alkylating agent, an enediyne, a lexitropsin, a duocarmycin, a taxane, a puromycin, a dolastatin, a maytansinoid, and a vinca alkaloid.

In some embodiments, the drug is a cytotoxic agent such as AFP or MMAF.

In some embodiments, the drug is an immunosuppressive agent such as gancyclovir, etanercept, cyclosporine, tacrolimus, rapamycin, cyclophosphamide, azathioprine, mycophenolate mofetil, methotrexate, cortisol, aldosterone, dexamethasone, a cyclooxygenase inhibitor, a 5-lipoxygenase inhibitor, or a leukotriene receptor antagonist.

See generally US 2007-0292441; US 2007-0292422; US 2007-0264266; and US 2006-0233794.

Linkers

The binding proteins described herein can be associated with a drug to form a binding protein-drug conjugate by being linked to the drug directly. In some embodiments, the binding protein is directly conjugated to the drug. Alternatively, the binding proteins described herein can be associated with a drug to form a binding protein-drug conjugate by use of a linker region between the drug and the binding protein. In some embodiments, the binding protein is conjugated to the drug via a linker. The linker can be cleavable under intracellular conditions, e.g., such that cleavage of the linker releases the drug from the binding protein in the intracellular environment. In some embodiments, the cleavable linker is a peptide linker cleavable by an intracellular protease. In some embodiments, the peptide linker is a dipeptide linker.

In some embodiments, the dipeptide linker is a val-cit (vc) linker or a phe-lys (fk) linker. In some embodiments, the cleavable linker is hydrolyzable at a pH of less than 5.5. In some embodiments, the hydrolyzable linker is a hydrazone linker. In some embodiments, the cleavable linker is a disulfide linker.

For example, in some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, which are known to hydrolyze dipeptide drug derivatives resulting in the release of active drug inside target cells (see, e.g., Dubowchik and Walker *Pharm. Therapeutics* 83:67-123 (1999)). In some embodiments, peptidyl linkers are cleavable by enzymes that are present in targeted cells (e.g., cancer cells). For example, a peptidyl linker that is cleavable by the thiol-dependent protease cathepsin-B, which is highly expressed in cancerous tissue, can be used (e.g., a Phe-Leu or a Gly-Phe-Leu-Gly linker (SEQ ID NO: 11)). Other such linkers are described, e.g., in U.S. Pat. No. 6,214,345. In some embodiments, the peptidyl linker cleavable by an intracellular protease is a Val-Cit (vc) linker or a Phe-Lys linker (fk) (see, e.g., U.S. Pat. No. 6,214,345, which describes the synthesis of doxorubicin with the val-cit linker). One advantage of using intracellular proteolytic release of the drug is that the drug can be attenuated when conjugated and the serum stabilities of the conjugates are typically high.

In some preferred embodiments, a vc linker is used in the binding protein-drug conjugates described herein. For example, a binding protein-vcAFP or a binding protein-vc-MMAF conjugate (e.g., a MMP-9 binding protein-vcAFP or a MMP-9 binding protein-vcMMAF conjugate) is prepared.

In other embodiments, the cleavable linker is pH-sensitive, i.e., sensitive to hydrolysis at certain pH values. For example, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal., ketal., or the like) can be used. See, e.g., U.S. Pat. Nos. 5,122,368; 5,824,805; 5,622,929; Dubowchik and Walker *Pharm. Therapeutics* 83:67-123 (1999); Neville et al. *Biol. Chem.* 264:14653-14661 (1989). Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929)).

In yet other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT (See, e.g., Thorpe et al. *Cancer Res.* 47:5924-5931 (1987); Wawrzynczak et al., In Immunoconjugates: Antibody Conjugates in Radioimagery and Therapy of Cancer (C. W. Vogel ed., Oxford U. Press, 1987). See also U.S. Pat. No. 4,880,935.

In yet other embodiments, the linker is a malonate linker (Johnson et al. *Anticancer Res.* 15:1387-93 (1995)), a maleimidobenzoyl linker (Lau et al. *Bioorg-Med-Chem.* 3(10): 1299-1304 (1995), or a 3'-N-amide analog (Lau et al. *Bioorg-Med-Chem.* 3(10):1305-12 (1995)).

In some embodiments, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of a binding protein-drug conjugate, are cleaved when the binding protein-drug conjugate is present in an extracellular environment (e.g., in plasma). Whether a linker is not substantially sensitive to the extracellular environment can be determined, for example, by incubating independently with plasma both (a) the binding protein-drug conjugate (the "conjugate sample") and (b) an equal molar amount of unconjugated binding protein or drug (the "control sample") for a predetermined time period (e.g., 2, 4, 8, 16, or 24 hours) and then comparing the amount of unconjugated binding protein or drug present in the conjugate sample with that present in control sample, as measured, for example, by high performance liquid chromatography.

In other, non-mutually exclusive embodiments, the linker promotes cellular internalization. In certain embodiments, the linker promotes cellular internalization when conjugated to the drug (i.e., in the milieu of the linker-drug moiety of the binding protein-drug conjugate described herein). In yet other embodiments, the linker promotes cellular internalization when conjugated to both the drug and the binding protein.

A variety of linkers that can be used with the present compositions and methods are described in WO 2004010957.

In some embodiments, the binding protein-drug conjugates described herein are used therapeutically in the treatment of a disorder (e.g., cancer or inflammation). In certain embodiments, it is desirable to only target a binding protein-drug conjugate to a cell that expresses the target to which the binding protein binds (e.g., to only target a MMP-9 expressing cell to which a MMP-9 binding protein binds, and not target a nearby "bystander" cell), e.g., to minimize toxicity. In other embodiments, it is desirable to target a binding protein-drug conjugate to a cell expressing the target to which the binding protein binds and also to bystander cells (e.g., to elicit a "bystander effect"). In some embodiments, a binding protein-drug conjugate (e.g., a MMP-9 binding protein-drug conjugate can be engineered to exert a precise killing of only antigen-presenting cells without damaging proximal antigen-negative tissues, e.g., by preparing thioether-linked conjugates. Alternatively, it can be engineered to produce a bystander effect, e.g., by preparing disulfide-linked conjugates.

For example, many solid tumors express targets (e.g., antigens) in a heterogeneous fashion and are populated with both target-positive and target-negative cells. The bystander cytotoxicity associated with disulfide linker-containing conjugates provides a rationale for treatment of sites of a disorder (e.g., tumors) with binding protein-drug conjugates even if the sites exhibit heterogeneous target expression. The bystander effect adds a degree of nonselective killing activity. Potentially, this could be a drawback if normal cells in tissues surrounding the site of disorder (e.g., tumor) are affected. However, as a potential advantage, the bystander cytotoxicity may damage tissues intricately involved in supporting the disorder, such as endothelial cells and pericytes of tumor neovasculature, or tumor stromal cells, resulting, for example, in enhanced antitumor activity of the binding protein-drug conjugate against tumors expressing the antigen either homogeneously or heterogeneously. See also Kovtum et al. *Cancer Res.* 66:3214 (2006).

Techniques for conjugating therapeutic agents to proteins (such as binding proteins, e.g., MMP-9 binding proteins) are known. See, e.g., Amon et al., "Monoclonal Antibodies For Immunotargeting Of Drugs In Cancer Therapy," in Monoclonal Antibodies And Cancer Therapy (Reisfeld et al eds., Alan R. Liss, Inc., 1985); Hellstrom et al., "Antibodies For Drug Delivery," in Controlled Drug Delivery (Robinson et al. eds., Marcel Deiker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al. eds., 1985); "Analysis, Results, and Future Prospective of the Therapeutic Use of Radiolabeled Antibody In Cancer Therapy," in Monoclonal Antibodies For Cancer Detection And Therapy (Baldwin et al. eds., Academic Press, 1985); and Thorpe et al. *Immunol. Rev.* 62:119-58 (1982). See also, e.g., US 2006-0233794 and PCT publication WO 89/12624.

Display Libraries

A display library is a collection of entities; each entity includes an accessible polypeptide component and a recoverable component that encodes or identifies the polypeptide component. The polypeptide component is varied so that different amino acid sequences are represented. The polypeptide component can be of any length, e.g. from three amino acids to over 300 amino acids. A display library entity can include more than one polypeptide component, for example, the two polypeptide chains of an sFab. In one exemplary implementation, a display library can be used to identify proteins that bind to MMP-9. In a selection, the polypeptide component of each member of the library is probed with MMP-9 (e.g., the catalytic domain of MMP-9 or other fragment) and if the polypeptide component binds to the MMP-9, the display library member is identified, typically by retention on a support.

Retained display library members are recovered from the support and analyzed. The analysis can include amplification and a subsequent selection under similar or dissimilar conditions. For example, positive and negative selections can be alternated. The analysis can also include determining the amino acid sequence of the polypeptide component and purification of the polypeptide component for detailed characterization.

A variety of formats can be used for display libraries. Examples include the following.

Phage Display: The protein component is typically covalently linked to a bacteriophage coat protein. The linkage results from translation of a nucleic acid encoding the protein component fused to the coat protein. The linkage can include a flexible peptide linker, a protease site, or an amino acid incorporated as a result of suppression of a stop codon. Phage display is described, for example, in U.S. Pat. No. 5,223,409; Smith (1985) Science 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem.* 274:18218-30; Hoogenboom et al. (1998) *Immunotechnology* 4:1-20; Hoogenboom et al. (2000) *Immunol Today* 2:371-8 and Hoet et al. (2005) *Nat. Biotechnol.* 23(3)344-8. Bacteriophage displaying the protein component can be grown and harvested using standard phage preparatory methods, e.g. PEG precipitation from growth media. After selection of individual display phages, the nucleic acid encoding the selected protein components can be isolated from cells infected with the selected phages or from the phage themselves, after amplification. Individual colonies or plaques can be picked, the nucleic acid isolated and sequenced.

Other Display Formats. Other display formats include cell based display (see, e.g., WO 03/029456), protein-nucleic acid fusions (see, e.g., U.S. Pat. No. 6,207,446), ribosome display (See, e.g., Mattheakis et al. (1994) *Proc. Natl. Acad. Sci. USA* 91:9022 and Hanes et al. (2000) *Nat. Biotechnol.* 18:1287-92; Hanes et al. (2000) *Methods Enzymol.* 328:404-30; and Schaffitzel et al. (1999) *J Immunol Methods.* 231(1-2):119-35), and *E. coli* periplasmic display (*J Immunol Methods.* 2005 Nov. 22; PMID: 16337958).

Scaffolds. Scaffolds useful for display include: antibodies (e.g., Fab fragments, single chain Fv molecules (scFV), single domain antibodies, camelid antibodies, and camelized antibodies); T-cell receptors; MHC proteins; extracellular domains (e.g., fibronectin Type III repeats, EGF repeats); protease inhibitors (e.g., Kunitz domains, ecotin, BPTI, and so forth); TPR repeats; trifoil structures; zinc finger domains; DNA-binding proteins; particularly monomeric DNA binding proteins; RNA binding proteins; enzymes, e.g., proteases (particularly inactivated proteases), RNase; chaperones, e.g., thioredoxin and heat shock proteins; intracellular signaling domains (such as SH2 and SH3 domains); linear and constrained peptides; and linear peptide substrates. Display libraries can include synthetic and/or natural diversity. See, e.g., US 2004-0005709.

Display technology can also be used to obtain binding proteins (e.g., antibodies) that bind particular epitopes of a target. This can be done, for example, by using competing non-target molecules that lack the particular epitope or are mutated within the epitope, e.g., with alanine. Such non-target molecules can be used in a negative selection procedure as described below, as competing molecules when binding a display library to the target, or as a pre-elution agent, e.g., to capture in a wash solution dissociating display library members that are not specific to the target.

Iterative Selection. In one preferred embodiment, display library technology is used in an iterative mode. A first display library is used to identify one or more binding proteins for a target. These identified binding proteins are then varied using a mutagenesis method to form a second display library. Higher affinity binding proteins are then selected from the second library, e.g., by using higher stringency or more competitive binding and washing conditions.

In some implementations, the mutagenesis is targeted to regions at the binding interface. If, for example, the identified binding proteins are antibodies, then mutagenesis can be directed to the CDR regions of the heavy or light chains as described herein. Further, mutagenesis can be directed to framework regions near or adjacent to the CDRs. In the case of antibodies, mutagenesis can also be limited to one or a few of the CDRs, e.g., to make precise step-wise improvements.

Exemplary mutagenesis techniques include: error-prone PCR, recombination, DNA shuffling, site-directed mutagenesis and cassette mutagenesis.

In one example of iterative selection, the methods described herein are used to first identify a protein from a display library that binds MMP-9 with at least a minimal binding specificity for a target or a minimal activity, e.g., an equilibrium dissociation constant for binding of less than 1 nM, 10 nM, or 100 nM. The nucleic acid sequence encoding the initial identified proteins are used as a template nucleic acid for the introduction of variations, e.g., to identify a second protein that has enhanced properties (e.g., binding affinity, kinetics, or stability) relative to the initial protein.

Off-Rate Selection. Since a slow dissociation rate can be predictive of high affinity, particularly with respect to interactions between polypeptides and their targets, the methods described herein can be used to isolate binding proteins with a desired (e.g., reduced) kinetic dissociation rate for a binding interaction to a target.

To select for slow dissociating binding proteins from a display library, the library is contacted to an immobilized target. The immobilized target is then washed with a first solution that removes non-specifically or weakly bound biomolecules. Then the bound binding proteins are eluted with a second solution that includes a saturating amount of free target or a target specific high-affinity competing monoclonal antibody, i.e., replicates of the target that are not attached to the particle. The free target binds to biomolecules that dissociate from the target. Rebinding is effectively prevented by the saturating amount of free target relative to the much lower concentration of immobilized target.

The second solution can have solution conditions that are substantially physiological or that are stringent. Typically, the solution conditions of the second solution are identical to the solution conditions of the first solution. Fractions of the second solution are collected in temporal order to distinguish early from late fractions. Later fractions include biomolecules that dissociate at a slower rate from the target than biomolecules in the early fractions.

Further, it is also possible to recover display library members that remain bound to the target even after extended incubation. These can either be dissociated using chaotropic conditions or can be amplified while attached to the target. For example, phage bound to the target can be contacted to bacterial cells.

Selecting or Screening for Specificity. The display library screening methods described herein can include a selection or screening process that discards display library members that bind to a non-target molecule. Examples of non-target molecules include streptavidin on magnetic beads, blocking agents such as bovine serum albumin, non-fat bovine milk, any capturing or target immobilizing monoclonal antibody, or non-transfected cells which do not express the human MMP-9 target.

In one implementation, a so-called "negative selection" step is used to discriminate between the target and related non-target molecule and a related, but distinct non-target molecules. The display library or a pool thereof is contacted to the non-target molecule. Members of the sample that do not bind the non-target are collected and used in subsequent selections for binding to the target molecule or even for subsequent negative selections. The negative selection step can be prior to or after selecting library members that bind to the target molecule.

In another implementation, a screening step is used. After display library members are isolated for binding to the target molecule, each isolated library member is tested for its ability to bind to a non-target molecule (e.g., a non-target listed above). For example, a high-throughput ELISA screen can be used to obtain this data. The ELISA screen can also be used to obtain quantitative data for binding of each library member to the target as well as for cross species reactivity to related targets or subunits of the target (e.g., mouse MMP-9) and also under different condition such as pH6 or pH 7.5. The non-target and target binding data are compared (e.g., using a computer and software) to identify library members that specifically bind to the target.

Other Exemplary Expression Libraries

Other types of collections of proteins (e.g., expression libraries) can be used to identify proteins with a particular property (e.g., ability to bind MMP-9 and/or ability to modulate MMP-9), including, e.g., protein arrays of antibodies (see, e.g., De Wildt et al. (2000) Nat. Biotechnol. 18:989-994), lambda gt11 libraries, two-hybrid libraries and so forth.

Exemplary Libraries

It is possible to immunize a non-human primate and recover primate antibody genes that can be displayed on phage (see below). From such a library, one can select antibodies that bind the antigen used in immunization. See, for example, Vaccine. (2003) 22(2):257-67 or Immunogenetics. (2005) 57(10):730-8. Thus one could obtain primate antibodies that bind and inhibit MMP-9 by immunizing a chimpanzee or macaque and using a variety of means to select or screen for primate antibodies that bind and inhibit MMP-9. One can also make chimeras of primatized Fabs with human constant regions, see Curr Opin Mol. Ther. (2004) 6(6):675-83. "PRIMATIZED antibodies, genetically engineered from cynomolgus macaque monkey and human components, are structurally indistinguishable from human antibodies. They may, therefore, be less likely to cause adverse reactions in humans, making them potentially suited for long-term, chronic treatment" Curr Opin Investig Drugs. (2001) 2(5): 635-8.

One exemplary type of library presents a diverse pool of polypeptides, each of which includes an immunoglobulin domain, e.g., an immunoglobulin variable domain. Of interest are display libraries where the members of the library include primate or "primatized" (e.g., such as human, non-human primate or "humanized") immunoglobin domains (e.g., immunoglobin variable domains) or chimeric primatized Fabs with human constant regions. Human or humanized immunoglobin domain libraries may be used to identify human or "humanized" antibodies that, for example, recognize human antigens. Because the constant and framework regions of the antibody are human, these antibodies may avoid themselves being recognized and targeted as antigens when administered to humans. The constant regions may also be optimized to recruit effector functions of the human immune system. The in vitro display selection process surmounts the inability of a normal human immune system to generate antibodies against self-antigens.

A typical antibody display library displays a polypeptide that includes a VH domain and a VL domain. An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay, 1988, Ann. Rev. Immunol. 6:381-405). The display library can display the antibody as a Fab fragment (e.g., using two polypeptide chains) or a single chain Fv (e.g., using a single polypeptide chain). Other formats can also be used.

As in the case of the Fab and other formats, the displayed antibody can include one or more constant regions as part of a light and/or heavy chain. In one embodiment, each chain includes one constant region, e.g., as in the case of a Fab. In other embodiments, additional constant regions are displayed.

Antibody libraries can be constructed by a number of processes (see, e.g., de Haard et al., 1999, J. Biol. Chem. 274: 18218-30; Hoogenboom et al., 1998, Immunotechnology 4:1-20; Hoogenboom et al., 2000, Immunol. Today 21:371-378, and Hoet et al. (2005) Nat. Biotechnol. 23(3)344-8. Further, elements of each process can be combined with those of other processes. The processes can be used such that variation is introduced into a single immunoglobulin domain (e.g., VH or VL) or into multiple immunoglobulin domains (e.g., VH and VL). The variation can be introduced into an immunoglobulin variable domain, e.g., in the region of one or more of CDR1, CDR2, CDR3, FR1, FR2, FR3, and FR4, referring to such regions of either and both of heavy and light chain variable domains. The variation(s) may be introduced into all three CDRs of a given variable domain, or into CDR1 and CDR2, e.g., of a heavy chain variable domain. Any combination is feasible. In one process, antibody libraries are constructed by inserting diverse oligonucleotides that encode CDRs into the corresponding regions of the nucleic acid. The oligonucleotides can be synthesized using monomeric nucleotides or trinucleotides. For example, Knappik et al., 2000, J. Mol. Biol. 296:57-86 describe a method for constructing CDR encoding oligonucleotides using trinucleotide synthesis and a template with engineered restriction sites for accepting the oligonucleotides.

In another process, an animal, e.g., a rodent, is immunized with MMP-9. The animal is optionally boosted with the antigen to further stimulate the response. Then spleen cells are isolated from the animal, and nucleic acid encoding VH and/or VL domains is amplified and cloned for expression in the display library.

In yet another process, antibody libraries are constructed from nucleic acid amplified from naïve germline immunoglobulin genes. The amplified nucleic acid includes nucleic acid encoding the VH and/or VL domain. Sources of immunoglobulin-encoding nucleic acids are described below. Amplification can include PCR, e.g., with primers that anneal to the conserved constant region, or another amplification method.

Nucleic acid encoding immunoglobulin domains can be obtained from the immune cells of, e.g., a primate (e.g., a human), mouse, rabbit, camel, or rodent. In one example, the cells are selected for a particular property. B cells at various stages of maturity can be selected. In another example, the B cells are naïve.

In one embodiment, fluorescent-activated cell sorting (FACS) is used to sort B cells that express surface-bound IgM, IgD, or IgG molecules. Further, B cells expressing different isotypes of IgG can be isolated. In another preferred embodiment, the B or T cell is cultured in vitro. The cells can be stimulated in vitro, e.g., by culturing with feeder cells or by adding mitogens or other modulatory reagents, such as antibodies to CD40, CD40 ligand or CD20, phorbol myristate acetate, bacterial lipopolysaccharide, concanavalin A, phytohemagglutinin, or pokeweed mitogen.

In another embodiment, the cells are isolated from a subject that has a disease of condition described herein, e.g., a cancer (e.g., metastatic cancer, e.g., metastatic breast cancer), an inflammatory disease (e.g., synovitis, atherosclerosis), rheumatoid arthritis, osteoarthritis, an ocular condition (e.g., macular degeneration), diabetes, Alzheimer's Disease, cerebral ischemia, endometriosis, fibrin-invasive activity, angiogenesis, or capillary tube formation In another embodiment, the cells are isolated from a transgenic non-human animal that includes a human immunoglobulin locus.

In one preferred embodiment, the cells have activated a program of somatic hypermutation. Cells can be stimulated to undergo somatic mutagenesis of immunoglobulin genes, for example, by treatment with anti-immunoglobulin, anti-CD40, and anti-CD38 antibodies (see, e.g., Bergthorsdottir et al., 2001, *J. Immunol.* 166:2228). In another embodiment, the cells are naïve.

The nucleic acid encoding an immunoglobulin variable domain can be isolated from a natural repertoire by the following exemplary method. First, RNA is isolated from the immune cell. Full length (i.e., capped) mRNAs are separated (e.g. by degrading uncapped RNAs with calf intestinal phosphatase). The cap is then removed with tobacco acid pyrophosphatase and reverse transcription is used to produce the cDNAs.

The reverse transcription of the first (antisense) strand can be done in any manner with any suitable primer. See, e.g., de Haard et al., 1999, *J. Biol. Chem.* 274:18218-30. The primer binding region can be constant among different immunoglobulins, e.g., in order to reverse transcribe different isotypes of immunoglobulin. The primer binding region can also be specific to a particular isotype of immunoglobulin. Typically, the primer is specific for a region that is 3' to a sequence encoding at least one CDR. In another embodiment, poly-dT primers may be used (and may be preferred for the heavy-chain genes).

A synthetic sequence can be ligated to the 3' end of the reverse transcribed strand. The synthetic sequence can be used as a primer binding site for binding of the forward primer during PCR amplification after reverse transcription. The use of the synthetic sequence can obviate the need to use a pool of different forward primers to fully capture the available diversity.

The variable domain-encoding gene is then amplified, e.g., using one or more rounds. If multiple rounds are used, nested primers can be used for increased fidelity. The amplified nucleic acid is then cloned into a display library vector.

Secondary Screening Methods

After selecting candidate library members that bind to a target, each candidate library member can be further analyzed, e.g., to further characterize its binding properties for the target, e.g., MMP-9, or for binding to other protein, e.g., another metalloproteinase. Each candidate library member can be subjected to one or more secondary screening assays. The assay can be for a binding property, a catalytic property, an inhibitory property, a physiological property (e.g., cytotoxicity, renal clearance, immunogenicity), a structural property (e.g., stability, conformation, oligomerization state) or another functional property. The same assay can be used repeatedly, but with varying conditions, e.g., to determine pH, ionic, or thermal sensitivities.

As appropriate, the assays can use a display library member directly, a recombinant polypeptide produced from the nucleic acid encoding the selected polypeptide, or a synthetic peptide synthesized based on the sequence of the selected polypeptide. In the case of selected Fabs, the Fabs can be evaluated or can be modified and produced as intact IgG proteins. Exemplary assays for binding properties include the following.

ELISA. Binding proteins can be evaluated using an ELISA assay. For example, each protein is contacted to a microtitre plate whose bottom surface has been coated with the target, e.g., a limiting amount of the target. The plate is washed with buffer to remove non-specifically bound polypeptides. Then the amount of the binding protein bound to the target on the plate is determined by probing the plate with an antibody that can recognize the binding protein, e.g., a tag or constant portion of the binding protein. The antibody is linked to a detection system (e.g., an enzyme such as alkaline phosphatase or horse radish peroxidase (HRP) which produces a colorimetric product when appropriate substrates are provided).

Homogeneous Binding Assays. The ability of a binding protein described herein to bind a target can be analyzed using a homogenous assay, i.e., after all components of the assay are added, additional fluid manipulations are not required. For example, fluorescence resonance energy transfer (FRET) can be used as a homogenous assay (see, for example, Lakowicz et al., U.S. Pat. No. 5,631,169; Stavrianopoulos, et al., U.S. Pat. No. 4,868,103). A fluorophore label on the first molecule (e.g., the molecule identified in the fraction) is selected such that its emitted fluorescent energy can be absorbed by a fluorescent label on a second molecule (e.g., the target) if the second molecule is in proximity to the first molecule. The fluorescent label on the second molecule fluoresces when it absorbs to the transferred energy. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A binding event that is configured for monitoring by FRET can be conveniently measured through standard fluorometric detection means, e.g., using a fluorimeter. By titrating the amount of the first or second binding molecule, a binding curve can be generated to estimate the equilibrium binding constant.

Another example of a homogenous assay is ALPHASCREEN™ (Packard Bioscience, Meriden Conn.). ALPHASCREEN™ uses two labeled beads. One bead generates singlet oxygen when excited by a laser. The other bead generates a light signal when singlet oxygen diffuses from the first bead and collides with it. The signal is only generated when the two beads are in proximity. One bead can be attached to the display library member, the other to the target. Signals are measured to determine the extent of binding.

Surface Plasmon Resonance (SPR). The interaction of binding protein and a target can be analyzed using SPR. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether, 1988, Surface Plasmons Springer Verlag; Sjolander and Urbaniczky, 1991, *Anal. Chem.* 63:2338-2345; Szabo et al., 1995, *Curr. Opin. Struct. Biol.* 5:699-705 and on-line resources provide by BIAcore International AB (Uppsala, Sweden). BIAcore Flexchip can be used to compare and rank interactions in real time, in terms of kinetics, affinity or specificity without the use of labels.

Information from SPR can be used to provide an accurate and quantitative measure of the equilibrium dissociation constant ($K_d$), and kinetic parameters, including $K_{on}$ and $K_{off}$, for the binding of a binding protein to a target. Such data can be used to compare different biomolecules. For example, selected proteins from an expression library can be compared to identify proteins that have high affinity for the target or that have a slow $K_{off}$. This information can also be used to develop structure-activity relationships (SAR). For example, the kinetic and equilibrium binding parameters of matured versions of a parent protein can be compared to the parameters of the parent protein. Variant amino acids at given positions can be identified that correlate with particular binding parameters, e.g., high affinity and slow $K_{off}$. This information can be combined with structural modeling (e.g., using homology modeling, energy minimization, or structure determination by x-ray crystallography or NMR). As a result, an understanding of the physical interaction between the protein and its target can be formulated and used to guide other design processes.

Cellular Assays. Binding proteins can be screened for ability to bind to cells which transiently or stably express and display the target of interest on the cell surface. For example, MMP-9 binding proteins can be fluorescently labeled and binding to MMP-9 in the presence of absence of antagonistic antibody can be detected by a change in fluorescence intensity using flow cytometry e.g., a FACS machine.

Other Exemplary Methods for Obtaining MMP-9 Binding Antibodies

In addition to the use of display libraries, other methods can be used to obtain a MMP-9 binding antibody. For example, MMP-9 protein or a region thereof can be used as an antigen in a non-human animal, e.g., a rodent.

In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies (Mabs) derived from the genes with the desired specificity may be produced and selected. See, e.g., XENOMOUSE™, Green et al., 1994, *Nat. Gen.* 7:13-21; U.S. 2003-0070185, WO 96/34096, published Oct. 31, 1996, and PCT Application No. PCT/US96/05928, filed Apr. 29, 1996.

In another embodiment, a monoclonal antibody is obtained from the non-human animal, and then modified, e.g., humanized or deimmunized. Winter describes a CDR-grafting method that may be used to prepare the humanized antibodies (UK Patent Application GB 2188638A, filed on Mar. 26, 1987; U.S. Pat. No. 5,225,539. All of the CDRs of a particular human antibody may be replaced with at least a portion of a non-human CDR or only some of the CDRs may be replaced with non-human CDRs. It is only necessary to replace the number of CDRs required for binding of the humanized antibody to a predetermined antigen.

Humanized antibodies can be generated by replacing sequences of the Fv variable region that are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. No. 5,585,089, U.S. Pat. No. 5,693,761 and U.S. Pat. No. 5,693,762. Those methods include isolating, manipulating, and expressing the nucleic acid sequences that encode all or part of immunoglobulin Fv variable regions from at least one of a heavy or light chain. Numerous sources of such nucleic acid are available. For example, nucleic acids may be obtained from a hybridoma producing an antibody against a predetermined target, as described above. The recombinant DNA encoding the humanized antibody, or fragment thereof, can then be cloned into an appropriate expression vector.

Reducing Immunogenicity of MMP-9 Binding Proteins

Immunoglobin MMP-9 binding proteins (e.g., IgG or Fab MMP-9 binding proteins) may be modified to reduce immunogenicity. Reduced immunogenicity is desirable in MMP-9 binding proteins intended for use as therapeutics, as it reduces the chance that the subject will develop an immune response against the therapeutic molecule. Techniques useful for reducing immunogenicity of MMP-9 binding proteins include deletion/modification of potential human T cell epitopes and 'germlining' of sequences outside of the CDRs (e.g., framework and Fc).

An MMP-9-binding antibody may be modified by specific deletion of human T cell epitopes or "deimmunization" by the methods disclosed in WO 98/52976 and WO 00/34317. Briefly, the heavy and light chain variable regions of an antibody are analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the VH and VL sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable regions, or preferably, by single amino acid substitutions. As far as possible conservative substitutions are made, often but not exclusively, an amino acid common at this position in human germline antibody sequences may be used. Human germline sequences are disclosed in Tomlinson, I. A. et al., 1992, *J. Mol. Biol.* 227:776-798; Cook, G. P. et al., 1995, *Immunol. Today* Vol. 16 (5): 237-242; Chothia, D. et al., 1992, *J. Mol. Bio.* 227:799-817. The V BASE directory provides a comprehensive directory of human immunoglobulin variable region sequences (compiled by Tomlinson, I. A. et al. MRC Centre for Protein Engineering, Cambridge, UK). After the deimmunizing changes are identified, nucleic acids encoding $V_H$ and $V_L$ can be constructed by mutagenesis or other synthetic methods (e.g., de novo synthesis, cassette replacement, and so forth). Mutagenized variable sequence can, optionally, be fused to a human constant region, e.g., human IgG1 or κ constant regions.

In some cases a potential T cell epitope will include residues which are known or predicted to be important for antibody function. For example, potential T cell epitopes are usually biased towards the CDRs. In addition, potential T cell epitopes can occur in framework residues important for antibody structure and binding. Changes to eliminate these potential epitopes will in some cases require more scrutiny, e.g., by making and testing chains with and without the change. Where possible, potential T cell epitopes that overlap the CDRs were eliminated by substitutions outside the CDRs. In some cases, an alteration within a CDR is the only option, and thus variants with and without this substitution should be tested. In other cases, the substitution required to remove a potential T cell epitope is at a residue position within the framework that might be critical for antibody binding. In these cases, variants with and without this substitution should be tested. Thus, in some cases several variant deimmunized heavy and light chain variable regions were designed and various heavy/light chain combinations tested in order to identify the optimal deimmunized antibody. The choice of the final deimmunized antibody can then be made by considering the binding affinity of the different variants in conjunction with the extent of deimmunization, i.e., the number of potential T cell epitopes remaining in the variable region. Deimmunization can be used to modify any antibody, e.g., an antibody that includes a non-human sequence, e.g., a synthetic antibody, a murine antibody other non-human monoclonal antibody, or an antibody isolated from a display library.

MMP-9 binding antibodies are "germlined" by reverting one or more non-germline amino acids in framework regions to corresponding germline amino acids of the antibody, so long as binding properties are substantially retained. Similar methods can also be used in the constant region, e.g., in constant immunoglobulin domains.

Antibodies that bind to MMP-9, e.g., an antibody described herein, may be modified in order to make the variable regions of the antibody more similar to one or more germline sequences. For example, an antibody can include one, two, three, or more amino acid substitutions, e.g., in a framework, CDR, or constant region, to make it more similar to a reference germline sequence. One exemplary germlining method can include identifying one or more germline sequences that are similar (e.g., most similar in a particular database) to the sequence of the isolated antibody. Mutations (at the amino acid level) are then made in the isolated antibody, either incrementally or in combination with other mutations. For example, a nucleic acid library that includes sequences encoding some or all possible germline mutations is made. The mutated antibodies are then evaluated, e.g., to identify an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a framework and/or constant region. For example, a germline framework and/or constant region residue can be from a germline sequence that is similar (e.g., most similar) to the non-variable region being modified. After mutagenesis, activity (e.g., binding or other functional activity) of the antibody can be evaluated to determine if the germline residue or residues are tolerated (i.e., do not abrogate activity). Similar mutagenesis can be performed in the framework regions.

Selecting a germline sequence can be performed in different ways. For example, a germline sequence can be selected if it meets a predetermined criteria for selectivity or similarity, e.g., at least a certain percentage identity, e.g., at least 75, 80, 85, 90, 91, 92, 93, 94, 95, 96, 97, 98, 99, or 99.5% identity. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but may including using two germline sequences that separately contribute to the amino-terminal portion and the carboxy-terminal portion. In other implementations more than one or two germline sequences are used, e.g., to form a consensus sequence.

In one embodiment, with respect to a particular reference variable domain sequence, e.g., a sequence described herein, a related variable domain sequence has at least 30, 40, 50, 60, 70, 80, 90, 95 or 100% of the CDR amino acid positions that are not identical to residues in the reference CDR sequences, residues that are identical to residues at corresponding positions in a human germline sequence (i.e., an amino acid sequence encoded by a human germline nucleic acid).

In one embodiment, with respect to a particular reference variable domain sequence, e.g., a sequence described herein, a related variable domain sequence has at least 30, 50, 60, 70, 80, 85, 90, 91, 92, 93, 94, 95, 96, 97, 98, 99 or 100% of the FR regions identical to FR sequence from a human germline sequence, e.g., a germline sequence related to the reference variable domain sequence.

Accordingly, it is possible to isolate an antibody which has similar activity to a given antibody of interest, but is more similar to one or more germline sequences, particularly one or more human germline sequences. For example, an antibody can be at least 90, 91, 92, 93, 94, 95, 96, 97, 98, 99, or 99.5% identical to a germline sequence in a region outside the CDRs (e.g., framework regions). Further, an antibody can include at least 1, 2, 3, 4, or 5 germline residues in a CDR region, the germline residue being from a germline sequence of similar (e.g., most similar) to the variable region being modified. Germline sequences of primary interest are human germline sequences. The activity of the antibody (e.g., the binding activity as measured by $K_A$) can be within a factor or 100, 10, 5, 2, 0.5, 0.1, and 0.001 of the original antibody.

Germline sequences of human immunoglobin genes have been determined and are available from a number of sources, including the international ImMunoGeneTics information System® (IMGT), available via the world wide web at imgt.cines.fr, and the V BASE directory (compiled by Tomlinson, I. A. et al. MRC Centre for Protein Engineering, Cambridge, UK, available via the world wide web at vbase.mrc-cpe.cam.ac.uk).

Exemplary germline reference sequences for $V_{kappa}$ include: O12/O2, O18/O8, A20, A30, L14, L1, L15, L4/18a, L5/L19, L8, L23, L9, L24, L11, L12, O11/O1, A17, A1, A18, A2, A19/A3, A23, A27, A11, L2/L16, L6, L20, L25, B3, B2, A26/A10, and A14. See, e.g., Tomlinson et al., 1995, *EMBO J.* 14(18):4628-3.

A germline reference sequence for the HC variable domain can be based on a sequence that has particular canonical structures, e.g., 1-3 structures in the H1 and H2 hypervariable loops. The canonical structures of hypervariable loops of an immunoglobulin variable domain can be inferred from its sequence, as described in Chothia et al., 1992, *J. Mol. Biol.* 227:799-817; Tomlinson et al., 1992, *J. Mol. Biol.* 227:776-798); and Tomlinson et al., 1995, *EMBO J.* 14(18):4628-38. Exemplary sequences with a 1-3 structure include: DP-1, DP-8, DP-12, DP-2, DP-25, DP-15, DP-7, DP-4, DP-31, DP-32, DP-33, DP-35, DP-40, 7-2, hv3005, hv3005f3, DP-46, DP-47, DP-58, DP-49, DP-50, DP-51, DP-53, and DP-54.

Protein Production

Standard recombinant nucleic acid methods can be used to express a protein that binds to MMP-9. Generally, a nucleic acid sequence encoding the protein is cloned into a nucleic acid expression vector. Of course, if the protein includes multiple polypeptide chains, each chain can be cloned into an expression vector, e.g., the same or different vectors, that are expressed in the same or different cells.

Antibody Production. Some antibodies, e.g., Fabs, can be produced in bacterial cells, e.g., *E. coli* cells. For example, if the Fab is encoded by sequences in a phage display vector that includes a suppressible stop codon between the display entity and a bacteriophage protein (or fragment thereof), the vector nucleic acid can be transferred into a bacterial cell that cannot suppress a stop codon. In this case, the Fab is not fused to the gene III protein and is secreted into the periplasm and/or media.

Antibodies can also be produced in eukaryotic cells. In one embodiment, the antibodies (e.g., scFv's) are expressed in a yeast cell such as *Pichia* (see, e.g., Powers et al., 2001, *J. Immunol. Methods.* 251:123-35), Hanseula, or *Saccharomyces*.

In one preferred embodiment, antibodies are produced in mammalian cells. Preferred mammalian host cells for expressing the clone antibodies or antigen-binding fragments thereof include Chinese Hamster Ovary (CHO cells) (including dhfr-CHO cells, described in Urlaub and Chasin, 1980, *Proc. Natl. Acad. Sci. USA* 77:4216-4220, used with a DHFR selectable marker, e.g., as described in Kaufman and Sharp, 1982, *Mol. Biol.* 159:601 621), lymphocytic cell lines, e.g., NS0 myeloma cells and SP2 cells, COS cells, HEK293T cells (*J. Immunol. Methods* (2004) 289(1-2):65-80.), and a cell from a transgenic animal, e.g., a transgenic mammal. For example, the cell is a mammary epithelial cell.

In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr host cells with methotrexate selection/amplification) and the neo gene (for G418 selection).

In an exemplary system for recombinant expression of an antibody, or antigen-binding portion thereof, a recombinant expression vector encoding both the antibody heavy chain and the antibody light chain is introduced into dhfr⁻ CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G coupled matrix.

For antibodies that include an Fc domain, the antibody production system may produce antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcg receptors and complement C1q (Burton and Woof, 1992, *Adv. Immunol.* 51:1-84; Jefferis et al., 1998, *Immunol. Rev.* 163:59-76). In one embodiment, the Fc domain is produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

Characterization of MMP-9 Binding Proteins

Binding of MMP-9 binding proteins to cells expressing MMP-9 can be characterized in a number assays known in the art, including FACS (Fluorescence Activated Cell Sorting), immunofluorescence, and immunocytochemistry. MMP-9 binding protein is contacted with cells and/or tissues which express or contain MMP-9, and binding is detected in accordance with the method being used. For example, a fluorescent detection system (e.g., fluorescent-labeled secondary antibody) employed for FACS and immunofluorescence analysis, or a enzymatic system is used for immunocytochemistry are generally used in these assays can be performed on non-perm. MMP-9 binding proteins can be characterized as to cellular binding by FACS (Fluorescence Activated Cell Sorting) using cells expressing MMP-9. Individual cells held in a thin stream of fluid are passed through one or more laser beams cause light to scatter and fluorescent dyes to emit light at various frequencies. Photomultiplier tubes (PMT) convert light to electrical signals and cell data is collected. Forward and side scatter are used for preliminary identification of cells. Forward and side scatter are used to exclude debris and dead cells. Fluorescent labeling allows investigation of cell structure and function. Cell autofluorescence is generated by labeling cell structures with fluorescent dyes. FACS collects fluorescence signals in one to several channels corresponding to different laser excitation and fluorescence emission wavelength. Immunofluorescence, the most widely used application, involves the staining of cells with antibodies conjugated to fluorescent dyes such as fluorescein and phycoerythrin (PE). This method can be used to label MMP-9 on the cell surface of MDA-MB-231 cells using biotinylated MMP-9 binding proteins. Biotin is used in these two-step detection systems in concert with conjugated steptavidin. Biotin is typically conjugated to proteins via primary amines (i.e., lysines). Usually, between 1.5 and 3 biotin molecules are conjugated to each antibody. A second fluorescently conjugated antibody (streptavidin/PE) is added which is specific for biotin.

MMP-9 binding proteins can be characterized in cultured cells expressing the MMP-9 antigen. The method generally used is immunocytochemistry. Immunocytochemistry involves the use of antibodies that recognize parts of the receptor that are exposed to the outside environment when expressed at the cell surface (the 'primary antibody'). If the experiment is carried out in intact cells, such an antibody will only bind to surface expressed receptors. Biotinylated or non-biotinylated MMP-9 binding proteins can be used. The secondary antibody is then either a streptavidin/HRP antibody (for biotinylated MMP-9 binding protein) or an anti-human IgG/HRP (for non-biotinylated MMP-9 binding protein). The staining can then be detected using an inverted microscope. The assay can be performed in the absence of MMP-9 binding protein and in presence of 10 μg/mL of MMP-9 binding protein.

MMP-9 binding proteins can be characterized in assays that measure their modulatory activity toward MMP-9 or fragments thereof in vitro or in vivo. For example, MMP-9 can be combined with a substrate such as Mca-Pro-Leu-Ala-Cys(Mob)-Trp-Ala-Arg-Dap(Dnp)-NH$_2$ (SEQ ID NO: 12) under assay conditions permitting cleavage by MMP-9. The assay is performed in the absence of the MMP-9 binding protein, and in the presence of increasing concentrations of the MMP-9 binding protein. The concentration of binding protein at which 50% of the MMP-9 activity (e.g., binding to the substrate) is inhibited is the $IC_{50}$ value (Inhibitory Concentration 50%) or $EC_{50}$ (Effective Concentration 50%) value for that binding protein. Within a series or group of binding proteins, those having lower $IC_{50}$ or $EC_{50}$ values are considered more potent inhibitors of MMP-9 than those binding proteins having higher $IC_{50}$ or $EC_{50}$ values. Exemplary binding proteins have an $IC_{50}$ value of less than 800 nM, 400 nM, 100 nM, 25 nM, 5 nM, or 1 nM, e.g., as measured in an in vitro assay for inhibition of MMP-9 activity when the MMP-9 is at 2 pM.

MMP-9 binding proteins may also be characterized with reference to the activity of MMP-9 on substrates (e.g., collagen, gelatin). For example, cleavage of gelatin by MMP-9 can be detected in zymography. The method is based on a SDS gel impregnated with a substrate, which is degraded by the proteases resolved during the incubation period. Coomassie blue staining of the gels reveals proteolytic fragments as white bands on a dark blue background. Within a certain range, the band intensity can be related linearly to the amount of the protease loaded. Cells expressing both MMP-9 and MMP-2 are used in this assay. The assay is performed in the absence of the MMP-9 binding protein, and in the presence of increasing concentrations of the MMP-9 binding protein. The concentration of binding protein at which 50% of the MMP-2 activity (e.g., binding to the substrate) is inhibited is the $IC_{50}$ value (Inhibitory Concentration 50%) or $EC_{50}$ (Effective Concentration 50%) value for that binding protein. Within a series or group of binding proteins, those having lower $IC_{50}$ or $EC_{50}$ values are considered more potent inhibitors of MMP-9 than those binding proteins having higher $IC_{50}$ or $EC_{50}$ values. Exemplary binding proteins have an $IC_{50}$ value of less than 800 nM, 400 nM, 100 nM, 25 nM, 5 nM, or 1 nM, e.g., as measured in an in vitro assay for inhibition of MMP-9 activity.

The binding proteins can also be evaluated for selectivity toward MMP-9. For example, a MMP-9 binding protein can be assayed for its potency toward MMP-9 and a panel of MMPs and other enzymes, e.g., human and/or mouse enzymes, e.g., MMP-1, -2, -3, -7, -8, -12, -13, -14, -16, -17, -24, and TACE, and an $IC_{50}$ value or $EC_{50}$ value can be determined for each MMP. In one embodiment, a compound that demonstrates a low $IC_{50}$ value or $EC_{50}$ value for the MMP-9, and a higher $IC_{50}$ value or $EC_{50}$ value, e.g., at least 2-, 5-, or 10-fold higher, for another MMP within the test panel (e.g., MMP-1, -10) is considered to be selective toward MMP-9.

MMP-9 binding proteins can be evaluated for their ability to inhibit MMP-9 in a cell based assay, e.g., in situ zymography, e.g., in Colo205 cells or MCF-7 cells.

A pharmacokinetics study in rat, mice, or monkey can be performed with MMP-9 binding proteins for determining MMP-9 half-life in the serum. Likewise, the effect of the binding protein can be assessed in vivo, e.g., in an animal model for a disease, for use as a therapeutic, for example, to treat a disease or condition described herein, e.g., a cancer (e.g., metastatic cancer, e.g., metastatic breast cancer), an inflammatory disease (e.g., chronic obstructive pulmonary disease (COPD), asthma, rhinitis (e.g., allergic rhinitis), inflammatory bowel disease, synovitis, rheumatoid arthritis), heart failure, septic shock, neuropathic pain, inflammatory pain, osteoarthritis, or an ocular condition (e.g., macular degeneration).

Pharmaceutical Compositions

In another aspect, the disclosure provides compositions, e.g., pharmaceutically acceptable compositions or pharmaceutical compositions, which include an MMP-9-binding protein, e.g., an antibody molecule, other polypeptide or peptide identified as binding to MMP-9 described herein. The MMP-9 binding protein can be formulated together with a pharmaceutically acceptable carrier. Pharmaceutical compositions include therapeutic compositions and diagnostic compositions, e.g., compositions that include labeled MMP-9 binding proteins for in vivo imaging.

A pharmaceutically acceptable carrier includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal, or epidermal administration (e.g., by injection or infusion), although carriers suitable for inhalation and intranasal administration are also contemplated. Depending on the route of administration, the MMP-9 binding protein may be coated in a material to protect the compound from the action of acids and other natural conditions that may inactivate the compound.

A pharmaceutically acceptable salt is a salt that retains the desired biological activity of the parent compound and does not impart any undesired toxicological effects (see e.g., Berge, S. M., et al., 1977, *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids, and the like. Base addition salts include those derived from alkaline earth metals, such as sodium, potassium, magnesium, calcium, and the like, as well as from nontoxic organic amines, such as N,N'-dibenzylethylenediamine, N-methylglucamine, chloroprocaine, choline, diethanolamine, ethylenediamine, procaine, and the like.

The compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Many compositions are in the form of injectable or infusible solutions, such as compositions similar to those used for administration of humans with antibodies. An exemplary mode of administration is parenteral (e.g., intravenous, subcutaneous, intraperitoneal, intramuscular). In one embodiment, the MMP-9 binding protein is administered by intravenous infusion or injection. In another preferred embodiment, the MMP-9 binding protein is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The composition can be formulated as a solution, microemulsion, dispersion, liposome, or other ordered structure suitable to high drug concentration. Sterile injectable solutions can be prepared by incorporating the binding protein in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An MMP-9 binding protein can be administered by a variety of methods, although for many applications, the preferred route/mode of administration is intravenous injection or infusion. For example, for therapeutic applications, the MMP-9 binding protein can be administered by intravenous infusion at a rate of less than 30, 20, 10, 5, or 1 mg/min to reach a dose of about 1 to 100 mg/m$^2$ or 7 to 25 mg/m$^2$. The route and/or mode of administration will vary depending upon the desired results. In certain embodiments, the active compound may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are available. See, e.g., Sustained and Controlled Release Drug Delivery Systems, J. R. Robinson, ed., 1978, Marcel Dekker, Inc., New York.

Pharmaceutical compositions can be administered with medical devices. For example, in one embodiment, a pharmaceutical composition disclosed herein can be administered with a device, e.g., a needleless hypodermic injection device, a pump, or implant.

In certain embodiments, an MMP-9 binding protein can be formulated to ensure proper distribution in vivo. For example, the blood-brain barrier (BBB) excludes many highly hydrophilic compounds. To ensure that the therapeutic compounds disclosed herein cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties that are selectively transported into specific cells or organs, thus enhance targeted drug delivery (see, e.g., V. V. Ranade, 1989, *J. Clin. Pharmacol.* 29:685).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms can be dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody disclosed herein is 0.1-20 mg/kg, more preferably 1-10 mg/kg. An anti-MMP-9 antibody can be administered, e.g., by intravenous infusion, e.g., at a rate of less than 30, 20, 10, 5, or 1 mg/min to reach a dose of about 1 to 100 mg/m$^2$ or about 5 to 30 mg/m$^2$. For binding proteins smaller in molecular weight than an antibody, appropriate amounts can be proportionally less. Dosage values may vary with the type and severity of the condition to be alleviated. For a particular subject, specific dosage regimens can be adjusted over time according to the individual need and the professional judgment of the person administering or supervising the administration of the compositions.

The pharmaceutical compositions disclosed herein may include a "therapeutically effective amount" or a "prophylactically effective amount" of an MMP-9 binding protein disclosed herein. A "therapeutically effective amount" refers to an amount effective, at dosages and for periods of time necessary, to achieve the desired therapeutic result. A therapeutically effective amount of the composition may vary according to factors such as the disease state, age, sex, and weight of the individual, and the ability of the protein to elicit a desired response in the individual. A therapeutically effective amount is also one in which any toxic or detrimental effects of the composition is outweighed by the therapeutically beneficial effects.

A "therapeutically effective dosage" preferably modulates a measurable parameter, e.g., levels of circulating IgG antibodies or enzymatic activity, by a statistically significant degree or at least about 20%, more preferably by at least about 40%, even more preferably by at least about 60%, and still more preferably by at least about 80% relative to untreated subjects. The ability of a compound to modulate a measurable parameter, e.g., a disease-associated parameter, can be evaluated in an animal model system predictive of efficacy in human disorders and conditions, e.g., a cancer (e.g., metastatic cancer, e.g., metastatic breast cancer), an inflammatory disease (e.g., chronic obstructive pulmonary disease (COPD), asthma, rhinitis (e.g., allergic rhinitis), inflammatory bowel disease, synovitis, rheumatoid arthritis), heart failure, septic shock, neuropathic pain, inflammatory pain, osteoarthritis, or an ocular condition (e.g., macular degeneration). Alternatively, this property of a composition can be evaluated by examining the ability of the compound to modulate a parameter in vitro.

A "prophylactically effective amount" refers to an amount effective, at dosages and for periods of time necessary, to achieve the desired prophylactic result. Typically, because a prophylactic dose is used in subjects prior to or at an earlier stage of disease, the prophylactically effective amount will be less than the therapeutically effective amount.

Stabilization and Retention

In one embodiment, an MMP-9 binding protein is physically associated with a moiety that improves its stabilization and/or retention in circulation, e.g., in blood, serum, lymph, or other tissues, e.g., by at least 1.5, 2, 5, 10, or 50 fold. For example, an MMP-9 binding protein can be associated with a polymer, e.g., a substantially non-antigenic polymer, such as polyalkylene oxides or polyethylene oxides. Suitable polymers will vary substantially by weight. Polymers having molecular number average weights ranging from about 200 to about 35,000 (or about 1,000 to about 15,000, and 2,000 to about 12,500) can be used. For example, an MMP-9 binding protein can be conjugated to a water soluble polymer, e.g., hydrophilic polyvinyl polymers, e.g. polyvinylalcohol and polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

An MMP-9 binding protein can also be associated with a carrier protein, e.g., a serum albumin, such as a human serum albumin. For example, a translational fusion can be used to associate the carrier protein with the MMP-9 binding protein.

Kits

An MMP-9 binding protein described herein can be provided in a kit, e.g., as a component of a kit. For example, the kit includes (a) an MMP-9 binding protein, e.g., a composition that includes an MMP-9 binding protein, and, optionally (b) informational material. The informational material can be descriptive, instructional, marketing or other material that relates to the methods described herein and/or the use of an MMP-9 binding protein for the methods described herein.

The informational material of the kits is not limited in its form. In one embodiment, the informational material can include information about production of the compound, molecular weight of the compound, concentration, date of expiration, batch or production site information, and so forth. In one embodiment, the informational material relates to using the binding protein to treat, prevent, or diagnosis of disorders and conditions, e.g., a cancer (e.g., metastatic cancer, e.g., metastatic breast or colon cancer), an inflammatory disease (e.g., chronic obstructive pulmonary disease (COPD), asthma, rhinitis (e.g., allergic rhinitis), inflammatory bowel disease, synovitis, rheumatoid arthritis), heart failure, septic shock, neuropathic pain, inflammatory pain, osteoarthritis, or an ocular condition (e.g., macular degeneration).

In one embodiment, the informational material can include instructions to administer an MMP-9 binding protein in a suitable manner to perform the methods described herein, e.g., in a suitable dose, dosage form, or mode of administration (e.g., a dose, dosage form, or mode of administration described herein). In another embodiment, the informational material can include instructions to administer an MMP-9 binding protein to a suitable subject, e.g., a human, e.g., a human having, or at risk for, a disorder or condition described herein, e.g., a cancer (e.g., metastatic cancer, e.g., metastatic breast cancer), an inflammatory disease (e.g., chronic obstructive pulmonary disease (COPD), asthma, rhinitis (e.g., allergic rhinitis), inflammatory bowel disease, synovitis, rheumatoid arthritis), heart failure, septic shock, neuropathic pain, inflammatory pain, osteoarthritis, or an ocular condition (e.g., macular degeneration). For example, the material can include instructions to administer an MMP-9 binding protein to a patient with a disorder or condition described herein, e.g., a cancer (e.g., metastatic cancer, e.g., metastatic breast cancer), an inflammatory disease (e.g., chronic obstructive pulmonary disease (COPD), asthma, rhinitis (e.g., allergic rhinitis), inflammatory bowel disease, synovitis, rheumatoid arthritis), heart failure, septic shock, neuropathic pain, inflammatory pain, osteoarthritis, or an ocular condition (e.g., macular degeneration). The informational material of the kits is not limited in its form. In many cases, the informational material, e.g., instructions, is provided in print but may also be in other formats, such as computer readable material.

An MMP-9 binding protein can be provided in any form, e.g., liquid, dried or lyophilized form. It is preferred that an MMP-9 binding protein be substantially pure and/or sterile. When an MMP-9 binding protein is provided in a liquid solution, the liquid solution preferably is an aqueous solution, with a sterile aqueous solution being preferred. When an MMP-9 binding protein is provided as a dried form, reconstitution generally is by the addition of a suitable solvent. The solvent, e.g., sterile water or buffer, can optionally be provided in the kit.

The kit can include one or more containers for the composition containing an MMP-9 binding protein. In some embodiments, the kit contains separate containers, dividers or compartments for the composition and informational material. For example, the composition can be contained in a bottle, vial, or syringe, and the informational material can be contained association with the container. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of an MMP-9 binding protein. For example, the kit includes a plurality of syringes, ampules, foil packets, or blister packs, each containing a single unit dose of an MMP-9 binding protein. The containers of the kits can be air tight, waterproof (e.g., impermeable to changes in moisture or evaporation), and/or light-tight.

The kit optionally includes a device suitable for administration of the composition, e.g., a syringe, inhalant, dropper (e.g., eye dropper), swab (e.g., a cotton swab or wooden swab), or any such delivery device. In one embodiment, the device is an implantable device that dispenses metered doses of the binding protein. The disclosure also features a method of providing a kit, e.g., by combining components described herein.

Treatments

Proteins that bind to MMP-9 and identified by the method described herein and/or detailed herein have therapeutic and prophylactic utilities, particularly in human subjects. These binding proteins are administered to a subject to treat, prevent, and/or diagnose a variety of disorders, including e.g., a cancer (e.g., metastatic cancer, e.g., metastatic breast or colon cancer), an inflammatory disease (e.g., chronic obstructive pulmonary disease (COPD), asthma, rhinitis (e.g., allergic rhinitis), inflammatory bowel disease, synovitis, rheumatoid arthritis), heart failure, septic shock, neuropathic pain, inflammatory pain, osteoarthritis, or an ocular condition (e.g., macular degeneration), or even to cells in culture, e.g. in vitro or ex vivo. Treating includes administering an amount effective to alleviate, relieve, alter, remedy, ameliorate, improve or affect the disorder, the symptoms of the disorder or the predisposition toward the disorder. The treatment may also delay onset, e.g., prevent onset, or prevent deterioration of a disease or condition.

Exemplary disorders include a cancer (e.g., metastatic cancer, e.g., metastatic breast or colon cancer), an inflammatory disease (e.g., chronic obstructive pulmonary disease (COPD), asthma, rhinitis (e.g., allergic rhinitis), inflammatory bowel disease, synovitis, rheumatoid arthritis), heart failure, septic shock, neuropathic pain, inflammatory pain, osteoarthritis, or an ocular condition (e.g., macular degeneration). Some of these disorders are discussed above. Still other disorders that can be treated using an MMP-9 binding protein include: aortic aneurysms, periodontitis, autoimmune blistering disorders of the skin, dermal photoaging.

As used herein, an amount of an target-binding agent effective to prevent a disorder, or a prophylactically effective amount of the binding agent refers to an amount of a target binding agent, e.g., an MMP-9 binding protein, e.g., an anti-MMP-9 antibody described herein, which is effective, upon single- or multiple-dose administration to the subject, for preventing or delaying the occurrence of the onset or recurrence of a disorder, e.g., a disorder described herein.

A binding agent described herein can be used to reduce angiogenesis in a subject, e.g., to treat a cancer (e.g., a solid tumor) or an angiogenesis-associated disorder. The method includes administering the binding to the subject, e.g., in an amount effective to modulate angiogenesis, a symptom of the disorder, or progression of the disorder. The agent (e.g., an MMP-9 binding protein, e.g., an anti-MMP-9 antibody) may be administered multiple times (e.g., at least two, three, five, or ten times) before a therapeutically effective amount is attained. Methods of administering MMP-9 binding proteins and other agents are also described in "Pharmaceutical Compositions." Suitable dosages of the molecules used can depend on the age and weight of the subject and the particular drug used. The binding proteins can be used as competitive agents to inhibit, reduce an undesirable interaction, e.g., between a natural or pathological agent and the MMP-9. The dose of the MMP-9 binding protein can be the amount sufficient to block 90%, 95%, 99%, or 99.9% of the activity of MMP-9 in the patient, especially at the site of disease. Depending on the disease, this may require 0.1, 1.0, 3.0, 6.0, or 10.0 mg/Kg. For an IgG having a molecular mass of 150,000 g/mole (two binding sites), these doses correspond to approximately 18 nM, 180 nM, 540 nM, 1.08 µM, and 1.8 µM of binding sites for a 5 L blood volume.

In one embodiment, the MMP-9 binding proteins are used to inhibit an activity (e.g., inhibit at least one activity of, reduce proliferation, migration, growth or viability) of a cell, e.g., a cancer cell in vivo. The binding proteins can be used by themselves or conjugated to an agent, e.g., a cytotoxic drug, cytotoxin enzyme, or radioisotope. This method includes: administering the binding protein alone or attached to an agent (e.g., a cytotoxic drug), to a subject requiring such treatment. For example, MMP-9 binding proteins that do not substantially inhibit MMP-9 may be used to deliver nanoparticles containing agents, such as toxins, to MMP-9 associated cells or tissues, e.g., tumors.

Because the MMP-9 binding proteins recognize MMP-9-expressing cells and can bind to cells that are associated with (e.g., in proximity of or intermingled with) cancer cells, e.g., cancerous lung, liver, colon, breast, ovarian, epidermal, laryngeal, and cartilage cells, and particularly metastatic cells thereof, leukemia, B cell lymphoma, and multiple myeloma, MMP-9 binding proteins can be used to inhibit (e.g., inhibit at least one activity, reduce growth and proliferation, or kill) any such cells and inhibit carcinogenesis. Reducing MMP-9 activity near a cancer can indirectly inhibit (e.g., inhibit at least one activity, reduce growth and proliferation, or kill) the cancer cells which may be dependent on the MMP-9 activity for metastasis, activation of growth factors, and so forth.

Alternatively, the binding proteins bind to cells in the vicinity of the cancerous cells, but are sufficiently close to the cancerous cells to directly or indirectly inhibit (e.g., inhibit at least one activity, reduce growth and proliferation, or kill) the cancers cells. Thus, the MMP-9 binding proteins (e.g., modified with a toxin, e.g., a cytotoxin) can be used to selectively inhibit cells in cancerous tissue (including the cancerous cells themselves and cells associated with or invading the cancer).

The binding proteins may be used to deliver an agent (e.g., any of a variety of cytotoxic and therapeutic drugs) to cells and tissues where MMP-9 is present. Exemplary agents include a compound emitting radiation, molecules of plants, fungal, or bacterial origin, biological proteins, and mixtures thereof. The cytotoxic drugs can be intracellularly acting cytotoxic drugs, such as toxins short range radiation emitters, e.g., short range, high energy α-emitters.

To target MMP-9 expressing cells, particularly cancerous cells, a prodrug system can be used. For example, a first binding protein is conjugated with a prodrug which is activated only when in close proximity with a prodrug activator. The prodrug activator is conjugated with a second binding protein, preferably one which binds to a non competing site on the target molecule. Whether two binding proteins bind to competing or non competing binding sites can be determined by conventional competitive binding assays. Exemplary drug prodrug pairs are described in Blakely et al., (1996) Cancer Research, 56:3287 3292.

The MMP-9 binding proteins can be used directly in vivo to eliminate antigen-expressing cells via natural complement-dependent cytotoxicity (CDC) or antibody dependent cellular cytotoxicity (ADCC). The binding proteins described herein can include complement binding effector domain, such as the Fc portions from IgG1, -2, or -3 or corresponding portions of IgM which bind complement. In one embodiment, a population of target cells is ex vivo treated with a binding agent described herein and appropriate effector cells. The treatment can be supplemented by the addition of complement or serum containing complement. Further, phagocytosis of target cells coated with a binding protein described herein can be improved by binding of complement proteins. In another embodiment target, cells coated with the binding protein which includes a complement binding effector domain are lysed by complement.

Methods of administering MMP-9 binding proteins are described in "Pharmaceutical Compositions." Suitable dosages of the molecules used will depend on the age and weight of the subject and the particular drug used. The binding proteins can be used as competitive agents to inhibit or reduce an undesirable interaction, e.g., between a natural or pathological agent and the MMP-9.

The MMP-9 binding protein can be used to deliver macro and micromolecules, e.g., a gene into the cell for gene therapy purposes into the endothelium or epithelium and target only those tissues expressing the MMP-9. The binding proteins may be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short range radiation emitters, including, for example, short range, high energy α emitters, as described herein.

In the case of polypeptide toxins, recombinant nucleic acid techniques can be used to construct a nucleic acid that encodes the binding protein (e.g., antibody or antigen-binding fragment thereof) and the cytotoxin (or a polypeptide component thereof) as translational fusions. The recombinant nucleic acid is then expressed, e.g., in cells and the encoded fusion polypeptide isolated.

Alternatively, the MMP-9 binding protein can be coupled to high energy radiation emitters, for example, a radioisotope, such as $^{131}$I, a γ-emitter, which, when localized at a site, results in a killing of several cell diameters. See, e.g., S. E. Order, "Analysis, Results, and Future Prospective of the Therapeutic Use of Radiolabeled Antibody in Cancer Therapy", *Monoclonal Antibodies for Cancer Detection and Therapy*, R. W. Baldwin et al. (eds.), pp 303 316 (Academic Press 1985). Other suitable radioisotopes include a emitters, such as $^{212}$Bi, $^{23}$Bi, and $^{211}$At, and b emitters, such as $^{186}$Re and $^{90}$Y. Moreover, $^{177}$Lu may also be used as both an imaging and cytotoxic agent.

Radioimmunotherapy (RIT) using antibodies labeled with $^{131}$I, $^{90}$Y, and $^{177}$Lu is under intense clinical investigation. There are significant differences in the physical characteristics of these three nuclides and as a result, the choice of radionuclide is very critical in order to deliver maximum radiation dose to a tissue of interest. The higher beta energy particles of $^{90}$Y may be good for bulky tumors. The relatively low energy beta particles of $^{131}$I are ideal, but in vivo dehalogenation of radioiodinated molecules is a major disadvantage for internalizing antibody. In contrast, 177Lu has low energy beta particle with only 0.2-0.3 mm range and delivers much lower radiation dose to bone marrow compared to $^{90}$Y. In addition, due to longer physical half-life (compared to $^{90}$Y), the residence times are higher. As a result, higher activities (more mCi amounts) of $^{177}$Lu labeled agents can be administered with comparatively less radiation dose to marrow. There have been several clinical studies investigating the use of 177Lu labeled antibodies in the treatment of various cancers. (Mulligan T et al., 1995, *Clin. Canc. Res.* 1: 1447-1454; Meredith R F, et al., 1996, *J. Nucl. Med.* 37:1491-1496; Alvarez R D, et al., 1997, *Gynecol. Oncol.* 65: 94-101).

Exemplary Diseases and Conditions

The MMP-9 binding proteins described herein are useful to treat diseases or conditions in which MMP-9 is implicated, e.g., a disease or condition described herein, or to treat one or more symptoms associated therewith. In some embodiments, the MMP-9 binding protein (e.g., MMP-9 binding IgG or Fab) inhibits MMP-9 activity, e.g., catalytic activity.

Examples of such diseases and conditions include a cancer (e.g., leukemia, B cell lymphoma, multiple myeloma, metastatic cancer, e.g., metastatic breast or colon cancer), an inflammatory disease (e.g., chronic obstructive pulmonary disease (COPD), asthma, rhinitis (e.g., allergic rhinitis), inflammatory bowel disease, synovitis, rheumatoid arthritis), heart failure, septic shock, neuropathic pain, inflammatory pain, osteoarthritis, or an ocular condition (e.g., macular degeneration). A therapeutically effective amount of a MMP-9 binding protein is administered to a subject having or suspected of having a disorder in which MMP-9 is implicated, thereby treating (e.g., ameliorating or improving a symptom or feature of a disorder, slowing, stabilizing or halting disease progression) the disorder.

The MMP-9 binding protein is administered in a therapeutically effective amount. A therapeutically effective amount of an MMP-9 binding protein is the amount which is effective, upon single or multiple dose administration to a subject, in treating a subject, e.g., curing, alleviating, relieving or improving at least one symptom of a disorder in a subject to a degree beyond that expected in the absence of such treatment. A therapeutically effective amount of the composition may vary according to factors such as the disease state, age, sex, and weight of the individual, and the ability of the compound to elicit a desired response in the individual. A therapeutically effective amount is also one in which any toxic or detrimental effects of the composition is outweighed by the therapeutically beneficial effects.

A therapeutically effective amount can be administered, typically an amount of the compound which is effective, upon single or multiple dose administration to a subject, in treating a subject, e.g., curing, alleviating, relieving or improving at least one symptom of a disorder in a subject to a degree beyond that expected in the absence of such treatment. A therapeutically effective amount of the composition may vary according to factors such as the disease state, age, sex, and weight of the individual, and the ability of the compound to elicit a desired response in the individual. A therapeutically effective amount is also one in which any toxic or detrimental effects of the composition is outweighed by the therapeutically beneficial effects. A therapeutically effective dosage preferably modulates a measurable parameter, favorably, relative to untreated subjects. The ability of a compound to inhibit a measurable parameter can be evaluated in an animal model system predictive of efficacy in a human disorder.

Dosage regimens can be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Cancer

Matrix metalloproteases (MMPs), such as MMP-9, are believed to contribute to cancer by cleaving components of the ECM and basement membranes, thereby allowing cancer cells to penetrate and infiltrate the subjacent stromal matrix. Additionally, a number of growth-factor receptors, cell adhesion molecules, chemokines, cytokines, apoptotic ligands, and angiogenic factors are substrates of MMPs. Hence, MMP activity may cause activation of growth factors, suppression of tumor cell apoptosis, destruction of chemokine gradients developed by host immune response, or release of angiogenic factors. MMPs may facilitate tumor growth by promoting the release of cell proliferation factors such as insulin-like growth factors which are bound to specific binding proteins (IG-FBPs) (Manes et al., 1997 J. Biol. Chem. 272: 25706-25712).

Collagenases, including MMP-9 and MMP-2, have been found at elevated levels in melanoma and in cancers of the colon, breast, lung, prostate, and bladder. Usually, these elevated levels correlate with higher tumor grade and invasiveness. MMP-2 levels are significantly elevated in the serum of patients with metastatic lung cancer, and in those patients with high levels, response to chemotherapy is diminished. MMP-9 may contribute to tumor invasiveness and recurrence.

Accordingly, the disclosure provides methods of treating (e.g., slowing, eliminating, or reversing tumor growth, preventing or reducing, either in number or size, metastases, reducing or eliminating tumor cell invasiveness, providing an increased interval to tumor progression, or increasing disease-free survival time) cancer (e.g., breast cancer, including Her2+, Her2−, ER+, ER−, Her2+/ER+, Her2+/ER−, Her2−/ER+, and Her2−/ER− breast cancer), head and neck cancer, oral cavity cancer, laryngeal cancer, chondrosarcoma, ovarian cancer, lung cancer, prostate cancer, colon cancer (e.g., primary or metastatic colon cancer), testicular carcinoma, melanoma, leukemia, B cell lymphoma, multiple myeloma, brain tumors (e.g., astrocytomas, glioblastomas, gliomas)) by administering an effective amount of an MMP-9 binding protein (e.g., an anti-MMP-9 IgG or Fab). In some embodiments, the MMP-9 binding protein inhibits MMP-9 activity.

In certain embodiments, the MMP-9 binding protein is administered as a single agent treatment. In other embodiments, the MMP-9 binding protein is administered in combination with an additional anti-cancer agent.

Also provided are methods of preventing or reducing risk of developing cancer, by administering an effective amount of an MMP-9 binding protein to a subject at risk of developing cancer, thereby reducing the subject's risk of developing a cancer.

The disclosure further provides methods of modulating (e.g. reducing or preventing) angiogenesis at a tumor site by administering an effective amount of an MMP-9 binding protein, thereby reducing or preventing angiogenesis at the tumor site. The MMP-9 binding protein may be administered as a single agent therapy or in combination with additional agents.

Also provided are methods for reducing extracellular matrix (ECM) degradation by a tumor, comprising administering an effective amount of an MMP-9 binding protein to a subject, thereby reducing ECM degradation by a tumor in the subject.

The disclosed methods are useful in the prevention and treatment of solid tumors, soft tissue tumors, and metastases thereof. Solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine. Additional exemplary solid tumors include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastrointestinal system carcinomas, colon carcinoma, pancreatic cancer, breast cancer, genitourinary system carcinomas, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, endocrine system carcinomas, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Metastases of the aforementioned cancers can also be treated or prevented in accordance with the methods described herein. Blood cancers (e.g., leukemia, B cell lymphoma) and multiple myeloma can also be treated and/or prevented using the methods described herein.

Guidance for determination of a therapeutically effective amount for treatment of cancer may be obtained by reference to in vivo models of the cancer to be treated. For example, the amount of a MMP-9 binding protein that is a therapeutically effective amount in a rodent or Libechov minipig model of cancer may be used to guide the selection of a dose that is a therapeutically effective amount. A number of rodent models of human cancers are available, including nude mouse/tumor xenograft systems (e.g., melanoma xenografts; see, e.g., Trikha et al. Cancer Research 62:2824-2833 (2002)) and murine models of breast cancer or glioma (e.g., Kuperwasser et al., Cancer Research 65, 6130-6138, (2005); Bradford et al., Br J Neurosurg. 3(2):197-210 (1989)). A melanoblastoma-bearing Libechov minipig (MeLiM) is available as an animal model of melanoma (e.g., Boisgard et al., Eur J Nucl Med Mol Imaging 30(6):826-34 (2003)).

Synovitis

Synovitis is a condition characterized by inflammation of the synovium, a tissue normally only a few cell layers thick. In synovitis, the synovium can become thickened, more cellular, and engorged with fluid. Synovitis can cause pain and inflammation within the affected joint, and is commonly seen in arthritic conditions (e.g., rheumatoid arthritis).

Active synovial MMP-2 is associated with radiographic erosions in patients with early synovitis (Goldbach-Mansky et al, 2000, Arthritis Res, 2:145-153). Synovial tissue expressions of MMP-2 and TIMP-2 are virtually undetectable in normal synovial tissue samples. The synovial tissue samples of patients with erosive disease have significantly higher levels of active MMP-2 than did those of patients without erosions. This may reflect augmented activation of MMP-2 by increased levels of MMP-9 and low levels of TIMP-2 seen in these tissues. Thus, active MMP-2 can contribute to the development and/or progression of rheumatoid arthritis and osteoarthritis.

Increased levels of MMP-9 have been found in the synovial fluid in subjects with arthritis (compared with normal individuals). The disclosure provides methods of treating (e.g., ameliorating, stabilizing, reducing, or eliminating a symptom of synovitis such as pain, joint swelling, synovial thickening, increased synovial fluid) synovitis by administering a therapeutically effective amount of a MMP-9 binding protein. Also provided are methods which combine MMP-9 binding protein therapy with additional therapies. Current therapies for synovitis include anti-inflammatory medications (e.g. NSAIDS and ibuprofen), cortisone injections into the joint, and surgical treatment (e.g., synovectomy). One or more of these treatments can be used in combination with an MMP-9 binding protein (e.g., an inhibitory MMP-9 binding protein, e.g., an anti-MMP-9 IgG or Fab) to treat this condition.

Guidance for determination of a therapeutically effective amount of an MMP-9 binding protein may be obtained from an animal model of synovitis. Rodent models of synovitis are available, including a rat model of synovitis-like inflammation (Cirino et al., J Rheumatol. 21(5):824-9 (1994)), and a model of carrageenan synovitis in male Wistar rats (Walsh et al. Lab Invest. 78(12):1513-21 (1998)).

Rheumatoid Arthritis and Associated Conditions

Rheumatoid arthritis (RA) is an autoimmune, chronic inflammatory disease that causes joint swelling and pain and normally results in joint destruction. RA generally follows a relapsing/remitting course, with "flares" of disease activity interspersed with remissions of disease symptoms. RA is associated with a number of additional inflammatory disorders, including Sjogren's syndrome (dry eyes and mouth caused by inflammation of tear and saliva glands), pleuritis (inflammation of the pleura that causes pain upon deep breath and coughing), rheumatoid nodules (nodular sites of inflammation that develop within the lungs), pericarditis (inflammation of the pericardium that causes pain when lying down or leaning forward), Felty syndrome (splenomegaly and leucopenia observed in conjunction with RA, making the subject prone to infection), and vasculitis (an inflammation of the blood vessels which can block blood flow). MMP-9 and MMP-16 have been implicated in rheumatoid arthritis.

Symptoms of active RA include fatigue, lack of appetite, low grade fever, muscle and joint aches, and stiffness. Muscle and joint stiffness are usually most notable in the morning and after periods of inactivity. During flares, joints frequently become red, swollen, painful, and tender, generally as a consequence of synovitis.

Treatment for rheumatoid arthritis involves a combination of medications, rest, joint strengthening exercises, and joint protection. Two classes of medications are used in treating rheumatoid arthritis: anti-inflammatory "first-line drugs," and Disease-Modifying Antirheumatic Drugs (DMARDs)." The first-line drugs, include NSAIDS (e.g., aspirin, naproxen, ibuprofen, and etodolac) and cortisone (corticosteroids). DMARDS, such as gold (e.g., gold salts, gold thioglucose, gold thiomalate, oral gold), methotrexate, sulfasalazine, D-penicillamine, azathioprine, cyclophosphamide, chlorambucil, and cyclosporine, leflunomide, etanercept, infliximab, anakinra, and adalimumab, and hydroxychloroquine, promote disease remission and prevent progressive joint destruction, but they are not anti-inflammatory agents.

Increased levels of MMP-9 have been found in the synovial fluid in subjects with arthritis (compared with normal individuals). The disclosure provides methods of treating (e.g., ameliorating, stabilizing, or eliminating one or more symptoms or ameliorating or stabilizing the subject's score on a RA scale) rheumatoid arthritis by administering a therapeutically effective amount of a MMP-9 binding protein to a subject having or suspected of having RA. Additionally provides are methods of treating RA by administering a therapeutically effective amount of a MMP-9 binding protein and at least one NSAID and/or DMARDS.

Further provided are methods of treating (e.g., ameliorating, stabilizing, or eliminating one or more symptoms) rheumatoid arthritis associated disorders (Sjogren's syndrome, pleuritis, pulmonary rheumatoid nodules, pericarditis, Felty syndrome, and vasculitis) by administering a therapeutically effective amount of an MMP-9 binding protein.

Scales useful for assessing RA and symptoms of RA include the Rheumatoid Arthritis Severity Scale (RASS; Bardwell et al., (2002) *Rheumatology* 41(1):38-45), SF-36 Arthritis Specific Health Index (ASHI; Ware et al., (1999) *Med. Care.* 37(5 Suppl):MS40-50), Arthritis Impact Measurement Scales or Arthritis Impact Measurement Scales 2 (AIMS or AIMS2; Meenan et al. (1992) *Arthritis Rheum.* 35(1):1-10); the Stanford Health Assessment Questionnaire (HAQ), HAQII, or modified HAQ (see, e.g., Pincus et al. (1983) *Arthritis Rheum.* 26(11):1346-53).

Guidance for the determination of the dosage that delivers a therapeutically effective amount of a MMP-9 binding protein may be obtained from animal models of rheumatoid arthritis, such as collagen-induced arthritis (CIA), which is induced, typically in rodents, by immunization with autologous or heterologous type II collagen in adjuvant (Williams et al. Methods Mol. Med. 98:207-16 (2004)).

COPD

Chronic Obstructive Pulmonary Disease (COPD), also known as chronic obstructive airway disease (COAD), is a group of diseases characterized by the pathological limitation of airflow in the airway that is not fully reversible. COPD is the umbrella term for chronic bronchitis, emphysema and a range of other lung disorders. It is most often due to tobacco smoking, but can be due to other airborne irritants such as coal dust, asbestos or solvents, as well as congenital conditions such as alpha-1-antitrypsin deficiency.

The main symptoms of COPD include dyspnea (shortness of breath) lasting for months or perhaps years, possibly accompanied by wheezing, and a persistent cough with sputum production. It is possible the sputum may contain blood (hemoptysis) and become thicker, usually due to damage of the blood vessels of the airways. Severe COPD could lead to cyanosis caused by a lack of oxygen in the blood. In extreme cases it could lead to cor pulmonale due to the extra work required by the heart to get blood to flow through the lungs.

COPD is particularly characterised by the spirometric measurement of a ratio of forced expiratory volume over 1 second ($FEV_1$) to forced vital capacity (FVC) being <0.7 and the $FEV_1$<80% of the predicted value as measured by a plethysmograph. Other signs include a rapid breathing rate (tachypnea) and a wheezing sound heard through a stethoscope. Pulmonary emphysema is NOT the same as subcutaneous emphysema, which is a collection of air under the skin that may be detected by the crepitus sounds produced on palpation.

Treatment for COPD includes inhalers that dilate the airways (bronchodilators) and sometimes theophylline. The COPD patient must stop smoking. In some cases inhaled steroids are used to suppress lung inflammation, and, in severe cases or flare-ups, intravenous or oral steroids are given. Antibiotics are used during flare-ups of symptoms as infections can worsen COPD. Chronic, low-flow oxygen, non-invasive ventilation, or intubation may be needed in some cases. Surgery to remove parts of the disease lung has been shown to be helpful for some patients with COPD. Lung rehabilitation programs may help some patients. Lung transplant is sometimes performed for severe cases. Bronchodilators that can be used include:

There are several types of bronchodilators used clinically with varying efficacy: for example, $\beta_2$ agonists, $M_3$ antimuscarinics, leukotriene antagonists, cromones, corticosteroids, and xanthines. These drugs relax the smooth muscles of the airway allowing for improved airflow. $\beta_2$ agonists include: Salbutamol (Ventolin), Bambuterol, Clenbuterol, Fenoterol, and Formoterol, and long acting $\beta_2$ agonists (LABAs) such as Salmeterol. $M_3$ muscarinic antagonists (anticholinergics) include the quaternary $M_3$ muscarinic antagonist Ipratropium, which is widely prescribed with the $\beta_2$ agonist salbutamol, Ipratropium, and Tiotropium, which can be combined with a LABA and inhaled steroid. Cromones include Cromoglicate and Nedocromil. Leukotriene antagonists can be used and include Montelukast, Pranlukast, Zafirlukast. Xanthines include theophylline, methylxanthines, theobromine. More aggressive EMR interventions include IV $H_1$ antihistamines and IV dexamethasone. Phosphodiesterase-4 antagonists include roflumilast and cilomilast. Corticosteroids can be used and include glucocorticoids, beclomethasone, mometasone, and fluticasone. Corticosteroids are often combined with bronchodilators in a single inhaler. Salmeterol and fluticasone can be combined (Advair). TNF antagonists include cachexin, cachectin infliximab, adalimumab and etanercept.

The disclosure provides methods of treating COPD (e.g., ameliorating symptoms or the worsening of COPD) by administering a therapeutically effective amount of a MMP-9 binding protein (e.g., an inhibitory MMP-9 binding protein, e.g., an anti-MMP-9 IgG or Fab) to a subject having or suspected of having COPD. Also provided are methods of treating COPD by administering a therapeutically effective amount of a MMP-9 binding protein with another COPD treatment (e.g., $\beta_2$ agonists, $M_3$ antimuscarinics, leukotriene antagonists, cromones, corticosteroids, and xanthines).

Guidance regarding the efficacy and dosage an MMP-9 binding protein which will deliver a therapeutically effective amount of the protein can be obtained from an animal model of COPD, see e.g., PCT publication WO 2007/084486 and references cited therein.

Asthma

Asthma is a chronic condition involving the respiratory system in which the airway occasionally constricts, becomes inflamed, and is lined with excessive amounts of mucus, often in response to one or more triggers. These episodes may be triggered by such things as exposure to an environmental stimulant (or allergen) such as cold air, warm air, moist air, exercise or exertion, or emotional stress. In children, the most common triggers are viral illnesses such as those that cause the common cold. This airway narrowing causes symptoms such as wheezing, shortness of breath, chest tightness, and coughing. The airway constriction responds to bronchodilators.

In some individuals asthma is characterized by chronic respiratory impairment. In others it is an intermittent illness marked by episodic symptoms that may result from a number of triggering events, including upper respiratory infection, stress, airborne allergens, air pollutants (such as smoke or traffic fumes), or exercise. Some or all of the following symptoms may be present in those with asthma: dyspnea, wheezing, stridor, coughing, an inability for physical exertion. Some asthmatics who have severe shortness of breath and tightening of the lungs never wheeze or have stridor and their symptoms may be confused with a COPD-type disease.

An acute exacerbation of asthma is commonly referred to as an asthma attack. The clinical hallmarks of an attack are shortness of breath (dyspnea) and either wheezing or stridor.

During an asthma episode, inflamed airways react to environmental triggers such as smoke, dust, or pollen. The airways narrow and produce excess mucus, making it difficult to breathe. In essence, asthma is the result of an immune response in the bronchial airways.

The airways of asthmatics are "hypersensitive" to certain triggers/stimuli. In response to exposure to these triggers, the bronchi (large airways) contract into spasm (an "asthma attack"). Inflammation soon follows, leading to a further narrowing of the airways and excessive mucus production, which leads to coughing and other breathing difficulties.

The most effective treatment for asthma is identifying triggers, such as pets or aspirin, and limiting or eliminating exposure to them. Desensitization is currently the only known "cure" to the disease.

Symptomatic control of episodes of wheezing and shortness of breath is generally achieved with fast-acting bronchodilators.

Relief medication: Short-acting, selective beta$_2$-adrenoceptor agonists, such as salbutamol (albuterol USAN), levalbuterol, terbutaline and bitolterol, can be used. Older, less selective adrenergic agonists, such as inhaled epinephrine and ephedrine tablets, can be used. Anticholinergic medications, such as ipratropium bromide may be used.

Preventative medication: Current treatment protocols recommend prevention medications such as an inhaled corticosteroid, which helps to suppress inflammation and reduces the swelling of the lining of the airways, in anyone who has frequent (greater than twice a week) need of relievers or who has severe symptoms. If symptoms persist, additional preventive drugs are added until the asthma is controlled. With the proper use of prevention drugs, asthmatics can avoid the complications that result from overuse of relief medications. Preventive agents include: inhaled glucocorticoids (e.g., ciclesonide, beclomethasone, budesonide, flunisolide, fluticasone, mometasone, and triamcinolone), leukotriene modifiers (e.g., montelukast, zafirlukast, pranlukast, and zileuton), mast cell stabilizers (e.g., cromoglicate (cromolyn), and nedocromil), antimuscarinics/anticholinergics (e.g., ipratropium, oxitropium, and tiotropium), methylxanthines (e.g., theophylline and aminophylline), antihistamines, an IgE blocker such as omalizumab, methotrexate).

Long-acting beta$_2$-adrenoceptor agonists can be used and include salmeterol, formoterol, bambuterol, and sustained-release oral albuterol. Combinations of inhaled steroids and long-acting bronchodilators are becoming more widespread; the most common combination currently in use is fluticasone/salmeterol (Advair in the United States, and Seretide in the United Kingdom). Another combination is budesonide/formoterol which is commercially known as Symbicort.

Concentrations of MMP-9 are increased in the bronchoalveolar lavage fluid (BAL), sputum, bronchi, and serum of asthmatic subjects compared with normal individuals. The disclosure provides methods of treating asthma (e.g., ameliorating symptoms or the worsening of asthma) by administering a therapeutically effective amount of a MMP-9 binding protein (e.g., an inhibitory MMP-9 binding protein, e.g., an anti-MMP-9 IgG or Fab) to a subject having or suspected of having asthma. Also provided are methods of treating asthma by administering a therapeutically effective amount of a MMP-9 binding protein with another asthma treatment (e.g., glucocorticoids, leukotriene modifiers, mast cell stabilizers, antimuscarinics/anticholinergics, antihistamines, an IgE blocker, methotrexate.

Guidance regarding the efficacy and dosage an MMP-9 binding protein which will deliver a therapeutically effective amount of the protein can be obtained from an animal model of asthma, see e.g., U.S. Pat. No. 5,602,302, or European Pat. No. EP1192944 B1, and references cited therein.

Rhinitis

Rhinitis is the medical term describing irritation and inflammation of some internal areas of the nose. The primary symptom of rhinitis is a runny nose. It is caused by chronic or acute inflammation of the mucous membrane of the nose due to viruses, bacteria or irritants. The inflammation results in the generating of excessive amounts of mucus producing a runny nose, nasal congestion and post-nasal drip. Rhinitis has also been found to adversely affect more than just the nose, throat, and eyes. It has been associated with sleeping problems, problems with the ears, and even been linked to learning problems Rhinitis is caused by an increase in histamine. This increase is likely caused by airborne allergens. These allergens may affect an individual's nose, throat, or eyes and cause an increase in fluid production within these areas. There are two types of Rhinitis that the general population may suffer from: allergic rhinitis and nonallergic rhinitis. Rhinitis is considered IgE-mediated when the sufferer is classified as having allergic rhinitis.

The typical method of diagnosis and monitoring of allergic rhinitis is skin testing, also known as "scratch testing" and "prick testing" due to the series of pricks and/or scratches made into the patient's skin. Small amounts of suspected allergens and/or their extracts (pollen, grass, mite proteins, peanut extract, etc.) are introduced to sites on the skin marked with pen or dye.

The management of rhinitis is mainly medical. Treatment for seasonal rhinitis is only needed during the appropriate time of the year. Current treatments include: antihistamine pills and sprays, leukotriene antagonists, nasal corticosteroid sprays, decongestant pills or sprays, allergen immunotherapy saline irrigation of sinus cavities through the use of a neti pot or by other means; nasal obstruction in perennial rhinitis may be treated by surgery.

The disclosure provides methods of treating rhinitis (e.g., allergic rhinitis) (e.g., ameliorating symptoms or the worsening of rhinitis) by administering a therapeutically effective amount of a MMP-9 binding protein (e.g., an inhibitory MMP-9 binding protein, e.g., an anti-MMP-9 IgG or Fab) to a subject having or suspected of having rhinitis. Also provided are methods of treating rhinitis by administering a therapeutically effective amount of a MMP-9 binding protein with another rhinitis treatment (e.g., $\beta_2$ agonists, $M_3$ antimuscarinics, leukotriene antagonists, cromones, corticosteroids, and xanthines).

Guidance regarding the efficacy and dosage an MMP-9 binding protein which will deliver a therapeutically effective amount of the protein can be obtained from an animal model of rhinitis, see e.g., Zhao et al. (2005) *Rhinology* 43:47-54, and references cited therein.

IBD

Inflammatory bowel disease (IBD) is a group of inflammatory conditions of the large intestine and, in some cases, the small intestine. The main forms of IBD are Crohn's disease and ulcerative colitis (UC). Accounting for far fewer cases are other forms of IBD: Collagenous colitis, Lymphocytic colitis, Ischaemic colitis, Diversion colitis, Behçet's syndrome, Infective colitis, and Indeterminate colitis.

The main difference between Crohn's disease and UC is the location and nature of the inflammatory changes. Crohn's can affect any part of the gastrointestinal tract, from mouth to anus (skip lesions), although a majority of the cases start in the terminal ileum. Ulcerative colitis, in contrast, is restricted to the colon and the rectum.

Microscopically, ulcerative colitis is restricted to the mucosa (epithelial lining of the gut), while Crohn's disease affects the whole bowel wall.

Finally, Crohn's disease and ulcerative colitis present with extra-intestinal manifestations (such as liver problems, arthritis, skin manifestations and eye problems) in different proportions.

Rarely, a definitive diagnosis of neither Crohn's disease nor ulcerative colitis can be made because of idiosyncrases in the presentation. In this case, a diagnosis of indeterminate colitis may be made.

Diagnosis: Although very different diseases, both may present with any of the following symptoms: abdominal pain, vomiting, diarrhea, hematochezia, weight loss, weight gain and various associated complaints or diseases (arthritis, pyoderma gangrenosum, primary sclerosing cholangitis). Diagnosis is generally by colonoscopy with biopsy of pathological lesions.

Treatment: Depending on the level of severity, IBD may require immunosuppression to control the symptoms. Immunosuppresives such as azathioprine, methotrexate, or 6-mercaptopurine can be used. More commonly, treatment of IBD requires a form of mesalamine. Often, steroids are used to control disease flares and were once acceptable as a maintenance drug. In use for several years in Crohns disease patients and recently in patients with Ulcerative Colitis, biologicals, such as Remicade, have been used. Severe cases may require surgery, such as bowel resection, strictureplasty or a temporary or permanent colostomy or ileostomy. Alternative medicine treatments for bowel disease exist in various forms, however such methods concentrate on controlling underlying pathology in order to avoid prolonged steroidal exposure or surgical excisement.

Usually the treatment is started by administering drugs, such as Prednisone, with high anti-inflammatory affects. Once the inflammation is successfully controlled, the patient is usually switched to a lighter drug, such as Asacol—a mesalamine, to keep the disease in remission. If unsuccessful, a combination of the aforementioned immunosurppression drugs with a mesalamine (which may also have an anti-inflammatory effect) may or may not be administered, depending on the patient.

The disclosure provides methods of treating IBD (e.g., ameliorating symptoms or the worsening of IBD) by administering a therapeutically effective amount of a MMP-9 binding protein (e.g., an inhibitory MMP-9 binding protein, e.g., an anti-MMP-9 IgG or Fab) to a subject having or suspected of having IBD. Also provided are methods of treating IBD by administering a therapeutically effective amount of a MMP-9 binding protein with another IBD treatment (e.g., azathioprine, methotrexate, 6-mercaptopurine, a mesalamine, Remicade).

Guidance regarding the efficacy and dosage an MMP-9 binding protein which will deliver a therapeutically effective amount of the protein can be obtained from animal models of IBD, see e.g., those described in U.S. Pat. No. 6,114,382, PCT publication WO 2004/071186 and references cited therein.

Ocular Conditions

Macular Degeneration. Macular degeneration progressively destroys the macula, the central portion of the retina, impairing central vision, leading to difficulty with reading, driving, and/or other daily activities that require fine central vision. While there are a number of different forms of macular degeneration, the most common is age-related macular degeneration (AMD). AMD presents as either "dry" or "wet", with the wet type being far more common. In wet AMD, fluid leaking from newly formed subretinal blood vessels (subretinal neovascularization) distorts the macula and impairs vision. Symptoms of AMD include loss or impairment in central vision (generally slowing in dry AMD and rapidly in wet AMD) and abnormal visual perception of straight lines (e.g., straight lines appear wavy). Supplements of zinc and the antioxidants vitamin C, vitamin E and beta-carotene reportedly slow the progression of wet AMD.

The disclosure provides methods of treating (e.g., ameliorating vision, stabilizing vision degradation, or reducing the rate of vision degradation) AMD (wet AMD or dry AMD) by administering a therapeutically effective amount of a MMP-9 binding protein (e.g., an inhibitory MMP-9 binding protein, e.g., an anti-MMP-9 IgG or Fab) to a subject having or suspected of having AMD. Also provided are methods of treating AMD by administering a therapeutically effective amount of a MMP-9 binding protein with another AMD treatment (e.g., zinc, vitamin C, vitamin E and/or beta-carotene).

Guidance regarding the efficacy and dosage an MMP-9 binding protein which will deliver a therapeutically effective amount of the protein can be obtained from an animal model of macular degeneration, e.g., a *Coturnix coturnix* japonica (Japanese quail) model of macular degeneration (U.S. Pat. No. 5,854,015), or wound creation on the Bruch's membrane of a C57BL/6J mouse, e.g., with a krypton laser (US App. No. 20030181531).

Corneal Disease. Keratoconus is a progressive disease where the cornea thins and changes shape. The resulting distortion (astigmatism) frequently causes nearsightedness. Keratoconus may also cause swelling and scarring of the cornea and vision loss.

The disclosure provides methods of treating (e.g., improving or stabilizing vision, or improving, stabilizing, reducing eliminating, or preventing corneal scarring) keratoconus in a subject having or suspected of having keratoconus by administering an effective amount of a MMP-9 binding protein (e.g., an inhibitory MMP-9 binding protein, e.g., an anti-MMP-9 IgG or Fab).

Guidance regarding the efficacy and dosage an MMP-9 binding protein which will deliver a therapeutically effective amount of the protein can be obtained from an animal model of keratoconus, e.g., the inbred SKC mouse line, which serves as a model for a subset of keratoconus (Tachibana et al. Investig Opthalmol Visual Sci, 43:51-57 (2002)).

Corneal Infection. Also provided are methods of treating (e.g., preventing, reducing, stabilizing or eliminating corneal scarring as a result of the infection) corneal infection by administering an effective amount of a MMP-9 binding protein (e.g., an inhibitory MMP-9 binding protein, e.g., an anti-MMP-9 IgG or Fab) to a subject having or suspected of having a corneal infection. Additionally, methods are provided for treatment of corneal infection by administering a MMP-9 binding protein and a therapeutic agent which treats the infectious agent (e.g., an antibiotic or anti-viral agent).

Guidance regarding the efficacy and dosage an MMP-9 binding protein which will deliver a therapeutically effective amount of the protein can be obtained from an animal model of corneal infection, e.g., a rabbit model of experimental keratomycosis, in which keratitis is induced with a standardized inoculum of *Candida albicans* (SC 5314) placed on a debrided cornea (Goldblum et al. Antimicrob Agents Chemother 49:1359-1363 (2005)).

Osteoarthritis

Osteoarthritis, also known as degenerative arthritis, is characterized by the breakdown and eventual loss of the cartilage of one or more joints. Osteoarthritis commonly affects the hands, feet, spine, and large weight-bearing joints, such as the hips and knees. The disclosure provides methods of treating (e.g., stabilizing, reducing, or eliminating joint pain, stabilizing or improving performance on general health or osteoarthritis scales) osteoarthritis by administering a therapeutically effective amount of a MMP-9 binding protein (e.g., an inhibitory MMP-9 binding protein, e.g., an anti-MMP-9 IgG or Fab) to a subject having or suspected of having osteoarthritis.

Current medical treatment of osteoarthritis includes conservative measures (e.g., rest, weight reduction, physical and occupational therapy) and medications such as acetaminophen, pain-relieving creams applied to the skin over the joints such as capsaicin, salycin, methyl salicylate, and menthol, nonsteroidal anti-inflammatory drugs (NSAIDs) such as aspirin, ibuprofen, nabumetone, and naproxen, and Cox-2 inhibitors. The disclosure further provides methods of treating osteoarthritis by administering a therapeutically effective amount of a MMP-9 binding protein (e.g., an inhibitory MMP-9 binding protein, e.g., an anti-MMP-9 IgG or Fab) and another osteoarthritis therapy (e.g. acetaminophen, a topical pain-relieving cream, a nonsteroidal anti-inflammatory drug (NSAID) such as aspirin, ibuprofen, nabumetone, or naproxen, or a Cox-2 inhibitor).

Scales useful for the assessment of osteoarthritis include the Knee Injury and Osteoarthritis Outcome Score (KOOS; Roos et al. (1998) *J. Orthop. Sports Phys. Ther.* 28(2):88-96), Western Ontario and McMaster Universities Osteoarthrtis Index (WOMAC; Roos et al. (2003) *Health Qual. Life Outcomes* 1(1):17), and the 36-item Short Form General Health Scale (SF-36 GHS), as well as other assessment tools known in the art.

Guidance regarding the efficacy and dosage an MMP-9 binding protein which will deliver a therapeutically effective amount of the protein can be obtained from an animal model of osteoarthritis, e.g., injection of mono-iodoacetate (MIA) into the femorotibial joint of rodents which promotes loss of articular cartilage similar to that noted in human osteoarthritis (Guzman et al. Toxicol Pathol. 31(6):619-24 (2003)), or transection of the anterior cruciate ligament (ACL) in canines to induce osteoarthritis (Fife and Brandt J Clin Invest. 84(5): 1432-1439 (1989)).

Heart Failure

Heart failure is caused by any condition which reduces the efficiency of the myocardium, or heart muscle, through damage or overloading. As such, it can be caused by as diverse an array of conditions as myocardial infarction, hypertension and amyloidosis. Over time these increases in workload will produce changes to the heart itself. Congestive heart failure (CHF), congestive cardiac failure (CCF) or just heart failure, is a condition that can result from any structural or functional cardiac disorder that impairs the ability of the heart to fill with or pump a sufficient amount of blood through the body.

Other related terms include ischemic cardiomyopathy (implying that the cause of heart failure is coronary artery disease) and dilated cardiomyopathy (which is a description of echocardiographic findings characteristic of heart failure but which does not suggest any specific etiology).

Congestive heart failure exacerbation or decompensated heart failure (DHF) refer to episodes in which a patient with known chronic heart failure acutely develops symptoms.

Symptoms are dependent on two factors. The first is based on the side of the heart, right or left, that is involved. The second factor is based on the type of failure, either diastolic or systolic. Symptoms and presentation may be indistinguishable making diagnosis impossible based on symptoms.

Given that the left side of the heart pumps blood from the lungs to the organs, failure to do so leads to congestion of the lung veins and symptoms that reflect this, as well as reduced supply of blood to the tissues. The predominant respiratory symptom is shortness of breath on exertion (dyspnea, dyspnée d'effort)—or in severe cases at rest—and easy fatigueability. Orthopnea is increasing breathlessness on reclining. Paroxysmal nocturnal dyspnea is a nighttime attack of severe breathlessness, usually several hours after going to sleep. Poor circulation to the body leads to dizziness, confusion and diaphoresis and cool extremities at rest.

The right side of the heart pumps blood returned from the tissues to the lungs to exchange $CO_2$ for $O_2$. Hence, failure of the right side leads to congestion of peripheral tissues. This may lead to peripheral edema or anasarca and nocturia. In more severe cases, ascites and hepatomegaly may develop.

Heart failure may decompensate easily; this may occur as the result of any intercurrent illness (such as pneumonia), but specifically myocardial infarction, anaemia, hyperthyroidism or arrhythmias. These place additional strain on the heart muscle, which may cause symptoms to rapidly worsen. Excessive fluid or salt intake (including intravenous fluids for unrelated indications, but more commonly from dietary indiscretion), and medication that causes fluid retention (such as NSAIDs and thiazolidinediones), may also precipitate decompensation.

In examining a patient with possible heart failure, a health professional would look for particular signs. General signs indicating heart failure are a laterally displaced apex beat (as the heart is enlarged) and a gallop rhythm (additional heart sounds) in case of decompensation. Heart murmurs may indicate the presence of valvular heart disease, either as a cause (e.g. aortic stenosis) or as a result (e.g. mitral regurgitation) of the heart failure.

Predominant left-sided clinical signs are tachypnea and increased work of breathing (signs of respiratory distress not specific to heart failure), rales or crackles, which suggests the development of pulmonary edema, dullness of the lung fields to percussion and diminished breath sounds at the bases of the lung, which suggests the development of a pleural effusion (fluid collection in the pleural cavity) that is transudative in nature, and cyanosis which suggests hypoxemia, caused by the decreased rate of diffusion of oxygen from fluid-filled alveoli to the pulmonary capillaries.

Right-sided signs are peripheral edema, ascites and hepatomegaly, an increased jugular venous pressure, which can be increased further by the hepatojugular reflux, and a parasternal heave.

Causes of left-side heart failure include: hypertension (high blood pressure), aortic and mitral valve disease, aortic coarctation. Causes of right-side heart failure include pulmonary hypertension (e.g. due to chronic lung disease), pulmonary or tricuspid valve disease. Causes of both types include: Ischemic heart disease (due to insufficient vascular supply, usually as a result of coronary artery disease); this may be chronic or due to acute myocardial infarction (a heart attack), chronic arrhythmias (e.g. atrial fibrillation), cardiomyopathy of any cause, cardiac fibrosis, chronic severe anemia, thyroid disease (hyperthyroidism and hypothyroidism).

Treatments of heart failure include: moderate physical activity, bed rest, weight reduction, monitoring weight, sodium restriction, fluid restriction, diuretic agents, vasodilator agents, positive inotropes, ACE inhibitors, beta blockers, and aldosterone antagonists (e.g., spironolactone), angiotensin II receptor antagonist therapy (also referred to as $AT_1$-antagonists or angiotensin receptor blockers) (particularly using candesartan). Diuretics include loop diuretics (e.g., furosemide, bumetanide), thiazide diuretics (e.g., hydrochlorothiazide, chlorthalidone, chlorthiazide), potassium-sparing diuretics (e.g., amiloride), spironolactone, eplerenone. Beta blockers include bisoprolol, carvedilol, and extended-release metoprolol. Positive inotropes include digoxin, dobutamine. Phosphodiesterase inhibitors such as milrinone are sometimes utilized in severe cardiomyopathy. Alternative vasodilators include the combination of isosorbide dinitrate/hydralazine. Aldosterone receptor antagonists include spironolactone and the related drug eplerenone. Recombinant neuroendocrine hormones can also be used and include Nesiritide, a recombinant form of B-natriuretic peptide. Vasopressin receptor antagonists that can be used include tolvaptan and conivaptan. Devices and surgery options include cardiac resynchronization therapy (CRT; pacing both the left and right ventricles), through implantation of an bi-ventricular pacemaker, or surgical remodelling of the heart, an implantable cardioverter-defibrillator (ICD), left ventricular assist devices (LVADs).

The disclosure provides methods of treating heart failure (e.g., ameliorating symptoms or the worsening of heart failure) by administering a therapeutically effective amount of a MMP-9 binding protein (e.g., an inhibitory MMP-9 binding protein, e.g., an anti-MMP-9 IgG or Fab) to a subject having or suspected of having heart failure. Also provided are methods of treating heart failure by administering a therapeutically effective amount of a MMP-9 binding protein with another heart failure treatment (e.g., a diuretic agent, a vasodilator agent, a positive inotrope, an ACE inhibitor, a beta blocker, and an aldosterone antagonist (e.g., spironolactone), angiotensin II receptor antagonist therapy (also referred to as $AT_1$-antagonists or angiotensin receptor blockers)).

Guidance regarding the efficacy and dosage an MMP-9 binding protein which will deliver a therapeutically effective amount of the protein can be obtained from an animal model of heart failure, see e.g., U.S. Pat. No. 7,166,762 and references cited therein.

Septic Shock

Septic shock is a serious medical condition caused by decreased tissue perfusion and oxygen delivery as a result of infection and sepsis. It can cause multiple organ failure and death. Its most common victims are children, immunocompromised individuals, and the elderly, as their immune systems cannot cope with the infection as well as healthy adults are able. The mortality rate from septic shock is approximately 50%.

Symptoms include: Refractory hypotension—hypotension despite adequate fluid resuscitation. In adults it is defined as a systolic blood pressure <90 mmHg, or a MAP<60 mmHg, without the requirement for inotropic support, or a reduction of 40 mmHg in the systolic blood pressure from baseline. In children, it is BP<2 SD of the normal blood pressure. In addition to the two criteria above, two or more of the following can be present: Hyperventilation (high respiratory rate) >20 breaths per minute or, on blood gas, a $PaCO_2$ less than 32 mmHg, and/or White blood cell count <4000 cells/mm$^3$ or >12000 cells/mm$^3$ (<4×10$^9$ or >12×10$^9$ cells/L).

A subclass of distributive shock, shock refers specifically to decreased tissue perfusion resulting in end-organ dysfunction. Cytokines TNFα, IL-1β, IL-6 released in a large scale inflammatory response results in massive vasodilation, increased capillary permeability, decreased systemic vascular resistance, and hypotension. Hypotension reduces tissue perfusion pressure and thus tissue hypoxia ensues. Finally, in an attempt to offset decreased blood pressure, ventricular dilatation and myocardial dysfunction will occur.

The process of infection by bacteria or fungi can result in systemic signs and symptoms that are variously described. In rough order of severity, these are bacteremia or fungemia; septicemia; sepsis, severe sepsis or sepsis syndrome; septic shock; refractory septic shock; multiple organ dysfunction syndrome, and death.

The condition develops as a response to certain microbial molecules which trigger the production and release of cellular mediators, such as tumor necrosis factors (TNF); these act to stimulate immune response. Besides TNFα, other cytokines involved in the development of septic shock include interleukin-1β, and interferon γ.

Treatment primarily consists of 1) Volume resuscitation 2) Early antibiotic administration 3) Rapid source identification and control and 4) Support of major organ dysfunction. Among the choices for pressors, norepinephrine (optionally plus dobutamine as needed for cardiac output) or epinephrine can be used. Antimmediator agents may be of some limited use in severe clinical situations: Corticosteroids, especially if combined with a mineralocorticoid, can reduce mortality among patients who have relative adrenal insufficiency; or recombinant activated protein C (drotrecogin alpha). A sophorolipid mixture can be used.

The disclosure provides methods of treating septic shock by administering a therapeutically effective amount of a MMP-9 binding protein (e.g., an inhibitory MMP-9 binding protein, e.g., an anti-MMP-9 IgG or Fab) to a subject having or suspected of having septic shock. Also provided are methods of treating septic shock by administering a therapeutically effective amount of a MMP-9 binding protein with another septic shock treatment (e.g., corticosteroid, sophorolipid mixture, or antibiotics).

Guidance regarding the efficacy and dosage an MMP-9 binding protein which will deliver a therapeutically effective amount of the protein can be obtained from an animal model of septic shock, see e.g., U.S. Pat. No. 7,262,178, and references cited therein.

Neuropathic Pain

Neuropathic pain is a complex, chronic pain state that usually is accompanied by tissue injury. With neuropathic pain, the nerve fibers themselves might be damaged, dysfunctional, or injured. These damaged nerve fibers send incorrect signals to other pain centers. The impact of a nerve fiber injury includes a change in nerve function both at the site of injury and areas around the injury.

Neuropathic pain often seems to have no obvious cause. It responds poorly to standard pain treatment and occasionally might get worse instead of better over time. For some people, it can lead to serious disability. One example of neuropathic pain is called phantom limb syndrome. This occurs when an arm or a leg has been removed because of illness or injury, but the brain still gets pain messages from the nerves that originally carried impulses from the missing limb. These nerves now seem to misfire and cause pain. Some common causes of neuropathic pain include: alcoholism, amputation, back, leg, and hip problems, cancer chemotherapy, diabetes, facial nerve problems, HIV infection or AIDS, multiple sclerosis, shingles, and spine surgery.

Some symptoms of neuropathic pain include shooting pain, burning pain, tingling, and numbness.

Improvement is often possible with proper treatment. Treatments include: administering an NSAID, an analgesic (e.g., with morphine), an anticonvulsant drug (e.g., an anticonvulsant described in U.S. Pat. No. 5,760,007), an antidepressant drug, or other pain reliever. If another condition, such as diabetes, is involved, better management of that disorder might alleviate the neuropathic pain. In cases that are difficult to treat, a pain specialist might use invasive or implantable device therapies to effectively manage the pain. Electrical stimulation of the nerves involved in neuropathic pain generation might significantly control the pain symptoms.

MMP-9 and MMP-2 have been found to play roles in the development of neuropathic pain. MMP-9 is upregaulated in the early phase of neuropathic pain development, while MMP-2 is upregulated in the late phase of neuropathic pain development. Targeting and inhibition of MMP-9 and/or MMP-2 is a therapeutic approach to treating neuropathic pain. The disclosure provides methods of treating neuropathic pain by administering a therapeutically effective amount of a MMP-9 binding protein (e.g., an inhibitory MMP-9 binding protein, e.g., an anti-MMP-9 IgG or Fab) to a subject having or suspected of having neuropathic pain. Also provided are methods of treating neuropathic pain by administering a therapeutically effective amount of a MMP-9 binding protein with another neuropathic pain treatment (e.g., an NSAID, an analgesic (e.g., with morphine), an anticonvulsant drug, an antidepressant drug, or other pain reliever; invasive or implantable device therapies).

Guidance regarding the efficacy and dosage an MMP-9 binding protein which will deliver a therapeutically effective amount of the protein can be obtained from an animal model of neuropathic pain, such as the L5 spinal nerve ligation (SNL) animal model, see e.g., Kawasaki et al., Feb. 10, 2008, Nat. Med. advance on-line publication doi:10.1038/nm1723. See also U.S. Pat. No. 5,760,007 and references cited therein.

Inflammatory Pain

Inflammatory pain is precipitated by an insult to the integrity of tissues at a cellular level. This can happen, e.g., with penetration wounds, burns, extreme cold, fractures, arthritis, autoimmune conditions, excessive stretching, infections and vasoconstriction. Multiple chemicals can mediate the inflammatory process. For example, vascular components, fibroblastic components and tissue cell components can be involved. For example, mast cells release histamines and 5HT; macrophages activate fibroblasts, which in turn release interleukins and Tumor Necrosis Factor; cycloloxygenase activates prostaglandin and leukotrienes. The inflammatory mediators can directly affect nociceptors or may sensitize them to touch or movement, even some distance from the inflammatory field.

Treatments of inflammatory pain include nonsteroidal anti-inflammatory drugs (NSAIDs) and corticosteroids. Anti-inflammatory drugs include: ibuprofen, naproxen, naproxen sodium, aspirin, ketoprofen, valdecoxib, celecoxib, sulindac, oxaprozin, salsalate, piroxicam, indomethacin, etodolac, meloxicam, nabumetone, ketorolac tromethamine, rofecoxib.

Guidance regarding the efficacy and dosage an MMP-9 binding protein which will deliver a therapeutically effective amount of the protein can be obtained from an animal model of inflammatory pain, such as intraplantar injection of Carrageenan in an animal model, see e.g., Jabakhanji et al., Molecular Pain 2006, 2:1.

Endometriosis

Endometriosis is a common medical condition characterized by growth beyond or outside the uterus of endometrium, the tissue that normally lines the uterus. In endometriosis, the endometrium is found to be growing outside the uterus, on or in other areas of the body. Normally, the endometrium is shed each month during the menstrual cycle; however, in endometriosis, the misplaced endometrium is usually unable to exit the body. The endometriotic tissues still detach and bleed, but the result is far different: internal bleeding, degenerated blood and tissue shedding, inflammation of the surrounding areas, pain, and formation of scar tissue may result. In addition, depending on the location of the growths, interference with the normal function of the bowel, bladder, small intestines and other organs within the pelvic cavity can occur. In very rare cases, endometriosis has also been found in the skin, the lungs, the eye, the diaphragm, and the brain.

A major symptom of endometriosis is severe recurring pain. The amount of pain a woman feels is not necessarily related to the extent or stage (1 through 4) of endometriosis. Some women will have little or no pain despite having extensive endometriosis affecting large areas or having endometriosis with scarring. On the other hand, women may have severe pain even though they have only a few small areas of endometriosis.

Symptoms of endometriosis can include (but are not limited to): Painful, sometimes disabling menstrual cramps (dysmenorrhea), pain may get worse over time (progressive pain), chronic pain (typically lower back pain and pelvic pain, also abdominal), painful sex (dyspareunia), painful bowel movements (dyschezia) or painful urination (dysuria), heavy menstrual periods (menorrhagia) nausea and vomiting, premenstrual or intermenstrual spotting (bleeding between periods), and infertility and subfertility. Endometriosis may lead to fallopian tube obstruction. Bowel obstruction (possibly including vomiting, crampy pain, diarrhea, a rigid and tender abdomen, and distention of the abdomen, depending on where the blockage is and what is causing it) or complete urinary retention. In addition, women who are diagnosed with endometriosis may have gastrointestinal symptoms that may mimic irritable bowel syndrome, as well as fatigue.

Patients who rupture an endometriotic cyst may present with an acute abdomen as a medical emergency. Endometriotic cysts in the thoracic cavity may cause some form of thoracic endometriosis syndrome, most often catamenial pneumothorax.

Diagnosis. Health history and a physical examination can in many patients lead the physician to suspect the diagnosis. Use of imaging tests (e.g., ultrasound and magnetic resonance imaging (MRI)) may identify larger endometriotic areas, such as nodules or endometriotic cysts. The only sure way to confirm an endometriosis diagnosis is by laparoscopy. The diagnosis is based on the characteristic appearance of the disease, if necessary corroborated by a biopsy. Laparoscopy also allows for surgical treatment of endometriosis.

Treatment. Generally, endometriosis-directed drug therapy (other than the oral contraceptive pill) is utilized after a confirmed surgical diagnosis of endometriosis. Treatments include: NSAIDs and other pain medication, commonly used in conjunction with other therapy; Gonadotropin Releasing Hormone (GnRH) Agonist; Hormone suppression therapy; Progesterone or Progestins; avoiding products with xenoestrogens, which have a similar effect to naturally produced estrogen and can increase growth of the endometrium; continuous hormonal contraception; suppressive steroids such as Danazol (Danocrine) and gestrinone; aromatase inhibitors. Surgical treatment is usually a good choice if endometriosis is extensive, or very painful. Surgical treatments range from minor to major surgical procedures. Laparoscopy is very useful not only to diagnose endometriosis, but to treat it—endometriotic tissue can be ablated or removed in an attempt to restore normal anatomy. Laparotomy can be used for more extensive surgery either in attempt to restore normal anatomy. Other procedures include hysterectomy, bilateral salpingo-oophorectomy (removal of the fallopian tubes and ovaries), bowel resection. For patients with extreme pain, a presacral neurectomy may be indicated where the nerves to the uterus are cut.

MMP-9 is upregulated in endometriosis and may contribute to survival and invasion of endometriosis. The disclosure provides methods of treating endometriosis by administering a therapeutically effective amount of a MMP-9 binding protein (e.g., an inhibitory MMP-9 binding protein, e.g., an anti-MMP-9 IgG or Fab) to a subject having or suspected of having endometriosis. Also provided are methods of treating endometriosis by administering a therapeutically effective amount of a MMP-9 binding protein with another endometriosis treatment (e.g., corticosteroid, sophorolipid mixture, or antibiotics).

Guidance regarding the efficacy and dosage an MMP-9 binding protein which will deliver a therapeutically effective amount of the protein can be obtained from an animal model of endometriosis, see e.g., U.S. Pat. Nos. 6,429,353 and 7,220,890, and references cited therein.

Combination Therapies

The MMP-9 binding proteins described herein, e.g., anti-MMP-9 Fabs or IgGs, can be administered in combination with one or more of the other therapies for treating a disease or condition associated with MMP-9 activity, e.g., a disease or condition described herein. For example, an MMP-9 binding protein can be used therapeutically or prophylactically with surgery, another MMP-9 inhibitor, e.g., a small molecule inhibitor, another anti-MMP-9 Fab or IgG (e.g., another Fab or IgG described herein), an anti-MMP-9/-2 binding protein (e.g., IgG or Fab, e.g., 539A-M0237-D02 or a protein containing one or more heavy and/or light chains CDRs thereof), an anti-MMP14 binding protein (e.g., IgG or Fab, e.g., DX-2400, or a protein described in U.S. Pub. App. No. 2007-0217997), peptide inhibitor, or small molecule inhibitor. Examples of other MMP-9 inhibitors that can be used in combination therapy with an MMP-9 binding protein described herein are provided herein.

One or more small-molecule MMP inhibitors can be used in combination with one or more MMP-9 binding proteins described herein. For example, the combination can result in a lower dose of the small-molecule inhibitor being needed, such that side effects are reduced.

The MMP-9 binding proteins described herein can be administered in combination with one or more of the other therapies for treating cancers, including, but not limited to: surgery; radiation therapy, and chemotherapy. For example, proteins that inhibit MMP-9 or that inhibit a downstream event of MMP-9 activity (e.g., cleavage of pro-MMP-2 to MMP-2) can also be used in combination with other anti-cancer therapies, such as radiation therapy, chemotherapy, surgery, or administration of a second agent. For example, the second agent can be a Tie-1 inhibitor (e.g., Tie-1 binding proteins; see e.g., U.S. Ser. No. 11/199,739 and PCT/US2005/0284, both filed Aug. 9, 2005). As another example, the second agent can be an anti-MMP14 binding protein (e.g., IgG or Fab, e.g., DX-2400, or a protein described in U.S. Pub. App. No. 2007-0217997). As another example, the second agent can be one that targets or negatively regulates the VEGF signaling pathway. Examples of this latter class include VEGF antagonists (e.g., anti-VEGF antibodies such as bevacizumab) and VEGF receptor antagonists (e.g., anti-VEGF receptor antibodies). One particularly preferred combination includes bevacizumab. As a further example, the second agent is an inhibitor of plasmin, such as a kunitz domain-containing protein or polypeptide (e.g., a plasmin-inhibiting kunitz domain disclosed in U.S. Pat. No. 6,010,880, such as a protein or polypeptide comprising the amino acid sequence MHSF-CAFKAETGPCRARFDRWFFNIFTRQ-CEEFIYGGCEGNQNRFESLEECKKMCTRD (SEQ ID NO:1)). As another example, the second agent is an agent that binds to Her2, such as a Her2-binding antibody (e.g., trastuzumab). The combination can further include 5-FU and leucovorin, and/or irinotecan.

Inhibitors of MMP-9 (e.g., the MMP-9 binding proteins disclosed herein) can potentiate the activity of an agent that targets Her2 (e.g., a Her2-binding antibody such as trastuzumab). Accordingly, in one combination therapy for the treatment of breast cancer, the second therapy is an agent that binds Her2, such as a Her2-binding antibody (e.g., trastuzumab). When an MMP-9 binding protein is used in a combination therapy with a Her2 binding agent, the dose of the Her2 binding agent may be reduced from the dose of the Her2 binding agent when administered not in combination with an MMP-9 binding protein (e.g., is at least 10%, 25%, 40%, or 50% less than the dose of the Her2 binding agent when administered not in combination with a MMP-9 binding protein). For example, the dose of trastuzumab, when administered in a combination therapy with an MMP-9 binding protein is less than about 4.0, 3.6, 3.0, 2.4, or 2 mg/kg as an initial (loading) dose, and less than about 2.0, 1.8, 1.5, 1.2, or 1 mg/kg in subsequent doses.

The MMP-9 binding proteins described herein can also be administered in combination with one or more other therapies for treating ocular disorders, such as surgical or medical (e.g., administration of a second agent) therapies. For example, in treatment of age-related macular degeneration (e.g., wet age-related macular degeneration), an MMP-9 binding protein may be administered in conjunction with (e.g., before, during, or after) laser surgery (laser photocoagulation or photocoagulation therapy). As another example, the MMP-9 binding protein can be administered in combination with a second agent, such as a VEGF antagonist (e.g., an anti-VEGF antibody such as bevacizumab or ranibizumab) or a VEGF receptor antagonist (e.g., anti-VEGF receptor antibodies).

The term "combination" refers to the use of the two or more agents or therapies to treat the same patient, wherein the use or action of the agents or therapies overlap in time. The agents or therapies can be administered at the same time (e.g., as a single formulation that is administered to a patient or as two separate formulations administered concurrently) or sequentially in any order. Sequential administrations are administrations that are given at different times. The time between administration of the one agent and another agent can be minutes, hours, days, or weeks. The use of an MMP-9 binding protein described herein can also be used to reduce the dosage of another therapy, e.g., to reduce the side-effects associated with another agent that is being administered, e.g., to reduce the side-effects of an anti-VEGF antibody such as bevacizumab. Accordingly, a combination can include administering a second agent at a dosage at least 10, 20, 30, or 50% lower than would be used in the absence of the MMP-9 binding protein.

In addition, a subject can be treated for an angiogenesis-associated disorder, e.g., a cancer, by administering to the subject a first and second agent. For example, the first agent modulates early stage angiogenesis and the second agent modulates a subsequent stage of angiogenesis or also modulates early stage angiogenesis. The first and second agents can be administered using a single pharmaceutical composition or can be administered separately. In one embodiment, the first agent is a VEGF pathway antagonist (e.g., an inhibitor of a VEGF (e.g., VEGF-A, -B, or -C) or a VEGF receptor (e.g., KDR or VEGF receptor III (Flt4)) or a bFGF pathway antagonist (e.g., an antibody that binds to bFGF or a bFGF receptor). Other VEGF pathway antagonists are also described, herein and elsewhere. In one embodiment, the second agent inhibits or decreases the mobility or invasiveness of tumor cells. For example, the second agent comprises an MMP-9 binding protein. For example, the second agent is an MMP-9 binding protein described herein.

Once a tumor reaches a certain size (e.g., ~1-2 mm), the tumor requires new vasculature prior to increasing its mass. An early stage of tumor angiogenesis can include a signal from the tumor, e.g., secretion of VEGF, to stimulate the growth of new blood vessels from the host and infiltration of the tumor by the vessels. VEGF can, for example, stimulate proliferation of endothelial cells that are then assembled into blood vessels. A late stage of tumor growth can include metastasis, mobility and invasiveness of tumor cells. This mobility and invasiveness may involve the action of matrix metalloproteinases, e.g., MMP-9, MMP-16, or MMP-24. Thus, an effective therapy to treat angiogenesis-related disorders can involve a combination of an agent that modulates an early stage angiogenesis (e.g., VEGF pathway antagonists, e.g., anti-VEGF (e.g., bevacizumab) or anti-VEGF receptor (e.g., anti-KDR) antibodies; or antagonists of other pro-angiogenic pathways, e.g., anti-bFGF antibodies or anti-bFGF receptor (e.g., anti-bFGF receptor-1, -2, -3) antibodies) and an agent that modulates a late stage of tumor growth can include metastasis, mobility and invasiveness of tumor cells (e.g., antagonists of MMP-9 (e.g., anti-MMP-9 antibodies (e.g., an antibody disclosed herein)). One or more of these agents can be used in combination. One or more of these agents may also be used in combination with other anti-cancer therapies, such as radiation therapy or chemotherapy.

Exemplary VEGF receptor antagonists include inhibitors of a VEGF (e.g., VEGF-A, -B, or -C, for example bevacizumab), modulators of VEGF expression (e.g., INGN-241, oral tetrathiomolybdate, 2-methoxyestradiol, 2-methoxyestradiol nanocrystal dispersion, bevasiranib sodium, PTC-299, Veglin), inhibitors of a VEGF receptor (e.g., KDR or VEGF receptor III (Flt4), for example anti-KDR antibodies, VEGFR2 antibodies such as CDP-791, IMC-1121B, VEGFR2 blockers such as CT-322), VEGFR3 antibodies such as mF4-31C1 from Imclone Systems, modulators of VEGFR expression (e.g., VEGFR1 expression modulator Sima-027) or inhibitors of VEGF receptor downstream signaling.

Exemplary inhibitors of VEGF include bevacizumab, pegaptanib, ranibizumab, NEOVASTAT®, AE-941, VEGF Trap, and PI-88.

Exemplary VEGF receptor antagonists include inhibitors of VEGF receptor tyrosine kinase activity. 4-[4-(1-Amino-1-methylethyl)phenyl]-2-[4-(2-morpholin-4-yl-ethyl)phenylamino]pyrimidine-5-carbonitrile (JNJ-17029259) is one of a structural class of 5-cyanopyrimidines that are orally available, selective, nanomolar inhibitors of the vascular endothelial growth factor receptor-2 (VEGF-R2). Additional examples include: PTK-787/ZK222584(Astra-Zeneca), SU5416, SU11248 (Pfizer), and ZD6474 ([N-(4-bromo-2-fluorophenyl)-6-methoxy-7-[(1-methylpiperidin-4-yl)methoxy]quinazolin-4-amine]), vandetanib, cediranib, AG-013958, CP-547632, E-7080, XL-184, L-21649, and ZK-304709. Other VEGF antagonist agents are broad specificity tyrosine kinase inhibitors, e.g., SU6668 (see, e.g., Bergers, B. et al., 2003 J. Clin. Invest. 111:1287-95), sorafenib, sunitinib, pazopanib, vatalanib, AEE-788, AMG-706, axitinib, BIBF-1120, SU-14813, XL-647, XL-999, ABT-869, BAY-57-9352, BAY-73-4506, BMS-582664, CEP-7055, CHIR-265, OSI-930, and TKI-258. Also useful are agents that down regulate VEGF receptors on the cell surface, such as fenretinide, and agents which inhibit VEGF receptor downstream signaling, such as squalamine The second agent or therapy can also be another anti-cancer agent or therapy. Non-limiting examples of anti-cancer agents include, e.g., anti-microtubule agents, topoisomerase inhibitors, antimetabolites, mitotic inhibitors, alkylating agents, intercalating agents, agents capable of interfering with a signal transduction pathway, agents that promote apoptosis, radiation, and antibodies against other tumor-associated antigens (including naked antibodies, immunotoxins and radioconjugates). Examples of the particular classes of anti-cancer agents are provided in detail as follows: antitubulin/antimicrotubule, e.g., paclitaxel, vincristine, vinblastine, vindesine, vinorelbin, taxotere; topoisomerase I inhibitors, e.g., irinotecan, topotecan, camptothecin, doxorubicin, etoposide, mitoxantrone, daunorubicin, idarubicin, teniposide, amsacrine, epirubicin, merbarone, piroxantrone hydrochloride; antimetabolites, e.g., fluorouracil (5 FU), methotrexate, 6 mercaptopurine, 6 thioguanine, fludarabine phosphate, cytarabine/Ara C, trimetrexate, gemcitabine, acivicin, alanosine, pyrazofurin, N-Phosphoracetyl-L-Asparate=PALA, pentostatin, 5 azacitidine, 5 Aza 2' deoxycytidine, ara A, cladribine, 5 fluorouridine, FUDR, tiazofurin, N-[5-[N-(3,4-dihydro-2-methyl-4-oxoquinazolin-6-ylmethyl)-N-methylamino]-2-thenoyl]-L-glutamic acid; alkylating agents, e.g., cisplatin, carboplatin, mitomycin C, BCNU=Carmustine, melphalan, thiotepa, busulfan, chlorambucil, plicamycin, dacarbazine, ifosfamide phosphate, cyclophosphamide, nitrogen mustard, uracil mustard, pipobroman, 4 ipomeanol; agents acting via other mechanisms of action, e.g., dihydrolenperone, spiromustine, and desipeptide; biological response modifiers, e.g., to enhance anti-tumor responses, such as interferon; apoptotic agents, such as actinomycin D; and anti-hormones, for example anti-estrogens such as tamoxifen or, for example antiandrogens such as 4'-cyano-3-(4-fluorophenylsulphonyl)-2-hydroxy-2-methyl-3'-(trifluoromethyl)propionanilide.

A combination therapy can include administering an agent that reduces the side effects of other therapies. The agent can be an agent that reduces the side effects of anti-cancer treatments. For example, the agent can be leucovorin.

Combination therapies that include administering an MMP-9 binding protein or other binding protein described herein can also be used to treat a subject having or at risk for another angiogenesis related disorder (e.g., a disorder other than cancer, e.g., disorders that include undesired endothelial cell proliferation or undesirable inflammation, e.g., rheumatoid arthritis).

Diagnostic Uses

Proteins that bind to MMP-9 and identified by the method described herein and/or detailed herein have in vitro and in vivo diagnostic utilities. The MMP-9 binding proteins described herein (e.g., the proteins that bind and inhibit, or the proteins that bind but do not inhibit MMP-9) can be used, e.g., for in vivo imaging, e.g., during a course of treatment for a disease or condition in which MMP-9 is active, e.g., a disease or condition described herein, or in diagnosing a disease or condition described herein.

In one aspect, the disclosure provides a diagnostic method for detecting the presence of an MMP-9, in vitro or in vivo (e.g., in vivo imaging in a subject). The method can include localizing MMP-9 within a subject or within a sample from a subject. With respect to sample evaluation, the method can include, for example: (i) contacting a sample with MMP-9 binding protein; and (ii) detecting location of the MMP-9 binding protein in the sample.

An MMP-9 binding protein can also be used to determine the qualitative or quantitative level of expression of MMP-9 in a sample. The method can also include contacting a reference sample (e.g., a control sample) with the binding protein, and determining a corresponding assessment of the reference sample. A change, e.g., a statistically significant change, in the formation of the complex in the sample or subject relative to the control sample or subject can be indicative of the presence of MMP-9 in the sample. In one embodiment, the MMP-9 binding protein does not cross react with another metalloproteinase.

The MMP-9 binding proteins are also useful for in vivo tumor imaging. Better clinical endpoints are needed to monitor the efficacy of drugs, such as MMP-inhibitors, that are designed to block enzymatic function (Zucker et al, 2001, Nature Medicine 7:655-656). Imaging of tumors in vivo by using labeled MMP-9 binding proteins could be of help to target the delivery of the binding protein to tumors for cancer diagnosis, intraoperative tumor detection, and for investigations of drug delivery and tumor physiology. MMP-9 binding proteins can be used to monitor native enzymatic activity in vivo at invasive sites. Another exemplary method includes: (i) administering the MMP-9 binding protein to a subject; and (iii) detecting location of the MMP-9 binding protein in the subject. The detecting can include determining location or time of formation of the complex.

The MMP-9 binding protein can be directly or indirectly labeled with a detectable substance to facilitate detection of the bound or unbound antibody. Suitable detectable substances include various enzymes, prosthetic groups, fluorescent materials, luminescent materials and radioactive materials.

Complex formation between the MMP-9 binding protein and MMP-9 can be detected by evaluating the binding protein bound to the MMP-9 or unbound binding protein. Conventional detection assays can be used, e.g., an enzyme-linked immunosorbent assays (ELISA), a radioimmunoassay (RIA) or tissue immunohistochemistry. Further to labeling the MMP-9 binding protein, the presence of MMP-9 can be assayed in a sample by a competition immunoassay utilizing standards labeled with a detectable substance and an unlabeled MMP-9 binding protein. In one example of this assay, the biological sample, the labeled standards, and the MMP-9 binding protein are combined and the amount of labeled standard bound to the unlabeled binding protein is determined. The amount of MMP-9 in the sample is inversely proportional to the amount of labeled standard bound to the MMP-9 binding protein.

Fluorophore and chromophore labeled proteins can be prepared. Because antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer, 1968, Science 162:526 and Brand, L. et al., 1972, Annu. Rev. Biochem. 41:843 868. The proteins can be labeled with fluorescent chromophore groups by conventional procedures such as those disclosed in U.S. Pat. Nos. 3,940,475, 4,289,747, and 4,376,110. One group of fluorescers having a number of the desirable properties described above is the xanthene dyes, which include the fluoresceins and rhodamines. Another group of fluorescent compounds are the naphthylamines. Once labeled with a fluorophore or chromophore, the protein can be used to detect the presence or localization of the MMP-9 in a sample, e.g., using fluorescent microscopy (such as confocal or deconvolution microscopy).

Histological Analysis. Immunohistochemistry can be performed using the proteins described herein. For example, in the case of an antibody, the antibody can be synthesized with a label (such as a purification or epitope tag), or can be detectably labeled, e.g., by conjugating a label or label-binding group. For example, a chelator can be attached to the antibody. The antibody is then contacted to a histological preparation, e.g., a fixed section of tissue that is on a microscope slide. After an incubation for binding, the preparation is washed to remove unbound antibody. The preparation is then analyzed, e.g., using microscopy, to identify if the antibody bound to the preparation.

Of course, the antibody (or other polypeptide or peptide) can be unlabeled at the time of binding. After binding and washing, the antibody is labeled in order to render it detectable.

Protein Arrays. The MMP-9 binding protein can also be immobilized on a protein array. The protein array can be used as a diagnostic tool, e.g., to screen medical samples (such as isolated cells, blood, sera, biopsies, and the like). Of course, the protein array can also include other binding proteins, e.g., that bind to MMP-9 or to other target molecules.

Methods of producing polypeptide arrays are described, e.g., in De Wildt et al., 2000, Nat. Biotechnol. 18:989-994; Lueking et al., 1999, Anal. Biochem. 270:103-111; Ge, 2000, Nucleic Acids Res. 28, e3, I-VII; MacBeath and Schreiber, 2000, Science 289:1760-1763; WO 01/40803 and WO 99/51773A1. Polypeptides for the array can be spotted at high speed, e.g., using commercially available robotic apparati, e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer.

For example, the array can be an array of antibodies, e.g., as described in De Wildt, supra. Cells that produce the proteins can be grown on a filter in an arrayed format. Polypeptide production is induced, and the expressed polypeptides are immobilized to the filter at the location of the cell. A protein array can be contacted with a labeled target to determine the extent of binding of the target to each immobilized polypeptide. Information about the extent of binding at each address of the array can be stored as a profile, e.g., in a computer database. The protein array can be produced in replicates and used to compare binding profiles, e.g., of a target and a non-target.

FACS (Fluorescence Activated Cell Sorting). The MMP-9 binding protein can be used to label cells, e.g., cells in a sample (e.g., a patient sample). The binding protein is also attached (or attachable) to a fluorescent compound. The cells can then be sorted using fluorescence activated cell sorter (e.g., using a sorter available from Becton Dickinson Immunocytometry Systems, San Jose Calif.; see also U.S. Pat. Nos. 5,627,037; 5,030,002; and 5,137,809). As cells pass through the sorter, a laser beam excites the fluorescent compound while a detector counts cells that pass through and determines whether a fluorescent compound is attached to the cell by detecting fluorescence. The amount of label bound to each cell can be quantified and analyzed to characterize the sample.

The sorter can also deflect the cell and separate cells bound by the binding protein from those cells not bound by the binding protein. The separated cells can be cultured and/or characterized.

In Vivo Imaging. Also featured is a method for detecting the presence of a MMP-9 expressing tissues in vivo. The method includes (i) administering to a subject (e.g., a patient having, e.g., a cancer (e.g., metastatic cancer, e.g., metastatic breast cancer), an inflammatory disease (e.g., chronic obstructive pulmonary disease (COPD), asthma, rhinitis (e.g., allergic rhinitis), inflammatory bowel disease, synovitis, rheumatoid arthritis), heart failure, septic shock, neuropathic pain, osteoarthritis, or an ocular condition (e.g., macular degeneration)) an anti-MMP-9 antibody, conjugated to a detectable marker; (ii) exposing the subject to a means for detecting said detectable marker to the MMP-9 expressing tissues or cells. For example, the subject is imaged, e.g., by NMR or other tomographic means.

Examples of labels useful for diagnostic imaging include radiolabels such as $^{131}$I, $^{111}$In, $^{123}$I, $^{99m}$Tc, $^{32}$P, $^{125}$I, $^{3}$H, $^{14}$C, and $^{188}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short range radiation emitters, such as isotopes detectable by short range detector probes can also be employed. The protein can be labeled with such reagents; for example, see Wensel and Meares, 1983, *Radioimmunoimaging and Radioimmunotherapy*, Elsevier, New York for techniques relating to the radiolabeling of antibodies and D. Colcher et al., 1986, *Meth. Enzymol.* 121: 802 816.

The binding protein can be labeled with a radioactive isotope (such as $^{14}$C, $^{3}$H, $^{35}$S, $^{125}$I, $^{32}$P, $^{131}$I). A radiolabeled binding protein can be used for diagnostic tests, e.g., an in vitro assay. The specific activity of a isotopically-labeled binding protein depends upon the half life, the isotopic purity of the radioactive label, and how the label is incorporated into the antibody.

In the case of a radiolabeled binding protein, the binding protein is administered to the patient, is localized to cells bearing the antigen with which the binding protein reacts, and is detected or "imaged" in vivo using known techniques such as radionuclear scanning using e.g., a gamma camera or emission tomography. See e.g., A. R. Bradwell et al., "Developments in Antibody Imaging", *Monoclonal Antibodies for Cancer Detection and Therapy*, R. W. Baldwin et al., (eds.), pp 65 85 (Academic Press 1985). Alternatively, a positron emission transaxial tomography scanner, such as designated Pet VI located at Brookhaven National Laboratory, can be used where the radiolabel emits positrons (e.g., $^{11}$C, $^{18}$F, $^{15}$O, and $^{13}$N).

MRI Contrast Agents. Magnetic Resonance Imaging (MRI) uses NMR to visualize internal features of living subject, and is useful for prognosis, diagnosis, treatment, and surgery. MRI can be used without radioactive tracer compounds for obvious benefit. Some MRI techniques are summarized in EP-A-0 502 814. Generally, the differences related to relaxation time constants T1 and T2 of water protons in different environments is used to generate an image. However, these differences can be insufficient to provide sharp high resolution images.

The differences in these relaxation time constants can be enhanced by contrast agents. Examples of such contrast agents include a number of magnetic agents paramagnetic agents (which primarily alter T1) and ferromagnetic or superparamagnetic (which primarily alter T2 response). Chelates (e.g., EDTA, DTPA and NTA chelates) can be used to attach (and reduce toxicity) of some paramagnetic substances (e.g., $Fe^{+3}$, $Mn^{+2}$, $Gd^{+3}$). Other agents can be in the form of particles, e.g., less than 10 mm to about 10 nM in diameter). Particles can have ferromagnetic, antiferromagnetic, or superparamagnetic properties. Particles can include, e.g., magnetite ($Fe_3O_4$), $\gamma$-$Fe_2O_3$, ferrites, and other magnetic mineral compounds of transition elements. Magnetic particles may include: one or more magnetic crystals with and without nonmagnetic material. The nonmagnetic material can include synthetic or natural polymers (such as sepharose, dextran, dextrin, starch and the like.

The MMP-9 binding protein can also be labeled with an indicating group containing of the NMR active $^{19}$F atom, or a plurality of such atoms inasmuch as (i) substantially all of naturally abundant fluorine atoms are the $^{19}$F isotope and, thus, substantially all fluorine containing compounds are NMR active; (ii) many chemically active polyfluorinated compounds such as trifluoracetic anhydride are commercially available at relatively low cost; and (iii) many fluorinated compounds have been found medically acceptable for use in humans such as the perfluorinated polyethers utilized to carry oxygen as hemoglobin replacements. After permitting such time for incubation, a whole body MRI is carried out using an apparatus such as one of those described by Pykett, 1982, *Sci. Am.* 246:78 88 to locate and image tissues expressing MMP-9.

The contents of all references, pending patent applications and published patents, cited throughout this application are hereby expressly incorporated by reference. The following examples provide further illustrate and are not limiting.

EXAMPLES

Example 1

Selection and Screening of Anti-MMP-9 Fabs and IgGs

Two strategies were employed to identify anti-MMP-9 antibodies:

(1) Capture of a non-biotinylated form of MMP-9 (PMA-activated) by a biotinylated binding but not inhibiting Fab with the subsequent immobilization of the biotinylated entity on a streptavidin coated surface; and (2) MMP-9 (PMA activated) in solution. Phage, suitably depleted (e.g., previous contact with streptavidin) were allowed to interact with the target, unbound phage washed away and the output sampled and/or amplified for the next round of selection. This was repeated until the output phage in ELISA analysis indicate a high percentage of binders. 128/2076 unique sFabs were identified by ELISA and sequencing.

After sequencing analysis, the phage display were converted into sFabs and then into IgG1s. Their ability to inhibit MMP-9 and other MMPs (1, 3, 7, 8, 9, 10, 12, 13, 14) was determined by usual means. Compounds were initially screened at 1 µM against MMP-9 and those compounds that inhibited MMP-9>80% were subjected to additional screens against purified recombinant human MMPs. For these additional screens, an $IC_{50}$ value was determined.

Example 2

Exemplary Clone Identified

539A-M0166-F10 is a selective inhibitor of human MMP-9 ($IC_{50}$=1.8±0.3 nM). 539A-M0166-F10 does not inhibit activity of mouse MMP-9. 539A-M0166-F10 potently inhibits activity of hMMP-9 on tumor sections.

Example 3

CDR Amino Acid Sequences of MMP-9 Binding Anti-MMP-9 Binding Fabs

CDR sequences of MMP-9 binding proteins are summarized in Table 3.

TABLE 3

CDR Sequences of MMP-9 Binding Proteins (SEQ ID NOS 13-324, respectively, in order appearance)

| Isolate | Initial Name | Groups | LV-CDR1 | LV-CDR2 | LV-CDR3 | HV-CDR1 | HV-CDR2 | HV-CDR3 |
|---|---|---|---|---|---|---|---|---|
| 539A-R0017-A02 | 539A-M0071-A05 | 1 | RASQGISNYLA | AASNLQS | QQYKTYPFT | PYRMH | YIGSSGGPTAYADSVKG | ARAGTFFDS |
| 539A-R0017-A03 | 539A-M0071-A06 | 2 | RSSQSLVSSNGNTYLN | YKVSNRDS | MQGTHWPYT | MYRMM | YIGSSGGMTSYADSVKG | DSVFRGERDAFDI |
| 539A-R0017-A04 | 539A-M0071-D03 | 3 | RASQSISSSFLA | GASSRAT | QQTYSTPLT | KYSMV | VISPSGGYTGYADSVKG | MRVPAAIGGWLDP |
| 539A-R0017-A05 | 539A-M0071-D11 | 4 | RASQNIGKFLA | GASTLQL | QKYDSALWT | GYGMW | SISPSGGWTFYADSVKG | VKVRHGGGFDY |
| 539A-R0017-A06 | 539A-M0071-E02 | 5 | KSSQNVLLSSNSKNYLA | WASTRES | QQYYSIPWS | NYRMS | SIGSSGGQTMYADSVKG | SHPVSGGVFDF |
| 539A-R0017-A07 | 539A-M0071-E03 | 6 | RASQGISSWLA | YATSSLQS | QQSKSFPPT | RYRMN | YIGSSGGNTAYADSVKG | RRIGVGAKGGGTFDI |
| 539A-R0017-A08 | 539A-M0071-E10 | 7 | RASQSVSSYLA | DASNRAT | QQRSNWPLT | HYRMY | YIGSSGGMTSYADSVKG | SDRSGDNYYGMDY |
| 539A-R0017-A09 | 539A-M0071-E12 | 8 | RASQSISSDLN | AASSLQS | QQSYSTPVT | DYRMF | SISSSGGFTNYADSVKG | DQGGTVVVVATADY |
| 539A-R0017-A11 | 539A-M0071-F10 | 9 | RASQSISSWLA | KASSLES | QQYNSYPWT | KYKMF | SIGSSGGATSYADSVKG | GGFWSGYYGY |
| 539A-R0017-A12 | 539A-M0071-G11 | 10 | RASETVRYGQVA | DASKRAT | QQRSNWPLT | LYRMN | YIGSSGGATAYADSVKG | SMRGGHLDS |
| 539A-R0017-B01 | 539A-M0071-H05 | 11 | SGDKLGDKYAS | QDRKRPS | QAWDSNTVV | HYDMW | RIVPSGGLTTYADSVKG | HSFWSGYYGAFDI |
| 539A-R0017-B02 | 539A-M0071-H10 | 12 | RASQGISSWLA | AASTLQS | QPTYSTSWT | TYSMV | RIGSSGGDTFYADSVKG | DRADTVVTAGGDYYYYGMDV |
| 539A-R0017-B03 | 539A-M0072-B02 | 13 | RASQSISSWLA | KASSLES | QQYNSYPWT | NYKMH | SIGSSGGMTSYADSVKG | RDWQHLAGDAFDF |
| 539A-R0017-B04 | 539A-M0072-C04 | 14 | RASQGIRNDLG | AASSLQS | QQLNSYPPT | PYRMH | RIGSSGGATSYADSVKG | DGIAVAGIAFDI |
| 539A-R0017-B05 | 539A-M0072-C12 | 15 | RASQDIRSSLA | AASSLQS | QQANSFPPT | SYRMQ | YIGSSGGMTSYADSVKG | GSWRGGSQYFDY |
| 539A-R0017-B06 | 539A-M0072-F02 | 16 | RASQSISSYLN | AASSLQS | QQSYSTPRT | HYVMS | SIGSSGGDTHYADSVKG | VWISGSYLDAFDI |
| 539A-R0017-B07 | 539A-M0072-F05 | 17 | RASQSISSHLA | GASNRAT | QQRSNWPPT | AYRMQ | YIGSSGGQTSYADSVKG | DPVGAKYYGMDV |
| 539A-R0017-B08 | 539A-M0072-G08 | 18 | RASQSVSSYLA | DASNRAT | QQRSNWPIT | AYGMV | VIRSSGGPTSYADSVKG | AGGGTYLDY |
| 539A-R0017-B09 | 539A-M0072-H07 | 19 | RASQSVSSNLA | GASTRAT | HQYNDWPLT | PYKMY | YIGSSGGMTSYADSVKG | RGYSSGPLRY |
| 539A-R0017-B10 | 539A-M0072-H08 | 20 | RASQSISSTITYLN | AASNRAT | QQRSNWPPT | DYKMW | SIRSSGGPIGYADSVKG | ETNQMGMDV |

TABLE 3-continued

CDR Sequences of MMP-9 Binding Proteins (SEQ ID NOS 13-324, respectively, in order appearance)

| Isolate | Initial Name | Groups | LV-CDR1 | LV-CDR2 | LV-CDR3 | HV-CDR1 | HV-CDR2 | HV-CDR3 |
|---|---|---|---|---|---|---|---|---|
| 539A-R0017-B11 | 539A-M0072-H10 | 21 | RASQSVSSYLA | DASNRAT | QQRGNWPIT | PYRMS | SIGSSGGQTSYADSVKG | EPPGYYFDS |
| 539A-R0017-B12 | 539A-M0073-C11 | 22 | RASQSVSSYLA | DASNRAT | QQRSNWPIT | NYRMH | WISSSGGPTSYADSVKG | GGSYRHNNVFDI |
| 539A-R0014-A05 | 539A-M0073-G10 | 23 | RASQTVSRNYLA | DASKRAT | QQRSNWPPT | LYRMV | SFGPSGGPTMYADSVKG | RGYTVDVNAFDI |
| 539A-R0017-C02 | 539A-M0073-G12 | 24 | RASQSVSSNLA | GASTRAT | QQYNKWPQT | IYRMH | YIGSSGGNTSYADSVKG | EWVGSSAALDY |
| 539A-R0017-C03 | 539A-M0074-D05 | 25 | KSSQSVLYSSNNKNYLA | WASTRES | QQSYSTPLT | AYRMH | YIGSSGGMTTYADSVKG | STVTTLDY |
| 539A-R0017-C04 | 539A-M0074-D09 | 26 | RASQSVRSYLA | DVSNRAT | QQRSNWPLT | MYRMI | WIGSSGGQTSYADSVKG | GLWCDN |
| 539A-R0017-C05 | 539A-M0074-E11 | 27 | RASQSVSSYLA | GASSRAI | QQYGSSTRT | QYRMF | YIGSSGGMTSYADSVKG | SMGYGDAFDI |
| 539A-R0017-C06 | 539A-M0074-G03 | 28 | RASQTISSYYLA | GASSRAA | QQYGVSPPYS | YYNMV | VISPSGGWTPYADSVKG | EVGGSGWLGDAFDI |
| 539A-R0017-C07 | 539A-M0075-A07 | 29 | RASQGISSALA | DASSLES | QQFHTYPFT | TYRMV | YIGSSGGQTAYADSVKG | HNRAIGTFDY |
| 539A-R0017-C08 | 539A-M0075-B09 | 30 | KSSQSILYSSNNRNYLA | WASTRES | QHYYTAPYT | GYSMH | SIWPSGGYTRYADSVKG | GNDSDSFAYRF |
| 539A-R0017-C09 | 539A-M0075-D06 | 31 | RTSQSVSDSLA | DASNRAT | QQRGSWPIT | NYRMM | YIGSSGGMTSYADSVKG | ETNWNDLGRYFDY |
| 539A-R0017-C10 | 539A-M0075-D11 | 32 | RASHSVGGGYLA | DAFNRAT | QQRSEWPWT | RYKMS | YIGSSGGMTSYADSVKG | DLTATGYFDY |
| 539A-R0017-C11 | 539A-M0075-D12 | 33 | RASQGISSWLA | GASSLES | QQANSFPPT | DYRMT | WIGSSGGQTSYADSVKG | GTPRVASYFDY |
| 539A-R0017-C12 | 539A-M0075-F03 | 34 | RASQSVGSDYLA | AASTRAT | QQRSSWPPT | KYYMV | YISPSGGGTYYADSVKG | NYYDSSGTRGAFDI |
| 539A-R0017-D01 | 539A-M0075-G09 | 35 | KSSQSVLYSSNNKNYLA | WASTRES | QQYYSTPLT | EYRMT | YIGSSGGMTTYADSVKG | GSGSGYDS |
| 539A-R0017-D02 | 539A-M0075-G12 | 36 | RASQGIRNDLG | AASSLQS | QQTITFPLT | SYRMM | WISSSGGSTGYADSVKG | TTVTRVGSFYFDL |
| 539A-R0017-D03 | 539A-M0075-H05 | 37 | TGTSSDVGYYNYVS | DVSARPS | CSYAGSYTYV | MYYMQ | SIRSSGGFTSYADSVKG | GLRLDM |
| 539A-R0017-D04 | 539A-M0076-D03 | 38 | RASQGIRNDLD | SASNLQS | LQHNSFPLT | LYRMN | YIGSSGGATAYADSVKG | GAWYLDS |
| 539A-R0017-D05 | 539A-M0076-D07 | 39 | RASQSVSTFLA | DASNRAT | QQYASPPRT | GYYMS | SISPSGGNTEYAESVKG | DSGQTFYYAFDI |
| 539A-R0017-D06 | 539A-M0076-E11 | 40 | RASQGISRWLA | DASNRAT | QQRSNWPPRLT | FYHMS | SIGPSGGWTNYADSVKG | DGGLEGMDV |
| 539A-R0017-D07 | 539A-M0076-H03 | 41 | RASQGVSNYLA | AASTLQS | QKYNSAPYT | NYSMG | GIYSSGGYTQYADSVKG | GHYVWDSGWYSAFDI |
| 539A-R0017-D08 | 539A-M0078-G07 | 42 | RASQSVSSDLA | GVSTKAT | QQYHNWPPLT | SYTME | WISPSGGYTFYADSVKG | GYSYGSIDL |
| 539A-R0017-D09 | 539A-M0081-B03 | 43 | RASQGISSWLA | AASSLQS | QQANSFPYLT | TYMMM | SIWSGGSTFYADSVKG | GVVPALDY |
| 539A-R0017-D10 | 539A-M0081-D05 | 44 | RASESISRNLA | GAATRVA | QQANTFPFT | MYRMS | YIGSSGGPTAYADSVKG | EGDARVPAAIGY |
| 539A-R0017-D11 | 539A-M0081-E01 | 45 | RASQSISSYLN | AASSLQS | QQSYSTPRT | HYVMS | SIGSSGGDTHYADSVKG | VWISGSYLDAFDI |
| 539A-R0017-D12 | 539A-M0081-G03 | 46 | RTSHNVANFLA | DAYNRAT | QQRANWPLS | RYPME | YISSSGGWTSYADSVKG | DGLELFGGWLES |
| 539A-R0017-E01 | 539A-M0082-F03 | 47 | RASQSTSNSLS | AASRLQS | QQSWRTPLT | QYWMT | GIGPSGGPTTYADSVKG | HSTTVTTNFDY |
| 539A-R0017-E03 | 539A-M0082-G08 | 48 | RASQSISSYLN | AASSLQS | QQSYSTPRT | MYYMY | SIRSSGGETQYADSVKG | VWISGSYLDAFDI |

TABLE 3-continued

CDR Sequences of MMP-9 Binding Proteins (SEQ ID NOS 13-324, respectively, in order appearance)

| Isolate | Initial Name | Groups | LV-CDR1 | LV-CDR2 | LV-CDR3 | HV-CDR1 | HV-CDR2 | HV-CDR3 |
|---|---|---|---|---|---|---|---|---|
| 539A-R0017-E04 | 539A-M0082-G09 | 49 | RATQYISNYVN | AASSLQS | QQANSFPPT | AYSMH | RLGSSGGPTSYADSVKG | RSSYGRGFDY |
| 539A-R0017-E05 | 539A-M0083-A05 | 50 | RASQSISSYLN | AASSLQS | QQSYSTPRT | HYPMS | YIYSSGGDTEYADSVKG | YGSGGWMTYGLDV |
| 539A-R0017-E06 | 539A-M0084-E03 | 51 | RASQSIDTYLN | AASKLED | QQSYSSPGIT | HYDMS | SIWPSGGVTWYADSVKG | GGYNNYYYALDV |
| 539A-R0017-E08 | 539A-M0085-H01 | 52 | RASQNIAGLLA | KASTLES | QQYSFNSGT | KYHMH | SISPSGGVTSYADSVKG | DACSGGTCQLDY |

Example 4

CDR Amino Acid Sequences of MMP-9 Binding Anti-MMP-9 Binding Fabs

Unique Fab on phage sequences SC-014 SR-001 539A-M00166, SC-015 SR-001 539A-M0167, SC-016 SR-001 539A-M0168

1. SC-014 SR-001 539A-M00166 (phage was depleted on biotinylated Fab M0076-D03 immobilized streptavidin beads were selected against MMP-9 captured by Fab D03 immobilized on streptavidin beads)

42 intact clones (both LV and HV); all clones unique to this selection arm, except for 1 clone that was found also in SC-015 SR-001 (plate M0167)

2. SC-015 SR-001 539A-M0167 (a similar procedure as above was followed but the Fab used during depletion and selection was M0078-G07)

24 intact clones (both LV and HV); all clones unique to this selection arm, except for 1 clone described above and second clone found in previous selection attempts (more on that later)

3. SC-016 SR-001 539A-M0168 (phage depleted on D03 streptavidin beads were incubated with MMP-9 in solution and subsequently the MMP-9 with or without phage captured onto D03 streptavidin beads)

18 intact clones (both LV and HV); all clones unique to this selection arm.

CDRs of clones with complete sequence summarized in Table 4.

TABLE 4

Unique Fab on phage sequences SC-014 SR-001 539A-M00166, SC-015 SR-001 539A-M0167, SC-016 SR-001 539A-M0168 (SEQ ID NOS 325-801, respectively, in order appearance)

| Isolate | Initial Name | Groups | LV-CDR1 | LV-CDR2 | LV-CDR3 |
|---|---|---|---|---|---|
| 539A-R0027-A02 | 539A-M0166-A02 | 1 | RASQSVSSSYLA | GASSRAT | QQYGSSPLT |
| 539A-R0027-A06 | 539A-M0166-A06 | 2 | RASQSISSYLN | AASSLQS | QQTYITPPIT |
| 539A-R0027-A07 | 539A-M0166-A07 | 3 | KSSQSVLYSSNNKNYLA | WASTRES | QQYYSTPPT |
| 539A-R0027-A10 | 539A-M0166-A10 | 4 | QGDSLRSYYAS | GKNNRPS | QAWDSSTVV |
| 539A-R0027-B01 | 539A-M0166-B01 | 5 | RASQSVSSSYLA | GASSRAP | QQYGSSYT |
| 539A-R0027-B03 | 539A-M0166-B03 | 6 | TGTSSDVGGYNYVS | EVSKRPS | SSYAGTNNFV |
| 539A-R0027-B06 | 539A-M0166-B06 | 7 | SGSSSNIGSNTVN | SNNQRPS | AAWDDSVSGVV |
| 539A-R0027-B08 | 539A-M0166-B08 | 8 | RASQTINNWLA | KAFNLES | QQYDTYSWT |
| 539A-R0027-B11 | 539A-M0166-B11 | 9 | RASQGISSWLA | GATSLES | QQSNSFPLT |
| 539A-R0027-C01 | 539A-M0166-C01 | 10 | RASQSVTGNYLA | GVSSRAT | QQYGSAPFA |
| 539A-R0027-C03 | 539A-M0166-C03 | 11 | RASEDIRSALA | GASSLES | LQHSNYPAT |
| 539A-R0027-C04 | 539A-M0166-C04 | 12 | RSSQSLLHSNGYNYLD | LGSNRAS | MQARQTPWT |
| 539A-R0027-C05 | 539A-M0166-C05 | 13 | TGTSSDVGGYNFVS | DVSNRPS | SSYTRSSTVI |
| 539A-R0027-C07 | 539A-M0166-C07 | 14 | RTSLSISSNLA | DASTRAT | QQYETLPLT |
| 539A-R0027-C09 | 539A-M0166-C09 | 15 | RASQAIRHDLG | EVSNLQS | QQLNSYPRT |
| 539A-R0027-D02 | 539A-M0166-D02 | 17 | KSSQSVLYSSNNKNYLA | WASTRES | QQYYSTPPT |
| 539A-R0027-D04 | 539A-M0166-D04 | 18 | TGTTRDVGGYDYVS | EVNNRPS | NSYAGSNKLI |

TABLE 4-continued

Unique Fab on phage sequences SC-014 SR-001 539A-M00166, SC-015 SR-001 539A-M0167, SC-016 SR-001 539A-M0168
(SEQ ID NOS 325-801, respectively, in order appearance)

| | | | | | |
|---|---|---|---|---|---|
| 539A-R0027-D05 | 539A-M0166-D05 | 19 | RASHIIIRYLN | SASTLQG | QQSYSSPLT |
| 539A-R0027-D06 | 539A-M0166-D06 | 20 | RASQSVSSSYLA | GASSRAT | QQYGSSVT |
| 539A-R0027-D09 | 539A-M0166-D09 | 21 | SGDELGFGSVC | YEDNRRPS | QAWATTTVI |
| 539A-R0027-D11 | 539A-M0166-D11 | 23 | TGTSSDVGGYNYVS | EVSNRPS | SSYTSRSTPYV |
| 539A-R0027-E03 | 539A-M0166-E03 | 24 | SGGSSNIGSNYVS | NNNQRPS | AAWDDSLSSAV |
| 539A-R0027-E11 | 539A-M0166-E11 | 25 | RASQSISSYLN | AASSLQS | QQSYSTPLT |
| 539A-R0027-E12 | 539A-M0166-E12 | 26 | QATQDISNYLN | DASILET | LQHNRYPWT |
| 539A-R0027-F01 | 539A-M0166-F01 | 27 | GGINIGSKSVH | YFDSDRPS | QVWDSRSDQYV |
| 539A-R0027-F02 | 539A-M0166-F02 | 28 | RASQSVTSSYVA | GASSRAT | QQYEDSTHS |
| 539A-R0027-F09 | 539A-M0166-F09 | 29 | SGDKLGDKFAS | QDRKRPS | QVWDITSDHRGV |
| 539A-R0027-F10 | 539A-M0166-F10 | 30 | SGSSSNIGSNTVT | NNYERPS | ATWDDSLIANYV |
| 539A-R0027-G02 | 539A-M0166-G02 | 31 | RASQSVSSGSLA | ATSSRAS | QQCGDSPRT |
| 539A-R0027-G04 | 539A-M0166-G04 | 32 | RASQGISNWLA | GASSLQS | QQDNSFPLT |
| 539A-R0027-G10 | 539A-M0166-G10 | 34 | SGNNLGNKFVY | QDTKRPS | QAWDSSTAV |
| 539A-R0027-H01 | 539A-M0166-H01 | 35 | SGSSYNIGVYDVY | TNNQRPS | AAWDDSLSGSWM |
| 539A-R0027-H02 | 539A-M0166-H02 | 36 | SQSVSSSYLA | GASSRAT | QQYGSSRT |
| 539A-R0027-H03 | 539A-M0166-H03 | 37 | TGTSSDVGGYNYVS | EVNNRPS | SSYTHRNSFV |
| 539A-R0027-H04 | 539A-M0166-H04 | 38 | TRSSGSITSNFVQ | EDKRRPS | QSYDFTNQI |
| 539A-R0027-H08 | 539A-M0166-H08 | 39 | SGDKLGDKYAC | QDSKRPS | QAWDSMSVV |
| 539A-R0027-H10 | 539A-M0166-H10 | 40 | RASQSVSSNLA | GASTRAT | QHYDRYPLT |
| 539A-R0027-H11 | 539A-M0166-H11 | 41 | QASQDINTYLN | DASNLET | QQYDNLRT |
| 539A-R0028-A03 | 539A-M0167-A03 | 42 | RASQSVTSTFLA | GASSRAT | QQCGSSPFA |
| 539A-R0028-A08 | 539A-M0167-A08 | 43 | RASQSVSSNLA | GASTRAT | QQRSVWPWT |
| 539A-R0028-B01 | 539A-M0167-B01 | 44 | QASQDISNYLN | DASNLET | QQYDNLP |
| 539A-R0028-B03 | 539A-M0167-B03 | 45 | RASQSISVSLH | GASSLQS | QQSYRIPPT |
| 539A-R0028-B10 | 539A-M0167-B10 | 47 | GGDNIGGRSVQ | DDGDRPL | QAWDSSRDHPV |
| 539A-R0028-C11 | 539A-M0167-C11 | 48 | RASQSVSSSYLA | GASSRAT | QQYGSSPLT |
| 539A-R0028-D01 | 539A-M0167-D01 | 49 | KTSHRISSSYLA | GTSHRAT | HQRSNWPQT |
| 539A-R0028-D02 | 539A-M0167-D02 | 50 | TGTGSDVGDYNYVS | DVSNRPS | SSYTNSSVI |
| 539A-R0028-D03 | 539A-M0167-D03 | 51 | RASQSISSYLN | AASSLQS | QQSYSTPF |
| 539A-R0028-D08 | 539A-M0167-D08 | 52 | TGATSDIGTYDLVS | EVTNRPS | SSYTRTNTVI |
| 539A-R0028-D12 | 539A-M0167-D12 | 53 | RASQSISSYLN | AASSLQS | QQSYSTPLT |
| 539A-R0028-E01 | 539A-M0167-E01 | 54 | RASQSISSYLN | AASSLQS | QQSYSTPLT |
| 539A-R0028-E04 | 539A-M0167-E04 | 55 | RASQSISSYLN | AASTLQS | QHLNTYPIT |
| 539A-R0028-E05 | 539A-M0167-E05 | 56 | KSSQNVLLSSNSKNYLA | WASTRES | QQYYSIPWS |
| 539A-R0028-E06 | 539A-M0167-E06 | 57 | RASQSISSWLA | KASSLES | QQYDTYPLT |
| 539A-R0028-E08 | 539A-M0167-E08 | 58 | RASESISSYVA | GASNRAT | QQYGSSPPLT |
| 539A-R0028-F01 | 539A-M0167-F01 | 59 | TLSSGHSNYAIA | KLFSDGRHNKGD | QTWVAGIVV |

TABLE 4-continued

Unique Fab on phage sequences SC-014 SR-001 539A-M00166, SC-015 SR-001 539A-M0167, SC-016 SR-001 539A-M0168
(SEQ ID NOS 325-801, respectively, in order appearance)

| | | | | | |
|---|---|---|---|---|---|
| 539A-R0028-F02 | 539A-M0167-F02 | 60 | RASQSISSWLA | KASSLES | QQYDTYPLT |
| 539A-R0028-F04 | 539A-M0167-F04 | 61 | RASQPVSSTYLA | DTSKRAT | QQYGRSPYT |
| 539A-R0028-F06 | 539A-M0167-F06 | 62 | RASQSIATYLN | AATSLQS | QQTKIFPTWT |
| 539A-R0028-F07 | 539A-M0167-F07 | 63 | RASHRVTGYLN | ATSTVQS | QQSYSAFR |
| 539A-R0028-F10 | 539A-M0167-F10 | 64 | TGTSSDVGAYNYVS | DVSNRPS | SSYTSSSTRV |
| 539A-R0028-G10 | 539A-M0167-G10 | 65 | SGETLGGQFAS | QNTKRPS | QAWDTNTVV |
| 539A-R0029-A01 | 539A-M0168-A01 | 66 | TGTSSDVGAYNYVS | EVSNRPS | NSYTTSATLV |
| 539A-R0029-A11 | 539A-M0168-A11 | 67 | SGSSSNIGTNTLN | GNNQRPS | ATWDDSLIGPV |
| 539A-R0029-B02 | 539A-M0168-B02 | 68 | SGDKLGDKFVS | QDSKRPS | QAWDSSTFYV |
| 539A-R0029-B05 | 539A-M0168-B05 | 69 | RASQNIRSFLA | KTSNLQS | QQYYTYSWT |
| 539A-R0029-C01 | 539A-M0168-C01 | 70 | SSQSLLHSDGKTYLY | EASNRFS | MQSIELPRT |
| 539A-R0029-C03 | 539A-M0168-C03 | 71 | TLSSGYSNYAIA | RVNSDGSHSKGD | QTWGMGILVV |
| 539A-R0029-C07 | 539A-M0168-C07 | 72 | SGSSSNIGTNTLN | ANNQRPS | AAWDDSLSGL |
| 539A-R0029-C08 | 539A-M0168-C08 | 73 | TGTSNDVGGYNYVS | EVSNRPS | NSYTSSRTWV |
| 539A-R0029-C09 | 539A-M0168-C09 | 74 | RASQGISNYLA | DASSLES | QQFNSYPLT |
| 539A-R0029-D04 | 539A-M0168-D04 | 75 | TGTSSDVGGYNYVS | EVSKRPS | SSYAGSNNLGV |
| 539A-R0029-D09 | 539A-M0168-D09 | 76 | RASQVISSWLA | AASSLQS | QQYNSYPWA |
| 539A-R0029-D12 | 539A-M0168-D12 | 77 | TGTNTDVGGYNYVA | DVSNRPS | SSFTSRSTHV |
| 539A-R0029-E01 | 539A-M0168-E01 | 78 | RTSQDVRNWVA | MASTLQS | QQADTFPWT |
| 539A-R0029-F02 | 539A-M0168-F02 | 79 | RASQNIHSYLH | AASTLQR | HQSYMSPPT |
| 539A-R0029-F07 | 539A-M0168-F07 | 80 | RASQSVSSNYLA | HADNR | QQYGTSPGVT |
| 539A-R0029-H01 | 539A-M0168-H01 | 81 | TGTSSDVGAYNYVS | DVSDRPS | CSYARASTFSYV |
| 539A-R0029-H02 | 539A-M0168-H02 | 82 | QASQDINIYLN | DASNLEP | QRFDDLYT |
| 539A-R0029-H03 | 539A-M0168-H03 | 83 | QASQDIDNYLN | DASNLET | QQYDDLPRDT |
| 539A-R0029-H07 | 539A-M0168-H07 | 84 | SGGSSNIENNTVN | GDTERPS | ATWDDTLDGYV |

| Isolate | HV-CDR1 | HV-CDR2 | HV-CDR3 |
|---|---|---|---|
| 539A-R0027-A02 | MYGMP | VISPSGGSTTYADSVKG | GTPYYYDSSYNGGRAFDI |
| 539A-R0027-A06 | PYLMH | YIVPSGGNTFYADSVKG | GIGVASGLGSRYLDY |
| 539A-R0027-A07 | PYMMA | RIGSWTNYADSVKG | RSRDGYKGGFDY |
| 539A-R0027-A10 | IYWMM | YISPSGGMTSYADSVKG | GIYCSSTSCYDYFDY |
| 539A-R0027-B01 | VYMMP | YISSSGGKTEYADSVKG | DGAAAGPWDYYYYGLDV |
| 539A-R0027-B03 | HYWMK | SIVPSGGVTYYADSVKG | DLTNMAFDI |
| 539A-R0027-B06 | RYKMS | YIYSSGGLTMYADSVKG | DGGVVEAEDLFDY |
| 539A-R0027-B08 | WYGMS | SIWSSGGYTGYADSVKG | GSGSYIAY |
| 539A-R0027-B11 | PYAMR | SIDPSGGPTYYADSVKG | RGRYYYDSYDAFDI |
| 539A-R0027-C01 | YYYMY | YIYPSGGFTSYADSVKG | LLGGTVPPPDY |
| 539A-R0027-C03 | LYLMM | GIYPSGGYTQYADSVKG | DKGRWDLLGWYFDL |
| 539A-R0027-C04 | VYFMP | YIYPSGGRTFYADSVKG | QDSSGWYYFDY |

TABLE 4-continued

Unique Fab on phage sequences SC-014 SR-001 539A-M00166, SC-015 SR-001
539A-M0167, SC-016 SR-001 539A-M0168
(SEQ ID NOS 325-801, respectively, in order appearance)

```
539A-R0027-C05  MYNMY  YIVPSDGWTPYADSVKG  EDPSISGYINAFDI

539A-R0027-C07  WYEMF  SIYPSGGLTPYADSVKG  DIHAIFGPFYYYYGMDV

539A-R0027-C09  QYLMW  YIVPSGGYTLYADSVKG  SQALRFLESPGAFDI

539A-R0027-D02  MYYMD  GISSGGFTAYADSVKG   EGGYCSSTSCYVDY

539A-R0027-D04  VYPMP  VISPSGGHTTYADSVKG  SVPLYYFDY

539A-R0027-D05  PYSMN  RIVPSGGFTLYADSVKG  VGSSSWYLPYFDY

539A-R0027-D06  NYPMW  YIVSSGGTMYADSVKG   CSSGWYVNYYYYGMDV

539A-R0027-D09  KYMMQ  VIVSSGGFTWYADSVKG  HLWYYYGMDV

539A-R0027-D11  QYR    SIYPSGGPTGYADSVKG  GYSTGFYNSGGYFDY

539A-R0027-E03  TYYMN  SIVSSGGYTEYADSVKG  DGLPVVAATFNYYYYYMDV

539A-R0027-E11  KYFMG  VISPSGGYTYYADSVKG  WGSSWYYFDY

539A-R0027-E12  SYGMP  VIYPSGGNTPYADSVKG  GYYDILTGYYGPNWFDP

539A-R0027-F01  DYQME  VIRPSGGKTAYADSVKG  AELGYCSGGSCYFDGAWFDP

539A-R0027-F02  TYNMP  RIYSSGGYTPYADSVNG  QGLDDDIWTDYRDF

539A-R0027-F09  DYIMW  RIYSSGGFTNYADSVKG  DLGGLSFADY

539A-R0027-F10  PYLMN  SIYSSGGGTGYADSVKG  IYHSSSGPFYGMDV

539A-R0027-G02  WYRMP  YIGPSGGDTVYADSVKG  RGGYEFDF

539A-R0027-G04  PYRMP  YIYPSGGNTGYADSVKG  SYDFWSGYWFDY

539A-R0027-G10  DYIM   WISSSGGGTTYADSVKG  VSPYSSGWYPYNWFDP

539A-R0027-H01  DYWMY  YIYSSGGFTGYADSVKG  KVADSGMNWFDP

539A-R0027-H02  FYGMN  GIGSSGYTPYADSVKG   AYDFWSGYQELDY

539A-R0027-H03  VYGMP  WIYSSGGKTEYVDSVKG  DPVRFLEWLWGIDY

539A-R0027-H04  QYVMP  YIVPSGGETDYADSVKG  LDDSSGWYSFDY

539A-R0027-H08  LYYMW  WIYPSGGYTPYADSVKG  GIHSGSYSGQDY

539A-R0027-H10  FYPMV  WIGPSGGTTKYADSVKG  DWGYYYDSGSRLDY

539A-R0027-H11  WYYMR  RIVSSGGDTPYADSVKG  EVGPRSFDS

539A-R0028-A03  FYYMW  SIGSSGGFTEYADSVKG  EDYDYVWGSYRSPFFDY

539A-R0028-A08  DYSMD  SISPSGGWTIYADSVKG  SSGDFWSGYYPYYMDV

539A-R0028-B01  LTLWF  GISPSGGKTIYADSVKG  DWYCGGGSCFDWYFDL

539A-R0028-B03  KYFME  SIWSSGGYTIYADSVKG  SPSDDFWSGYHGGAFDI

539A-R0028-B10  GYYMP  WIGPSGGNTLYADSVKG  ASYIVATIPQYFDY

539A-R0028-C11  KYDME  SIVPSGGFTDYADSVKG  DSSSWYKRFDP

539A-R0028-D01  VYNML  YIYSSGGHTIYADSVKG  QAGVGWQLEPDNWFDP

539A-R0028-D02  PYMMA  RIYPSGGETTYADSVKG  GQSYCSSTSCYPYYYYGMDV

539A-R0028-D03  PYVMP  YIGPSGGNTRYADSVKG  DLLSGYDYYYYPLDV

539A-R0028-D08  PYKMF  YIRSSGGKTHYADSVKG  DSNAPYYYDSSGYDAFDI
```

TABLE 4-continued

Unique Fab on phage sequences SC-014 SR-001 539A-M00166, SC-015 SR-001 539A-M0167, SC-016 SR-001 539A-M0168
(SEQ ID NOS 325-801, respectively, in order appearance)

```
539A-R0028-D12  TYGMT  SISPSGGATRYVDSVKG  EDL

539A-R0028-E01  KYFMG  VISPSGGYTYYADSVKG  WGSSWYYFDY

539A-R0028-E04  PYMME  SYIGSSGGYTKYADSVKG ILGGDYFDY

539A-R0028-E05  NYRMS  SIGSSGGQTMYADSVKG  SHPVSGGVFDF

539A-R0028-E06  SYWMH  GIYPSGGNTNYADSVKG  VIYDFWSGYYFDY

539A-R0028-E08  RYTMM  YIGSSGGVTSYADSVKG  DPRDYSDYRGGYWYFDL

539A-R0028-F01  RYLMM  YIYPSGGSTTYADSVKG  DRVVVAATPLTGFDY

539A-R0028-F02  SYWMH  GIYPSGGNTNYADSVKG  VIYDFWSGYYFDY

539A-R0028-F04  PYIMK  SISSSGGPTNYADSVKG  SYSNYPRRFFDY

539A-R0028-F06  AYLMD  VIYSSGGPTMYADSVKG  WCSSGWYPQCHN

539A-R0028-F07  DYIMP  RIYPSGGPTWYADSVKG  DTTSGDYFDL

539A-R0028-F10  LYVMF  RIRPSGGVTDYADSVKG  DTRYDYDFWSGYYTGFFDI

539A-R0028-G10  KYWMQ  WIYPSGGNTPYADSVKG  SGSRPSYYYYYGMDV

539A-R0029-A01  LYYMY  GIVPSGGRTDYADSVKG  GLLRFLEWLLYPFDY

539A-R0029-A11  PYSME  SIRPSGGLTAYADSVKG  WLGFDILTGYFDY

539A-R0029-B02  FTL    GIYSSGGLTWYADSVKG  DGVLYYSYYGMEV

539A-R0029-B05  GYWMK  SIYPSGGKTPYADSVKG  WPTSDYGGKYWFDP

539A-R0029-C01  PYYMQ  RISSSGGPTNYADSVKG  GYGHGLDY

539A-R0029-C03  QYRMP  WIWPSGGWTQYADSVKG  GDSSGYPYYFDY

539A-R0029-C07  FYTMR  SIGSSGGYTGYADSVKG  RHYGGNSPYYFDY

539A-R0029-C08  PYEMN  GIVPSGGITMYADSVKG  DNRNPVMVMIDY

539A-R0029-C09  HYYMP  SIYSSGGVTWYADSVKG  VSYDSSGYYPFDY

539A-R0029-D04  MYYML  SIYSSGGMTMYADSVKG  VGIAVAGPALDY

539A-R0029-D09  KYIMM  WIYSSGGNTNYADSVKG  EGAYSGSYGGDAFDI

539A-R0029-D12  HYPMP  YIYPSGGVTPYADSVKG  DPPYYDFWSGYYTS

539A-R0029-E01  MYSMN  SIVSSGGDTRYADSVKG  DISGYYPPYFDY

539A-R0029-F02  WYMMG  VIYPSGGHTPYADSVKG  DHIRTASGAFWFDP

539A-R0029-F07  IYTME  RISPSGGDTIYADSVKG  TKGVDCSGGSCYRAGIDY

539A-R0029-H01  MYWMG  SIVSSGGWTQYADSVKG  DHDSSGYWFDD

539A-R0029-H02  VYGMY  RIGPSGGMTYYADSVKG  ERLPYGDHQHYFDY

539A-R0029-H03  VYWML  YIYSSGGWTVYADSVKG  VVFESGDFWSGYPYYFDY

539A-R0029-H07  VYIMG  SIYSSGGSTNYADSVKG  RGDWGSVGFDP
```

Example 5

CDR Sequences of MMP-9 Binding Fabs

Unique Fab on phage sequences SC-017 SR-001 539A-M00166, SC-018 SR-001 539A-M0167, SC-019 SR-001 539A-M0168: Results are summarized in Table 5.

TABLE 5

Unique sequence clones found in the SC17-19 phage screening.
(SEQ ID NOS 802-926, respectively, in order appearance)

| Isolate | Initial Name | L-Info | Project Reps | LV-CDR1 | LV-CDR2 | LV-CDR3 | HV-CDR1 | HV-CDR2 | HV-CDR3 |
|---|---|---|---|---|---|---|---|---|---|
| 539A-R0031-A04 | 539A-M0186-B05 | L.KU | 3 | RASQSISGWLA | KASTLES | QQYDSYPYT | YMN | VISPSGGTTNYADSVKG | GSSIAARPLDY |
| 539A-R0031-B10 | 539A-M0186-E08 | L.KU | 1 | RASQSIGSYLN | AVSSLQS | QQSYSNPIS | DYTME | GISPSGGYTDYADSVKG | NLITMIVVGEFDY |
| 539A-R0031-C12 | 539A-M0186-G11 | L.LU | 2 | SGSSSNIGGNRVN | STNQRPS | AAWDDTLNGPV | NYDMM | SIGSSGGITFYADSVKG | EYSSGWPLDY |
| 539A-R0031-D10 | 539A-M0196-A01 | L.KU | 1 | RASQSISTFLN | AASSLQS | QQSYSTPPIT | RYDML | GISPSGGFTTYADSVKG | PALYYYGSGRLKAFDI |
| 539A-R0031-E07 | 539A-M0196-B03 | L.KU | 1 | RSSQSLLHSNGYNYLD | LGSYRAS | MQALQTPIT | RYQMG | SISPSGGGTVYADSVKG | NYYYMDV |
| 539A-R0031-E09 | 539A-M0196-B05 | L.KU | 1 | RASQGIRNDLG | AASSLQS | LQHNSYPFT | AYRMQ | YIGSSGGQTSYADSVKG | AKPGRPFDF |
| 539A-R0031-E12 | 539A-M0196-B08 | L.KU | 1 | RASQSISSYLN | AASSLQS | QQSYSTPHT | HYVMS | SIGSSGGDTHYADSVKG | VWISGSYLDAFDI |
| 539A-R0031-F07 | 539A-M0196-C07 | L.KU | 1 | RSSQSLLLSNGYNYLD | LGSHRAS | MQALQTPVIT | KYMMF | SIYPSGGWTYYADSVKG | LGYPPY |
| 539A-R0031-F08 | 539A-M0196-C09 | L.KU | 9 | RASQSISSWLA | KASFLKS | QQYNSYPFT | HYIMF | GIYPSGGFTYYADSVKG | GHDAFDI |
| 539A-R0031-G07 | 539A-M0196-D11 | L.KU | 1 | RASQSVGSQLA | DASTRAT | HQYDNWPHT | FYRMS | WIGSSGGPTSYADSVKG | SGGVAGTFGY |
| 539A-R0031-G08 | 539A-M0196-D12 | L.KU | 1 | RASQSISHWLA | KASSLQS | QQYDSYPFT | PYYMS | VISPSGGVTHYADSVKG | SSSSSWYAFDY |
| 539A-R0031-G11 | 539A-M0196-E03 | L.KU | 1 | RASQFISHWLA | KSSTLKS | QQYDSVPYT | YYGML | YISPSGGFTKYADSVKG | DLSSGGFDY |
| 539A-R0031-H09 | 539A-M0196-F04 | L.KU | 1 | RASQTISSWLA | RASTLKS | QQYDSYRYT | KYYMG | YIGSSGGYTNYADSVKG | PQLAFDI |
| 539A-R0032-A02 | 539A-M0196-G03 | L.LU | 2 | AGSSSNIGSNSVY | SNNKRPS | AAWDDSLRSVV | RYGML | VIYPSGGVTWYADSVKG | PATMVRY |
| 539A-R0032-B05 | 539A-M0206-C04 | L.KU | 1 | RVSQSVSSSYLA | GASSRAT | QQRSNWPPIT | VYAMH | SIVPSGGVTLYADSVKG | SSSSFLYYYGMDV |
| 539A-R0032-B09 | 539A-M0206-E10 | L.LU | 1 | TGTSSDVGGYNYVS | EVGNRPS | SSYTSSSTWV | LYVMQ | VIVPSGGDTYYADSVKG | GYCTGGVCYLGFDC |
| 539A-R0032-B11 | 539A-M0206-F05 | L.LU | 1 | RSSQSLLHSDGYNYLD | LGSNRAS | MQALQTPLT | WYTMA | SIWSSGGQTQYADSVKG | PGLPIAGSFHGDFDL |
| 539A-R0032-B12 | 539A-M0206-F08 | L.LU | 2 | RANQVISTWLS | TASTLQS | QQANSFPIT | HYPMI | SIRPSGGDTKYADSVKG | METGYDILTGYYIRWRYFDY |
| 539A-R0032-C01 | 539A-M0206-F10 | L.LU | 1 | SGSSSNIGSNYVY | INDHRPS | AVWDDSLSGWV | DYFMY | SIGPSGGWTWYADSVKG | GTGSFDY |
| 539A-R0032-C06 | 539A-M0206-G09 | L.LU | 1 | SGSSSNIGSNYVY | TNNQRPS | ATWDDDLSGPV | KYAMY | SIVSSGGETHYADSVKG | GGQWLPYYFDS |
| 539A-R0032-C08 | 539A-M0206-H09 | L.KU | 1 | RASQSVSTNLA | GASTRAT | QQYGSSQLT | NYRMI | RISSSGGNTQYADSVKG | AGGYSYGPPTYYYYGMDV |

Example 6

Affinity Ranking of MMP-9 Binding Fabs

Affinity ranking of 24 Fabs from the R0017 plate was performed by BIACORE® Flexchip. Results are summarized in Table 6.

TABLE 6

Affinity ranking by Flexchip

| Difference from reference | spot content | ka | kd | KD | rmax average |
|---|---|---|---|---|---|
| 1794.8151 | Anti-MMP-9 | No Binding * | No Binding * | — | |
| 13678.9169 | anti-His | No Binding * | No Binding * | — | |
| 314.5676 | PBS | No Binding * | No Binding * | — | |
| 845.8099 | TIMP-1 | No Binding * | No Binding * | — | |
| 1746.5973 | 539A-M0081-D05 | 4.10E+04 | 2.04E−04 | 4.97E−09 | 9.20E+01 |
| 1725.9598 | 539A-M0076-D03 | 5.97E+04 | 3.51E−04 | 5.88E−09 | 3.68E+02 |
| 1454.5212 | 539A-M0072-H07 | 1.42E+05 | 1.01E−03 | 7.13E−09 | 3.59E+01 |
| 1744.5526 | 539A-M0075-D12 | 6.77E+04 | 6.53E−04 | 9.65E−09 | 2.88E+02 |
| 1889.4882 | 539A-M0075-B09 | 1.38E+05 | 1.57E−03 | 1.14E−08 | 1.90E+02 |
| 1539.5203 | 539A-M0075-A07 | 1.18E+05 | 1.61E−03 | 1.36E−08 | 1.93E+02 |
| 1756.4697 | 539A-M0076-D07 | 5.78E+04 | 1.02E−03 | 1.76E−08 | 3.03E+02 |
| 1527.4429 | 539A-M0081-G03 | 5.93E+04 | 1.13E−03 | 1.91E−08 | 9.80E+01 |
| 1661.5067 | 539A-M0072-F02 | 5.30E+04 | 1.24E−03 | 2.33E−08 | 3.23E+02 |
| 1428.5431 | 539A-M0071-E12 | 9.11E+04 | 2.18E−03 | 2.40E−08 | 9.71E+01 |
| 2059.7763 | 539A-M0082-G08 | 4.36E+04 | 1.13E−03 | 2.60E−08 | 2.82E+02 |
| 1952.6749 | 539A-M0076-E11 | 6.55E+04 | 1.79E−03 | 2.73E−08 | 8.38E+01 |
| 1561.9125 | 539A-M0072-H10 | 2.32E+05 | 6.96E−03 | 3.00E−08 | 8.78E+01 |
| 1673.6221 | 539A-M0072-C04 | 1.42E+05 | 5.07E−03 | 3.58E−08 | 7.42E+01 |
| 2073.5321 | 539A-M0084-E03 | 1.10E+05 | 4.60E−03 | 4.18E−08 | 2.82E+02 |
| 2062.6144 | 539A-M0082-G09 | 1.62E+05 | 7.54E−03 | 4.66E−08 | 9.33E+01 |
| 1911.293 | 539A-M0073-C11 | 9.54E+04 | 4.49E−03 | 4.71E−08 | 1.76E+02 |
| 1840.1489 | 539A-M0072-G08 | 7.42E+04 | 3.82E−03 | 5.15E−08 | 3.22E+02 |
| 1774.4522 | 539A-M0071-E02 | 4.82E+04 | 2.69E−03 | 5.58E−08 | 2.37E+02 |
| 1804.1611 | 539A-M0075-F03 | 9.17E+04 | 5.64E−03 | 6.15E−08 | 1.37E+02 |
| 2037.2009 | 539A-M0081-E01 | 3.33E+04 | 2.17E−03 | 6.52E−08 | 3.34E+02 |
| 1598.526 | 539A-M0071-D03 | 6.46E+04 | 5.30E−03 | 8.20E−08 | 2.62E+02 |
| 1989.357 | 539A-M0075-G12 | 1.51E+05 | 1.30E−02 | 8.63E−08 | 1.20E+02 |

No Binding * an air bubble was introduced to the flowcell during the injection.

Example 7

Competition Experiments

Results of the competition experiments are summarized in Table 7.

| Isolate | M0078-G07 | M0081-D05 | M0076-D03 | M0072-H07 | M0075-D12 |
|---|---|---|---|---|---|
| KD (nM) | 3.1 | 5.0 | 5.9 | 7.1 | 9.6 |
| epitope | B | A | A | A | A |
| t½ (min) | 25 | 57 | 33 | 11 | 18 |

R0025-B12_M0131-F06 used for competition.

Example 8

As shown in FIG. 1A, antibody 539A-M0166-F10 has an IC50 of 4.3±1.9 nM on human MMP-9 activity. The IC50 is ~33 nM for the 539A-M0166-F10 Fab.

FIG. 1B shows that 539A-M0166-F10 is specific for human MMP-9 (hMMP-9) as compared to the other human (h) and murine (m) MMPs tested.

The residual enzyme activity was measured in the presence of 1 μM antibody (Fab or hIgG-1, as indicated in FIG. 1B). The human MMP-1, -2, -3, -7, -8, -9, -10, -12, -13, and -14 were obtained from BIOMOL (Human MMP-9: SE-244, BIOMOL; Human MMP-14: SE-259, BIOMOL; Human MMP-1, -2, -8, -13: MMP MultiPack-1 from BIOMOL; Human MMP-3, -7, -10, -12: MMP MultiPack-2 from BIOMOL). The mouse MMP-2 and -9 were from R&D (Mouse MMP-9: 909-MM, R&D Mouse MMP-2: 924-MP, R&D). The substrate was Mca-Pro-Lys-Pro-Leu-Ala-Leu-Dap (Dnp)-Ala-Arg-NH2 (SEQ ID NO: 951) (M-2225, Bachem) for human MMP-3, and Mca-Lys-Pro-Leu-Gly-Leu-Dap (Dnp)-Ala-Arg-NH2 (SEQ ID NO: 952) (M-2350, Bachem) for all the other enzymes. The substrate concentration in the assay was 10 μm.

Example 9

539A-M0166-F10 also decreases MMP-9 activity in MCF-7 and Colo205 tumors, as measured by in situ zymography (data not shown).

Example 10

The DNA and amino acid sequences of variable regions of 539A-M0166-F10 sFAB are as follows:

539A-M0166-F10 (phage/SFAB) VL leader +VL
SEQ ID NO: 2:
TTCTATTCTCACAGTGCACAGAGCGAATTGACTCAGCCACCGTCAGCGTC

TGCGGCCCCCGGGCAGAGGGTCACCATCTCTTGTTCTGGAAGCAGCTCCA

ACATCGGAAGTAACACTGTAACCTGGTACCAGAAGCTCCCAGGAACGG

CCCCCAAGCTCCTCATTTACAATAATTATGAGCGGCCCTCAGGGGTCCCT

GCCCGATTCTCTGGCTCCAAGTCTGGCACCTCAGCCTCCCTGGCCATCAG

TGGGCTCCAGTCTGAGGATGAGGCTGATTATTACTGTGCAACATGGGAT

GACAGCCTGATTGCCAATTACGTCTTCGGAAGTGGGACCAAGGTCACCG

-continued

TCCTAGGTCAGCCCAAGGCCAACCCC

SEQ ID NO: 3:
FYSHSAQSELTQPPSASAAPGQRVTISCSGSSSNIGSNTVTWYQKLPGTA

PKLLIYNNYERPSGVPARFSGSKSGTSASLAISGLQSEDEADYYCATWDD

SLIANYVFGSGTKVTVLGQPKANP

539A-M0166-F10 (phage/SFAB) VH leader +VH
SEQ ID NO: 4:
ATGAAGAAGCTCCTCTTTGCTATCCCGCTCGTCGTTCCTTTTGTGGCCCA

GCCGGCCATGGCCGAAGTTCAATTGTTAGAGTCTGGTGGCGGTCTTGTT

CAGCCTGGTGGTTCTTTACGTCTTTCTTGCGCTGCTTCCGGATTCACTTT

CTCTCCTTACCTTATGAATTGGGTTCGCCAAGCTCCTGGTAAAGGTTTG

GAGTGGGTTTCTTCTATCTATTCTTCTGGTGGCGGTACTGGTTATGCTGA

CTCCGTTAAAGGTCGCTTCACTATCTCTAGAGACAACTCTAAGAATAC

TCTCTACTTGCAGATGAACAGCTTAAGGGCTGAGGACACGGCCGTGTA

TTACTGTGCGAGAATATACCATAGCAGCAGTGGACCTTTCTACGGTATG

GACGTCTGGGGCCAAGGGACCACGGTCACCGTCTCAAGCGCCTCCACC

AAGGGCCCATCGGTCTTCCCGCTAGCACCCTCCTCCAAGAGC

SEQ ID NO: 5:
MKKLLFAIPLVVPFVAQPAMAEVQLLESGGGLVQPGGSLRLSCAASGFTF

SPYLMNWVRQAPGKGLEWVSSIYSSGGGTGYADSVKGRFTISRDNSKNT

LYLQMNSLRAEDTAVYYCARIYHSSSGPFYGMDVWGQGTTVTVSSAST

KGPSVFPLAPSSKS

Example 11

Experiments were performed to characterize the interaction of the M0166-F10 hIgG1 with human MMP-9. The Ki was measured and the inhibition mechanism was determined. The results show that inhibition of human MMP-9 by M0166-F10 appears to follow a competitive model, with a Ki value equal to 0.3±0.5 nM.

The experiments were performed as follows:
Materials:
Substrate: Mca-KPLGL-Dap(Dnp)-AR-NH$_2$ (SEQ ID NO: 952) (M-2350) from BACHEM (521575). A 10 mM stock solution was prepared in DMSO.
Human MMP-9 catalytic domain (BIOMOL, SE-244), stock solution at 0.24 mg/ml.
M0166-F10 hIgG1: 2551-095. Dialysed against TCN. Stock solution at 0.226 mg/ml.
Experiments were performed in TCNB: 50 mM Tris/HCl, 10 mM CaCl$_2$, 150 mM NaCl, 0.05% Brij 35, pH 7.5. 96-well black plates from Perkin Elmer (6005270).
Spectramax M2e to measure fluorescence emission of the substrate upon hydrolysis (temperature control set at 30° C.; $\lambda_{exc}$=328 nm and $\lambda_{em}$=393 nm).
Procedure:
90 μl of the enzyme (final concentration=0.6 nM) was preincubated with 90 μl of various concentrations (0-100 nM final) of M0166-F10 for 1.5 h at 30° C. 20 μl the substrate was then added to a final concentration ranging from 3 to 15 μM, and initial rates were recorded. Each data point was measured in triplicate, and initial rates were averaged.

Averaged initial rates were plotted against the M0166-F10 concentration for each substrate concentration, and IC$_{50}$'s were calculated using the following equation:

$$y = \frac{\text{Range}}{1 + \left(\frac{x}{IC_{50}}\right)^s}$$

Figure 2:
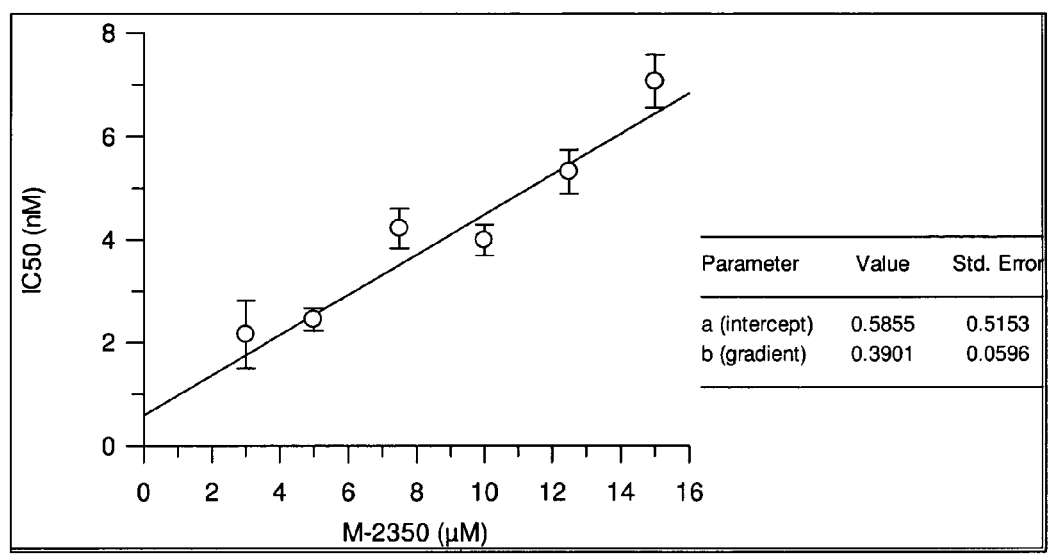
FIG. 2 is a line graph showing measured IC$_{50}$ (nM) versus substrate concentration (µM) of an MMP-9 binding protein (539A-M0166-F10).
Figure 3:
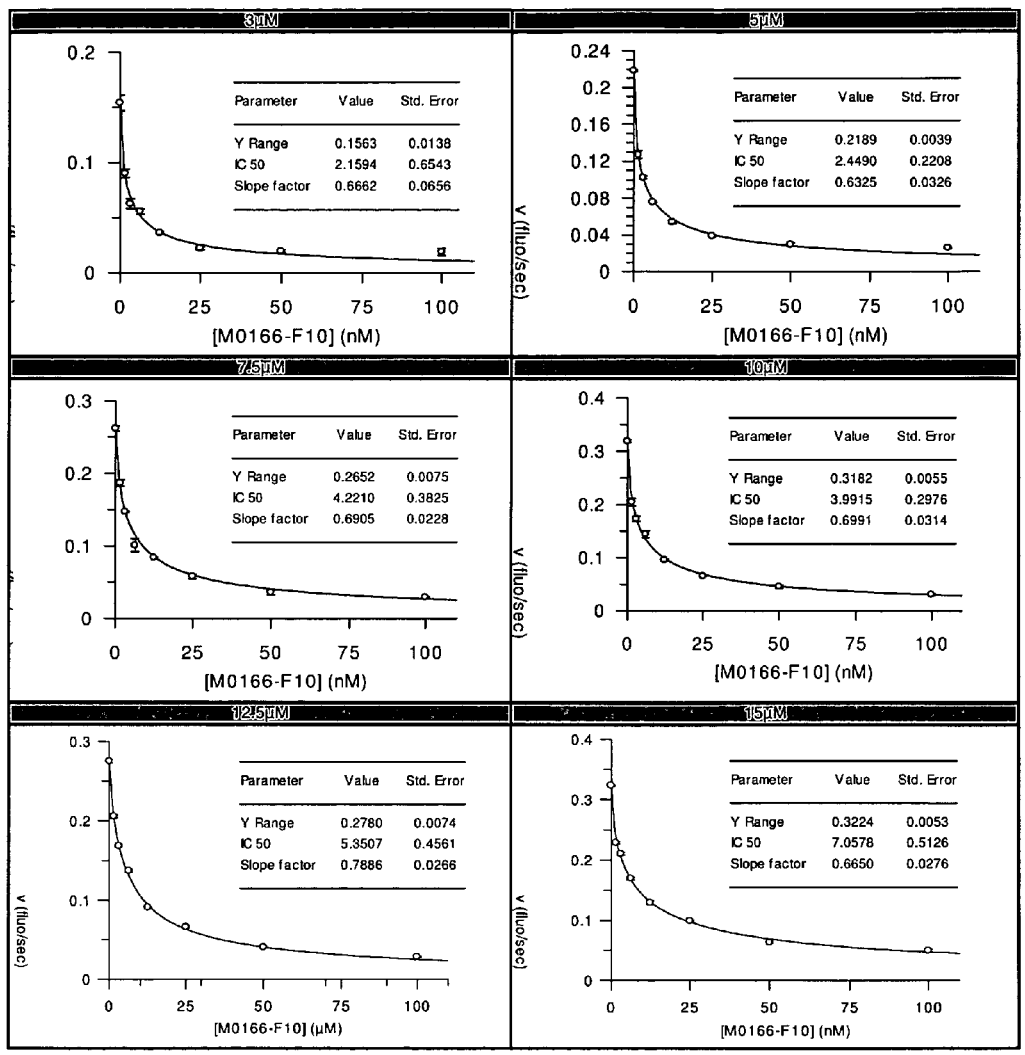
FIG. 3 is a series of line graphs showing IC$_{50}$ measurements at various concentrations of substrate of an MMP-9 binding protein (539A-M0166-F10).
Figure 4:
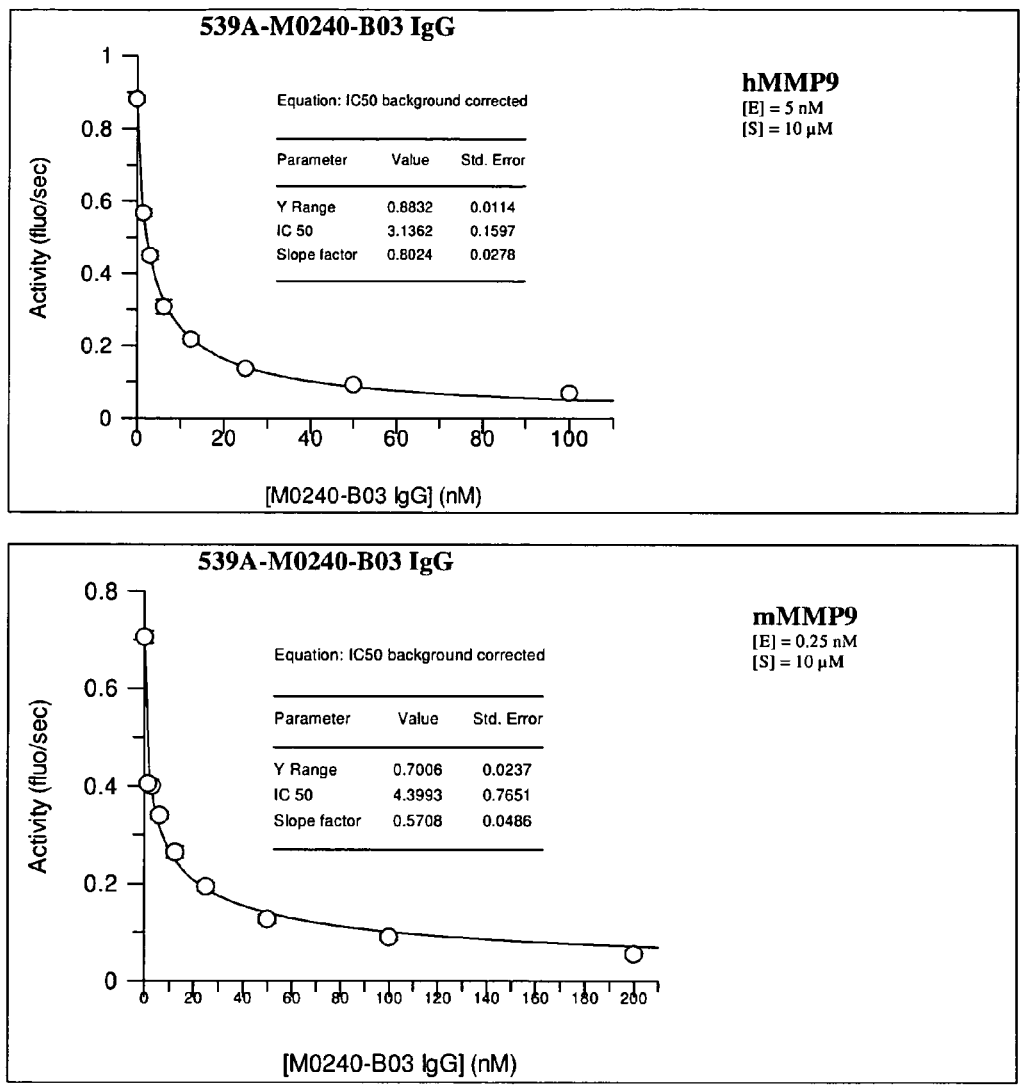
FIG. 4 is a set of two line graphs showing IC$_{50}$ measurements at 10 µM concentration of substrate (human MMP-9—top panel, or mouse MMP-9—bottom panel) of an MMP-9 binding protein (539A-M0240-B03).
Figure 6B:
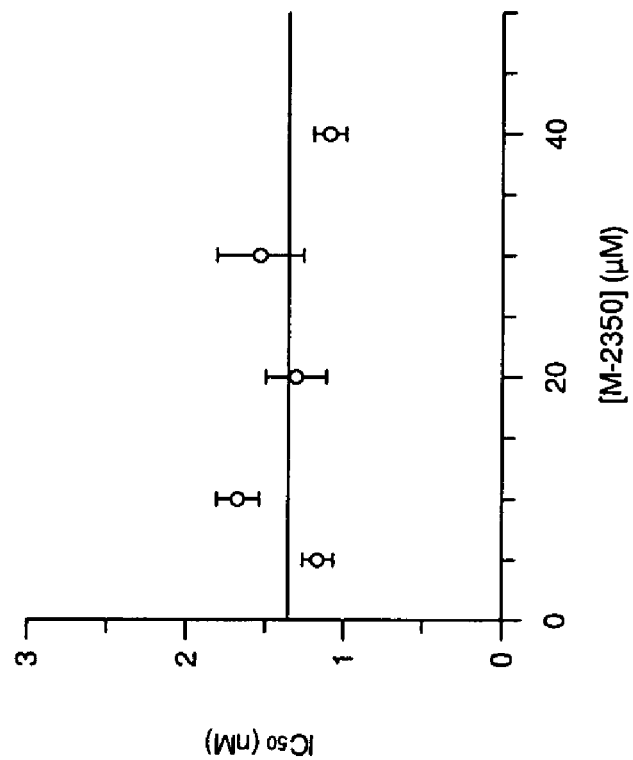
FIGS. 6A and 6B are two line graphs showing IC$_{50}$ (nM) versus substrate concentration (µM) of an MMP-9/-2 binding protein (539A-M0237-D02).
Figure 6A:
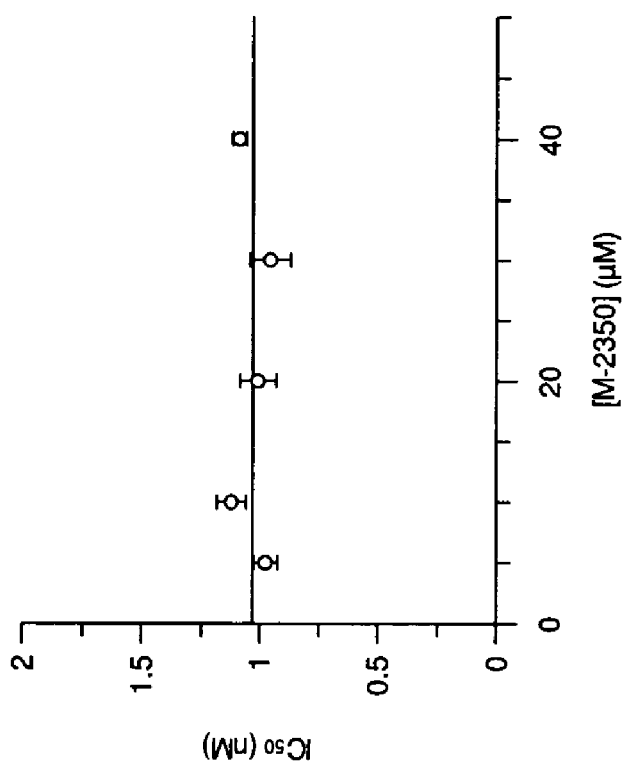

The IC$_{50}$ values were then plotted against the substrate concentration.
Results
The plot of the measured IC$_{50}$ (nM) vs. the substrate concentration (μM) is shown in FIG. 2. The IC$_{50}$ increases linearly with the substrate concentration, which indicates that M0166-F10 behaves as a competitive inhibitor of the human MMP-9.
For a competitive inhibition model, the following equation applies:

$$IC_{50} = K_i + \frac{E}{2} + \frac{K_i}{K_m}[S]$$

and therefore the value of the K$_i$ can be calculated from the intercept. Here, K$_i$=0.3±0.5 nM.
The IC$_{50}$ measurements for M0166-F10 at various concentrations of substrate Mca-KPLGL-Dap(Dnp)-AR-NH$_2$ (SEQ ID NO: 952) from BACHEM (M-2350) (3 μM, 5 μM, 7.5 μM, 10 μM, 12.5 μM, and 15 μM) are shown in FIG. 3.
FIG. 4 shows the IC50 measurements for an MMP-9 binding protein (539A-M0240-B03) at 10 mM concentration of human MMP-9 (top) or mouse MMP-9 (bottom).
The results in FIG. 5 show that an MMP-9 binding protein (539A-M0240-B03) inhibits human and mouse MMP-9 but not human MMP-1, -2, -3, -7, -8, -10, -12, and -14.
The results in FIGS. 6A and 6B show IC$_{50}$ (nM) versus substrate concentration (μM) of an MMP-9/-2 binding protein (539A-M0237-D02). Human MMP-9 (FIG. 6A) and mouse MMP-9 (FIG. 6B) were used as substrates.

Example 12

Exemplary Clone Identified

539A-M0240-B03 is a selective inhibitor of MMP-9. 539A-M0240-B03 can decrease or inhibit the activity of human and mouse MMP-9.
The sequences of the complememtarity determining regions (CDRs) of 539A-M0240-B03 light chain (LC) and heavy chain (HC) are as follows:

```
LC CDR1: TGTSSDVGGYNYVS (SEQ ID NO: 953)
LC CDR2: DVSKRPS (SEQ ID NO: 954)
LC CDR3: CSYAGSYTLV (SEQ ID NO: 955)
HC CDR1: TYQMV (SEQ ID NO: 956)
HC CDR2: VIYPSGGPTVYADSVKG (SEQ ID NO: 957)
HC CDR3: GEDYYDSSGPGAFDI (SEQ ID NO: 958)
```

Example 13

Additional MMP-9 Binding Proteins

A protein containing the HC CDR sequences of 539A-M0240-B03 and the light chain sequence shown below can be used in the methods described herein. A protein containing the LC CDRs shown below and the HC CDRs of 539A-M0240-B03, or a protein containing the LC variable region (light V gene) shown below and the 539A-M0240-B03 HC CDRs can also be used in the methods described herein. The protein can include a constant region sequence, such as the constant region (LC-lambda1) shown below.

chain and heavy chain variable regions (LV and HV, respectively) shown below can also be used in the methods described herein.

539A-M0240-B03: Parental isolate (sFab; IgG-pBh1(f)).
539A-X0034-C02 (GS clone): DX-2802: Germlined, sequence optimized. The entire antibody fragment, contain-

```
Light V gene = VL2_2e; J gene = JL3
FR1-L                     CDR1-L            FR2-L           CDR2-L
QSALTQPRSVSGSPGQSVTISC TGTSSDVGGYNYVS WYQQHPGKAPKLMIY DVSKRPS GVPD FR3-L                                 CDR3-L       FR4-L
RFSGSKSGNTASLTISGLQAEDEADYYC CSYAGSYTLV FGGGTKLTVL (SEQ ID NO: 959)

LC-lambda1
GQPKAAPSVTLFPPSSEELQANKATLVCLISDFYPGAVTVAWKADSSPVKAGVETTTPSKQSNNKYAASSYLSLTPEQWKSHRSYS
CQVTHEGSTVEKTVAPTECS (SEQ ID NO: 960)
CDR regions are in bold.
```

The amino acid and nucleic acid sequences for another exemplary protein that can be used in the methods described herein are provided below. A protein containing the LC and HC CDRs shown below, or a protein containing the light ing the signal sequence, variable region and constant region of both the light and heavy chains were sequenced. The sequence data is available in 539A-R0108-A01 (539A-X0034-C02).

```
Light Chain
Light V gene = VL2_2e 2e.2.2/V1-3/DPL12
Light J gene = JL3

FR1-L                     CDR1-L            FR2-L           CDR2-L
539A-M0240-B03:   QYELTQPRSVSGSPGQSVTISC TGTSSDVGGYNYVS WYQQHPGKAPKLMIY DVSKRPS  GVPD
                          FR3-H                                 CDR3-L       FR4-L
539A-M0240-B03:   RFSGSKSGNTASLTISGLQAEDEADYYC CSYAGSYTLV FGGGTKLTVL   (SEQ ID NO: 927)
Heavy Chain
Heavy V gene: VH3_3-23 DP-47/V3-23
Heavy J gene: JH3

FR1-H                     CDR1-H      FR2-H           CDR2-H
539A-M0240-B03:   EVQLLESGGGLVQPGGSLRLSCAASGFTFS TYQMV WVRQAPGKGLEWVS VIYPSGGPTVYADSVKG
                          FR3-H                                 CDR3-H       FR4-H
539A-M0240-B03:   RFTISRDNSKNTLYLQMNSLRAEDTAVYYCAR GEDYYDSSGPGAFDI WGQGTMVTVSS   (SEQ ID NO: 928)
Light Variable
539A-M0240-B03-Light: Parental clone (sFab; IgG in pBh1(f)) light variable Q   Y   E   L   T   Q   P   R   S   V   S   G   S   P   G   Q   S   V   T   I
539A-M0240-B03:   CAGTACGAATTGACTCAGCCTCGCTCAGTGTCCGGGTCTCCTGGACAGTCAGTCACCATC
                  S   C   T   G   T   S   S   D   V   G   G   Y   N   Y   V   S   W   Y   Q   Q
539A-M0240-B03:   TCCTGCACTGGAACCAGCAGTGATGTTGGTGGTTATAACTATGTCTCCTGGTACCAACAG
                  H   P   G   K   A   P   K   L   M   I   Y   D   V   S   K   R   P   S   G   V
539A-M0240-B03:   CACCCAGGCAAAGCCCCCAAACTCATGATTTATGATGTCAGTAAGCGGCCCTCAGGGGTC
                  P   D   R   F   S   G   S   K   S   G   N   T   A   S   L   T   I   S   G   L
539A-M0240-B03:   CCTGATCGCTTCTCTGGCTCCAAGTCTGGCAACACGGCCTCCCTGACCATCTCTGGGCTC
                  Q   A   E   D   E   A   D   Y   Y   C   C   S   Y   A   G   S   Y   T   L   V
539A-M0240-B03:   CAGGCTGAGGATGAGGCTGATTATTACTGCTGCTCATATGCAGGCAGCTACACTTTGGTG
                  F   G   G   T   K   L   T   V   L   (SEQ ID NO: 930)
539A-M0240-B03:   TTCGGCGGAGGGACCAAGCTGACCGTCCTA (SEQ ID NO: 929)
Heavy Variable
539a-M0240-B03-Heavy: Parental clone (sFab; IgG in pBh1 (f)) Heavy variable E   V   Q   L   L   E   S   G   G   G   L   V   Q   P   G   G   S   L   R   L
539A-M0240-B03:   GAAGTTCAATTGTTAGAGTCTGGTGGCGGTCTTGTTCAGCCTGGTGGTTCTTTACGTCTT
                  S   C   A   A   S   G   F   T   F   S   T   Y   Q   M   V   W   V   R   Q   A
539A-M0240-B03:   TCTTGCGCTGCTTCCGGATTCACTTTCTCTACTTACCAGATGGTTTGGGTTCGCCAAGCT
                  P   G   K   G   L   E   W   V   S   V   I   Y   P   S   G   G   P   T   V   Y
539A-M0240-B03:   CCTGGTAAAGGTTTGGAGTGGGTTTCTGTTATCTATCCTTCTGGTGGCCCTACTGTTTAT
                  A   D   S   V   K   G   R   F   T   I   S   R   D   N   S   K   N   T   L   Y
539A-M0240-B03:   GCTGACTCCGTTAAAGGTCGCTTCACTATCTCTAGAGACAACTCTAAGAATACTCTCTAC
```

```
                          L  Q  M  N  S  L  R  A  E  D  T  A  V  Y  Y  C  A  R  G  E
539A-M0240-B03: TTGCAGATGAACAGCTTAAGGGCTGAGGACACGGCCGTGTATTACTGTGCGAGAGGGGAG

D  Y  Y  D  S  S  G  P  G  A  F  D  I  W  G  Q  G  T  M  V  T  V  S  S (SEQ ID NO: 932)

539A-M0240-B03: GACTACTATGATAGTAGTGGCCCGGGGGCTTTTGATATCTGGGGCCAAGGGACAATGGTCACCGTCTCAAGC (SEQ ID NO: 931)
```

The amino acid and nucleic acid sequences for another exemplary protein that can be used in the methods described herein are provided below. A protein containing the LC and HC CDRs shown below, or a protein containing the light chain and heavy chain variable regions (LV and HV, respectively) shown below can also be used in the methods described herein. A protein containing the light chain and heavy chain (designated as LV+LC and HV+HC, respectively, below) sequences can also be used.

```
Light Chain
Light V gene = VL2_2e 2e.2.2/V1-3/DPL12
Light J gene = JL3

FR1-L                    CDR1-L              FR2-L              CDR2-L
539A-X0034-C02(DX-2803): QSALTQPRSVSGSPGQVTISC TGTSSDVGGYNYVS WYQQHPGKAPKLMIY DVSKRPS GVPD
                         FR3-L                        CDR3-L        FR4-L
539A-X0034-C02(DX-2802): RFSGSKSGNTASLTISGLQAEDEADYYC GSYAGSYTLV FGGGTKLTVL    (SEQ ID NO: 933)
Heavy Chain
Heavy V gene: VH3_3-23 DP-47/V3-23
Heavy J gene: JH3

FR1-H                              CDR1-H   FR2-H            CDR2-H
539A-X0034-C02(DX-2802): EVQLLESGGGLVQPGGSLRLSCAASGFTFS TYQMV WVRQAPGKGLEWVS VIYPSGGPTVYAADSVKG
                         FR3-H                         CDR3-H             FR4-H
539A-X0034-C02(DX-2802): RFTISRDNSKNTLYLQMNSLRAEDTAVYCAR GEDYYDSSGPGAFDI WGQGTMVTVSS (SEQ ID NO: 934)
Light Variable
539A-X0034-C02(DX-2802)-Light: Germlined, codon optimized in GS vector 539A-X0034-C02(DX-2802): CAGAGCGCCCTGACCCAGCCCAGAAGCGTGTCCGGCAGCCCAGGCCAGAGCGTGACCATC
                          Q  S  A  L  T  Q  P  R  S  V  S  G  S  P  G  Q  S  V  T  I
539A-X0034-C02(DX-2802): AGCTGCACCGGCACCAGCAGCGACGTGGGCGGCTACAACTACGTGTCCTGGTATCAGCAG
                          S  C  T  G  T  S  S  D  V  G  G  Y  N  Y  V  S  W  Y  Q  Q
539A-X0034-C02(DX-2802): CACCCCGGCAAGGCCCCCAAGCTGATGATCTACGACGTGTCCAAGAGGCCCAGCGGCGTG
                          H  P  G  K  A  P  K  L  M  I  Y  D  V  S  K  R  P  S  G  V
539A-X0034-C02(DX-2802): CCCGACAGGTTCAGCGGCAGCAAGAGCGGCAACACCGCCAGCCTGACCATCTCCGGACTG
                          P  D  R  F  S  G  S  K  S  G  N  T  A  S  L  T  I  S  G  L
539A-X0034-C02(DX-2802): CAGGCCGAGGACGAGGCCGACTACTACTGCTGCAGCTACGCCGGCAGCTACACCCTGGTC
                          Q  A  E  D  E  A  D  Y  Y  C  C  S  Y  A  G  S  Y  T  L  V
539A-X0034-C02(DX-2802): TTCGGCGGAGGGACCAGCTGACCGTGCTG (SEQ ID NO: 935)
                          F  G  G  G  T  K  L  T  V  L  (SEQ ID NO: 936)
Heavy Variable
539A-X0034-C02(DX-2802)-Heavy: Germlined, condon optimized in GS vector 539A-X0034-C02(DX-2802): GAGGTGCAATTGCTGGAAAGCGGCGGAGGACTGGTGCAGCCAGGCGGCAGCCTGAGGCTG
                          E  V  Q  L  L  E  S  G  G  G  L  V  Q  P  G  G  S  L  R  L
539A-X0034-C02(DX-2802): TCCTGCGCCGCCAGCGGCTTCACCTTCAGCACCTACCAGATGGTGTGGGTGCGCCAGGCC
                          S  C  A  A  S  G  F  T  F  S  T  Y  Q  M  V  W  V  R  Q  A
539A-X0034-C02(DX-2802): CCAGGCAAGGGCCTGGAATGGGTGTCCGTGATCTACCCCAGCGGCGGACCCACCGTGTAC
                          P  G  K  G  L  E  W  V  S  V  I  Y  P  S  G  G  P  T  V  Y
539A-X0034-C02(DX-2802): GCCGACAGCGTGAAGGGCAGGTTCACCATCAGCAGGGACAACAGCAAGAACACCCTGTAC (SEQ ID NO: 937)

ADSVKG R F T I S R D N S K N T L Y (SEQ ID NO: 938)

539A-X0034-C02(DX-2802): CTGCAGATGAACAGCCTGAGGGCCGAGGACACCGCCGTGTACTACTGCGCCAGGGGCGAG
                          L  Q  M  N  S  L  R  A  E  D  T  A  V  Y  Y  C  A  R  G  E
539A-X0034-C02(DX-2802): GACTACTACGACAGCAGCGGCCCAGGCGCCTTCGACATCTGGGGCCAGGGCACAATGGTGACCGTGTCCAGC
                          D  Y  Y  D  S  S  G  P  G  A  F  D  I  W  G  Q  G  T  M  V  T  V  S  S
```

```
>539A-X0034-C02(DX-2802): LV + LC dna
CAGAGCGCCCTGACCCAGCCCAGAAGCGTGTCCGGCAGCCCAGGCCAGAGCGTGACCATCAGCTGCACCGGCACCAGCAGCGACGTGGGCGGCTACA
ACTACGTGTCCTGGTATCAGCAGCACCCCGGCAAGGCCCCCAAGCTGATGATCTACGACGTGTCCAAGAGGCCCAGCGGCGTGCCCGACAGGTTCAG
CGGCAGCAAGAGCGGCAACACCGCCAGCCTGACCATCTCCGGACTGCAGGCCGAGGACGAGGCCGACTACTACTGCTGCAGCTACGCCGGCAGCTAC
ACCCTGGTGTTCGGCGGAGGGACCAAGCTGACCGTGCTGGGCCAGCCCAAGGCTGCCCCCAGCGTGACCCTGTTCCCCCCCAGCAGCGAGGAACTGC
AGGCCAACAAGGCCACACTGGTGTGCCTGATCAGCGACTTCTACCCAGGCGCCGTGACCGTGGCCTGGAAGGCCGACAGCAGCCCCGTGAAGGCCGG
CGTGGAGACAACCACCCCCAGCAAGCAGAGCAACAACAAGTACGCCGCCAGCAGCTACCTGAGCCTGACCCCCGAGCAGTGGAAGTCCCACAGGTCC
TACAGCTGCCAGGTGACCCACGAGGGCAGCACCGTGGAGAAAACCGTGGCCCCCACCGAGTGTAGCTGATGA (SEQ ID NO: 939)
>539A-X0034-C02(DX-2802): HV + HC dna
GAGGTGCAATTGCTGGAAAGCGGCGGAGGACTGGTGCAGCCAGGCGGCAGCCTGAGGCTGTCCTGCGCCGCCAGCGGCTTCACCTTCAGCACCTACCAGAT
GGTGTGGGTGCGCCAGGCCCCAGGCAAGGGCCTGGAATGGGTGTCCGTGATCTACCCAGCGGCGGACCCACCGTGTACGCCGACAGCGTGAAGGGCAGGT
TCACCATCAGCAGGGACAACAGCAAGAACACCCTGTACCTGCAGATGAACAGCCTGAGGGCCGAGGACACCGCCGTGTACTACTGCGCCAGGGGCGAGGAC
TACGACAGCAGCGGCCCAGGCGCCTTCGACATCTGGGGCCAGGGCACAATGGTGACCGTGTCCAGCGCCAGCACCAAGGGCCCCAGCGTGTTCCCGCTAGC
ACCTTCCTCCAAGTCCACCTCTGGCGGCACCGCCGCTCTGGGCTGCCTGGTGAAGGACTACTTCCCTGACGCCTGTGACCGTGAGCTGGAACTCTGGCGCC
CTGACCTCCGGCGTCGATACCTTCCCTGCCGTGCTGCAGTCCTCCGGCCTGTACTCCCTGTCCTCCGTGGTGACAGTGCCTTCCTCCTCCTGGGCACCCAG
ACCTACATCTGCAACGTGAACCACAAGCCTTCCAACACCAAGGTGGACAAGCGGGTGGAGCCTAAGTCCTGCGACAAGACCCACACCTGCCCTCCCTGCCC
TGCCCCTGAGCTGCTGGGCGGACCCTCCGTGTTCCTGTTCCCTCCTAAGCCTAAGGACACCCTGATGATCTCCCGGACCCCTGAGGTGACCTGCGTGGTGG
TGGACGTGTCCCACGCGGACCCAGAGGTGAAGTTTAATTGGTATGTGGACGGCGTGGAGGTCCACAACGCCAAGACCAAGCCTGGGAGGAACAGTACAAC
TCCACCTACCGGGTGGTGTCCGTGCTGACCGTGCTGCACCAGGACTGGCTGAACGGCAAGGAATACAAGTGCAAAGTCTCCAACAAGGCCCTGCCTGCCCC
CATCGAGAAAACCATCTCCAAGGCCAAGGGCCAGCCTCGCCAGGCCCGTGTACACCCTGCCTCCTAGCCGGGAGGAAATGACCAAGAACCAGGTGTCCC
TGACTGTCTGGTGAAGGGCTTCTACCCTTCCGATATCGCCGTGGAGTGGGAGTCCAACGGCCAGCCTGAGAACAACTACAAGACCACCCCTCCTGTGCTGG
ACTCCGACGGCTCCTTCTTCCTGTACTCCAAGVTGACCGTGGACAAGTCCCGGTGGCAGCAGGGCAACGTGTTCTCCTGCTCCGTGATGCACGAGGCCCTG
CACAACCACTACACCCAGAAGTCCCTGTCCCTGAGCCCTGGCAAGTGA (SEQ ID NO: 940)
>539A-X0034-C02(DX-2802): LV + LC aa
QSALTQPRSVSGSPGQSVTISCTGTSSDVGGYNYVSWYQQHPGKAPKLMIYDVSKRPSGVPDRFSGSKSGNTASLTISGLQAEDEADYYCCSYAGSYTLVF
GGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHE
GSTVEKTVAPTECSss (SEQ ID NO: 941)
>539A-X0034-C02(DX-2802): HV + HC aa
EVQLLESGGGLVQPGGSLRLSCAASGFTFSTYQMVWVRQAPGKGLEWVSVIYPSGGPTVYADSVKGRFTISRDNSKNTLYLQMNSLRAEDTAVYYCARGED
YYDSSGPGAFDIWGQGTMVTVSSASTKGPSVFPLAPSSKSTSGGTAALGCLVKDYFPEPVTVSWNSGALTSGVHTFPAVLQSSGLYSLSSVVTVPSSSLGT
QTYICNVNHKPSNTKVDKRVEPKSCDKTHTCPPCPAPELLGGPSVFLFPPKPKDTLMISRTPEVTCVVVDVSHEDPEVKFNYVDGVEVHNAKTKPREEQYN
STYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLPGKs (SEQ ID NO: 942)
```

Example 14

Studies with Colon Cancer Cells

Figure 7:
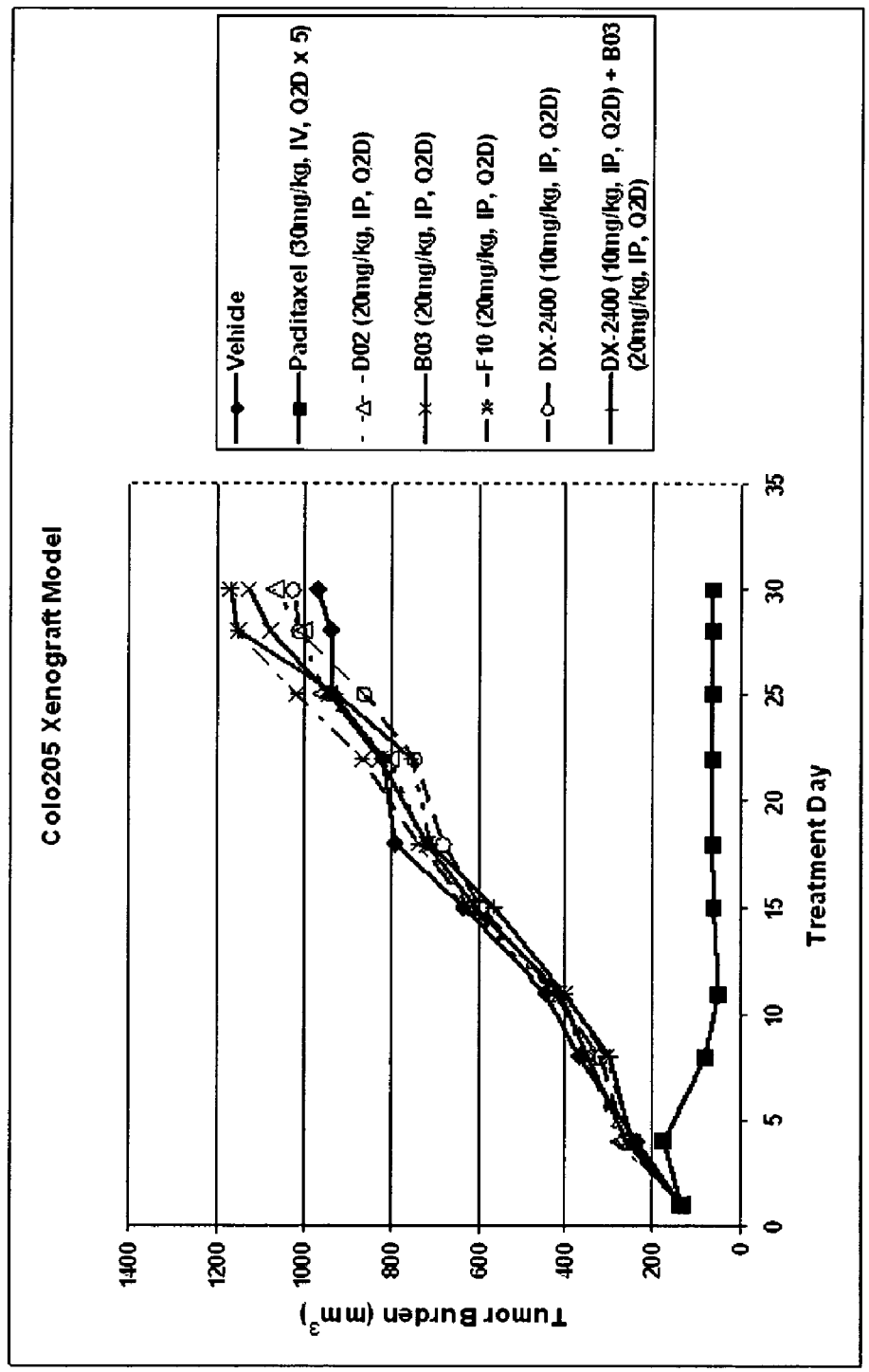
FIG. 7 is a line graph showing activity of MMP-9 binding proteins in a Colo205 colon xenograft cancer model.

The efficacies of novel antibodies DL8, DL12, DL15 and DL2 in the Colo205 colon carcinoma model were evaluated. The antibodies were tested alone or in combination. The results are shown in FIG. 7.

Drugs and Treatment:

| | | | 1 Drug/Testing Agent | | | | 2 Drug/Testing Agent | | | |
|---|---|---|---|---|---|---|---|---|---|---|
| Gr. | N | Agent | Vehicle | mg/kg | Route | Schedule | Agent | Vehicle | mg/kg | Route | Schedule |
| 1[#] | 10 | vehicle | PBS | — | ip | qod to end | — | — | — | — | — |
| 2 | 10 | paclitaxel | 5% EC | 30 | iv | qod × 5 | — | — | — | — | — |
| 3 | 10 | DL8 | PBS | 20 | ip | qod to end | — | — | — | — | — |
| 4 | 10 | DL12 | PBS | 20 | ip | qod to end | — | — | — | — | — |
| 5 | 10 | DL15 | PBS | 20 | ip | qod to end | — | — | — | — | — |
| 6 | 10 | DL2 | Citrate buffer | 10 | ip | qod to end | — | — | — | — | — |
| 7 | 10 | DL2 | Citrate buffer | 10 | ip | qod to end | DL12 | PBS | 20 | ip | qod to end |

[#]Control Group

Procedures:
Set up HRLN female nu/nu mice with 1×10⁶ Colo205 tumor cells in 50% Matrigel subcutaneously (sc) in flank
Do a pair match when tumors reach an average size of 100-150 mg, and begin treatment
Body Weight: daily for the first five days and then biwk to end
Caliper Measurement: biwk to end
Final body weights and calipers should be taken on the last day of the study.
Endpoint TGI (tumor growth inhibition). Animals are to be monitored as a group. The endpoint of the experiment is a mean tumor weight in Control Group of 1 gms or 45 days, whichever comes first. When the endpoint is reached, all the animals are to be euthanized.

Study Conditions:
Statistical analysis of the data will be performed using:
  Kruskal-Wallis with post hoc Dunn's test Groups 3-7 vs Group 1 and Group 7 vs Groups 4 and 6
  Mann-Whitney test GroupI vs Group 2
Clinical agent PACLITAXEL is for use as a positive control only
Dosing:
Prepare dosing solutions:
  DL2, DL8, DL12, DL15—every week, store at 4° C.
  paclitaxel—every dose, store at room temp
DL12=B03 in PBS=539A-M0240-B03 IgG1 (h/mMMP-9 antibody inhibitor) (parental) (539A-M0240-B03 listed above)
DL8=D02 in PBS=539A-M0237-D02 IgG1 (MMP-9/-2 dual reactive antibody inhibitor) (parental)
DL15=F10 in PBS=539A-M0166-F10 IgG1 (hMMP-9 antibody inhibitor) (parental)
DL2=DX-2400 in citrate buffer solution.
paclitaxel=paclitaxel in 5% Ethanol: 5% Cremophor EL: 90% D5W
vehicle=PBS
Dosing volume=10 mL/kg (0.200 mL/20 g mouse). Adjust volume accordingly for body weight.

Save remaining compound for future use
Discard remaining dosing solution
Sampling:
Sampling 1
  Timepoint: 24 hours post 5th dose of DL10 (Day 10)
  All Groups, the 6 Animals closest to mean:
  Blood Collection
    Collect full volume blood by terminal cardiac puncture under $CO_2$ anesthesia
    Process blood for:
      Serum (anti-coagulant—none, preservation—freeze, shipping condition—−80° C.)
Sampling 2
  Timepoint: 24 hours post 10th dose of DL10 (Day 20)
  All Groups, same animals sampled in Sampling 1:
  Blood Collection as above
Sampling 3
  Timepoint: at endpoint (24 hrs post last DL dose)
  All Groups All Animals:
  Blood Collection
    Collect full volume blood by terminal cardiac puncture under $CO_2$ anesthesia
    Process blood for:
      Serum (anti-coagulant—none, preservation—freeze, shipping condition—−80° C.)
  Organ Collection
    Tumor (weigh sample, divide into 2 parts)
      Part 1: preservation—snapfreeze in a cryovial, shipping condition—−80° C.
      Part 2: preservation—OCT, shipping condition—−80° C.

539A-M0166-F10: The variable domain sequences for 539A-M0166-F10 are provided above.

DX-2400: DX-2400 is an inhibitory MMP-14 binding antibody. The variable domain sequences for DX-2400 are:

```
VL:                                                                    (SEQ ID NO: 944)
           FR1------------------ CDR1------- FR2------------ CDR2---
DX-2400    DIQMTQSPSSLSASVGDRVTITC RASQSVGTYLN WYQQKPGKAPKLLIY ATSNLRS GVPS

FR3----------------------- CDR3------ FR4-------
DX-2400    RFSGSGSGTDFTLTISSLQPEDFATYYC QQSYSIPRFT FGPGTKVDIK
CDR regions are in bold.

VH:
DX-2400    FR1--------------------------- CDR1- FR2----------- CDR2-------
           EVQLLESGGGLVQPGGSLRLSCAASGFTFS LYSMN WVRQAPGKGLEWVS SIYSSGGSTLY

DX-2400    CDR2-- FR3--------------------------- CDR3-- FR4---------
           ADSVKG RFTISRDNSKNTLYLQMNSLRAEDTAVYYCAR GRAFDI WGQGTMVTVSS (SEQ ID NO: 943)
CDR regions are in bold.
```

539A-M0237-D02: 539A-M0237-D02 is an inhibitory MMP-9/-2 dual reactive antibody.

The variable domain sequences for 539A-M0237-D02 are:

```
VH:
MKKLLFAIPLVVPFVAQPAMAEVQLLESGGGLVQPGGSLRLSCAASGFTF
SQYPMWWVRQAPGKGLEWVSYIVPSGGRTYYADSVKGRFTISRDNSKNTL
YLQMNSLRAEDTAVYYCAKDRAYGDYVGWNGFDYWGQGTLVTVSSASTKG
PSVFPLAPSSKS (SEQ ID NO: 945)

VL:
FYSHSAQDIQMTQSPATLSLSPGERATLSCRASQSISSFLAWYQQKPGQA
PRLLIYDASYRATGIPARFSGS GSGTDFTLTISSLEPEDYAVYYCQQRG
NWPITFGQGTRLEIKRTVAAPS (SEQ ID NO: 946)
```

Example 15

Studies with Colon Cancer Cells

Figure 8:
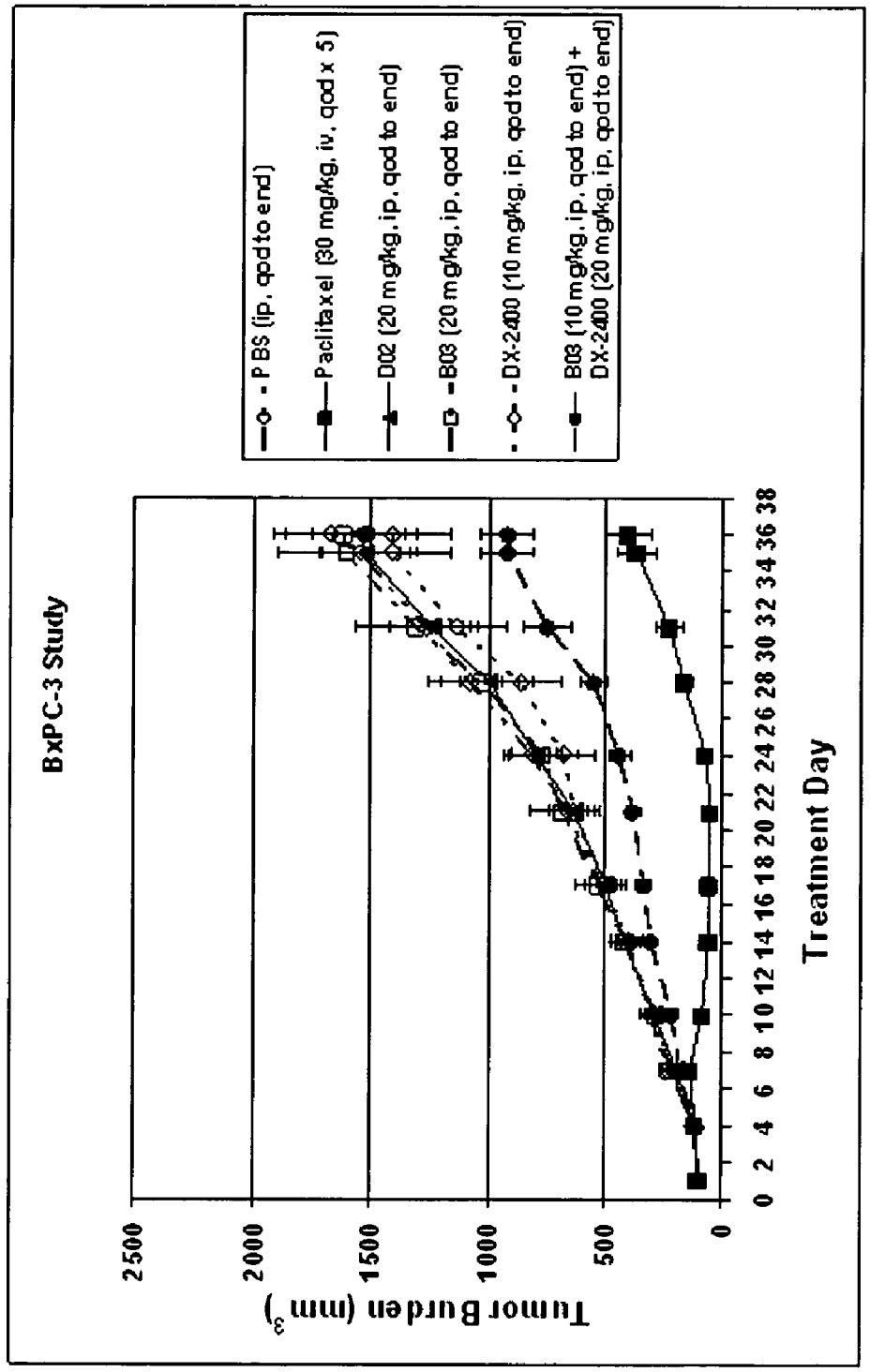
FIG. 8 is a line graph showing the efficacy of MMP-9 binding proteins in a BxPC-3 pancreatic cancer model.

The efficacies of novel antibodies DL8, DL12, and DL2 in the BxPC-3 pancreatic carcinoma model were evaluated. The antibodies were tested alone or in combination. The results are shown in FIG. 8.

Drugs and Treatment:

| Gr. | N | 1 Drug/Testing Agent | | | | | 2 Drug/Testing Agent | | | | |
|---|---|---|---|---|---|---|---|---|---|---|---|
| | | Agent | Vehicle | mg/kg | Route | Schedule | Agent | Vehicle | mg/kg | Route | Schedule |
| 1[#] | 10 | vehicle | PBS | — | ip | qod to end | — | — | — | — | — |
| 2 | 10 | paclitaxel | 5% EC | 30 | iv | qod × 5 | — | — | — | — | — |
| 3 | 10 | DL8 | PBS | 20 | ip | qod to end | — | — | — | — | — |
| 4 | 10 | DL12 | PBS | 20 | ip | qod to end | — | — | — | — | — |
| 5 | 10 | DL2 | Citrate buffer | 10 | ip | qod to end | — | — | — | — | — |
| 6 | 10 | DL2 | Citrate buffer | 10 | ip | qod to end | DL12 | PBS | 20 | ip | qod to end |

[#]Control Group

Procedures:
Set up HRLN female nu/nu mice with 1 mm$^3$ Bx-PC3 tumor fragments sc in flank
Do a pair match when tumors reach an average size of 80-120 mg, and begin treatment
Body Weight: 5/2 then biwk to end
Caliper Measurement: biwk to end
Final body weights and calipers should be taken on the last day of the study.
Endpoint TGI. Animals are to be monitored as a group. The endpoint of the experiment is a mean tumor weight in Control Group of 1 gms or 45 days, whichever comes first. When the endpoint is reached, all the animals are to be euthanized.
Study Conditions:
Statistical analysis of the data will be performed using:
  Kfuskal-Wallis with post hoc Dunn's test Groups 3-6 vs Group 1 and Group 6 vs Group 3 and Group 5
  Mann-Whitney test Group 1 vs Group 2
Clinical agent PACLITAXEL is for use as a positive control only
Dosing:
Prepare dosing solutions:
  DL2, DL8, DL12—every week, store at 4° C.
  paclitaxel—every dose, store at room temp
DL12=B03 in PBS
DL8=D02 in PBS
DL2=DX-2400 in citrate buffer solution
paclitaxel=paclitaxel in 5% Ethanol: 5% Cremophor EL: 90% D5W
vehicle=PBS
Dosing volume=10 mL/kg (0.200 mL/20 g mouse). Adjust volume accordingly for body weight.
Save remaining compound for future use
Discard remaining dosing solution
Sampling:
Sampling 1
  Timepoint: 24 hours post 5$^{th}$ dose (Day 10)
  All Groups 6 Animals closest to mean:
    Blood Collection
      Collect full volume blood by terminal cardiac puncture under CO$_2$ anesthesia
      Process blood for:
        Serum (anti-coagulant—none, preservation—freeze, shipping condition—−80° C.)
Sampling 2
  Timepoint: 24 hours post 10$^{th}$ dose (Day 20)
  All Groups same animals sampled in Sampling 1:
  Blood Collection as above
Sampling 3
  Timepoint: at endpoint (24 hours post last dose)

All Groups All Animals:
Blood Collection
  Collect full volume blood by terminal cardiac puncture under CO$_2$ anesthesia
  Process blood for:
    Serum (anti-coagulant—none, preservation—freeze, shipping condition—−80° C.)
Organ Collection
  Tumor (weigh sample, divide into 2 parts)
    Part 1: preservation—snap freeze in a cryovial, shipping condition—−80° C.
    Part 2: preservation—OCT, shipping condition—−80° C.

Example 16

Collagen-Induced Arthritis Model

Collagen-induced arthritis (CIA) is produced by the immunization of susceptible strains of rat/mice with native type II collagen.
Collagen is emulsified in Complete Freund's Adjuvant (CFA) and injected subQ (100 µg collagen: 100 µg CFA/mouse) at the base of the tail. Ten mice are injected subQ with 0.05 ml of distilled water/CFA emulsion. A booster injection of collagen in incomplete adjuvant is given IP 21 days after the initial immunization.
Disease is due to an auto-immune response induced upon immunization with collagen.
Drugs and Treatments

| Group No. | No. Mice | Test Material | Dose (mg/kg) | ROA (route of administration) |
|---|---|---|---|---|
| 1 | 10 | Vehicle | N/A | IP, qod |
| 2 | 10 | 539A-M0240-B03 | 20 | IP, qod |
| 3 | 10 | Methotrexate | 3 | IP, QD |
| 4 | 10 | Vehicle | NON-sensitized mice | IP, qod |

Figure 9:
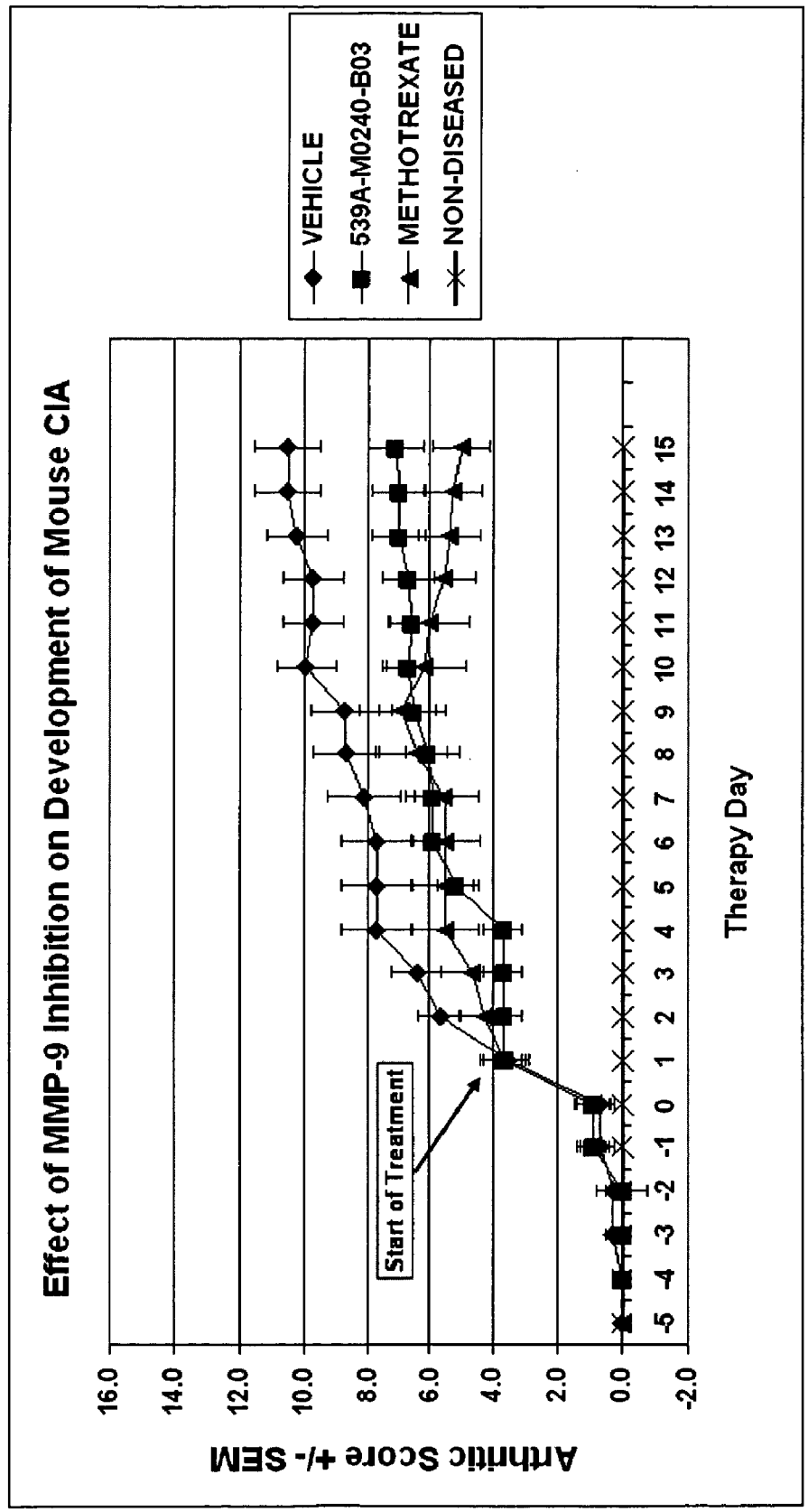
FIG. 9 is a line graph showing the efficacy of an MMP-9 binding protein (539A-M0240-B03) in a mouse collagen-induced arthritis model.

The joints were scored for severity of arthritis as follows, and the results are shown in FIG. 9.
0=no visible effects of arthritis
1=edema and erythema of one digit or joint
2=edema and erythema of two joints
3=edema and erythema of more than two joint
4=severe arthritis of the entire paw and digits, accompanied by ankylosis of the ankle and deformity of the limb. The score for each limb was summed and recorded as the arthritic index (AI) for each individual animal.

Figure 10:
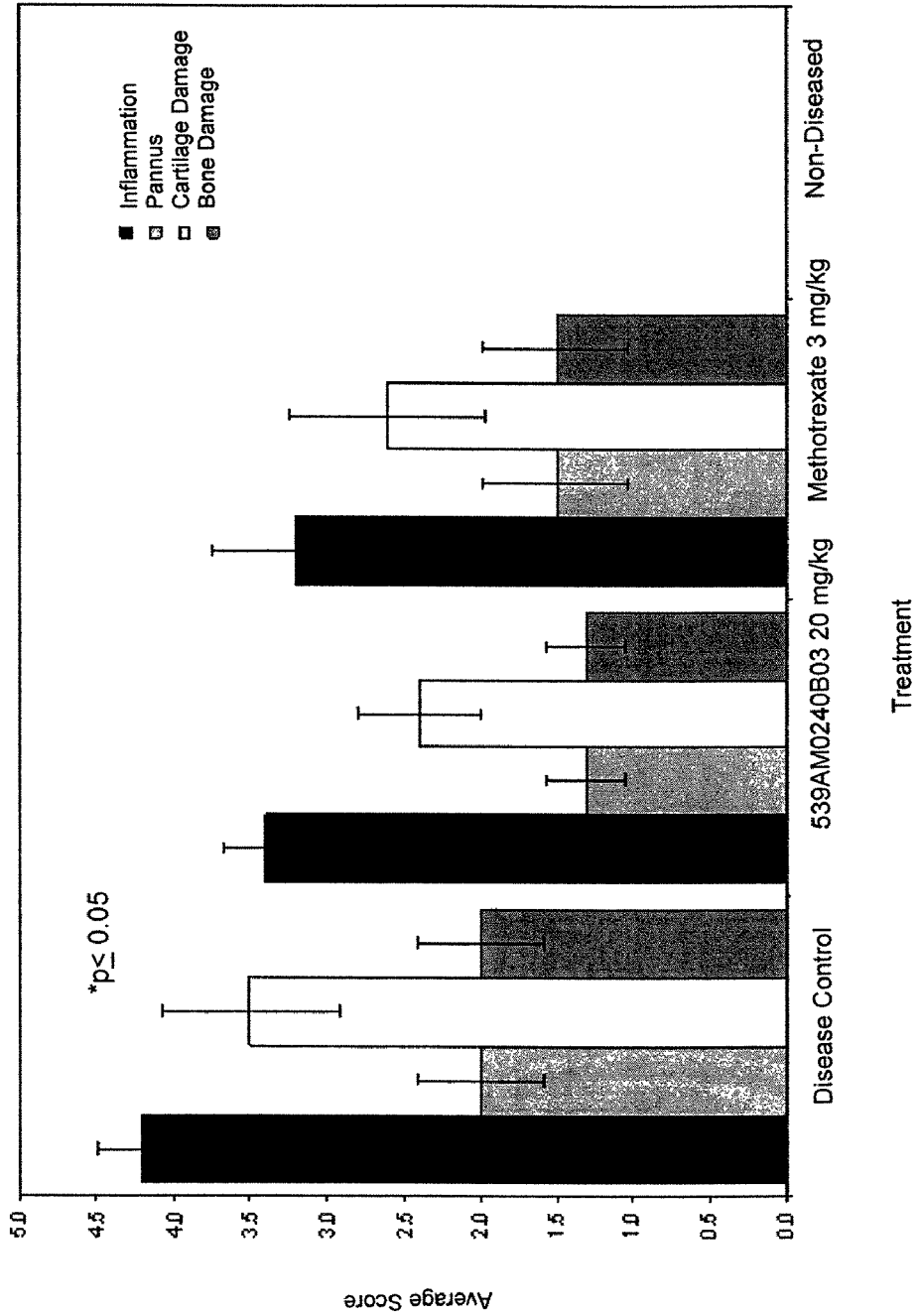
FIG. 10 is a diagram showing effects of disease and treatment on joint parameters of MMP-9 binding protein (539A-M0240-B03) in a mouse collagen-induced arthritis model.

The joints were scored for inflammation, pannus, cartilage damage and bone resorption as follows, and the results are shown in FIG. 10.

Inflammation Scoring
- 0=Normal
- 1=Minimal infiltration of inflammatory cells in synovium and periarticular tissue of affected joints.
- 2=Mild infiltration, if paws, restricted to affected joints
- 3=Moderate infiltration with moderate edema, if paws, restricted to affected joints.
- 4=Marked infiltration affecting most areas with marked edema
- 5=Severe diffuse infiltration with severe edema Pannus
- 0=Normal
- 1=Minimal infiltration of pannus in cartilage and subchondral bone
- 2=Mild infiltration with marginal zone destruction of hard tissue in affected joints.
- 3=Moderate infiltration with moderate hard tissue destruction in affected joints.
- 4=Marked infiltration with marked destruction of joint architecture, most joints.
- 5=Severe infiltration associated with total or near total destruction of joint architecture, affects all joints.

Cartilage Damage
- 0=Normal
- 1=Minimal=minimal to mild loss of toluidine blue staining with no obvious chondrocyte loss or collagen disruption in affected joints
- 2=Mild=mild loss of toluidine blue staining with focal mild (superficial)chondrocyte loss and/or collagen disruption in affected joints.
- 3=Moderate=moderate loss of toluidine blue staining with multifocal moderate (depth to middle zone) chondrocyte loss and/or collagen disruption in affected joints
- 4=Marked=marked loss of toluidine blue staining with multifocal marked (depth to deep zone) chondrocyte loss and/or collagen disruption in most joints
- 5=Severe=severe diffuse loss of toluidine blue staining with multifocal severe (depth to tide mark) chondrocyte loss and/or collagen disruption in all joints.

Bone Resorption
- 0=Normal
- 1=Minimal=small areas of resorption, not readily apparent on low magnification, rare osteoclasts in affected joints
- 2=Mild=more numerous areas of, not readily apparent on low magnification, osteoclasts more numerous in affected joints
- 3=Moderate=obvious resorption of medullary trabecular and cortical bone without full thickness defects in cortex, loss of some medullary trabeculae, lesion apparent on low magnification, osteoclasts more numerous in affected joints
- 4=Marked=Full thickness defects in cortical bone, often with distortion of profile of remaining A number of embodiments of the invention have been described. Nevertheless, it will be understood that various modifications may be made without departing from the spirit and scope of the invention. Accordingly, other embodiments are within the scope of the following claims.

What is claimed is:

1. An isolated antibody that binds to human Matrix Metalloproteinase-9 (MMP-9), wherein the antibody comprises a heavy chain variable domain comprising a HC-CDR1 comprising the amino acid sequence of SEQ ID NO: 956, a HC-CDR2 comprising the amino acid sequence of SEQ ID NO: 957, a HC-CDR3 comprising the amino acid sequence of SEQ ID NO: 958, and a light chain variable region comprising an LC-CDR1 comprising the amino acid sequence of SEQ ID NO: 953, a LC-CDR2 comprising the amino acid sequence of SEQ ID NO: 954, and a LC-CDR3 region comprising the amino acid sequence of SEQ ID NO: 955.

2. An anti-MMP-9 antibody-drug conjugate, wherein the conjugate comprises the isolated antibody of claim 1 and a drug.

3. The conjugate of claim 2, wherein the drug is a cytotoxic or cytostatic agent.

4. A composition comprising the isolated antibody of claim 1 and a pharmaceutically acceptable carrier.

* * * * *